US012569546B2

(12) United States Patent
Homan et al.

(10) Patent No.: US 12,569,546 B2
(45) Date of Patent: Mar. 10, 2026

(54) NEOANTIGEN IMMUNOTHERAPIES

(71) Applicant: IOGENETICS, LLC, Madison, WI (US)

(72) Inventors: Jane Homan, Hillpoint, WI (US); Robert D. Bremel, Hillpoint, WI (US)

(73) Assignee: IOGENETICS, LLC, Madison, WI (US)

( * ) Notice: Subject to any disclaimer, the term of this patent is extended or adjusted under 35 U.S.C. 154(b) by 869 days.

(21) Appl. No.: 16/898,924

(22) Filed: Jun. 11, 2020

(65) Prior Publication Data

US 2020/0390873 A1     Dec. 17, 2020

Related U.S. Application Data

(60) Provisional application No. 62/983,197, filed on Feb. 28, 2020, provisional application No. 62/859,962, filed on Jun. 11, 2019.

(51) Int. Cl.
*A61K 39/00* (2006.01)
*A61K 40/11* (2025.01)
(Continued)

(52) U.S. Cl.
CPC .. *A61K 39/0011* (2013.01); *A61K 39/001104* (2018.08); *A61K 39/001106* (2018.08); *A61K 39/001151* (2018.08); *A61K 39/001162* (2018.08); *A61K 39/001163* (2018.08); *A61K 40/11* (2025.01); *A61K 40/4201* (2025.01); *A61K 40/4204* (2025.01);
(Continued)

(58) Field of Classification Search
CPC . A61K 39/0011; A61K 45/06; A61K 2039/80
See application file for complete search history.

(56) References Cited

U.S. PATENT DOCUMENTS

| | | | | |
|---|---|---|---|---|
| 10,706,955 B2 * | 7/2020 | Bremel | ............... | G16B 40/20 |
| 2016/0101170 A1 * | 4/2016 | Hacohen | ............... | A61P 37/04 |
| | | | | 424/277.1 |
| 2017/0161430 A1 * | 6/2017 | Bremel | ............ | G01N 33/6878 |

FOREIGN PATENT DOCUMENTS

| | | | |
|---|---|---|---|
| WO | 2005097202 A2 | 10/2005 |
| WO | 2012092426 A1 | 7/2012 |
| | (Continued) | |

OTHER PUBLICATIONS

Schumacher et al. Neoantigens in cancer immunotherapy. Apr. 3, 2015 • vol. 348 Issue 6230 (Year: 2015).*

(Continued)

*Primary Examiner* — Janet L Andres
*Assistant Examiner* — Brian Hartnett
(74) *Attorney, Agent, or Firm* — Casimir Jones, S.C.; J. Mitchell Jones

(57) ABSTRACT

This invention provides a method for maximizing the immune response to mutated tumor specific proteins, either by means of stimulation of dendritic cells or T cells in vitro followed by administration of these cells to a patient, or by means of administration of a neoantigen vaccine in which de novo peptides, or their encoding nucleic acids, have been designed to ensure an appropriate level of binding affinity to a particular cancer patient's MHC alleles. This invention further provides for modulating the immune response in an immunopathology other than cancer.

7 Claims, 20 Drawing Sheets

Specification includes a Sequence Listing.

(51) Int. Cl.
    *A61K 40/42*      (2025.01)
    *A61K 45/06*      (2006.01)

(52) U.S. Cl.
    CPC ...... *A61K 40/4205* (2025.01); *A61K 2039/54*
          (2013.01); *A61K 45/06* (2013.01); *A61K*
        *2239/47* (2023.05); *A61K 2239/55* (2023.05)

(56)             References Cited

FOREIGN PATENT DOCUMENTS

WO      WO-2016159875 A1 * 10/2016  .............  A61K 35/15
WO          2017001491 A2     1/2017

OTHER PUBLICATIONS

International Search Report & Written Opinion, International Patent Application No. PCT/US2020/037206, mailed Nov. 13, 2020, 20 pages.
Bentzen et al. Evolution of MHC-based technologies used for detection of antigen-responsive T cells. Cancer Immunology, immunotherapy. May 1, 2017, vol. 66, No. 5, p. 657-66.
European Patent Office, Extended European Search report for EP Application No. 20823678.6 mailed Jun. 12, 2023.

* cited by examiner

Mutant position 8

| Locus | 1st digit | N Missing Hits | ∑ Hits | 25%tile Hits | Median Hits | 75%tile Hits | σ Hit: |
|---|---|---|---|---|---|---|---|
| A | 03 | 2 | 6040 | 9.06 | 12.18 | 15.82 | 9.5 |
| A | 11 | 10 | 6227 | 7.72 | 10.01 | 12.66 | 6.6 |
| A | 01 | 91 | 1599 | 0.03 | 2.56 | 6.74 | 3.5 |
| A | 80 | 317 | 1487 | 3.00 | 8.00 | 10.00 | 3.7 |
| A | 36 | 259 | 1458 | 3.42 | 5.33 | 7.17 | 2.3 |
| A | 34 | 142 | 1359 | 1.38 | 2.46 | 4.31 | 2.8 |
| A | 68 | 97 | 1215 | 0.30 | 1.95 | 3.68 | 3.0 |
| A | 69 | 319 | 1111 | 2.50 | 4.00 | 9.20 | 3.3 |
| A | 66 | 319 | 808 | 1.10 | 2.90 | 5.81 | 2.7 |
| A | 30 | 43 | 626 | 0.15 | 0.22 | 1.97 | 1.9 |
| A | 74 | 296 | 533 | 1.58 | 2.35 | 2.65 | 0.9 |
| A | 32 | 3 | 479 | 0.18 | 0.28 | 1.62 | 1.0 |
| A | 25 | 124 | 295 | 0.11 | 0.43 | 0.59 | 0.9 |
| A | 23 | 340 | 262 | 0.02 | 1.82 | 1.82 | 1.0 |
| A | 24 | 66 | 258 | 0.02 | 0.03 | 1.71 | 0.9 |
| A | 43 | 448 | 231 | 2.00 | 3.00 | 3.00 | 0.8 |
| A | 26 | 208 | 222 | 0.03 | 0.06 | 0.88 | 1.1 |
| A | 31 | 193 | 167 | 0.03 | 0.12 | 0.28 | 0.7 |
| A | 29 | 356 | 163 | 0.09 | 0.72 | 1.47 | 0.8 |
| A | 33 | 244 | 157 | 0.03 | 0.13 | 1.73 | 0.7 |
| A | 02 | 116 | 8 | 0.00 | 0.01 | 0.02 | 0.0 |

| Locus | 1st digit | N Missing Hits | ∑ Hits | 25%tile Hits | Median Hits | 75%tile Hits | σ Hit: |
|---|---|---|---|---|---|---|---|
| B | 07 | 0 | 12288 | 13.31 | 19.34 | 34.29 | 11.4 |
| B | 42 | 275 | 8020 | 20.92 | 35.33 | 40.17 | 12.6 |
| B | 81 | 118 | 7977 | 3.20 | 18.00 | 32.85 | 14.9 |
| B | 83 | 220 | 7540 | 2.00 | 32.00 | 38.00 | 16.2 |
| B | 52 | 1 | 7390 | 9.82 | 13.24 | 17.44 | 5.9 |
| B | 78 | 86 | 4368 | 2.71 | 8.57 | 15.43 | 7.3 |
| B | 51 | 7 | 3768 | 0.38 | 4.71 | 12.40 | 7.5 |
| B | 48 | 26 | 3223 | 1.80 | 2.80 | 8.50 | 6.5 |
| B | 56 | 1 | 2367 | 0.56 | 1.59 | 6.08 | 5.8 |
| B | 82 | 274 | 2244 | 2.00 | 5.60 | 15.80 | 7.2 |
| B | 67 | 196 | 1966 | 1.00 | 2.00 | 11.00 | 5.8 |
| B | 55 | 268 | 1838 | 3.08 | 4.31 | 11.02 | 4.9 |
| B | 53 | 188 | 1392 | 1.35 | 1.92 | 6.27 | 3.1 |
| B | 35 | 2 | 1225 | 0.02 | 0.21 | 4.57 | 3.0 |
| B | 58 | 207 | 1138 | 0.88 | 2.50 | 5.60 | 3.0 |
| B | 54 | 350 | 1040 | 2.00 | 3.00 | 9.00 | 4.2 |
| B | 14 | 257 | 985 | 0.76 | 0.85 | 3.46 | 5.0 |
| B | 49 | 274 | 913 | 1.63 | 3.63 | 4.88 | 2.1 |
| B | 18 | 320 | 839 | 0.08 | 1.89 | 1.93 | 5.8 |
| B | 50 | 255 | 584 | 1.19 | 1.86 | 2.76 | 1.1 |
| B | 40 | 134 | 573 | 0.40 | 1.38 | 1.88 | 1.1 |
| B | 37 | 212 | 500 | 0.18 | 0.79 | 1.62 | 1.7 |
| B | 46 | 384 | 430 | 0.88 | 2.00 | 5.00 | 1.7 |
| B | 15 | 1 | 417 | 0.11 | 0.35 | 1.19 | 1.0 |
| B | 57 | 365 | 360 | 0.09 | 1.83 | 4.58 | 1.9 |
| B | 44 | 33 | 319 | 0.03 | 0.10 | 1.74 | 0.8 |
| B | 45 | 352 | 307 | 1.74 | 1.74 | 2.00 | 0.4 |
| B | 39 | 39 | 224 | 0.06 | 0.19 | 0.36 | 0.7 |
| B | 13 | 136 | 193 | 0.07 | 0.15 | 0.86 | 0.7 |
| B | 41 | 310 | 182 | 0.07 | 0.24 | 1.79 | 0.8 |
| B | 47 | 438 | 177 | 1.00 | 2.00 | 2.00 | 0.4 |
| B | 59 | 454 | 154 | 2.00 | 2.00 | 2.00 | 0.4 |
| B | 38 | 357 | 141 | 0.07 | 0.10 | 1.73 | 0.8 |
| B | 08 | 63 | 139 | 0.08 | 0.14 | 0.19 | 0.5 |
| B | 27 | 213 | 25 | 0.02 | 0.04 | 0.10 | 0.1 |

FIG. 8 (cont'd)

| Locus | 1st digit | N Missing Hits | ∑ Hits | 25%tile Hits | Median Hits | 75%tile Hits | σ Hit |
|---|---|---|---|---|---|---|---|
| C | 12 | 0 | 6437 | 6.67 | 11.33 | 18.05 | 6.3 |
| C | 07 | 0 | 6036 | 5.55 | 11.58 | 15.17 | 7.5 |
| C | 06 | 12 | 2422 | 1.56 | 4.16 | 7.24 | 3.4 |
| C | 16 | 35 | 2406 | 0.22 | 3.65 | 9.01 | 4.5 |
| C | 02 | 0 | 1834 | 0.07 | 0.84 | 4.55 | 4.5 |
| C | 01 | 10 | 1654 | 0.34 | 1.13 | 6.90 | 4.0 |
| C | 18 | 187 | 864 | 0.90 | 1.70 | 3.20 | 2.1 |
| C | 14 | 81 | 631 | 0.84 | 0.93 | 1.75 | 1.2 |
| C | 03 | 46 | 536 | 0.05 | 0.85 | 1.05 | 1.4 |
| C | 08 | 48 | 387 | 0.09 | 0.55 | 1.37 | 0.8 |
| C | 15 | 53 | 333 | 0.07 | 0.27 | 0.96 | 0.9 |
| C | 04 | 25 | 330 | 0.09 | 0.48 | 0.90 | 0.7 |
| C | 05 | 44 | 241 | 0.06 | 0.11 | 0.95 | 0.6 |

| Locus | 1st digit | N Missing Hits | ∑ Hits | 25%tile Hits | Median Hits | 75%tile Hits | σ Hit |
|---|---|---|---|---|---|---|---|
| DRB1 | 04 | 0 | 77344 | 12.06 | 46.85 | 280.86 | 157.3 |
| DRB1 | 01 | 0 | 63837 | 12.20 | 41.60 | 215.25 | 131.3 |
| DRB1 | 07 | 307 | 10385 | 18.00 | 43.00 | 72.50 | 32.6 |
| DRB1 | 09 | 307 | 10385 | 18.00 | 43.00 | 72.50 | 32.6 |
| DRB1 | 12 | 268 | 6272 | 9.08 | 16.50 | 44.06 | 17.4 |
| DRB1 | 08 | 296 | 2536 | 0.15 | 0.61 | 29.67 | 13.6 |
| DRB1 | 14 | 276 | 2103 | 1.10 | 2.23 | 22.75 | 9.8 |
| DRB1 | 11 | 346 | 1953 | 1.19 | 1.38 | 24.00 | 10.7 |
| DRB1 | 03 | 298 | 1914 | 0.22 | 0.78 | 24.00 | 10.5 |
| DRB1 | 13 | 306 | 1810 | 0.27 | 0.32 | 22.91 | 10.2 |
| DRB1 | 10 | 225 | 1258 | 1.00 | 1.00 | 7.00 | 4.8 |
| DRB1 | 16 | 360 | 263 | 1.00 | 1.00 | 2.00 | 0.6 |
| DRB1 | 15 | 360 | 253 | 1.00 | 1.00 | 1.87 | 0.5 |

SEQUENCE LISTING

<160> NUMBER OF SEQ ID NOS: 1095

<210> SEQ ID NO 1
<211> LENGTH: 5
<212> TYPE: PRT
<213> ORGANISM: Homo sapiens

<400> SEQUENCE: 1

Tyr Ser Phe Gly Val
1               5

<210> SEQ ID NO 2
<211> LENGTH: 5
<212> TYPE: PRT
<213> ORGANISM: Homo sapiens

<400> SEQUENCE: 2

Ser Phe Gly Val Ala
1               5

<210> SEQ ID NO 3
<211> LENGTH: 5
<212> TYPE: PRT
<213> ORGANISM: Homo sapiens

<400> SEQUENCE: 3

Gly Val Ala Thr Cys
1               5

<210> SEQ ID NO 4
<211> LENGTH: 5
<212> TYPE: PRT
<213> ORGANISM: Homo sapiens

<400> SEQUENCE: 4

Val Ala Thr Cys Val
1               5

<210> SEQ ID NO 5
<211> LENGTH: 5
<212> TYPE: PRT
<213> ORGANISM: Homo sapiens

<400> SEQUENCE: 5

Ser Phe Gly Val Ala
1               5

<210> SEQ ID NO 6
<211> LENGTH: 5
<212> TYPE: PRT
<213> ORGANISM: Homo sapiens

<400> SEQUENCE: 6

Phe Gly Val Ala Thr
1               5

<210> SEQ ID NO 7
<211> LENGTH: 5
<212> TYPE: PRT
<213> ORGANISM: Homo sapiens

<400> SEQUENCE: 7

Gly Val Ala Thr Cys
1               5

```
<210> SEQ ID NO 8
<211> LENGTH: 5
<212> TYPE: PRT
<213> ORGANISM: Homo sapiens

<400> SEQUENCE: 8

Tyr Ser Phe Gly Val
1               5

<210> SEQ ID NO 9
<211> LENGTH: 5
<212> TYPE: PRT
<213> ORGANISM: Homo sapiens

<400> SEQUENCE: 9

Ser Phe Gly Val Ala
1               5

<210> SEQ ID NO 10
<211> LENGTH: 5
<212> TYPE: PRT
<213> ORGANISM: Homo sapiens

<400> SEQUENCE: 10

Val Ala Thr Cys Val
1               5

<210> SEQ ID NO 11
<211> LENGTH: 5
<212> TYPE: PRT
<213> ORGANISM: Homo sapiens

<400> SEQUENCE: 11

Phe Gly Val Ala Thr
1               5

<210> SEQ ID NO 12
<211> LENGTH: 5
<212> TYPE: PRT
<213> ORGANISM: Homo sapiens

<400> SEQUENCE: 12

Phe Gly Arg Leu Ala
1               5

<210> SEQ ID NO 13
<211> LENGTH: 5
<212> TYPE: PRT
<213> ORGANISM: Homo sapiens

<400> SEQUENCE: 13

Thr Asp Phe Gly Arg
1               5

<210> SEQ ID NO 14
<211> LENGTH: 5
<212> TYPE: PRT
<213> ORGANISM: Homo sapiens

<400> SEQUENCE: 14

Asp Phe Gly Arg Leu
1               5

<210> SEQ ID NO 15
```

```
<211> LENGTH: 5
<212> TYPE: PRT
<213> ORGANISM: Homo sapiens

<400> SEQUENCE: 15

Gly Arg Leu Ala Lys
1               5

<210> SEQ ID NO 16
<211> LENGTH: 5
<212> TYPE: PRT
<213> ORGANISM: Homo sapiens

<400> SEQUENCE: 16

Arg Leu Ala Lys Leu
1               5

<210> SEQ ID NO 17
<211> LENGTH: 5
<212> TYPE: PRT
<213> ORGANISM: Homo sapiens

<400> SEQUENCE: 17

Asp Phe Gly Arg Leu
1               5

<210> SEQ ID NO 18
<211> LENGTH: 5
<212> TYPE: PRT
<213> ORGANISM: Homo sapiens

<400> SEQUENCE: 18

Phe Gly Arg Leu Ala
1               5

<210> SEQ ID NO 19
<211> LENGTH: 5
<212> TYPE: PRT
<213> ORGANISM: Homo sapiens

<400> SEQUENCE: 19

Asp Phe Gly Arg Leu
1               5

<210> SEQ ID NO 20
<211> LENGTH: 5
<212> TYPE: PRT
<213> ORGANISM: Homo sapiens

<400> SEQUENCE: 20

Phe Gly Arg Leu Ala
1               5

<210> SEQ ID NO 21
<211> LENGTH: 5
<212> TYPE: PRT
<213> ORGANISM: Homo sapiens

<400> SEQUENCE: 21

Arg Leu Ala Lys Leu
1               5

<210> SEQ ID NO 22
<211> LENGTH: 5
<212> TYPE: PRT
```

```
<213> ORGANISM: Homo sapiens

<400> SEQUENCE: 22

Leu Ile Lys Arg Gln
1               5

<210> SEQ ID NO 23
<211> LENGTH: 5
<212> TYPE: PRT
<213> ORGANISM: Homo sapiens

<400> SEQUENCE: 23

Ile Lys Arg Gln Arg
1               5

<210> SEQ ID NO 24
<211> LENGTH: 5
<212> TYPE: PRT
<213> ORGANISM: Homo sapiens

<400> SEQUENCE: 24

Lys Arg Gln Arg Gln
1               5

<210> SEQ ID NO 25
<211> LENGTH: 5
<212> TYPE: PRT
<213> ORGANISM: Homo sapiens

<400> SEQUENCE: 25

Arg Gln Arg Gln Gln
1               5

<210> SEQ ID NO 26
<211> LENGTH: 5
<212> TYPE: PRT
<213> ORGANISM: Homo sapiens

<400> SEQUENCE: 26

Gln Arg Gln Gln Lys
1               5

<210> SEQ ID NO 27
<211> LENGTH: 5
<212> TYPE: PRT
<213> ORGANISM: Homo sapiens

<400> SEQUENCE: 27

Ile Lys Arg Gln Arg
1               5

<210> SEQ ID NO 28
<211> LENGTH: 5
<212> TYPE: PRT
<213> ORGANISM: Homo sapiens

<400> SEQUENCE: 28

Arg Gln Arg Gln Gln
1               5

<210> SEQ ID NO 29
<211> LENGTH: 5
<212> TYPE: PRT
<213> ORGANISM: Homo sapiens
```

```
<400> SEQUENCE: 29

Leu Ile Lys Arg Gln
1               5

<210> SEQ ID NO 30
<211> LENGTH: 5
<212> TYPE: PRT
<213> ORGANISM: Homo sapiens

<400> SEQUENCE: 30

Thr Asp Val Gly Phe
1               5

<210> SEQ ID NO 31
<211> LENGTH: 5
<212> TYPE: PRT
<213> ORGANISM: Homo sapiens

<400> SEQUENCE: 31

Asp Val Gly Phe Ser
1               5

<210> SEQ ID NO 32
<211> LENGTH: 5
<212> TYPE: PRT
<213> ORGANISM: Homo sapiens

<400> SEQUENCE: 32

Val Gly Phe Ser Cys
1               5

<210> SEQ ID NO 33
<211> LENGTH: 5
<212> TYPE: PRT
<213> ORGANISM: Homo sapiens

<400> SEQUENCE: 33

Thr Asp Val Gly Phe
1               5

<210> SEQ ID NO 34
<211> LENGTH: 5
<212> TYPE: PRT
<213> ORGANISM: Homo sapiens

<400> SEQUENCE: 34

Asp Val Gly Phe Ser
1               5

<210> SEQ ID NO 35
<211> LENGTH: 5
<212> TYPE: PRT
<213> ORGANISM: Homo sapiens

<400> SEQUENCE: 35

Gly Phe Ser Cys Thr
1               5

<210> SEQ ID NO 36
<211> LENGTH: 5
<212> TYPE: PRT
<213> ORGANISM: Homo sapiens

<400> SEQUENCE: 36
```

```
Thr Asp Val Gly Phe
1               5

<210> SEQ ID NO 37
<211> LENGTH: 5
<212> TYPE: PRT
<213> ORGANISM: Homo sapiens

<400> SEQUENCE: 37

Val Gly Phe Ser Cys
1               5

<210> SEQ ID NO 38
<211> LENGTH: 5
<212> TYPE: PRT
<213> ORGANISM: Homo sapiens

<400> SEQUENCE: 38

Phe Ser Cys Thr Leu
1               5

<210> SEQ ID NO 39
<211> LENGTH: 5
<212> TYPE: PRT
<213> ORGANISM: Homo sapiens

<400> SEQUENCE: 39

Phe Ser Cys Thr Leu
1               5

<210> SEQ ID NO 40
<211> LENGTH: 5
<212> TYPE: PRT
<213> ORGANISM: Homo sapiens

<400> SEQUENCE: 40

Ala Thr Glu Val Lys
1               5

<210> SEQ ID NO 41
<211> LENGTH: 5
<212> TYPE: PRT
<213> ORGANISM: Homo sapiens

<400> SEQUENCE: 41

Glu Val Lys Ser Arg
1               5

<210> SEQ ID NO 42
<211> LENGTH: 5
<212> TYPE: PRT
<213> ORGANISM: Homo sapiens

<400> SEQUENCE: 42

Gly Leu Ala Thr Glu
1               5

<210> SEQ ID NO 43
<211> LENGTH: 5
<212> TYPE: PRT
<213> ORGANISM: Homo sapiens

<400> SEQUENCE: 43

Leu Ala Thr Glu Val
1               5
```

```
<210> SEQ ID NO 44
<211> LENGTH: 5
<212> TYPE: PRT
<213> ORGANISM: Homo sapiens

<400> SEQUENCE: 44

Ala Thr Glu Val Lys
1               5

<210> SEQ ID NO 45
<211> LENGTH: 5
<212> TYPE: PRT
<213> ORGANISM: Homo sapiens

<400> SEQUENCE: 45

Glu Val Lys Ser Arg
1               5

<210> SEQ ID NO 46
<211> LENGTH: 5
<212> TYPE: PRT
<213> ORGANISM: Homo sapiens

<400> SEQUENCE: 46

Ala Thr Glu Val Lys
1               5

<210> SEQ ID NO 47
<211> LENGTH: 5
<212> TYPE: PRT
<213> ORGANISM: Homo sapiens

<400> SEQUENCE: 47

Thr Glu Val Lys Ser
1               5

<210> SEQ ID NO 48
<211> LENGTH: 5
<212> TYPE: PRT
<213> ORGANISM: Homo sapiens

<400> SEQUENCE: 48

Glu Val Lys Ser Arg
1               5

<210> SEQ ID NO 49
<211> LENGTH: 5
<212> TYPE: PRT
<213> ORGANISM: Homo sapiens

<400> SEQUENCE: 49

Leu Ala Thr Met Val
1               5

<210> SEQ ID NO 50
<211> LENGTH: 5
<212> TYPE: PRT
<213> ORGANISM: Homo sapiens

<400> SEQUENCE: 50

Ala Thr Met Val Lys
1               5
```

-continued

```
<210> SEQ ID NO 51
<211> LENGTH: 5
<212> TYPE: PRT
<213> ORGANISM: Homo sapiens

<400> SEQUENCE: 51

Met Val Lys Ser Arg
1               5

<210> SEQ ID NO 52
<211> LENGTH: 5
<212> TYPE: PRT
<213> ORGANISM: Homo sapiens

<400> SEQUENCE: 52

Gly Leu Ala Thr Met
1               5

<210> SEQ ID NO 53
<211> LENGTH: 5
<212> TYPE: PRT
<213> ORGANISM: Homo sapiens

<400> SEQUENCE: 53

Ala Thr Met Val Lys
1               5

<210> SEQ ID NO 54
<211> LENGTH: 5
<212> TYPE: PRT
<213> ORGANISM: Homo sapiens

<400> SEQUENCE: 54

Thr Met Val Lys Ser
1               5

<210> SEQ ID NO 55
<211> LENGTH: 5
<212> TYPE: PRT
<213> ORGANISM: Homo sapiens

<400> SEQUENCE: 55

Met Val Lys Ser Arg
1               5

<210> SEQ ID NO 56
<211> LENGTH: 5
<212> TYPE: PRT
<213> ORGANISM: Homo sapiens

<400> SEQUENCE: 56

Leu Ala Thr Met Val
1               5

<210> SEQ ID NO 57
<211> LENGTH: 5
<212> TYPE: PRT
<213> ORGANISM: Homo sapiens

<400> SEQUENCE: 57

Ala Thr Met Val Lys
1               5

<210> SEQ ID NO 58
<211> LENGTH: 5
```

-continued

```
<212> TYPE: PRT
<213> ORGANISM: Homo sapiens

<400> SEQUENCE: 58

Thr Met Val Lys Ser
1               5

<210> SEQ ID NO 59
<211> LENGTH: 5
<212> TYPE: PRT
<213> ORGANISM: Homo sapiens

<400> SEQUENCE: 59

Met Val Lys Ser Arg
1               5

<210> SEQ ID NO 60
<211> LENGTH: 5
<212> TYPE: PRT
<213> ORGANISM: Homo sapiens

<400> SEQUENCE: 60

Ile Thr Lys Glu Gln
1               5

<210> SEQ ID NO 61
<211> LENGTH: 5
<212> TYPE: PRT
<213> ORGANISM: Homo sapiens

<400> SEQUENCE: 61

Glu Ile Thr Lys Glu
1               5

<210> SEQ ID NO 62
<211> LENGTH: 5
<212> TYPE: PRT
<213> ORGANISM: Homo sapiens

<400> SEQUENCE: 62

Met Asn Asp Ala Arg
1               5

<210> SEQ ID NO 63
<211> LENGTH: 5
<212> TYPE: PRT
<213> ORGANISM: Homo sapiens

<400> SEQUENCE: 63

Ala Arg His His Gly
1               5

<210> SEQ ID NO 64
<211> LENGTH: 5
<212> TYPE: PRT
<213> ORGANISM: Homo sapiens

<400> SEQUENCE: 64

Asp Ala Arg His His
1               5

<210> SEQ ID NO 65
<211> LENGTH: 5
<212> TYPE: PRT
<213> ORGANISM: Homo sapiens
```

<400> SEQUENCE: 65

Ala Arg His His Gly
1               5

<210> SEQ ID NO 66
<211> LENGTH: 5
<212> TYPE: PRT
<213> ORGANISM: Homo sapiens

<400> SEQUENCE: 66

Arg His His Gly Gly
1               5

<210> SEQ ID NO 67
<211> LENGTH: 5
<212> TYPE: PRT
<213> ORGANISM: Homo sapiens

<400> SEQUENCE: 67

Lys Gly Gly Arg Thr
1               5

<210> SEQ ID NO 68
<211> LENGTH: 5
<212> TYPE: PRT
<213> ORGANISM: Homo sapiens

<400> SEQUENCE: 68

Ala Gly Lys Gly Gly
1               5

<210> SEQ ID NO 69
<211> LENGTH: 5
<212> TYPE: PRT
<213> ORGANISM: Homo sapiens

<400> SEQUENCE: 69

Lys Gly Gly Arg Thr
1               5

<210> SEQ ID NO 70
<211> LENGTH: 5
<212> TYPE: PRT
<213> ORGANISM: Homo sapiens

<400> SEQUENCE: 70

Gly Gly Arg Thr Gly
1               5

<210> SEQ ID NO 71
<211> LENGTH: 5
<212> TYPE: PRT
<213> ORGANISM: Homo sapiens

<400> SEQUENCE: 71

Ala Gly Lys Gly Gly
1               5

<210> SEQ ID NO 72
<211> LENGTH: 5
<212> TYPE: PRT
<213> ORGANISM: Homo sapiens

<400> SEQUENCE: 72

-continued

```
Lys Gly Gly Arg Thr
1               5

<210> SEQ ID NO 73
<211> LENGTH: 5
<212> TYPE: PRT
<213> ORGANISM: Homo sapiens

<400> SEQUENCE: 73

Ala Gly Lys Gly Gln
1               5

<210> SEQ ID NO 74
<211> LENGTH: 5
<212> TYPE: PRT
<213> ORGANISM: Homo sapiens

<400> SEQUENCE: 74

Lys Gly Gln Arg Thr
1               5

<210> SEQ ID NO 75
<211> LENGTH: 5
<212> TYPE: PRT
<213> ORGANISM: Homo sapiens

<400> SEQUENCE: 75

Gly Gln Arg Thr Gly
1               5

<210> SEQ ID NO 76
<211> LENGTH: 5
<212> TYPE: PRT
<213> ORGANISM: Homo sapiens

<400> SEQUENCE: 76

Ala Gly Lys Gly Gln
1               5

<210> SEQ ID NO 77
<211> LENGTH: 5
<212> TYPE: PRT
<213> ORGANISM: Homo sapiens

<400> SEQUENCE: 77

Lys Gly Gln Arg Thr
1               5

<210> SEQ ID NO 78
<211> LENGTH: 7
<212> TYPE: PRT
<213> ORGANISM: Homo sapiens

<400> SEQUENCE: 78

Gly Lys Tyr Ser Phe Gly Val
1               5

<210> SEQ ID NO 79
<211> LENGTH: 7
<212> TYPE: PRT
<213> ORGANISM: Homo sapiens

<400> SEQUENCE: 79

Lys Tyr Ser Phe Gly Val Ala
```

-continued

```
1               5

<210> SEQ ID NO 80
<211> LENGTH: 7
<212> TYPE: PRT
<213> ORGANISM: Homo sapiens

<400> SEQUENCE: 80

Ser Phe Gly Val Ala Thr Cys
1               5

<210> SEQ ID NO 81
<211> LENGTH: 7
<212> TYPE: PRT
<213> ORGANISM: Homo sapiens

<400> SEQUENCE: 81

Gly Val Ala Thr Cys Val Lys
1               5

<210> SEQ ID NO 82
<211> LENGTH: 7
<212> TYPE: PRT
<213> ORGANISM: Homo sapiens

<400> SEQUENCE: 82

Val Ala Thr Cys Val Lys Lys
1               5

<210> SEQ ID NO 83
<211> LENGTH: 7
<212> TYPE: PRT
<213> ORGANISM: Homo sapiens

<400> SEQUENCE: 83

Gly Lys Tyr Ser Phe Gly Val
1               5

<210> SEQ ID NO 84
<211> LENGTH: 7
<212> TYPE: PRT
<213> ORGANISM: Homo sapiens

<400> SEQUENCE: 84

Gly Val Ala Thr Cys Val Lys
1               5

<210> SEQ ID NO 85
<211> LENGTH: 7
<212> TYPE: PRT
<213> ORGANISM: Homo sapiens

<400> SEQUENCE: 85

Val Ala Thr Cys Val Lys Lys
1               5

<210> SEQ ID NO 86
<211> LENGTH: 7
<212> TYPE: PRT
<213> ORGANISM: Homo sapiens

<400> SEQUENCE: 86

Gly Val Ala Thr Cys Val Lys
1               5
```

<210> SEQ ID NO 87
<211> LENGTH: 7
<212> TYPE: PRT
<213> ORGANISM: Homo sapiens

<400> SEQUENCE: 87

Ser Phe Gly Val Ala Thr Cys
1               5

<210> SEQ ID NO 88
<211> LENGTH: 7
<212> TYPE: PRT
<213> ORGANISM: Homo sapiens

<400> SEQUENCE: 88

Gly Val Ala Thr Cys Val Lys
1               5

<210> SEQ ID NO 89
<211> LENGTH: 7
<212> TYPE: PRT
<213> ORGANISM: Homo sapiens

<400> SEQUENCE: 89

Ile Thr Asp Phe Gly Arg Leu
1               5

<210> SEQ ID NO 90
<211> LENGTH: 7
<212> TYPE: PRT
<213> ORGANISM: Homo sapiens

<400> SEQUENCE: 90

Gly Arg Leu Ala Lys Leu Leu
1               5

<210> SEQ ID NO 91
<211> LENGTH: 7
<212> TYPE: PRT
<213> ORGANISM: Homo sapiens

<400> SEQUENCE: 91

Lys Ile Thr Asp Phe Gly Arg
1               5

<210> SEQ ID NO 92
<211> LENGTH: 7
<212> TYPE: PRT
<213> ORGANISM: Homo sapiens

<400> SEQUENCE: 92

Ile Thr Asp Phe Gly Arg Leu
1               5

<210> SEQ ID NO 93
<211> LENGTH: 7
<212> TYPE: PRT
<213> ORGANISM: Homo sapiens

<400> SEQUENCE: 93

Asp Phe Gly Arg Leu Ala Lys
1               5

<210> SEQ ID NO 94

```
<211> LENGTH: 7
<212> TYPE: PRT
<213> ORGANISM: Homo sapiens

<400> SEQUENCE: 94

Gly Arg Leu Ala Lys Leu Leu
1               5

<210> SEQ ID NO 95
<211> LENGTH: 7
<212> TYPE: PRT
<213> ORGANISM: Homo sapiens

<400> SEQUENCE: 95

Arg Leu Ala Lys Leu Leu Gly
1               5

<210> SEQ ID NO 96
<211> LENGTH: 7
<212> TYPE: PRT
<213> ORGANISM: Homo sapiens

<400> SEQUENCE: 96

Lys Ile Thr Asp Phe Gly Arg
1               5

<210> SEQ ID NO 97
<211> LENGTH: 7
<212> TYPE: PRT
<213> ORGANISM: Homo sapiens

<400> SEQUENCE: 97

Ile Thr Asp Phe Gly Arg Leu
1               5

<210> SEQ ID NO 98
<211> LENGTH: 7
<212> TYPE: PRT
<213> ORGANISM: Homo sapiens

<400> SEQUENCE: 98

Asp Phe Gly Arg Leu Ala Lys
1               5

<210> SEQ ID NO 99
<211> LENGTH: 7
<212> TYPE: PRT
<213> ORGANISM: Homo sapiens

<400> SEQUENCE: 99

Ile Lys Arg Gln Arg Gln Gln
1               5

<210> SEQ ID NO 100
<211> LENGTH: 7
<212> TYPE: PRT
<213> ORGANISM: Homo sapiens

<400> SEQUENCE: 100

Gly Ile Leu Ile Lys Arg Gln
1               5

<210> SEQ ID NO 101
<211> LENGTH: 7
<212> TYPE: PRT
```

<213> ORGANISM: Homo sapiens

<400> SEQUENCE: 101

Ile Leu Ile Lys Arg Gln Arg
1               5

<210> SEQ ID NO 102
<211> LENGTH: 7
<212> TYPE: PRT
<213> ORGANISM: Homo sapiens

<400> SEQUENCE: 102

Ile Lys Arg Gln Arg Gln Gln
1               5

<210> SEQ ID NO 103
<211> LENGTH: 7
<212> TYPE: PRT
<213> ORGANISM: Homo sapiens

<400> SEQUENCE: 103

Gln Arg Gln Gln Lys Ile Arg
1               5

<210> SEQ ID NO 104
<211> LENGTH: 7
<212> TYPE: PRT
<213> ORGANISM: Homo sapiens

<400> SEQUENCE: 104

Ile Lys Arg Gln Arg Gln Gln
1               5

<210> SEQ ID NO 105
<211> LENGTH: 7
<212> TYPE: PRT
<213> ORGANISM: Homo sapiens

<400> SEQUENCE: 105

Arg Gln Arg Gln Gln Lys Ile
1               5

<210> SEQ ID NO 106
<211> LENGTH: 7
<212> TYPE: PRT
<213> ORGANISM: Homo sapiens

<400> SEQUENCE: 106

Gln Arg Gln Gln Lys Ile Arg
1               5

<210> SEQ ID NO 107
<211> LENGTH: 7
<212> TYPE: PRT
<213> ORGANISM: Homo sapiens

<400> SEQUENCE: 107

Leu Ser Thr Asp Val Gly Phe
1               5

<210> SEQ ID NO 108
<211> LENGTH: 7
<212> TYPE: PRT
<213> ORGANISM: Homo sapiens

```
<400> SEQUENCE: 108

Ser Thr Asp Val Gly Phe Ser
1               5

<210> SEQ ID NO 109
<211> LENGTH: 7
<212> TYPE: PRT
<213> ORGANISM: Homo sapiens

<400> SEQUENCE: 109

Asp Val Gly Phe Ser Cys Thr
1               5

<210> SEQ ID NO 110
<211> LENGTH: 7
<212> TYPE: PRT
<213> ORGANISM: Homo sapiens

<400> SEQUENCE: 110

Gly Phe Ser Cys Thr Leu Val
1               5

<210> SEQ ID NO 111
<211> LENGTH: 7
<212> TYPE: PRT
<213> ORGANISM: Homo sapiens

<400> SEQUENCE: 111

Leu Ser Thr Asp Val Gly Phe
1               5

<210> SEQ ID NO 112
<211> LENGTH: 7
<212> TYPE: PRT
<213> ORGANISM: Homo sapiens

<400> SEQUENCE: 112

Ser Thr Asp Val Gly Phe Ser
1               5

<210> SEQ ID NO 113
<211> LENGTH: 7
<212> TYPE: PRT
<213> ORGANISM: Homo sapiens

<400> SEQUENCE: 113

Asp Val Gly Phe Ser Cys Thr
1               5

<210> SEQ ID NO 114
<211> LENGTH: 7
<212> TYPE: PRT
<213> ORGANISM: Homo sapiens

<400> SEQUENCE: 114

Gly Phe Ser Cys Thr Leu Val
1               5

<210> SEQ ID NO 115
<211> LENGTH: 7
<212> TYPE: PRT
<213> ORGANISM: Homo sapiens

<400> SEQUENCE: 115
```

```
Leu Ser Thr Asp Val Gly Phe
1               5

<210> SEQ ID NO 116
<211> LENGTH: 7
<212> TYPE: PRT
<213> ORGANISM: Homo sapiens

<400> SEQUENCE: 116

Ser Thr Asp Val Gly Phe Ser
1               5

<210> SEQ ID NO 117
<211> LENGTH: 7
<212> TYPE: PRT
<213> ORGANISM: Homo sapiens

<400> SEQUENCE: 117

Phe Ser Cys Thr Leu Val Cys
1               5

<210> SEQ ID NO 118
<211> LENGTH: 7
<212> TYPE: PRT
<213> ORGANISM: Homo sapiens

<400> SEQUENCE: 118

Leu Ser Thr Asp Val Gly Phe
1               5

<210> SEQ ID NO 119
<211> LENGTH: 7
<212> TYPE: PRT
<213> ORGANISM: Homo sapiens

<400> SEQUENCE: 119

Ser Thr Asp Val Gly Phe Ser
1               5

<210> SEQ ID NO 120
<211> LENGTH: 7
<212> TYPE: PRT
<213> ORGANISM: Homo sapiens

<400> SEQUENCE: 120

Gly Phe Ser Cys Thr Leu Val
1               5

<210> SEQ ID NO 121
<211> LENGTH: 7
<212> TYPE: PRT
<213> ORGANISM: Homo sapiens

<400> SEQUENCE: 121

Glu Val Lys Ser Arg Trp Ser
1               5

<210> SEQ ID NO 122
<211> LENGTH: 7
<212> TYPE: PRT
<213> ORGANISM: Homo sapiens

<400> SEQUENCE: 122

Leu Ala Thr Glu Val Lys Ser
1               5
```

```
<210> SEQ ID NO 123
<211> LENGTH: 7
<212> TYPE: PRT
<213> ORGANISM: Homo sapiens

<400> SEQUENCE: 123

Thr Glu Val Lys Ser Arg Trp
1               5

<210> SEQ ID NO 124
<211> LENGTH: 7
<212> TYPE: PRT
<213> ORGANISM: Homo sapiens

<400> SEQUENCE: 124

Glu Val Lys Ser Arg Trp Ser
1               5

<210> SEQ ID NO 125
<211> LENGTH: 7
<212> TYPE: PRT
<213> ORGANISM: Homo sapiens

<400> SEQUENCE: 125

Asp Phe Gly Leu Ala Thr Glu
1               5

<210> SEQ ID NO 126
<211> LENGTH: 7
<212> TYPE: PRT
<213> ORGANISM: Homo sapiens

<400> SEQUENCE: 126

Phe Gly Leu Ala Thr Glu Val
1               5

<210> SEQ ID NO 127
<211> LENGTH: 7
<212> TYPE: PRT
<213> ORGANISM: Homo sapiens

<400> SEQUENCE: 127

Thr Glu Val Lys Ser Arg Trp
1               5

<210> SEQ ID NO 128
<211> LENGTH: 7
<212> TYPE: PRT
<213> ORGANISM: Homo sapiens

<400> SEQUENCE: 128

Phe Gly Leu Ala Thr Met Val
1               5

<210> SEQ ID NO 129
<211> LENGTH: 7
<212> TYPE: PRT
<213> ORGANISM: Homo sapiens

<400> SEQUENCE: 129

Leu Ala Thr Met Val Lys Ser
1               5
```

```
<210> SEQ ID NO 130
<211> LENGTH: 7
<212> TYPE: PRT
<213> ORGANISM: Homo sapiens

<400> SEQUENCE: 130

Met Val Lys Ser Arg Trp Ser
1               5

<210> SEQ ID NO 131
<211> LENGTH: 7
<212> TYPE: PRT
<213> ORGANISM: Homo sapiens

<400> SEQUENCE: 131

Leu Ala Thr Met Val Lys Ser
1               5

<210> SEQ ID NO 132
<211> LENGTH: 7
<212> TYPE: PRT
<213> ORGANISM: Homo sapiens

<400> SEQUENCE: 132

Met Val Lys Ser Arg Trp Ser
1               5

<210> SEQ ID NO 133
<211> LENGTH: 7
<212> TYPE: PRT
<213> ORGANISM: Homo sapiens

<400> SEQUENCE: 133

Asp Phe Gly Leu Ala Thr Met
1               5

<210> SEQ ID NO 134
<211> LENGTH: 7
<212> TYPE: PRT
<213> ORGANISM: Homo sapiens

<400> SEQUENCE: 134

Phe Gly Leu Ala Thr Met Val
1               5

<210> SEQ ID NO 135
<211> LENGTH: 7
<212> TYPE: PRT
<213> ORGANISM: Homo sapiens

<400> SEQUENCE: 135

Leu Ala Thr Met Val Lys Ser
1               5

<210> SEQ ID NO 136
<211> LENGTH: 7
<212> TYPE: PRT
<213> ORGANISM: Homo sapiens

<400> SEQUENCE: 136

Thr Met Val Lys Ser Arg Trp
1               5

<210> SEQ ID NO 137
<211> LENGTH: 7
```

```
<212> TYPE: PRT
<213> ORGANISM: Homo sapiens

<400> SEQUENCE: 137

Glu Ile Thr Lys Glu Gln Glu
1               5

<210> SEQ ID NO 138
<211> LENGTH: 7
<212> TYPE: PRT
<213> ORGANISM: Homo sapiens

<400> SEQUENCE: 138

Leu Ser Glu Ile Thr Lys Glu
1               5

<210> SEQ ID NO 139
<211> LENGTH: 7
<212> TYPE: PRT
<213> ORGANISM: Homo sapiens

<400> SEQUENCE: 139

Lys Glu Gln Glu Lys Asp Phe
1               5

<210> SEQ ID NO 140
<211> LENGTH: 7
<212> TYPE: PRT
<213> ORGANISM: Homo sapiens

<400> SEQUENCE: 140

Glu Ile Thr Lys Glu Gln Glu
1               5

<210> SEQ ID NO 141
<211> LENGTH: 7
<212> TYPE: PRT
<213> ORGANISM: Homo sapiens

<400> SEQUENCE: 141

Thr Lys Glu Gln Glu Lys Asp
1               5

<210> SEQ ID NO 142
<211> LENGTH: 7
<212> TYPE: PRT
<213> ORGANISM: Homo sapiens

<400> SEQUENCE: 142

Lys Glu Gln Glu Lys Asp Phe
1               5

<210> SEQ ID NO 143
<211> LENGTH: 7
<212> TYPE: PRT
<213> ORGANISM: Homo sapiens

<400> SEQUENCE: 143

Arg His His Gly Gly Trp Thr
1               5

<210> SEQ ID NO 144
<211> LENGTH: 7
<212> TYPE: PRT
<213> ORGANISM: Homo sapiens
```

-continued

<400> SEQUENCE: 144

Lys Gln Met Asn Asp Ala Arg
1               5

<210> SEQ ID NO 145
<211> LENGTH: 7
<212> TYPE: PRT
<213> ORGANISM: Homo sapiens

<400> SEQUENCE: 145

Gln Met Asn Asp Ala Arg His
1               5

<210> SEQ ID NO 146
<211> LENGTH: 7
<212> TYPE: PRT
<213> ORGANISM: Homo sapiens

<400> SEQUENCE: 146

Asn Asp Ala Arg His His Gly
1               5

<210> SEQ ID NO 147
<211> LENGTH: 7
<212> TYPE: PRT
<213> ORGANISM: Homo sapiens

<400> SEQUENCE: 147

Cys Lys Ala Gly Lys Gly Gly
1               5

<210> SEQ ID NO 148
<211> LENGTH: 7
<212> TYPE: PRT
<213> ORGANISM: Homo sapiens

<400> SEQUENCE: 148

Gly Lys Gly Gly Arg Thr Gly
1               5

<210> SEQ ID NO 149
<211> LENGTH: 7
<212> TYPE: PRT
<213> ORGANISM: Homo sapiens

<400> SEQUENCE: 149

Gly Gly Arg Thr Gly Val Met
1               5

<210> SEQ ID NO 150
<211> LENGTH: 7
<212> TYPE: PRT
<213> ORGANISM: Homo sapiens

<400> SEQUENCE: 150

Gly Arg Thr Gly Val Met Ile
1               5

<210> SEQ ID NO 151
<211> LENGTH: 7
<212> TYPE: PRT
<213> ORGANISM: Homo sapiens

<400> SEQUENCE: 151

```
Cys Lys Ala Gly Lys Gly Gly
1               5

<210> SEQ ID NO 152
<211> LENGTH: 7
<212> TYPE: PRT
<213> ORGANISM: Homo sapiens

<400> SEQUENCE: 152

Gly Lys Gly Gly Arg Thr Gly
1               5

<210> SEQ ID NO 153
<211> LENGTH: 7
<212> TYPE: PRT
<213> ORGANISM: Homo sapiens

<400> SEQUENCE: 153

Gly Gly Arg Thr Gly Val Met
1               5

<210> SEQ ID NO 154
<211> LENGTH: 7
<212> TYPE: PRT
<213> ORGANISM: Homo sapiens

<400> SEQUENCE: 154

Cys Lys Ala Gly Lys Gly Gln
1               5

<210> SEQ ID NO 155
<211> LENGTH: 7
<212> TYPE: PRT
<213> ORGANISM: Homo sapiens

<400> SEQUENCE: 155

Gly Lys Gly Gln Arg Thr Gly
1               5

<210> SEQ ID NO 156
<211> LENGTH: 7
<212> TYPE: PRT
<213> ORGANISM: Homo sapiens

<400> SEQUENCE: 156

Gly Gln Arg Thr Gly Val Met
1               5

<210> SEQ ID NO 157
<211> LENGTH: 7
<212> TYPE: PRT
<213> ORGANISM: Homo sapiens

<400> SEQUENCE: 157

Gln Arg Thr Gly Val Met Ile
1               5

<210> SEQ ID NO 158
<211> LENGTH: 7
<212> TYPE: PRT
<213> ORGANISM: Homo sapiens

<400> SEQUENCE: 158

Gly Lys Gly Gln Arg Thr Gly
```

-continued

```
1               5

<210> SEQ ID NO 159
<211> LENGTH: 7
<212> TYPE: PRT
<213> ORGANISM: Homo sapiens

<400> SEQUENCE: 159

Lys Ala Gly Lys Gly Gln Arg
1               5

<210> SEQ ID NO 160
<211> LENGTH: 7
<212> TYPE: PRT
<213> ORGANISM: Homo sapiens

<400> SEQUENCE: 160

Gly Gln Arg Thr Gly Val Met
1               5

<210> SEQ ID NO 161
<211> LENGTH: 7
<212> TYPE: PRT
<213> ORGANISM: Homo sapiens

<400> SEQUENCE: 161

Gln Arg Thr Gly Val Met Ile
1               5

<210> SEQ ID NO 162
<211> LENGTH: 5
<212> TYPE: PRT
<213> ORGANISM: Homo sapiens

<400> SEQUENCE: 162

Ser Phe Gly Val Ala
1               5

<210> SEQ ID NO 163
<211> LENGTH: 5
<212> TYPE: PRT
<213> ORGANISM: Homo sapiens

<400> SEQUENCE: 163

Phe Gly Val Ala Thr
1               5

<210> SEQ ID NO 164
<211> LENGTH: 5
<212> TYPE: PRT
<213> ORGANISM: Homo sapiens

<400> SEQUENCE: 164

Gly Val Ala Thr Cys
1               5

<210> SEQ ID NO 165
<211> LENGTH: 5
<212> TYPE: PRT
<213> ORGANISM: Homo sapiens

<400> SEQUENCE: 165

Ser Phe Gly Val Ala
1               5
```

<210> SEQ ID NO 166
<211> LENGTH: 5
<212> TYPE: PRT
<213> ORGANISM: Homo sapiens

<400> SEQUENCE: 166

Gly Val Ala Thr Cys
1               5

<210> SEQ ID NO 167
<211> LENGTH: 5
<212> TYPE: PRT
<213> ORGANISM: Homo sapiens

<400> SEQUENCE: 167

Ser Phe Gly Val Ala
1               5

<210> SEQ ID NO 168
<211> LENGTH: 5
<212> TYPE: PRT
<213> ORGANISM: Homo sapiens

<400> SEQUENCE: 168

Phe Gly Val Ala Thr
1               5

<210> SEQ ID NO 169
<211> LENGTH: 5
<212> TYPE: PRT
<213> ORGANISM: Homo sapiens

<400> SEQUENCE: 169

Gly Val Ala Thr Cys
1               5

<210> SEQ ID NO 170
<211> LENGTH: 5
<212> TYPE: PRT
<213> ORGANISM: Homo sapiens

<400> SEQUENCE: 170

Tyr Ser Phe Gly Val
1               5

<210> SEQ ID NO 171
<211> LENGTH: 5
<212> TYPE: PRT
<213> ORGANISM: Homo sapiens

<400> SEQUENCE: 171

Gly Val Ala Thr Cys
1               5

<210> SEQ ID NO 172
<211> LENGTH: 5
<212> TYPE: PRT
<213> ORGANISM: Homo sapiens

<400> SEQUENCE: 172

Thr Asp Phe Gly Arg
1               5

<210> SEQ ID NO 173

```
<211> LENGTH: 5
<212> TYPE: PRT
<213> ORGANISM: Homo sapiens

<400> SEQUENCE: 173

Asp Phe Gly Arg Leu
1               5

<210> SEQ ID NO 174
<211> LENGTH: 5
<212> TYPE: PRT
<213> ORGANISM: Homo sapiens

<400> SEQUENCE: 174

Gly Arg Leu Ala Lys
1               5

<210> SEQ ID NO 175
<211> LENGTH: 5
<212> TYPE: PRT
<213> ORGANISM: Homo sapiens

<400> SEQUENCE: 175

Thr Asp Phe Gly Arg
1               5

<210> SEQ ID NO 176
<211> LENGTH: 5
<212> TYPE: PRT
<213> ORGANISM: Homo sapiens

<400> SEQUENCE: 176

Gly Arg Leu Ala Lys
1               5

<210> SEQ ID NO 177
<211> LENGTH: 5
<212> TYPE: PRT
<213> ORGANISM: Homo sapiens

<400> SEQUENCE: 177

Thr Asp Phe Gly Arg
1               5

<210> SEQ ID NO 178
<211> LENGTH: 5
<212> TYPE: PRT
<213> ORGANISM: Homo sapiens

<400> SEQUENCE: 178

Asp Phe Gly Arg Leu
1               5

<210> SEQ ID NO 179
<211> LENGTH: 5
<212> TYPE: PRT
<213> ORGANISM: Homo sapiens

<400> SEQUENCE: 179

Gly Arg Leu Ala Lys
1               5

<210> SEQ ID NO 180
<211> LENGTH: 5
<212> TYPE: PRT
```

<213> ORGANISM: Homo sapiens

<400> SEQUENCE: 180

Arg Leu Ala Lys Leu
1               5

<210> SEQ ID NO 181
<211> LENGTH: 5
<212> TYPE: PRT
<213> ORGANISM: Homo sapiens

<400> SEQUENCE: 181

Thr Asp Phe Gly Arg
1               5

<210> SEQ ID NO 182
<211> LENGTH: 5
<212> TYPE: PRT
<213> ORGANISM: Homo sapiens

<400> SEQUENCE: 182

Gly Arg Leu Ala Lys
1               5

<210> SEQ ID NO 183
<211> LENGTH: 5
<212> TYPE: PRT
<213> ORGANISM: Homo sapiens

<400> SEQUENCE: 183

Leu Ile Lys Arg Gln
1               5

<210> SEQ ID NO 184
<211> LENGTH: 5
<212> TYPE: PRT
<213> ORGANISM: Homo sapiens

<400> SEQUENCE: 184

Gln Arg Gln Gln Lys
1               5

<210> SEQ ID NO 185
<211> LENGTH: 5
<212> TYPE: PRT
<213> ORGANISM: Homo sapiens

<400> SEQUENCE: 185

Lys Arg Gln Arg Gln
1               5

<210> SEQ ID NO 186
<211> LENGTH: 5
<212> TYPE: PRT
<213> ORGANISM: Homo sapiens

<400> SEQUENCE: 186

Gln Arg Gln Gln Lys
1               5

<210> SEQ ID NO 187
<211> LENGTH: 5
<212> TYPE: PRT
<213> ORGANISM: Homo sapiens

```
<400> SEQUENCE: 187

Leu Ile Lys Arg Gln
1               5

<210> SEQ ID NO 188
<211> LENGTH: 5
<212> TYPE: PRT
<213> ORGANISM: Homo sapiens

<400> SEQUENCE: 188

Gln Arg Gln Gln Lys
1               5

<210> SEQ ID NO 189
<211> LENGTH: 5
<212> TYPE: PRT
<213> ORGANISM: Homo sapiens

<400> SEQUENCE: 189

Gly Phe Ser Cys Thr
1               5

<210> SEQ ID NO 190
<211> LENGTH: 5
<212> TYPE: PRT
<213> ORGANISM: Homo sapiens

<400> SEQUENCE: 190

Asp Val Gly Phe Ser
1               5

<210> SEQ ID NO 191
<211> LENGTH: 5
<212> TYPE: PRT
<213> ORGANISM: Homo sapiens

<400> SEQUENCE: 191

Gly Phe Ser Cys Thr
1               5

<210> SEQ ID NO 192
<211> LENGTH: 5
<212> TYPE: PRT
<213> ORGANISM: Homo sapiens

<400> SEQUENCE: 192

Asp Val Gly Phe Ser
1               5

<210> SEQ ID NO 193
<211> LENGTH: 5
<212> TYPE: PRT
<213> ORGANISM: Homo sapiens

<400> SEQUENCE: 193

Gly Phe Ser Cys Thr
1               5

<210> SEQ ID NO 194
<211> LENGTH: 5
<212> TYPE: PRT
<213> ORGANISM: Homo sapiens

<400> SEQUENCE: 194
```

Phe Ser Cys Thr Leu
1               5

<210> SEQ ID NO 195
<211> LENGTH: 5
<212> TYPE: PRT
<213> ORGANISM: Homo sapiens

<400> SEQUENCE: 195

Asp Val Gly Phe Ser
1               5

<210> SEQ ID NO 196
<211> LENGTH: 5
<212> TYPE: PRT
<213> ORGANISM: Homo sapiens

<400> SEQUENCE: 196

Gly Phe Ser Cys Thr
1               5

<210> SEQ ID NO 197
<211> LENGTH: 5
<212> TYPE: PRT
<213> ORGANISM: Homo sapiens

<400> SEQUENCE: 197

Gly Leu Ala Thr Glu
1               5

<210> SEQ ID NO 198
<211> LENGTH: 5
<212> TYPE: PRT
<213> ORGANISM: Homo sapiens

<400> SEQUENCE: 198

Glu Val Lys Ser Arg
1               5

<210> SEQ ID NO 199
<211> LENGTH: 5
<212> TYPE: PRT
<213> ORGANISM: Homo sapiens

<400> SEQUENCE: 199

Gly Leu Ala Thr Glu
1               5

<210> SEQ ID NO 200
<211> LENGTH: 5
<212> TYPE: PRT
<213> ORGANISM: Homo sapiens

<400> SEQUENCE: 200

Gly Leu Ala Thr Glu
1               5

<210> SEQ ID NO 201
<211> LENGTH: 5
<212> TYPE: PRT
<213> ORGANISM: Homo sapiens

<400> SEQUENCE: 201

Ala Thr Glu Val Lys
1               5

```
<210> SEQ ID NO 202
<211> LENGTH: 5
<212> TYPE: PRT
<213> ORGANISM: Homo sapiens

<400> SEQUENCE: 202

Gly Leu Ala Thr Glu
1               5

<210> SEQ ID NO 203
<211> LENGTH: 5
<212> TYPE: PRT
<213> ORGANISM: Homo sapiens

<400> SEQUENCE: 203

Ala Thr Glu Val Lys
1               5

<210> SEQ ID NO 204
<211> LENGTH: 5
<212> TYPE: PRT
<213> ORGANISM: Homo sapiens

<400> SEQUENCE: 204

Thr Glu Val Lys Ser
1               5

<210> SEQ ID NO 205
<211> LENGTH: 5
<212> TYPE: PRT
<213> ORGANISM: Homo sapiens

<400> SEQUENCE: 205

Glu Val Lys Ser Arg
1               5

<210> SEQ ID NO 206
<211> LENGTH: 5
<212> TYPE: PRT
<213> ORGANISM: Homo sapiens

<400> SEQUENCE: 206

Gly Leu Ala Thr Met
1               5

<210> SEQ ID NO 207
<211> LENGTH: 5
<212> TYPE: PRT
<213> ORGANISM: Homo sapiens

<400> SEQUENCE: 207

Met Val Lys Ser Arg
1               5

<210> SEQ ID NO 208
<211> LENGTH: 5
<212> TYPE: PRT
<213> ORGANISM: Homo sapiens

<400> SEQUENCE: 208

Gly Leu Ala Thr Met
1               5
```

```
<210> SEQ ID NO 209
<211> LENGTH: 5
<212> TYPE: PRT
<213> ORGANISM: Homo sapiens

<400> SEQUENCE: 209

Gly Leu Ala Thr Met
1               5

<210> SEQ ID NO 210
<211> LENGTH: 5
<212> TYPE: PRT
<213> ORGANISM: Homo sapiens

<400> SEQUENCE: 210

Ala Thr Met Val Lys
1               5

<210> SEQ ID NO 211
<211> LENGTH: 5
<212> TYPE: PRT
<213> ORGANISM: Homo sapiens

<400> SEQUENCE: 211

Thr Met Val Lys Ser
1               5

<210> SEQ ID NO 212
<211> LENGTH: 5
<212> TYPE: PRT
<213> ORGANISM: Homo sapiens

<400> SEQUENCE: 212

Gly Leu Ala Thr Met
1               5

<210> SEQ ID NO 213
<211> LENGTH: 5
<212> TYPE: PRT
<213> ORGANISM: Homo sapiens

<400> SEQUENCE: 213

Ala Thr Met Val Lys
1               5

<210> SEQ ID NO 214
<211> LENGTH: 5
<212> TYPE: PRT
<213> ORGANISM: Homo sapiens

<400> SEQUENCE: 214

Thr Met Val Lys Ser
1               5

<210> SEQ ID NO 215
<211> LENGTH: 5
<212> TYPE: PRT
<213> ORGANISM: Homo sapiens

<400> SEQUENCE: 215

Met Val Lys Ser Arg
1               5

<210> SEQ ID NO 216
<211> LENGTH: 5
```

```
<212> TYPE: PRT
<213> ORGANISM: Homo sapiens

<400> SEQUENCE: 216

Glu Ile Thr Lys Glu
1               5

<210> SEQ ID NO 217
<211> LENGTH: 5
<212> TYPE: PRT
<213> ORGANISM: Homo sapiens

<400> SEQUENCE: 217

Thr Lys Glu Gln Glu
1               5

<210> SEQ ID NO 218
<211> LENGTH: 5
<212> TYPE: PRT
<213> ORGANISM: Homo sapiens

<400> SEQUENCE: 218

Ser Glu Ile Thr Lys
1               5

<210> SEQ ID NO 219
<211> LENGTH: 5
<212> TYPE: PRT
<213> ORGANISM: Homo sapiens

<400> SEQUENCE: 219

Ile Thr Lys Glu Gln
1               5

<210> SEQ ID NO 220
<211> LENGTH: 5
<212> TYPE: PRT
<213> ORGANISM: Homo sapiens

<400> SEQUENCE: 220

Asn Asp Ala Arg His
1               5

<210> SEQ ID NO 221
<211> LENGTH: 5
<212> TYPE: PRT
<213> ORGANISM: Homo sapiens

<400> SEQUENCE: 221

Arg His His Gly Gly
1               5

<210> SEQ ID NO 222
<211> LENGTH: 5
<212> TYPE: PRT
<213> ORGANISM: Homo sapiens

<400> SEQUENCE: 222

Asp Ala Arg His His
1               5

<210> SEQ ID NO 223
<211> LENGTH: 5
<212> TYPE: PRT
<213> ORGANISM: Homo sapiens
```

<400> SEQUENCE: 223

Ala Arg His His Gly
1               5

<210> SEQ ID NO 224
<211> LENGTH: 5
<212> TYPE: PRT
<213> ORGANISM: Homo sapiens

<400> SEQUENCE: 224

Arg His His Gly Gly
1               5

<210> SEQ ID NO 225
<211> LENGTH: 5
<212> TYPE: PRT
<213> ORGANISM: Homo sapiens

<400> SEQUENCE: 225

Asn Asp Ala Arg His
1               5

<210> SEQ ID NO 226
<211> LENGTH: 5
<212> TYPE: PRT
<213> ORGANISM: Homo sapiens

<400> SEQUENCE: 226

Arg His His Gly Gly
1               5

<210> SEQ ID NO 227
<211> LENGTH: 5
<212> TYPE: PRT
<213> ORGANISM: Homo sapiens

<400> SEQUENCE: 227

Ala Gly Lys Gly Gly
1               5

<210> SEQ ID NO 228
<211> LENGTH: 5
<212> TYPE: PRT
<213> ORGANISM: Homo sapiens

<400> SEQUENCE: 228

Gly Arg Thr Gly Val
1               5

<210> SEQ ID NO 229
<211> LENGTH: 5
<212> TYPE: PRT
<213> ORGANISM: Homo sapiens

<400> SEQUENCE: 229

Ala Gly Lys Gly Gly
1               5

<210> SEQ ID NO 230
<211> LENGTH: 5
<212> TYPE: PRT
<213> ORGANISM: Homo sapiens

<400> SEQUENCE: 230

```
Gly Lys Gly Gly Arg
1               5

<210> SEQ ID NO 231
<211> LENGTH: 5
<212> TYPE: PRT
<213> ORGANISM: Homo sapiens

<400> SEQUENCE: 231

Gly Arg Thr Gly Val
1               5

<210> SEQ ID NO 232
<211> LENGTH: 5
<212> TYPE: PRT
<213> ORGANISM: Homo sapiens

<400> SEQUENCE: 232

Lys Gly Gly Arg Thr
1               5

<210> SEQ ID NO 233
<211> LENGTH: 5
<212> TYPE: PRT
<213> ORGANISM: Homo sapiens

<400> SEQUENCE: 233

Gly Arg Thr Gly Val
1               5

<210> SEQ ID NO 234
<211> LENGTH: 5
<212> TYPE: PRT
<213> ORGANISM: Homo sapiens

<400> SEQUENCE: 234

Ala Gly Lys Gly Gly
1               5

<210> SEQ ID NO 235
<211> LENGTH: 5
<212> TYPE: PRT
<213> ORGANISM: Homo sapiens

<400> SEQUENCE: 235

Lys Gly Gly Arg Thr
1               5

<210> SEQ ID NO 236
<211> LENGTH: 5
<212> TYPE: PRT
<213> ORGANISM: Homo sapiens

<400> SEQUENCE: 236

Gly Gly Arg Thr Gly
1               5

<210> SEQ ID NO 237
<211> LENGTH: 5
<212> TYPE: PRT
<213> ORGANISM: Homo sapiens

<400> SEQUENCE: 237

Ala Gly Lys Gly Gln
```

```
1               5

<210> SEQ ID NO 238
<211> LENGTH: 5
<212> TYPE: PRT
<213> ORGANISM: Homo sapiens

<400> SEQUENCE: 238

Ala Gly Lys Gly Gln
1               5

<210> SEQ ID NO 239
<211> LENGTH: 5
<212> TYPE: PRT
<213> ORGANISM: Homo sapiens

<400> SEQUENCE: 239

Gln Arg Thr Gly Val
1               5

<210> SEQ ID NO 240
<211> LENGTH: 5
<212> TYPE: PRT
<213> ORGANISM: Homo sapiens

<400> SEQUENCE: 240

Lys Gly Gln Arg Thr
1               5

<210> SEQ ID NO 241
<211> LENGTH: 5
<212> TYPE: PRT
<213> ORGANISM: Homo sapiens

<400> SEQUENCE: 241

Gln Arg Thr Gly Val
1               5

<210> SEQ ID NO 242
<211> LENGTH: 5
<212> TYPE: PRT
<213> ORGANISM: Homo sapiens

<400> SEQUENCE: 242

Ala Gly Lys Gly Gln
1               5

<210> SEQ ID NO 243
<211> LENGTH: 5
<212> TYPE: PRT
<213> ORGANISM: Homo sapiens

<400> SEQUENCE: 243

Lys Gly Gln Arg Thr
1               5

<210> SEQ ID NO 244
<211> LENGTH: 5
<212> TYPE: PRT
<213> ORGANISM: Homo sapiens

<400> SEQUENCE: 244

Gly Gln Arg Thr Gly
1               5
```

-continued

```
<210> SEQ ID NO 245
<211> LENGTH: 5
<212> TYPE: PRT
<213> ORGANISM: Homo sapiens

<400> SEQUENCE: 245

Lys Lys Gly Asn Tyr
1               5

<210> SEQ ID NO 246
<211> LENGTH: 5
<212> TYPE: PRT
<213> ORGANISM: Homo sapiens

<400> SEQUENCE: 246

Glu Lys Lys Gly Asn
1               5

<210> SEQ ID NO 247
<211> LENGTH: 5
<212> TYPE: PRT
<213> ORGANISM: Homo sapiens

<400> SEQUENCE: 247

Gly Asn Tyr Val Val
1               5

<210> SEQ ID NO 248
<211> LENGTH: 5
<212> TYPE: PRT
<213> ORGANISM: Homo sapiens

<400> SEQUENCE: 248

Glu Lys Lys Gly Asn
1               5

<210> SEQ ID NO 249
<211> LENGTH: 5
<212> TYPE: PRT
<213> ORGANISM: Homo sapiens

<400> SEQUENCE: 249

Lys Lys Gly Asn Tyr
1               5

<210> SEQ ID NO 250
<211> LENGTH: 5
<212> TYPE: PRT
<213> ORGANISM: Homo sapiens

<400> SEQUENCE: 250

Lys Gly Asn Tyr Val
1               5

<210> SEQ ID NO 251
<211> LENGTH: 5
<212> TYPE: PRT
<213> ORGANISM: Homo sapiens

<400> SEQUENCE: 251

Lys Gly Asn Tyr Val
1               5

<210> SEQ ID NO 252
```

```
<211> LENGTH: 5
<212> TYPE: PRT
<213> ORGANISM: Homo sapiens

<400> SEQUENCE: 252

Glu Glu Lys Lys Gly
1               5

<210> SEQ ID NO 253
<211> LENGTH: 5
<212> TYPE: PRT
<213> ORGANISM: Homo sapiens

<400> SEQUENCE: 253

Lys Gly Asn Tyr Val
1               5

<210> SEQ ID NO 254
<211> LENGTH: 5
<212> TYPE: PRT
<213> ORGANISM: Homo sapiens

<400> SEQUENCE: 254

Glu Glu Lys Lys Gly
1               5

<210> SEQ ID NO 255
<211> LENGTH: 5
<212> TYPE: PRT
<213> ORGANISM: Homo sapiens

<400> SEQUENCE: 255

Glu Lys Lys Gly Asn
1               5

<210> SEQ ID NO 256
<211> LENGTH: 5
<212> TYPE: PRT
<213> ORGANISM: Homo sapiens

<400> SEQUENCE: 256

Lys Gly Asn Tyr Val
1               5

<210> SEQ ID NO 257
<211> LENGTH: 5
<212> TYPE: PRT
<213> ORGANISM: Homo sapiens

<400> SEQUENCE: 257

Lys Lys Gly Asn Tyr
1               5

<210> SEQ ID NO 258
<211> LENGTH: 5
<212> TYPE: PRT
<213> ORGANISM: Homo sapiens

<400> SEQUENCE: 258

Glu Lys Lys Gly Asn
1               5

<210> SEQ ID NO 259
<211> LENGTH: 5
<212> TYPE: PRT
```

```
<213> ORGANISM: Homo sapiens

<400> SEQUENCE: 259

Glu Glu Lys Lys Gly
1               5

<210> SEQ ID NO 260
<211> LENGTH: 5
<212> TYPE: PRT
<213> ORGANISM: Homo sapiens

<400> SEQUENCE: 260

Lys Gly Asn Tyr Val
1               5

<210> SEQ ID NO 261
<211> LENGTH: 5
<212> TYPE: PRT
<213> ORGANISM: Homo sapiens

<400> SEQUENCE: 261

Glu Lys Lys Gly Asn
1               5

<210> SEQ ID NO 262
<211> LENGTH: 5
<212> TYPE: PRT
<213> ORGANISM: Homo sapiens

<400> SEQUENCE: 262

Lys Lys Gly Asn Tyr
1               5

<210> SEQ ID NO 263
<211> LENGTH: 5
<212> TYPE: PRT
<213> ORGANISM: Homo sapiens

<400> SEQUENCE: 263

Gly Asn Tyr Val Val
1               5

<210> SEQ ID NO 264
<211> LENGTH: 5
<212> TYPE: PRT
<213> ORGANISM: Homo sapiens

<400> SEQUENCE: 264

Glu Glu Lys Lys Gly
1               5

<210> SEQ ID NO 265
<211> LENGTH: 5
<212> TYPE: PRT
<213> ORGANISM: Homo sapiens

<400> SEQUENCE: 265

Gly Asn Tyr Val Val
1               5

<210> SEQ ID NO 266
<211> LENGTH: 5
<212> TYPE: PRT
<213> ORGANISM: Homo sapiens
```

```
<400> SEQUENCE: 266

Lys Lys Gly Asn Tyr
1               5

<210> SEQ ID NO 267
<211> LENGTH: 5
<212> TYPE: PRT
<213> ORGANISM: Homo sapiens

<400> SEQUENCE: 267

Glu Lys Lys Gly Asn
1               5

<210> SEQ ID NO 268
<211> LENGTH: 5
<212> TYPE: PRT
<213> ORGANISM: Homo sapiens

<400> SEQUENCE: 268

Glu Lys Lys Gly Asn
1               5

<210> SEQ ID NO 269
<211> LENGTH: 5
<212> TYPE: PRT
<213> ORGANISM: Homo sapiens

<400> SEQUENCE: 269

Lys Lys Gly Asn Tyr
1               5

<210> SEQ ID NO 270
<211> LENGTH: 5
<212> TYPE: PRT
<213> ORGANISM: Homo sapiens

<400> SEQUENCE: 270

Lys Gly Asn Tyr Val
1               5

<210> SEQ ID NO 271
<211> LENGTH: 5
<212> TYPE: PRT
<213> ORGANISM: Homo sapiens

<400> SEQUENCE: 271

Lys Gly Asn Tyr Val
1               5

<210> SEQ ID NO 272
<211> LENGTH: 5
<212> TYPE: PRT
<213> ORGANISM: Homo sapiens

<400> SEQUENCE: 272

Lys Gly Asn Tyr Val
1               5

<210> SEQ ID NO 273
<211> LENGTH: 5
<212> TYPE: PRT
<213> ORGANISM: Homo sapiens

<400> SEQUENCE: 273
```

```
Glu Glu Lys Lys Gly
1               5

<210> SEQ ID NO 274
<211> LENGTH: 5
<212> TYPE: PRT
<213> ORGANISM: Homo sapiens

<400> SEQUENCE: 274

Glu Lys Lys Gly Asn
1               5

<210> SEQ ID NO 275
<211> LENGTH: 5
<212> TYPE: PRT
<213> ORGANISM: Homo sapiens

<400> SEQUENCE: 275

Glu Glu Lys Lys Gly
1               5

<210> SEQ ID NO 276
<211> LENGTH: 5
<212> TYPE: PRT
<213> ORGANISM: Homo sapiens

<400> SEQUENCE: 276

Lys Lys Gly Asn Tyr
1               5

<210> SEQ ID NO 277
<211> LENGTH: 5
<212> TYPE: PRT
<213> ORGANISM: Homo sapiens

<400> SEQUENCE: 277

Lys Gly Asn Tyr Val
1               5

<210> SEQ ID NO 278
<211> LENGTH: 5
<212> TYPE: PRT
<213> ORGANISM: Homo sapiens

<400> SEQUENCE: 278

Glu Glu Lys Lys Gly
1               5

<210> SEQ ID NO 279
<211> LENGTH: 5
<212> TYPE: PRT
<213> ORGANISM: Homo sapiens

<400> SEQUENCE: 279

Glu Lys Lys Gly Asn
1               5

<210> SEQ ID NO 280
<211> LENGTH: 5
<212> TYPE: PRT
<213> ORGANISM: Homo sapiens

<400> SEQUENCE: 280

Lys Gly Asn Tyr Val
1               5
```

```
<210> SEQ ID NO 281
<211> LENGTH: 5
<212> TYPE: PRT
<213> ORGANISM: Homo sapiens

<400> SEQUENCE: 281

Glu Lys Lys Gly Asn
1               5

<210> SEQ ID NO 282
<211> LENGTH: 5
<212> TYPE: PRT
<213> ORGANISM: Homo sapiens

<400> SEQUENCE: 282

Gly Asn Tyr Val Val
1               5

<210> SEQ ID NO 283
<211> LENGTH: 5
<212> TYPE: PRT
<213> ORGANISM: Homo sapiens

<400> SEQUENCE: 283

Lys Lys Gly Asn Tyr
1               5

<210> SEQ ID NO 284
<211> LENGTH: 5
<212> TYPE: PRT
<213> ORGANISM: Homo sapiens

<400> SEQUENCE: 284

Glu Glu Lys Lys Gly
1               5

<210> SEQ ID NO 285
<211> LENGTH: 5
<212> TYPE: PRT
<213> ORGANISM: Homo sapiens

<400> SEQUENCE: 285

Met Glu Pro Cys Trp
1               5

<210> SEQ ID NO 286
<211> LENGTH: 5
<212> TYPE: PRT
<213> ORGANISM: Homo sapiens

<400> SEQUENCE: 286

Glu Pro Cys Trp Lys
1               5

<210> SEQ ID NO 287
<211> LENGTH: 5
<212> TYPE: PRT
<213> ORGANISM: Homo sapiens

<400> SEQUENCE: 287

Pro Cys Trp Lys Gln
1               5
```

```
<210> SEQ ID NO 288
<211> LENGTH: 5
<212> TYPE: PRT
<213> ORGANISM: Homo sapiens

<400> SEQUENCE: 288

Cys Trp Lys Gln Ile
1               5

<210> SEQ ID NO 289
<211> LENGTH: 5
<212> TYPE: PRT
<213> ORGANISM: Homo sapiens

<400> SEQUENCE: 289

Trp Lys Gln Ile Asp
1               5

<210> SEQ ID NO 290
<211> LENGTH: 5
<212> TYPE: PRT
<213> ORGANISM: Homo sapiens

<400> SEQUENCE: 290

Thr Tyr Arg Leu Met
1               5

<210> SEQ ID NO 291
<211> LENGTH: 5
<212> TYPE: PRT
<213> ORGANISM: Homo sapiens

<400> SEQUENCE: 291

Tyr Arg Leu Met Leu
1               5

<210> SEQ ID NO 292
<211> LENGTH: 5
<212> TYPE: PRT
<213> ORGANISM: Homo sapiens

<400> SEQUENCE: 292

Arg Leu Met Leu Tyr
1               5

<210> SEQ ID NO 293
<211> LENGTH: 5
<212> TYPE: PRT
<213> ORGANISM: Homo sapiens

<400> SEQUENCE: 293

Leu Met Leu Tyr Ser
1               5

<210> SEQ ID NO 294
<211> LENGTH: 5
<212> TYPE: PRT
<213> ORGANISM: Homo sapiens

<400> SEQUENCE: 294

Met Leu Tyr Ser Leu
1               5

<210> SEQ ID NO 295
<211> LENGTH: 5
```

-continued

```
<212> TYPE: PRT
<213> ORGANISM: Homo sapiens

<400> SEQUENCE: 295

Arg Phe Phe Met Leu
1               5

<210> SEQ ID NO 296
<211> LENGTH: 5
<212> TYPE: PRT
<213> ORGANISM: Homo sapiens

<400> SEQUENCE: 296

Phe Phe Met Leu Ala
1               5

<210> SEQ ID NO 297
<211> LENGTH: 5
<212> TYPE: PRT
<213> ORGANISM: Homo sapiens

<400> SEQUENCE: 297

Phe Met Leu Ala Trp
1               5

<210> SEQ ID NO 298
<211> LENGTH: 5
<212> TYPE: PRT
<213> ORGANISM: Homo sapiens

<400> SEQUENCE: 298

Met Leu Ala Trp Asn
1               5

<210> SEQ ID NO 299
<211> LENGTH: 5
<212> TYPE: PRT
<213> ORGANISM: Homo sapiens

<400> SEQUENCE: 299

Leu Ala Trp Asn Leu
1               5

<210> SEQ ID NO 300
<211> LENGTH: 5
<212> TYPE: PRT
<213> ORGANISM: Homo sapiens

<400> SEQUENCE: 300

Pro Arg Ala Gln Leu
1               5

<210> SEQ ID NO 301
<211> LENGTH: 5
<212> TYPE: PRT
<213> ORGANISM: Homo sapiens

<400> SEQUENCE: 301

Arg Ala Gln Leu Ser
1               5

<210> SEQ ID NO 302
<211> LENGTH: 5
<212> TYPE: PRT
<213> ORGANISM: Homo sapiens
```

-continued

<400> SEQUENCE: 302

Ala Gln Leu Ser Ser
1               5

<210> SEQ ID NO 303
<211> LENGTH: 5
<212> TYPE: PRT
<213> ORGANISM: Homo sapiens

<400> SEQUENCE: 303

Gln Leu Ser Ser Ala
1               5

<210> SEQ ID NO 304
<211> LENGTH: 5
<212> TYPE: PRT
<213> ORGANISM: Homo sapiens

<400> SEQUENCE: 304

Leu Ser Ser Ala Ser
1               5

<210> SEQ ID NO 305
<211> LENGTH: 5
<212> TYPE: PRT
<213> ORGANISM: Homo sapiens

<400> SEQUENCE: 305

Glu Lys Glu Leu Pro
1               5

<210> SEQ ID NO 306
<211> LENGTH: 5
<212> TYPE: PRT
<213> ORGANISM: Homo sapiens

<400> SEQUENCE: 306

Lys Glu Leu Pro Glu
1               5

<210> SEQ ID NO 307
<211> LENGTH: 5
<212> TYPE: PRT
<213> ORGANISM: Homo sapiens

<400> SEQUENCE: 307

Glu Leu Pro Glu Glu
1               5

<210> SEQ ID NO 308
<211> LENGTH: 5
<212> TYPE: PRT
<213> ORGANISM: Homo sapiens

<400> SEQUENCE: 308

Leu Pro Glu Glu Lys
1               5

<210> SEQ ID NO 309
<211> LENGTH: 5
<212> TYPE: PRT
<213> ORGANISM: Homo sapiens

<400> SEQUENCE: 309

Pro Glu Glu Lys Lys
1               5

<210> SEQ ID NO 310
<211> LENGTH: 5
<212> TYPE: PRT
<213> ORGANISM: Homo sapiens

<400> SEQUENCE: 310

Leu Gln Ala Leu Lys
1               5

<210> SEQ ID NO 311
<211> LENGTH: 5
<212> TYPE: PRT
<213> ORGANISM: Homo sapiens

<400> SEQUENCE: 311

Gln Ala Leu Lys Glu
1               5

<210> SEQ ID NO 312
<211> LENGTH: 5
<212> TYPE: PRT
<213> ORGANISM: Homo sapiens

<400> SEQUENCE: 312

Ala Leu Lys Glu Leu
1               5

<210> SEQ ID NO 313
<211> LENGTH: 5
<212> TYPE: PRT
<213> ORGANISM: Homo sapiens

<400> SEQUENCE: 313

Leu Lys Glu Leu Ala
1               5

<210> SEQ ID NO 314
<211> LENGTH: 5
<212> TYPE: PRT
<213> ORGANISM: Homo sapiens

<400> SEQUENCE: 314

Lys Glu Leu Ala Val
1               5

<210> SEQ ID NO 315
<211> LENGTH: 5
<212> TYPE: PRT
<213> ORGANISM: Homo sapiens

<400> SEQUENCE: 315

Phe Asp Lys Cys Ser
1               5

<210> SEQ ID NO 316
<211> LENGTH: 5
<212> TYPE: PRT
<213> ORGANISM: Homo sapiens

<400> SEQUENCE: 316

Asp Lys Cys Ser Glu

-continued

```
1               5

<210> SEQ ID NO 317
<211> LENGTH: 5
<212> TYPE: PRT
<213> ORGANISM: Homo sapiens

<400> SEQUENCE: 317

Lys Cys Ser Glu Leu
1               5

<210> SEQ ID NO 318
<211> LENGTH: 5
<212> TYPE: PRT
<213> ORGANISM: Homo sapiens

<400> SEQUENCE: 318

Cys Ser Glu Leu Arg
1               5

<210> SEQ ID NO 319
<211> LENGTH: 5
<212> TYPE: PRT
<213> ORGANISM: Homo sapiens

<400> SEQUENCE: 319

Ser Glu Leu Arg Glu
1               5

<210> SEQ ID NO 320
<211> LENGTH: 5
<212> TYPE: PRT
<213> ORGANISM: Homo sapiens

<400> SEQUENCE: 320

Gln Arg Asp Arg Lys
1               5

<210> SEQ ID NO 321
<211> LENGTH: 5
<212> TYPE: PRT
<213> ORGANISM: Homo sapiens

<400> SEQUENCE: 321

Arg Asp Arg Lys Glu
1               5

<210> SEQ ID NO 322
<211> LENGTH: 5
<212> TYPE: PRT
<213> ORGANISM: Homo sapiens

<400> SEQUENCE: 322

Asp Arg Lys Glu Ala
1               5

<210> SEQ ID NO 323
<211> LENGTH: 5
<212> TYPE: PRT
<213> ORGANISM: Homo sapiens

<400> SEQUENCE: 323

Arg Lys Glu Ala Leu
1               5
```

-continued

<210> SEQ ID NO 324
<211> LENGTH: 5
<212> TYPE: PRT
<213> ORGANISM: Homo sapiens

<400> SEQUENCE: 324

Lys Glu Ala Leu His
1               5

<210> SEQ ID NO 325
<211> LENGTH: 5
<212> TYPE: PRT
<213> ORGANISM: Homo sapiens

<400> SEQUENCE: 325

Thr Ala Ile Ile Glu
1               5

<210> SEQ ID NO 326
<211> LENGTH: 5
<212> TYPE: PRT
<213> ORGANISM: Homo sapiens

<400> SEQUENCE: 326

Ala Ile Ile Glu Glu
1               5

<210> SEQ ID NO 327
<211> LENGTH: 5
<212> TYPE: PRT
<213> ORGANISM: Homo sapiens

<400> SEQUENCE: 327

Ile Ile Glu Glu Ile
1               5

<210> SEQ ID NO 328
<211> LENGTH: 5
<212> TYPE: PRT
<213> ORGANISM: Homo sapiens

<400> SEQUENCE: 328

Ile Glu Glu Ile Val
1               5

<210> SEQ ID NO 329
<211> LENGTH: 5
<212> TYPE: PRT
<213> ORGANISM: Homo sapiens

<400> SEQUENCE: 329

Glu Glu Ile Val Ser
1               5

<210> SEQ ID NO 330
<211> LENGTH: 5
<212> TYPE: PRT
<213> ORGANISM: Homo sapiens

<400> SEQUENCE: 330

Pro Trp Lys Glu Pro
1               5

<210> SEQ ID NO 331

```
<211> LENGTH: 5
<212> TYPE: PRT
<213> ORGANISM: Homo sapiens

<400> SEQUENCE: 331

Trp Lys Glu Pro Thr
1               5

<210> SEQ ID NO 332
<211> LENGTH: 5
<212> TYPE: PRT
<213> ORGANISM: Homo sapiens

<400> SEQUENCE: 332

Lys Glu Pro Thr Ala
1               5

<210> SEQ ID NO 333
<211> LENGTH: 5
<212> TYPE: PRT
<213> ORGANISM: Homo sapiens

<400> SEQUENCE: 333

Glu Pro Thr Ala Phe
1               5

<210> SEQ ID NO 334
<211> LENGTH: 5
<212> TYPE: PRT
<213> ORGANISM: Homo sapiens

<400> SEQUENCE: 334

Pro Thr Ala Phe Gln
1               5

<210> SEQ ID NO 335
<211> LENGTH: 9
<212> TYPE: PRT
<213> ORGANISM: Homo sapiens

<400> SEQUENCE: 335

Lys Thr Phe Met Glu Pro Cys Trp Pro
1               5

<210> SEQ ID NO 336
<211> LENGTH: 9
<212> TYPE: PRT
<213> ORGANISM: Homo sapiens

<400> SEQUENCE: 336

Ala Gly Lys Glu Pro Cys Trp Lys Pro
1               5

<210> SEQ ID NO 337
<211> LENGTH: 9
<212> TYPE: PRT
<213> ORGANISM: Homo sapiens

<400> SEQUENCE: 337

Leu Ala Ala Cys Trp Lys Gln Ile Lys
1               5

<210> SEQ ID NO 338
<211> LENGTH: 9
<212> TYPE: PRT
```

<213> ORGANISM: Homo sapiens

<400> SEQUENCE: 338

Leu Asp Pro Tyr Arg Leu Met Leu Lys
1               5

<210> SEQ ID NO 339
<211> LENGTH: 9
<212> TYPE: PRT
<213> ORGANISM: Homo sapiens

<400> SEQUENCE: 339

Thr Gln Ser Met Leu Tyr Ser Leu Lys
1               5

<210> SEQ ID NO 340
<211> LENGTH: 9
<212> TYPE: PRT
<213> ORGANISM: Homo sapiens

<400> SEQUENCE: 340

Asp Asp Arg Phe Phe Met Leu Ala Lys
1               5

<210> SEQ ID NO 341
<211> LENGTH: 9
<212> TYPE: PRT
<213> ORGANISM: Homo sapiens

<400> SEQUENCE: 341

Glu Pro Ser Met Leu Ala Trp Asn Lys
1               5

<210> SEQ ID NO 342
<211> LENGTH: 9
<212> TYPE: PRT
<213> ORGANISM: Homo sapiens

<400> SEQUENCE: 342

Ser Gly Arg Leu Ala Trp Asn Leu Pro
1               5

<210> SEQ ID NO 343
<211> LENGTH: 9
<212> TYPE: PRT
<213> ORGANISM: Homo sapiens

<400> SEQUENCE: 343

Arg Phe Tyr Pro Arg Ala Gln Leu Pro
1               5

<210> SEQ ID NO 344
<211> LENGTH: 9
<212> TYPE: PRT
<213> ORGANISM: Homo sapiens

<400> SEQUENCE: 344

Glu Gly Arg Leu Ser Ser Ala Ser Lys
1               5

<210> SEQ ID NO 345
<211> LENGTH: 9
<212> TYPE: PRT
<213> ORGANISM: Homo sapiens -continued

```
<400> SEQUENCE: 345

Lys Gly Ser Glu Lys Glu Leu Pro Gln
1               5

<210> SEQ ID NO 346
<211> LENGTH: 9
<212> TYPE: PRT
<213> ORGANISM: Homo sapiens

<400> SEQUENCE: 346

Gly Gly Tyr Pro Glu Glu Lys Lys Pro
1               5

<210> SEQ ID NO 347
<211> LENGTH: 9
<212> TYPE: PRT
<213> ORGANISM: Homo sapiens

<400> SEQUENCE: 347

Val Glu Phe Leu Lys Glu Leu Ala Arg
1               5

<210> SEQ ID NO 348
<211> LENGTH: 9
<212> TYPE: PRT
<213> ORGANISM: Homo sapiens

<400> SEQUENCE: 348

Tyr Val Arg Lys Glu Leu Ala Val Gln
1               5

<210> SEQ ID NO 349
<211> LENGTH: 9
<212> TYPE: PRT
<213> ORGANISM: Homo sapiens

<400> SEQUENCE: 349

Lys Cys Phe Phe Asp Lys Cys Ser Asp
1               5

<210> SEQ ID NO 350
<211> LENGTH: 9
<212> TYPE: PRT
<213> ORGANISM: Homo sapiens

<400> SEQUENCE: 350

Val Cys Phe Asp Lys Cys Ser Glu Gln
1               5

<210> SEQ ID NO 351
<211> LENGTH: 9
<212> TYPE: PRT
<213> ORGANISM: Homo sapiens

<400> SEQUENCE: 351

Asp Val Met Lys Cys Ser Glu Leu Pro
1               5

<210> SEQ ID NO 352
<211> LENGTH: 9
<212> TYPE: PRT
<213> ORGANISM: Homo sapiens

<400> SEQUENCE: 352
```

```
Lys Pro Tyr Lys Glu Ala Leu His Pro
1               5

<210> SEQ ID NO 353
<211> LENGTH: 9
<212> TYPE: PRT
<213> ORGANISM: Homo sapiens

<400> SEQUENCE: 353

Lys Cys Lys Glu Glu Ile Val Ser Pro
1               5

<210> SEQ ID NO 354
<211> LENGTH: 9
<212> TYPE: PRT
<213> ORGANISM: Homo sapiens

<400> SEQUENCE: 354

Asp Ala Trp Glu Glu Ile Val Ser Tyr
1               5

<210> SEQ ID NO 355
<211> LENGTH: 9
<212> TYPE: PRT
<213> ORGANISM: Homo sapiens

<400> SEQUENCE: 355

Met Tyr Leu Lys Glu Pro Thr Ala Lys
1               5

<210> SEQ ID NO 356
<211> LENGTH: 9
<212> TYPE: PRT
<213> ORGANISM: Homo sapiens

<400> SEQUENCE: 356

Ile Val Arg Pro Thr Ala Phe Gln Gln
1               5

<210> SEQ ID NO 357
<211> LENGTH: 9
<212> TYPE: PRT
<213> ORGANISM: Homo sapiens

<400> SEQUENCE: 357

His Gly Val Glu Pro Cys Trp Lys Ile
1               5

<210> SEQ ID NO 358
<211> LENGTH: 9
<212> TYPE: PRT
<213> ORGANISM: Homo sapiens

<400> SEQUENCE: 358

Met Lys Gly Pro Cys Trp Lys Gln Phe
1               5

<210> SEQ ID NO 359
<211> LENGTH: 9
<212> TYPE: PRT
<213> ORGANISM: Homo sapiens

<400> SEQUENCE: 359

Arg Pro Ser Trp Lys Gln Ile Asp Phe
1               5
```

-continued

```
<210> SEQ ID NO 360
<211> LENGTH: 9
<212> TYPE: PRT
<213> ORGANISM: Homo sapiens

<400> SEQUENCE: 360

Phe Lys Asn Thr Tyr Arg Leu Met Leu
1               5

<210> SEQ ID NO 361
<211> LENGTH: 9
<212> TYPE: PRT
<213> ORGANISM: Homo sapiens

<400> SEQUENCE: 361

Arg Pro Arg Met Leu Tyr Ser Leu Met
1               5

<210> SEQ ID NO 362
<211> LENGTH: 9
<212> TYPE: PRT
<213> ORGANISM: Homo sapiens

<400> SEQUENCE: 362

Lys Ser Glu Phe Phe Met Leu Ala Arg
1               5

<210> SEQ ID NO 363
<211> LENGTH: 9
<212> TYPE: PRT
<213> ORGANISM: Homo sapiens

<400> SEQUENCE: 363

Gln Ala Arg Met Leu Ala Trp Asn Tyr
1               5

<210> SEQ ID NO 364
<211> LENGTH: 9
<212> TYPE: PRT
<213> ORGANISM: Homo sapiens

<400> SEQUENCE: 364

Arg Gln Glu Leu Ala Trp Asn Leu Trp
1               5

<210> SEQ ID NO 365
<211> LENGTH: 9
<212> TYPE: PRT
<213> ORGANISM: Homo sapiens

<400> SEQUENCE: 365

Lys Asn Val Leu Ser Ser Ala Ser Trp
1               5

<210> SEQ ID NO 366
<211> LENGTH: 9
<212> TYPE: PRT
<213> ORGANISM: Homo sapiens

<400> SEQUENCE: 366

Asp Ala Glu Glu Lys Glu Leu Pro Tyr
1               5
```

```
<210> SEQ ID NO 367
<211> LENGTH: 9
<212> TYPE: PRT
<213> ORGANISM: Homo sapiens

<400> SEQUENCE: 367

Asp Leu Ile Pro Glu Glu Lys Lys Phe
1               5

<210> SEQ ID NO 368
<211> LENGTH: 9
<212> TYPE: PRT
<213> ORGANISM: Homo sapiens

<400> SEQUENCE: 368

Val Leu Arg Gln Ala Leu Lys Glu Phe
1               5

<210> SEQ ID NO 369
<211> LENGTH: 9
<212> TYPE: PRT
<213> ORGANISM: Homo sapiens

<400> SEQUENCE: 369

Val Gly Asp Ala Leu Lys Glu Leu Met
1               5

<210> SEQ ID NO 370
<211> LENGTH: 9
<212> TYPE: PRT
<213> ORGANISM: Homo sapiens

<400> SEQUENCE: 370

Lys Ser Gln Leu Lys Glu Leu Ala Tyr
1               5

<210> SEQ ID NO 371
<211> LENGTH: 9
<212> TYPE: PRT
<213> ORGANISM: Homo sapiens

<400> SEQUENCE: 371

Trp Pro Ser Lys Glu Leu Ala Val Arg
1               5

<210> SEQ ID NO 372
<211> LENGTH: 9
<212> TYPE: PRT
<213> ORGANISM: Homo sapiens

<400> SEQUENCE: 372

Arg Ser Asn Lys Cys Ser Glu Leu Tyr
1               5

<210> SEQ ID NO 373
<211> LENGTH: 9
<212> TYPE: PRT
<213> ORGANISM: Homo sapiens

<400> SEQUENCE: 373

Leu Ala Glu Ile Ile Glu Glu Ile His
1               5

<210> SEQ ID NO 374
<211> LENGTH: 9
```

-continued

<212> TYPE: PRT
<213> ORGANISM: Homo sapiens

<400> SEQUENCE: 374

Lys Gly Glu Ile Glu Glu Ile Val Tyr
1               5

<210> SEQ ID NO 375
<211> LENGTH: 9
<212> TYPE: PRT
<213> ORGANISM: Homo sapiens

<400> SEQUENCE: 375

Leu Gly Ser Glu Glu Ile Val Ser Arg
1               5

<210> SEQ ID NO 376
<211> LENGTH: 9
<212> TYPE: PRT
<213> ORGANISM: Homo sapiens

<400> SEQUENCE: 376

Leu Pro Ser Lys Glu Pro Thr Ala Ala
1               5

<210> SEQ ID NO 377
<211> LENGTH: 9
<212> TYPE: PRT
<213> ORGANISM: Homo sapiens

<400> SEQUENCE: 377

Asn Ser Ala Pro Thr Ala Phe Gln Phe
1               5

<210> SEQ ID NO 378
<211> LENGTH: 9
<212> TYPE: PRT
<213> ORGANISM: Homo sapiens

<400> SEQUENCE: 378

Val Glu Ser Pro Cys Trp Lys Gln Ser
1               5

<210> SEQ ID NO 379
<211> LENGTH: 9
<212> TYPE: PRT
<213> ORGANISM: Homo sapiens

<400> SEQUENCE: 379

Ile Glu Arg Cys Trp Lys Gln Ile Glu
1               5

<210> SEQ ID NO 380
<211> LENGTH: 9
<212> TYPE: PRT
<213> ORGANISM: Homo sapiens

<400> SEQUENCE: 380

Cys Glu Arg Trp Lys Gln Ile Asp Asp
1               5

<210> SEQ ID NO 381
<211> LENGTH: 9
<212> TYPE: PRT
<213> ORGANISM: Homo sapiens

<400> SEQUENCE: 381

Thr Glu Thr Thr Tyr Arg Leu Met Val
1               5

<210> SEQ ID NO 382
<211> LENGTH: 9
<212> TYPE: PRT
<213> ORGANISM: Homo sapiens

<400> SEQUENCE: 382

Arg Glu Glu Leu Met Leu Tyr Ser Gln
1               5

<210> SEQ ID NO 383
<211> LENGTH: 9
<212> TYPE: PRT
<213> ORGANISM: Homo sapiens

<400> SEQUENCE: 383

Ile Glu Arg Met Leu Tyr Ser Leu Arg
1               5

<210> SEQ ID NO 384
<211> LENGTH: 9
<212> TYPE: PRT
<213> ORGANISM: Homo sapiens

<400> SEQUENCE: 384

Glu Glu Gln Phe Phe Met Leu Ala Gln
1               5

<210> SEQ ID NO 385
<211> LENGTH: 9
<212> TYPE: PRT
<213> ORGANISM: Homo sapiens

<400> SEQUENCE: 385

Ala Glu Lys Phe Met Leu Ala Trp Glu
1               5

<210> SEQ ID NO 386
<211> LENGTH: 9
<212> TYPE: PRT
<213> ORGANISM: Homo sapiens

<400> SEQUENCE: 386

Ser Gly Pro Met Leu Ala Trp Asn Arg
1               5

<210> SEQ ID NO 387
<211> LENGTH: 9
<212> TYPE: PRT
<213> ORGANISM: Homo sapiens

<400> SEQUENCE: 387

Thr Glu Val Leu Ala Trp Asn Leu Lys
1               5

<210> SEQ ID NO 388
<211> LENGTH: 9
<212> TYPE: PRT
<213> ORGANISM: Homo sapiens

<400> SEQUENCE: 388

-continued

```
Glu Glu Val Pro Arg Ala Gln Leu Pro
1               5

<210> SEQ ID NO 389
<211> LENGTH: 9
<212> TYPE: PRT
<213> ORGANISM: Homo sapiens

<400> SEQUENCE: 389

Asp Cys Ser Arg Ala Gln Leu Ser Ala
1               5

<210> SEQ ID NO 390
<211> LENGTH: 9
<212> TYPE: PRT
<213> ORGANISM: Homo sapiens

<400> SEQUENCE: 390

Gly His Phe Glu Leu Pro Glu Glu Met
1               5

<210> SEQ ID NO 391
<211> LENGTH: 9
<212> TYPE: PRT
<213> ORGANISM: Homo sapiens

<400> SEQUENCE: 391

Val Glu Leu Pro Glu Glu Lys Lys Ser
1               5

<210> SEQ ID NO 392
<211> LENGTH: 9
<212> TYPE: PRT
<213> ORGANISM: Homo sapiens

<400> SEQUENCE: 392

Phe Glu Ser Gln Ala Leu Lys Glu Val
1               5

<210> SEQ ID NO 393
<211> LENGTH: 9
<212> TYPE: PRT
<213> ORGANISM: Homo sapiens

<400> SEQUENCE: 393

Pro Glu Lys Ala Leu Lys Glu Leu Gln
1               5

<210> SEQ ID NO 394
<211> LENGTH: 9
<212> TYPE: PRT
<213> ORGANISM: Homo sapiens

<400> SEQUENCE: 394

Gln Cys Glu Leu Lys Glu Leu Ala Thr
1               5

<210> SEQ ID NO 395
<211> LENGTH: 9
<212> TYPE: PRT
<213> ORGANISM: Homo sapiens

<400> SEQUENCE: 395

Leu Cys Leu Phe Asp Lys Cys Ser Ser
```

-continued

```
1               5

<210> SEQ ID NO 396
<211> LENGTH: 9
<212> TYPE: PRT
<213> ORGANISM: Homo sapiens

<400> SEQUENCE: 396

Leu Glu Glu Cys Ser Glu Leu Arg Thr
1               5

<210> SEQ ID NO 397
<211> LENGTH: 9
<212> TYPE: PRT
<213> ORGANISM: Homo sapiens

<400> SEQUENCE: 397

Arg Glu Ala Thr Ala Ile Ile Glu Glu
1               5

<210> SEQ ID NO 398
<211> LENGTH: 9
<212> TYPE: PRT
<213> ORGANISM: Homo sapiens

<400> SEQUENCE: 398

Glu Glu His Ile Ile Glu Glu Ile Asp
1               5

<210> SEQ ID NO 399
<211> LENGTH: 9
<212> TYPE: PRT
<213> ORGANISM: Homo sapiens

<400> SEQUENCE: 399

Val Glu Arg Pro Thr Ala Phe Gln Gly
1               5

<210> SEQ ID NO 400
<211> LENGTH: 9
<212> TYPE: PRT
<213> ORGANISM: Homo sapiens

<400> SEQUENCE: 400

Leu Leu Arg Pro Cys Trp Lys Gln Ala
1               5

<210> SEQ ID NO 401
<211> LENGTH: 9
<212> TYPE: PRT
<213> ORGANISM: Homo sapiens

<400> SEQUENCE: 401

Pro Phe Asp Trp Lys Gln Ile Asp Pro
1               5

<210> SEQ ID NO 402
<211> LENGTH: 9
<212> TYPE: PRT
<213> ORGANISM: Homo sapiens

<400> SEQUENCE: 402

Ser Lys Ile Arg Leu Met Leu Tyr Ser
1               5
```

```
<210> SEQ ID NO 403
<211> LENGTH: 9
<212> TYPE: PRT
<213> ORGANISM: Homo sapiens

<400> SEQUENCE: 403

Arg Arg Tyr Leu Met Leu Tyr Ser Lys
1               5

<210> SEQ ID NO 404
<211> LENGTH: 9
<212> TYPE: PRT
<213> ORGANISM: Homo sapiens

<400> SEQUENCE: 404

Lys Lys Leu Met Leu Tyr Ser Leu Lys
1               5

<210> SEQ ID NO 405
<211> LENGTH: 9
<212> TYPE: PRT
<213> ORGANISM: Homo sapiens

<400> SEQUENCE: 405

Ser Ala Glu Arg Phe Phe Met Leu Lys
1               5

<210> SEQ ID NO 406
<211> LENGTH: 9
<212> TYPE: PRT
<213> ORGANISM: Homo sapiens

<400> SEQUENCE: 406

Asp Arg Arg Phe Phe Met Leu Ala Lys
1               5

<210> SEQ ID NO 407
<211> LENGTH: 9
<212> TYPE: PRT
<213> ORGANISM: Homo sapiens

<400> SEQUENCE: 407

Pro Gly Ser Met Leu Ala Trp Asn Lys
1               5

<210> SEQ ID NO 408
<211> LENGTH: 9
<212> TYPE: PRT
<213> ORGANISM: Homo sapiens

<400> SEQUENCE: 408

Lys Leu Lys Pro Arg Ala Gln Leu Leu
1               5

<210> SEQ ID NO 409
<211> LENGTH: 9
<212> TYPE: PRT
<213> ORGANISM: Homo sapiens

<400> SEQUENCE: 409

Leu Glu Leu Arg Ala Gln Leu Ser Ser
1               5

<210> SEQ ID NO 410
```

```
<211> LENGTH: 9
<212> TYPE: PRT
<213> ORGANISM: Homo sapiens

<400> SEQUENCE: 410

Ser Leu Arg Gln Leu Ser Ser Ala Leu
1               5

<210> SEQ ID NO 411
<211> LENGTH: 9
<212> TYPE: PRT
<213> ORGANISM: Homo sapiens

<400> SEQUENCE: 411

Ala Pro Phe Glu Lys Glu Leu Pro Arg
1               5

<210> SEQ ID NO 412
<211> LENGTH: 8
<212> TYPE: PRT
<213> ORGANISM: Homo sapiens

<400> SEQUENCE: 412

Trp Leu Gln Leu Pro Glu Glu Lys
1               5

<210> SEQ ID NO 413
<211> LENGTH: 9
<212> TYPE: PRT
<213> ORGANISM: Homo sapiens

<400> SEQUENCE: 413

Gln Cys Leu Pro Glu Glu Lys Lys Ser
1               5

<210> SEQ ID NO 414
<211> LENGTH: 9
<212> TYPE: PRT
<213> ORGANISM: Homo sapiens

<400> SEQUENCE: 414

Tyr Gln Met Leu Lys Glu Leu Ala Pro
1               5

<210> SEQ ID NO 415
<211> LENGTH: 9
<212> TYPE: PRT
<213> ORGANISM: Homo sapiens

<400> SEQUENCE: 415

Gln Trp Arg Phe Asp Lys Cys Ser Gln
1               5

<210> SEQ ID NO 416
<211> LENGTH: 9
<212> TYPE: PRT
<213> ORGANISM: Homo sapiens

<400> SEQUENCE: 416

Leu Gln His Asp Lys Cys Ser Glu Lys
1               5

<210> SEQ ID NO 417
<211> LENGTH: 9
<212> TYPE: PRT
```

<213> ORGANISM: Homo sapiens

<400> SEQUENCE: 417

Leu Lys Phe Lys Cys Ser Glu Leu Ala
1               5

<210> SEQ ID NO 418
<211> LENGTH: 9
<212> TYPE: PRT
<213> ORGANISM: Homo sapiens

<400> SEQUENCE: 418

Val Ile Leu Gln Arg Asp Arg Lys Lys
1               5

<210> SEQ ID NO 419
<211> LENGTH: 9
<212> TYPE: PRT
<213> ORGANISM: Homo sapiens

<400> SEQUENCE: 419

Phe Asp Trp Asp Arg Lys Glu Ala Gly
1               5

<210> SEQ ID NO 420
<211> LENGTH: 9
<212> TYPE: PRT
<213> ORGANISM: Homo sapiens

<400> SEQUENCE: 420

Ala Tyr Asp Lys Glu Ala Leu His Leu
1               5

<210> SEQ ID NO 421
<211> LENGTH: 9
<212> TYPE: PRT
<213> ORGANISM: Homo sapiens

<400> SEQUENCE: 421

Ala Ala Val Thr Ala Ile Ile Glu Lys
1               5

<210> SEQ ID NO 422
<211> LENGTH: 9
<212> TYPE: PRT
<213> ORGANISM: Homo sapiens

<400> SEQUENCE: 422

Pro Thr Cys Ile Glu Glu Ile Val Lys
1               5

<210> SEQ ID NO 423
<211> LENGTH: 9
<212> TYPE: PRT
<213> ORGANISM: Homo sapiens

<400> SEQUENCE: 423

Arg Arg Phe Glu Glu Ile Val Ser Asp
1               5

<210> SEQ ID NO 424
<211> LENGTH: 9
<212> TYPE: PRT
<213> ORGANISM: Homo sapiens -continued

```
<400> SEQUENCE: 424

Ser Thr Cys Trp Lys Glu Pro Thr Lys
1               5

<210> SEQ ID NO 425
<211> LENGTH: 9
<212> TYPE: PRT
<213> ORGANISM: Homo sapiens

<400> SEQUENCE: 425

Ala Met Lys Lys Glu Pro Thr Ala Leu
1               5

<210> SEQ ID NO 426
<211> LENGTH: 9
<212> TYPE: PRT
<213> ORGANISM: Homo sapiens

<400> SEQUENCE: 426

Ile Tyr Arg Glu Pro Thr Ala Phe Ser
1               5

<210> SEQ ID NO 427
<211> LENGTH: 9
<212> TYPE: PRT
<213> ORGANISM: Homo sapiens

<400> SEQUENCE: 427

Ala Ser Leu Glu Pro Cys Trp Lys His
1               5

<210> SEQ ID NO 428
<211> LENGTH: 9
<212> TYPE: PRT
<213> ORGANISM: Homo sapiens

<400> SEQUENCE: 428

Trp Leu Gln Leu Pro Glu Glu Lys Trp
1               5

<210> SEQ ID NO 429
<211> LENGTH: 5
<212> TYPE: PRT
<213> ORGANISM: Homo sapiens

<400> SEQUENCE: 429

Cys Trp Gln Asp Gln
1               5

<210> SEQ ID NO 430
<211> LENGTH: 5
<212> TYPE: PRT
<213> ORGANISM: Homo sapiens

<400> SEQUENCE: 430

Trp Lys Ile Gln Gln
1               5

<210> SEQ ID NO 431
<211> LENGTH: 5
<212> TYPE: PRT
<213> ORGANISM: Homo sapiens

<400> SEQUENCE: 431
```

```
Lys Asn Tyr Leu Met
1               5

<210> SEQ ID NO 432
<211> LENGTH: 5
<212> TYPE: PRT
<213> ORGANISM: Homo sapiens

<400> SEQUENCE: 432

Asn Thr Arg Met Leu
1               5

<210> SEQ ID NO 433
<211> LENGTH: 5
<212> TYPE: PRT
<213> ORGANISM: Homo sapiens

<400> SEQUENCE: 433

Tyr Arg Met Tyr Ser
1               5

<210> SEQ ID NO 434
<211> LENGTH: 5
<212> TYPE: PRT
<213> ORGANISM: Homo sapiens

<400> SEQUENCE: 434

Leu Met Tyr Leu Arg
1               5

<210> SEQ ID NO 435
<211> LENGTH: 5
<212> TYPE: PRT
<213> ORGANISM: Homo sapiens

<400> SEQUENCE: 435

Met Leu Ser Arg Trp
1               5

<210> SEQ ID NO 436
<211> LENGTH: 5
<212> TYPE: PRT
<213> ORGANISM: Homo sapiens

<400> SEQUENCE: 436

Gln Glu Phe Met Leu
1               5

<210> SEQ ID NO 437
<211> LENGTH: 5
<212> TYPE: PRT
<213> ORGANISM: Homo sapiens

<400> SEQUENCE: 437

Glu Arg Phe Leu Ala
1               5

<210> SEQ ID NO 438
<211> LENGTH: 5
<212> TYPE: PRT
<213> ORGANISM: Homo sapiens

<400> SEQUENCE: 438

Phe Phe Leu Trp Asn
1               5
```

```
<210> SEQ ID NO 439
<211> LENGTH: 5
<212> TYPE: PRT
<213> ORGANISM: Homo sapiens

<400> SEQUENCE: 439

Met Leu Trp Leu Glu
1               5

<210> SEQ ID NO 440
<211> LENGTH: 5
<212> TYPE: PRT
<213> ORGANISM: Homo sapiens

<400> SEQUENCE: 440

Leu Ala Asn Glu Ile
1               5

<210> SEQ ID NO 441
<211> LENGTH: 5
<212> TYPE: PRT
<213> ORGANISM: Homo sapiens

<400> SEQUENCE: 441

Met Pro Ala Leu Ser
1               5

<210> SEQ ID NO 442
<211> LENGTH: 5
<212> TYPE: PRT
<213> ORGANISM: Homo sapiens

<400> SEQUENCE: 442

Arg Ala Leu Ser Ala
1               5

<210> SEQ ID NO 443
<211> LENGTH: 5
<212> TYPE: PRT
<213> ORGANISM: Homo sapiens

<400> SEQUENCE: 443

Gln Leu Ser Ser Tyr
1               5

<210> SEQ ID NO 444
<211> LENGTH: 5
<212> TYPE: PRT
<213> ORGANISM: Homo sapiens

<400> SEQUENCE: 444

Leu Ser Ala Tyr Gln
1               5

<210> SEQ ID NO 445
<211> LENGTH: 5
<212> TYPE: PRT
<213> ORGANISM: Homo sapiens

<400> SEQUENCE: 445

Leu Gln Lys Leu Pro
1               5
```

```
<210> SEQ ID NO 446
<211> LENGTH: 5
<212> TYPE: PRT
<213> ORGANISM: Homo sapiens

<400> SEQUENCE: 446

Gln Glu Glu Pro Glu
1               5

<210> SEQ ID NO 447
<211> LENGTH: 5
<212> TYPE: PRT
<213> ORGANISM: Homo sapiens

<400> SEQUENCE: 447

Lys Glu Pro Glu Lys
1               5

<210> SEQ ID NO 448
<211> LENGTH: 5
<212> TYPE: PRT
<213> ORGANISM: Homo sapiens

<400> SEQUENCE: 448

Leu Pro Glu Lys Arg
1               5

<210> SEQ ID NO 449
<211> LENGTH: 5
<212> TYPE: PRT
<213> ORGANISM: Homo sapiens

<400> SEQUENCE: 449

Pro Glu Lys Arg Lys
1               5

<210> SEQ ID NO 450
<211> LENGTH: 5
<212> TYPE: PRT
<213> ORGANISM: Homo sapiens

<400> SEQUENCE: 450

Glu Val Gln Leu Lys
1               5

<210> SEQ ID NO 451
<211> LENGTH: 5
<212> TYPE: PRT
<213> ORGANISM: Homo sapiens

<400> SEQUENCE: 451

Val Leu Ala Lys Glu
1               5

<210> SEQ ID NO 452
<211> LENGTH: 5
<212> TYPE: PRT
<213> ORGANISM: Homo sapiens

<400> SEQUENCE: 452

Gln Ala Lys Leu Ala
1               5

<210> SEQ ID NO 453
<211> LENGTH: 5
```

<212> TYPE: PRT
<213> ORGANISM: Homo sapiens

<400> SEQUENCE: 453

Leu Lys Leu Val Asn
1               5

<210> SEQ ID NO 454
<211> LENGTH: 5
<212> TYPE: PRT
<213> ORGANISM: Homo sapiens

<400> SEQUENCE: 454

Lys Glu Ala Asn Tyr
1               5

<210> SEQ ID NO 455
<211> LENGTH: 5
<212> TYPE: PRT
<213> ORGANISM: Homo sapiens

<400> SEQUENCE: 455

Asp Lys Ser Leu Arg
1               5

<210> SEQ ID NO 456
<211> LENGTH: 5
<212> TYPE: PRT
<213> ORGANISM: Homo sapiens

<400> SEQUENCE: 456

Ser Glu Arg Pro Leu
1               5

<210> SEQ ID NO 457
<211> LENGTH: 5
<212> TYPE: PRT
<213> ORGANISM: Homo sapiens

<400> SEQUENCE: 457

Met Thr Ile Glu Glu
1               5

<210> SEQ ID NO 458
<211> LENGTH: 5
<212> TYPE: PRT
<213> ORGANISM: Homo sapiens

<400> SEQUENCE: 458

Ala Ile Glu Ile Val
1               5

<210> SEQ ID NO 459
<211> LENGTH: 5
<212> TYPE: PRT
<213> ORGANISM: Homo sapiens

<400> SEQUENCE: 459

Ile Glu Ile Ser Arg
1               5

<210> SEQ ID NO 460
<211> LENGTH: 5
<212> TYPE: PRT
<213> ORGANISM: Homo sapiens

<400> SEQUENCE: 460

Glu Glu Val Arg Asn
1               5

<210> SEQ ID NO 461
<211> LENGTH: 5
<212> TYPE: PRT
<213> ORGANISM: Homo sapiens

<400> SEQUENCE: 461

Gln Pro Lys Pro Thr
1               5

<210> SEQ ID NO 462
<211> LENGTH: 5
<212> TYPE: PRT
<213> ORGANISM: Homo sapiens

<400> SEQUENCE: 462

Trp Lys Pro Ala Phe
1               5

<210> SEQ ID NO 463
<211> LENGTH: 5
<212> TYPE: PRT
<213> ORGANISM: Homo sapiens

<400> SEQUENCE: 463

Glu Pro Ala Gln Cys
1               5

<210> SEQ ID NO 464
<211> LENGTH: 5
<212> TYPE: PRT
<213> ORGANISM: Homo sapiens

<400> SEQUENCE: 464

Pro Thr Phe Cys Val
1               5

<210> SEQ ID NO 465
<211> LENGTH: 15
<212> TYPE: PRT
<213> ORGANISM: Homo sapiens

<400> SEQUENCE: 465

Met Leu Met Trp Cys Trp Lys Gln Ile Asp Gln Asn His Gln Tyr
1               5                   10                  15

<210> SEQ ID NO 466
<211> LENGTH: 15
<212> TYPE: PRT
<213> ORGANISM: Homo sapiens

<400> SEQUENCE: 466

Gln Ile Ile Tyr Lys Asn Thr Tyr Arg Leu Met Leu Asp Gly Leu
1               5                   10                  15

<210> SEQ ID NO 467
<211> LENGTH: 15
<212> TYPE: PRT
<213> ORGANISM: Homo sapiens

<400> SEQUENCE: 467

-continued

Gln Ile Trp Ser Asn Thr Tyr Arg Leu Met Leu Thr Thr Val Gly
1               5                   10                  15

<210> SEQ ID NO 468
<211> LENGTH: 15
<212> TYPE: PRT
<213> ORGANISM: Homo sapiens

<400> SEQUENCE: 468

Asp Ser Leu Gly Tyr Arg Leu Met Leu Tyr Ser Asp Gln Gly Asp
1               5                   10                  15

<210> SEQ ID NO 469
<211> LENGTH: 15
<212> TYPE: PRT
<213> ORGANISM: Homo sapiens

<400> SEQUENCE: 469

Thr Leu Pro His Leu Met Leu Tyr Ser Leu Arg Ser Glu Asn Gly
1               5                   10                  15

<210> SEQ ID NO 470
<211> LENGTH: 15
<212> TYPE: PRT
<213> ORGANISM: Homo sapiens

<400> SEQUENCE: 470

Arg Lys Ile His Met Leu Tyr Ser Leu Arg Trp Gly Leu Ala Gln
1               5                   10                  15

<210> SEQ ID NO 471
<211> LENGTH: 15
<212> TYPE: PRT
<213> ORGANISM: Homo sapiens

<400> SEQUENCE: 471

Arg Asp Ile Gln Phe Phe Met Leu Ala Trp Asn His Gln Asp Leu
1               5                   10                  15

<210> SEQ ID NO 472
<211> LENGTH: 15
<212> TYPE: PRT
<213> ORGANISM: Homo sapiens

<400> SEQUENCE: 472

Ser Tyr Thr Phe Met Leu Ala Trp Asn Leu Glu Ser Asp Thr Glu
1               5                   10                  15

<210> SEQ ID NO 473
<211> LENGTH: 15
<212> TYPE: PRT
<213> ORGANISM: Homo sapiens

<400> SEQUENCE: 473

Ser Tyr Met Arg Leu Ala Trp Asn Leu Glu Ile Ser Ser Glu Ile
1               5                   10                  15

<210> SEQ ID NO 474
<211> LENGTH: 15
<212> TYPE: PRT
<213> ORGANISM: Homo sapiens

<400> SEQUENCE: 474

Leu Pro Leu Leu Met Pro Arg Ala Gln Leu Ser Gln Ser Gln Asp

-continued

```
1               5               10              15

<210> SEQ ID NO 475
<211> LENGTH: 15
<212> TYPE: PRT
<213> ORGANISM: Homo sapiens

<400> SEQUENCE: 475

Gln Arg Phe Gln Arg Ala Gln Leu Ser Ser Ala Ala Thr Pro Leu
1               5               10              15

<210> SEQ ID NO 476
<211> LENGTH: 15
<212> TYPE: PRT
<213> ORGANISM: Homo sapiens

<400> SEQUENCE: 476

Asp Gln Met Trp Gln Leu Ser Ser Ala Ser Tyr Leu Asp Thr Thr
1               5               10              15

<210> SEQ ID NO 477
<211> LENGTH: 15
<212> TYPE: PRT
<213> ORGANISM: Homo sapiens

<400> SEQUENCE: 477

Pro Ala Leu Ile Leu Ser Ser Ala Ser Tyr Gln Asn Ser Leu Pro
1               5               10              15

<210> SEQ ID NO 478
<211> LENGTH: 15
<212> TYPE: PRT
<213> ORGANISM: Homo sapiens

<400> SEQUENCE: 478

Thr Leu Leu Ile Leu Gln Glu Lys Glu Leu Pro Ala Leu Asn Thr
1               5               10              15

<210> SEQ ID NO 479
<211> LENGTH: 15
<212> TYPE: PRT
<213> ORGANISM: Homo sapiens

<400> SEQUENCE: 479

Tyr Ser Met Trp Gln Glu Lys Glu Leu Pro Glu Leu Ser Tyr Ser
1               5               10              15

<210> SEQ ID NO 480
<211> LENGTH: 15
<212> TYPE: PRT
<213> ORGANISM: Homo sapiens

<400> SEQUENCE: 480

Ala Tyr Leu Phe Lys Glu Leu Pro Glu Glu Lys Asp Asp Asp Lys
1               5               10              15

<210> SEQ ID NO 481
<211> LENGTH: 15
<212> TYPE: PRT
<213> ORGANISM: Homo sapiens

<400> SEQUENCE: 481

Pro Lys Leu Phe Leu Pro Glu Glu Lys Lys Arg Pro Gln Leu Pro
1               5               10              15
```

<210> SEQ ID NO 482
<211> LENGTH: 15
<212> TYPE: PRT
<213> ORGANISM: Homo sapiens

<400> SEQUENCE: 482

Leu Phe His Tyr Pro Glu Glu Lys Lys Arg Lys Asn Leu Arg Lys
1               5                   10                  15

<210> SEQ ID NO 483
<211> LENGTH: 15
<212> TYPE: PRT
<213> ORGANISM: Homo sapiens

<400> SEQUENCE: 483

Ser Leu Asn Leu Glu Val Leu Gln Ala Leu Lys Gly Thr Gly Leu
1               5                   10                  15

<210> SEQ ID NO 484
<211> LENGTH: 15
<212> TYPE: PRT
<213> ORGANISM: Homo sapiens

<400> SEQUENCE: 484

Phe Ser Arg Trp Gln Ala Leu Lys Glu Leu Ala Leu Ala Arg Pro
1               5                   10                  15

<210> SEQ ID NO 485
<211> LENGTH: 15
<212> TYPE: PRT
<213> ORGANISM: Homo sapiens

<400> SEQUENCE: 485

Phe Leu Asn Ile Leu Lys Glu Leu Ala Val Asn Leu Thr Gln Asp
1               5                   10                  15

<210> SEQ ID NO 486
<211> LENGTH: 15
<212> TYPE: PRT
<213> ORGANISM: Homo sapiens

<400> SEQUENCE: 486

Ser Ile Gln Trp Lys Glu Leu Ala Val Asn Tyr Tyr Lys Lys Glu
1               5                   10                  15

<210> SEQ ID NO 487
<211> LENGTH: 15
<212> TYPE: PRT
<213> ORGANISM: Homo sapiens

<400> SEQUENCE: 487

Phe Ile Leu Leu Asp Lys Cys Ser Glu Leu Arg Ala Asp Thr Pro
1               5                   10                  15

<210> SEQ ID NO 488
<211> LENGTH: 15
<212> TYPE: PRT
<213> ORGANISM: Homo sapiens

<400> SEQUENCE: 488

Ala Leu Lys Met Met Thr Ala Ile Ile Glu Glu Leu Ser Pro Ser
1               5                   10                  15

<210> SEQ ID NO 489

-continued

```
<211> LENGTH: 15
<212> TYPE: PRT
<213> ORGANISM: Homo sapiens

<400> SEQUENCE: 489

Ala Arg Phe Phe Ala Ile Ile Glu Glu Ile Val Gln Glu Ala Glu
1               5                   10                  15

<210> SEQ ID NO 490
<211> LENGTH: 15
<212> TYPE: PRT
<213> ORGANISM: Homo sapiens

<400> SEQUENCE: 490

Met Trp Leu Arg Ile Glu Glu Ile Val Ser Arg Asn Ser Asp Leu
1               5                   10                  15

<210> SEQ ID NO 491
<211> LENGTH: 15
<212> TYPE: PRT
<213> ORGANISM: Homo sapiens

<400> SEQUENCE: 491

Pro Asp Leu Trp Glu Glu Ile Val Ser Arg Asn Leu Gln Leu Ala
1               5                   10                  15

<210> SEQ ID NO 492
<211> LENGTH: 15
<212> TYPE: PRT
<213> ORGANISM: Homo sapiens

<400> SEQUENCE: 492

Asp Phe Tyr Val Pro Thr Ala Phe Gln Cys Val Pro Lys Thr Gln
1               5                   10                  15

<210> SEQ ID NO 493
<211> LENGTH: 15
<212> TYPE: PRT
<213> ORGANISM: Homo sapiens

<400> SEQUENCE: 493

Ile Ser Arg Leu Trp Lys Gln Ile Asp Gln Gln Tyr Ile Ile Ala
1               5                   10                  15

<210> SEQ ID NO 494
<211> LENGTH: 15
<212> TYPE: PRT
<213> ORGANISM: Homo sapiens

<400> SEQUENCE: 494

His Arg Ile Phe Lys Asn Thr Tyr Arg Leu Met Val Leu Leu His
1               5                   10                  15

<210> SEQ ID NO 495
<211> LENGTH: 15
<212> TYPE: PRT
<213> ORGANISM: Homo sapiens

<400> SEQUENCE: 495

Phe Ala Phe Arg Tyr Arg Leu Met Leu Tyr Ser Lys Gln Glu Phe
1               5                   10                  15

<210> SEQ ID NO 496
<211> LENGTH: 15
<212> TYPE: PRT
```

<213> ORGANISM: Homo sapiens

<400> SEQUENCE: 496

Met Gln Pro Gln Leu Met Leu Tyr Ser Leu Arg Ile Asp Lys Val
1               5                   10                  15

<210> SEQ ID NO 497
<211> LENGTH: 15
<212> TYPE: PRT
<213> ORGANISM: Homo sapiens

<400> SEQUENCE: 497

Arg Gln Arg Gln Met Leu Tyr Ser Leu Arg Trp Val Asp Arg Phe
1               5                   10                  15

<210> SEQ ID NO 498
<211> LENGTH: 15
<212> TYPE: PRT
<213> ORGANISM: Homo sapiens

<400> SEQUENCE: 498

Arg Gln Ile Arg Gln Glu Arg Phe Phe Met Leu Gln Arg Tyr Phe
1               5                   10                  15

<210> SEQ ID NO 499
<211> LENGTH: 15
<212> TYPE: PRT
<213> ORGANISM: Homo sapiens

<400> SEQUENCE: 499

Lys Met Leu Glu Glu Arg Phe Phe Met Leu Ala Lys Leu Tyr Pro
1               5                   10                  15

<210> SEQ ID NO 500
<211> LENGTH: 15
<212> TYPE: PRT
<213> ORGANISM: Homo sapiens

<400> SEQUENCE: 500

Arg Pro Gln Phe Phe Phe Met Leu Ala Trp Asn Asn Arg Leu Arg
1               5                   10                  15

<210> SEQ ID NO 501
<211> LENGTH: 15
<212> TYPE: PRT
<213> ORGANISM: Homo sapiens

<400> SEQUENCE: 501

Gln Val Ser His Met Leu Ala Trp Asn Leu Glu Phe Ile Gln Glu
1               5                   10                  15

<210> SEQ ID NO 502
<211> LENGTH: 15
<212> TYPE: PRT
<213> ORGANISM: Homo sapiens

<400> SEQUENCE: 502

Arg Arg Trp Leu Leu Ala Trp Asn Leu Glu Ile Cys Asp Leu Asp
1               5                   10                  15

<210> SEQ ID NO 503
<211> LENGTH: 15
<212> TYPE: PRT
<213> ORGANISM: Homo sapiens

<400> SEQUENCE: 503

Gly Val Tyr Leu Arg Ala Gln Leu Ser Ser Ala Pro Ile Pro Ala
1               5                   10                  15

<210> SEQ ID NO 504
<211> LENGTH: 15
<212> TYPE: PRT
<213> ORGANISM: Homo sapiens

<400> SEQUENCE: 504

Phe Glu Phe Leu Gln Leu Ser Ser Ala Ser Tyr Ala His Cys Arg
1               5                   10                  15

<210> SEQ ID NO 505
<211> LENGTH: 15
<212> TYPE: PRT
<213> ORGANISM: Homo sapiens

<400> SEQUENCE: 505

Lys Phe Leu His Leu Ser Ser Ala Ser Tyr Gln Trp Arg Ile Met
1               5                   10                  15

<210> SEQ ID NO 506
<211> LENGTH: 15
<212> TYPE: PRT
<213> ORGANISM: Homo sapiens

<400> SEQUENCE: 506

Pro Thr Leu Pro Glu Val Leu Gln Ala Leu Lys Ala Met Leu Glu
1               5                   10                  15

<210> SEQ ID NO 507
<211> LENGTH: 15
<212> TYPE: PRT
<213> ORGANISM: Homo sapiens

<400> SEQUENCE: 507

Arg Met Pro Leu Val Leu Gln Ala Leu Lys Glu Val Arg Ser Ile
1               5                   10                  15

<210> SEQ ID NO 508
<211> LENGTH: 15
<212> TYPE: PRT
<213> ORGANISM: Homo sapiens

<400> SEQUENCE: 508

Lys Ser Leu Phe Gln Ala Leu Lys Glu Leu Ala Leu Asn Pro Val
1               5                   10                  15

<210> SEQ ID NO 509
<211> LENGTH: 15
<212> TYPE: PRT
<213> ORGANISM: Homo sapiens

<400> SEQUENCE: 509

His Glu Lys Met Leu Lys Glu Leu Ala Val Asn Pro Asn Phe Leu
1               5                   10                  15

<210> SEQ ID NO 510
<211> LENGTH: 15
<212> TYPE: PRT
<213> ORGANISM: Homo sapiens

<400> SEQUENCE: 510

```
Glu Leu Trp Tyr Lys Glu Leu Ala Val Asn Tyr Trp Arg Leu Pro
1               5                   10                  15

<210> SEQ ID NO 511
<211> LENGTH: 15
<212> TYPE: PRT
<213> ORGANISM: Homo sapiens

<400> SEQUENCE: 511

His Glu Leu Trp Ser Glu Leu Arg Glu Pro Leu Leu Leu Ile Ser
1               5                   10                  15

<210> SEQ ID NO 512
<211> LENGTH: 15
<212> TYPE: PRT
<213> ORGANISM: Homo sapiens

<400> SEQUENCE: 512

Arg Tyr Leu Thr Met Thr Ala Ile Ile Glu Glu Tyr Asp Val Leu
1               5                   10                  15

<210> SEQ ID NO 513
<211> LENGTH: 15
<212> TYPE: PRT
<213> ORGANISM: Homo sapiens

<400> SEQUENCE: 513

Ser Leu Asn Val Gln Pro Trp Lys Glu Pro Thr Leu Val Ile Met
1               5                   10                  15

<210> SEQ ID NO 514
<211> LENGTH: 15
<212> TYPE: PRT
<213> ORGANISM: Homo sapiens

<400> SEQUENCE: 514

Asp Lys Phe Arg Trp Lys Glu Pro Thr Ala Phe Phe Lys Val Cys
1               5                   10                  15

<210> SEQ ID NO 515
<211> LENGTH: 15
<212> TYPE: PRT
<213> ORGANISM: Homo sapiens

<400> SEQUENCE: 515

Leu Lys Lys Gln Glu Pro Thr Ala Phe Gln Cys Leu Leu Ile Ile
1               5                   10                  15

<210> SEQ ID NO 516
<211> LENGTH: 15
<212> TYPE: PRT
<213> ORGANISM: Homo sapiens

<400> SEQUENCE: 516

Lys Pro Leu Tyr Pro Thr Ala Phe Gln Cys Val Pro Tyr Gln Met
1               5                   10                  15

<210> SEQ ID NO 517
<211> LENGTH: 5
<212> TYPE: PRT
<213> ORGANISM: Homo sapiens

<400> SEQUENCE: 517

Arg Asp Lys Ala Leu
1               5
```

-continued

```
<210> SEQ ID NO 518
<211> LENGTH: 5
<212> TYPE: PRT
<213> ORGANISM: Homo sapiens

<400> SEQUENCE: 518

Lys Glu Leu Gln Phe
1               5

<210> SEQ ID NO 519
<211> LENGTH: 5
<212> TYPE: PRT
<213> ORGANISM: Homo sapiens

<400> SEQUENCE: 519

Cys Ser Leu Glu Pro
1               5

<210> SEQ ID NO 520
<211> LENGTH: 5
<212> TYPE: PRT
<213> ORGANISM: Homo sapiens

<400> SEQUENCE: 520

Arg Ser Arg Arg Lys
1               5

<210> SEQ ID NO 521
<211> LENGTH: 5
<212> TYPE: PRT
<213> ORGANISM: Homo sapiens

<400> SEQUENCE: 521

Ala Val Asp Cys Ser
1               5

<210> SEQ ID NO 522
<211> LENGTH: 9
<212> TYPE: PRT
<213> ORGANISM: Homo sapiens

<400> SEQUENCE: 522

Lys Asp Lys Gly Phe Leu Ile Tyr Val
1               5

<210> SEQ ID NO 523
<211> LENGTH: 9
<212> TYPE: PRT
<213> ORGANISM: Homo sapiens

<400> SEQUENCE: 523

Lys Met Lys Leu Ile Tyr Leu Asp Ala
1               5

<210> SEQ ID NO 524
<211> LENGTH: 9
<212> TYPE: PRT
<213> ORGANISM: Homo sapiens

<400> SEQUENCE: 524

Lys Leu Lys Ile Tyr Leu Asp Val Gly
1               5
```

-continued

```
<210> SEQ ID NO 525
<211> LENGTH: 9
<212> TYPE: PRT
<213> ORGANISM: Homo sapiens

<400> SEQUENCE: 525

Lys Leu Leu Tyr Lys Asp Thr Leu Val
1               5

<210> SEQ ID NO 526
<211> LENGTH: 9
<212> TYPE: PRT
<213> ORGANISM: Homo sapiens

<400> SEQUENCE: 526

Lys Met Ser Thr Leu Trp Cys Ser Gly
1               5

<210> SEQ ID NO 527
<211> LENGTH: 9
<212> TYPE: PRT
<213> ORGANISM: Homo sapiens

<400> SEQUENCE: 527

Lys Leu Arg Leu Trp Cys Ser Pro Ala
1               5

<210> SEQ ID NO 528
<211> LENGTH: 5
<212> TYPE: PRT
<213> ORGANISM: Homo sapiens

<400> SEQUENCE: 528

Gly Phe Leu Ile Tyr
1               5

<210> SEQ ID NO 529
<211> LENGTH: 5
<212> TYPE: PRT
<213> ORGANISM: Homo sapiens

<400> SEQUENCE: 529

Leu Ile Tyr Leu Asp
1               5

<210> SEQ ID NO 530
<211> LENGTH: 5
<212> TYPE: PRT
<213> ORGANISM: Homo sapiens

<400> SEQUENCE: 530

Ile Tyr Leu Asp Val
1               5

<210> SEQ ID NO 531
<211> LENGTH: 5
<212> TYPE: PRT
<213> ORGANISM: Homo sapiens

<400> SEQUENCE: 531

Tyr Lys Asp Thr Leu
1               5

<210> SEQ ID NO 532
<211> LENGTH: 5
```

<212> TYPE: PRT
<213> ORGANISM: Homo sapiens

<400> SEQUENCE: 532

Thr Leu Trp Cys Ser
1               5

<210> SEQ ID NO 533
<211> LENGTH: 5
<212> TYPE: PRT
<213> ORGANISM: Homo sapiens

<400> SEQUENCE: 533

Leu Trp Cys Ser Pro
1               5

<210> SEQ ID NO 534
<211> LENGTH: 5
<212> TYPE: PRT
<213> ORGANISM: Homo sapiens

<400> SEQUENCE: 534

Tyr Glu Val Pro Lys
1               5

<210> SEQ ID NO 535
<211> LENGTH: 5
<212> TYPE: PRT
<213> ORGANISM: Homo sapiens

<400> SEQUENCE: 535

Leu Asn Tyr Glu Val
1               5

<210> SEQ ID NO 536
<211> LENGTH: 5
<212> TYPE: PRT
<213> ORGANISM: Homo sapiens

<400> SEQUENCE: 536

Asn Tyr Glu Val Pro
1               5

<210> SEQ ID NO 537
<211> LENGTH: 5
<212> TYPE: PRT
<213> ORGANISM: Homo sapiens

<400> SEQUENCE: 537

Glu Val Pro Lys Tyr
1               5

<210> SEQ ID NO 538
<211> LENGTH: 9
<212> TYPE: PRT
<213> ORGANISM: Homo sapiens

<400> SEQUENCE: 538

Leu Glu Leu Leu Asn Tyr Glu Val Lys
1               5

<210> SEQ ID NO 539
<211> LENGTH: 9
<212> TYPE: PRT
<213> ORGANISM: Homo sapiens

<400> SEQUENCE: 539

Lys Ala Thr Asn Tyr Glu Val Pro Arg
1               5

<210> SEQ ID NO 540
<211> LENGTH: 9
<212> TYPE: PRT
<213> ORGANISM: Homo sapiens

<400> SEQUENCE: 540

Ser Ile Val Tyr Glu Val Pro Lys Pro
1               5

<210> SEQ ID NO 541
<211> LENGTH: 9
<212> TYPE: PRT
<213> ORGANISM: Homo sapiens

<400> SEQUENCE: 541

Asp Met Leu Tyr Glu Val Pro Lys Ile
1               5

<210> SEQ ID NO 542
<211> LENGTH: 9
<212> TYPE: PRT
<213> ORGANISM: Homo sapiens

<400> SEQUENCE: 542

Thr Ile Ala Glu Val Pro Lys Tyr Arg
1               5

<210> SEQ ID NO 543
<211> LENGTH: 9
<212> TYPE: PRT
<213> ORGANISM: Homo sapiens

<400> SEQUENCE: 543

Ala Leu Ile His His Asn Thr Tyr Leu
1               5

<210> SEQ ID NO 544
<211> LENGTH: 10
<212> TYPE: PRT
<213> ORGANISM: Homo sapiens

<400> SEQUENCE: 544

Val Leu Glu Asn Phe Thr Ile Phe Leu Val
1               5                   10

<210> SEQ ID NO 545
<211> LENGTH: 10
<212> TYPE: PRT
<213> ORGANISM: Homo sapiens

<400> SEQUENCE: 545

Ser Val Leu Glu Asn Phe Thr Ile Phe Leu
1               5                   10

<210> SEQ ID NO 546
<211> LENGTH: 10
<212> TYPE: PRT
<213> ORGANISM: Homo sapiens

<400> SEQUENCE: 546

-continued

```
Val Leu Leu Gly Val Lys Leu Phe Gly Val
1               5                   10

<210> SEQ ID NO 547
<211> LENGTH: 9
<212> TYPE: PRT
<213> ORGANISM: Homo sapiens

<400> SEQUENCE: 547

Gln Met Arg Gly Val Lys Leu Phe Gly
1               5

<210> SEQ ID NO 548
<211> LENGTH: 9
<212> TYPE: PRT
<213> ORGANISM: Homo sapiens

<400> SEQUENCE: 548

Gly Met Asp Val Lys Leu Phe Gly Gly
1               5

<210> SEQ ID NO 549
<211> LENGTH: 9
<212> TYPE: PRT
<213> ORGANISM: Homo sapiens

<400> SEQUENCE: 549

Arg Met Arg Leu Phe Gly Val Gln Ala
1               5

<210> SEQ ID NO 550
<211> LENGTH: 9
<212> TYPE: PRT
<213> ORGANISM: Homo sapiens

<400> SEQUENCE: 550

Lys Leu Val Phe Gly Val Gln Asp Ala
1               5

<210> SEQ ID NO 551
<211> LENGTH: 9
<212> TYPE: PRT
<213> ORGANISM: Homo sapiens

<400> SEQUENCE: 551

Gly Met Ile His His Asn Thr Tyr Gly
1               5

<210> SEQ ID NO 552
<211> LENGTH: 9
<212> TYPE: PRT
<213> ORGANISM: Homo sapiens

<400> SEQUENCE: 552

Gln Thr Ile His Asn Thr Tyr Leu Val
1               5

<210> SEQ ID NO 553
<211> LENGTH: 9
<212> TYPE: PRT
<213> ORGANISM: Homo sapiens

<400> SEQUENCE: 553

Lys Gly Val Asn Thr Tyr Leu Cys Val
```

-continued

```
1               5

<210> SEQ ID NO 554
<211> LENGTH: 9
<212> TYPE: PRT
<213> ORGANISM: Homo sapiens

<400> SEQUENCE: 554

Lys Leu Arg Thr Tyr Leu Cys Phe Ser
1               5

<210> SEQ ID NO 555
<211> LENGTH: 9
<212> TYPE: PRT
<213> ORGANISM: Homo sapiens

<400> SEQUENCE: 555

Lys Gln Gln Tyr Leu Cys Phe Val Gly
1               5

<210> SEQ ID NO 556
<211> LENGTH: 9
<212> TYPE: PRT
<213> ORGANISM: Homo sapiens

<400> SEQUENCE: 556

Arg Leu Lys Val Leu Glu Asn Phe Val
1               5

<210> SEQ ID NO 557
<211> LENGTH: 9
<212> TYPE: PRT
<213> ORGANISM: Homo sapiens

<400> SEQUENCE: 557

Ala Leu Pro Leu Glu Asn Phe Thr Gly
1               5

<210> SEQ ID NO 558
<211> LENGTH: 9
<212> TYPE: PRT
<213> ORGANISM: Homo sapiens

<400> SEQUENCE: 558

Tyr Ser Ala Glu Asn Phe Thr Ile Val
1               5

<210> SEQ ID NO 559
<211> LENGTH: 9
<212> TYPE: PRT
<213> ORGANISM: Homo sapiens

<400> SEQUENCE: 559

Lys Thr Pro Asn Phe Thr Ile Phe Ala
1               5

<210> SEQ ID NO 560
<211> LENGTH: 9
<212> TYPE: PRT
<213> ORGANISM: Homo sapiens

<400> SEQUENCE: 560

Arg Gln Lys Phe Thr Ile Phe Leu Gly
1               5
```

<210> SEQ ID NO 561
<211> LENGTH: 5
<212> TYPE: PRT
<213> ORGANISM: Homo sapiens

<400> SEQUENCE: 561

Gly Val Lys Leu Phe
1               5

<210> SEQ ID NO 562
<211> LENGTH: 5
<212> TYPE: PRT
<213> ORGANISM: Homo sapiens

<400> SEQUENCE: 562

Val Lys Leu Phe Gly
1               5

<210> SEQ ID NO 563
<211> LENGTH: 5
<212> TYPE: PRT
<213> ORGANISM: Homo sapiens

<400> SEQUENCE: 563

Leu Phe Gly Val Gln
1               5

<210> SEQ ID NO 564
<211> LENGTH: 5
<212> TYPE: PRT
<213> ORGANISM: Homo sapiens

<400> SEQUENCE: 564

Phe Gly Val Gln Asp
1               5

<210> SEQ ID NO 565
<211> LENGTH: 5
<212> TYPE: PRT
<213> ORGANISM: Homo sapiens

<400> SEQUENCE: 565

His His Asn Thr Tyr
1               5

<210> SEQ ID NO 566
<211> LENGTH: 5
<212> TYPE: PRT
<213> ORGANISM: Homo sapiens

<400> SEQUENCE: 566

His Asn Thr Tyr Leu
1               5

<210> SEQ ID NO 567
<211> LENGTH: 5
<212> TYPE: PRT
<213> ORGANISM: Homo sapiens

<400> SEQUENCE: 567

Asn Thr Tyr Leu Cys
1               5

<210> SEQ ID NO 568

```
<211> LENGTH: 5
<212> TYPE: PRT
<213> ORGANISM: Homo sapiens

<400> SEQUENCE: 568

Thr Tyr Leu Cys Phe
1               5

<210> SEQ ID NO 569
<211> LENGTH: 5
<212> TYPE: PRT
<213> ORGANISM: Homo sapiens

<400> SEQUENCE: 569

Tyr Leu Cys Phe Val
1               5

<210> SEQ ID NO 570
<211> LENGTH: 5
<212> TYPE: PRT
<213> ORGANISM: Homo sapiens

<400> SEQUENCE: 570

Val Leu Glu Asn Phe
1               5

<210> SEQ ID NO 571
<211> LENGTH: 5
<212> TYPE: PRT
<213> ORGANISM: Homo sapiens

<400> SEQUENCE: 571

Leu Glu Asn Phe Thr
1               5

<210> SEQ ID NO 572
<211> LENGTH: 5
<212> TYPE: PRT
<213> ORGANISM: Homo sapiens

<400> SEQUENCE: 572

Glu Asn Phe Thr Ile
1               5

<210> SEQ ID NO 573
<211> LENGTH: 5
<212> TYPE: PRT
<213> ORGANISM: Homo sapiens

<400> SEQUENCE: 573

Asn Phe Thr Ile Phe
1               5

<210> SEQ ID NO 574
<211> LENGTH: 5
<212> TYPE: PRT
<213> ORGANISM: Homo sapiens

<400> SEQUENCE: 574

Phe Thr Ile Phe Leu
1               5

<210> SEQ ID NO 575
<211> LENGTH: 9
<212> TYPE: PRT
```

<213> ORGANISM: Homo sapiens

<400> SEQUENCE: 575

Ala Leu Tyr Gly Phe Val Pro Val Leu
1               5

<210> SEQ ID NO 576
<211> LENGTH: 9
<212> TYPE: PRT
<213> ORGANISM: Homo sapiens

<400> SEQUENCE: 576

Arg Thr Arg Ala Leu Tyr Gly Phe Val
1               5

<210> SEQ ID NO 577
<211> LENGTH: 9
<212> TYPE: PRT
<213> ORGANISM: Homo sapiens

<400> SEQUENCE: 577

Ser Ser Asp Leu Tyr Gly Phe Val Arg
1               5

<210> SEQ ID NO 578
<211> LENGTH: 9
<212> TYPE: PRT
<213> ORGANISM: Homo sapiens

<400> SEQUENCE: 578

Lys Asp Glu Leu Tyr Gly Phe Val Val
1               5

<210> SEQ ID NO 579
<211> LENGTH: 9
<212> TYPE: PRT
<213> ORGANISM: Homo sapiens

<400> SEQUENCE: 579

Leu Ala Asp Tyr Gly Phe Val Pro Asp
1               5

<210> SEQ ID NO 580
<211> LENGTH: 9
<212> TYPE: PRT
<213> ORGANISM: Homo sapiens

<400> SEQUENCE: 580

Lys Leu Arg Tyr Gly Phe Val Pro Ala
1               5

<210> SEQ ID NO 581
<211> LENGTH: 9
<212> TYPE: PRT
<213> ORGANISM: Homo sapiens

<400> SEQUENCE: 581

Lys Val Asp Gly Phe Val Pro Val Ala
1               5

<210> SEQ ID NO 582
<211> LENGTH: 9
<212> TYPE: PRT
<213> ORGANISM: Homo sapiens -continued

```
<400> SEQUENCE: 582

Arg Ser Asp Phe Val Pro Val Leu Asn
1               5

<210> SEQ ID NO 583
<211> LENGTH: 5
<212> TYPE: PRT
<213> ORGANISM: Homo sapiens

<400> SEQUENCE: 583

Ala Leu Tyr Gly Phe
1               5

<210> SEQ ID NO 584
<211> LENGTH: 5
<212> TYPE: PRT
<213> ORGANISM: Homo sapiens

<400> SEQUENCE: 584

Leu Tyr Gly Phe Val
1               5

<210> SEQ ID NO 585
<211> LENGTH: 5
<212> TYPE: PRT
<213> ORGANISM: Homo sapiens

<400> SEQUENCE: 585

Leu Tyr Gly Phe Val
1               5

<210> SEQ ID NO 586
<211> LENGTH: 5
<212> TYPE: PRT
<213> ORGANISM: Homo sapiens

<400> SEQUENCE: 586

Tyr Gly Phe Val Pro
1               5

<210> SEQ ID NO 587
<211> LENGTH: 5
<212> TYPE: PRT
<213> ORGANISM: Homo sapiens

<400> SEQUENCE: 587

Tyr Gly Phe Val Pro
1               5

<210> SEQ ID NO 588
<211> LENGTH: 5
<212> TYPE: PRT
<213> ORGANISM: Homo sapiens

<400> SEQUENCE: 588

Gly Phe Val Pro Val
1               5

<210> SEQ ID NO 589
<211> LENGTH: 5
<212> TYPE: PRT
<213> ORGANISM: Homo sapiens

<400> SEQUENCE: 589
```

```
Phe Val Pro Val Leu
1               5

<210> SEQ ID NO 590
<211> LENGTH: 10
<212> TYPE: PRT
<213> ORGANISM: Homo sapiens

<400> SEQUENCE: 590

Pro Ser Asp Thr Arg Gln Met Leu Phe Tyr
1               5                   10

<210> SEQ ID NO 591
<211> LENGTH: 9
<212> TYPE: PRT
<213> ORGANISM: Homo sapiens

<400> SEQUENCE: 591

Glu Gly Asp Phe Phe Pro Ser Asp Pro
1               5

<210> SEQ ID NO 592
<211> LENGTH: 9
<212> TYPE: PRT
<213> ORGANISM: Homo sapiens

<400> SEQUENCE: 592

Phe Glu Asp Phe Phe Pro Ser Asp Leu
1               5

<210> SEQ ID NO 593
<211> LENGTH: 9
<212> TYPE: PRT
<213> ORGANISM: Homo sapiens

<400> SEQUENCE: 593

Trp Asp Asp Phe Phe Pro Ser Asp Glu
1               5

<210> SEQ ID NO 594
<211> LENGTH: 5
<212> TYPE: PRT
<213> ORGANISM: Homo sapiens

<400> SEQUENCE: 594

Phe Phe Pro Ser Asp
1               5

<210> SEQ ID NO 595
<211> LENGTH: 9
<212> TYPE: PRT
<213> ORGANISM: Homo sapiens

<400> SEQUENCE: 595

Ala Val Asp Asp Phe Gly Arg Ala Arg
1               5

<210> SEQ ID NO 596
<211> LENGTH: 9
<212> TYPE: PRT
<213> ORGANISM: Homo sapiens

<400> SEQUENCE: 596

Ser Arg Asp Asp Phe Gly Arg Ala Arg
1               5
```

```
<210> SEQ ID NO 597
<211> LENGTH: 9
<212> TYPE: PRT
<213> ORGANISM: Homo sapiens

<400> SEQUENCE: 597

Leu Ser His Phe Gly Arg Ala Lys Phe
1               5

<210> SEQ ID NO 598
<211> LENGTH: 9
<212> TYPE: PRT
<213> ORGANISM: Homo sapiens

<400> SEQUENCE: 598

Phe Ala Glu Gly Arg Ala Lys Leu His
1               5

<210> SEQ ID NO 599
<211> LENGTH: 9
<212> TYPE: PRT
<213> ORGANISM: Homo sapiens

<400> SEQUENCE: 599

Tyr Gly His Arg Ala Lys Leu Leu Leu
1               5

<210> SEQ ID NO 600
<211> LENGTH: 9
<212> TYPE: PRT
<213> ORGANISM: Homo sapiens

<400> SEQUENCE: 600

Leu Ala Ile Thr Asp Phe Gly Arg Ala
1               5

<210> SEQ ID NO 601
<211> LENGTH: 9
<212> TYPE: PRT
<213> ORGANISM: Homo sapiens

<400> SEQUENCE: 601

Val Ala Ala Asp Phe Gly Arg Ala Tyr
1               5

<210> SEQ ID NO 602
<211> LENGTH: 9
<212> TYPE: PRT
<213> ORGANISM: Homo sapiens

<400> SEQUENCE: 602

Trp Gly Ile Phe Gly Arg Ala Lys Ala
1               5

<210> SEQ ID NO 603
<211> LENGTH: 9
<212> TYPE: PRT
<213> ORGANISM: Homo sapiens

<400> SEQUENCE: 603

Leu Glu Val Gly Arg Ala Lys Leu Leu
1               5
```

<210> SEQ ID NO 604
<211> LENGTH: 9
<212> TYPE: PRT
<213> ORGANISM: Homo sapiens

<400> SEQUENCE: 604

Pro Glu Ser Ser Gly Ile Ile Leu Arg
1               5

<210> SEQ ID NO 605
<211> LENGTH: 9
<212> TYPE: PRT
<213> ORGANISM: Homo sapiens

<400> SEQUENCE: 605

Gln Gln Met Pro Glu Gln Pro Ser Phe
1               5

<210> SEQ ID NO 606
<211> LENGTH: 9
<212> TYPE: PRT
<213> ORGANISM: Homo sapiens

<400> SEQUENCE: 606

Gly Leu Cys Glu Gln Pro Ser Gly Phe
1               5

<210> SEQ ID NO 607
<211> LENGTH: 9
<212> TYPE: PRT
<213> ORGANISM: Homo sapiens

<400> SEQUENCE: 607

His Ala Pro Gln Pro Ser Gly Ile Phe
1               5

<210> SEQ ID NO 608
<211> LENGTH: 9
<212> TYPE: PRT
<213> ORGANISM: Homo sapiens

<400> SEQUENCE: 608

Pro Ala Gly Pro Glu Gln Pro Ser Thr
1               5

<210> SEQ ID NO 609
<211> LENGTH: 9
<212> TYPE: PRT
<213> ORGANISM: Homo sapiens

<400> SEQUENCE: 609

Ala Ser Gly Glu Gln Pro Ser Gly Phe
1               5

<210> SEQ ID NO 610
<211> LENGTH: 9
<212> TYPE: PRT
<213> ORGANISM: Homo sapiens

<400> SEQUENCE: 610

Ser Gly Cys Gly Pro Arg Leu Leu Arg
1               5

<210> SEQ ID NO 611
<211> LENGTH: 9

-continued

```
<212> TYPE: PRT
<213> ORGANISM: Homo sapiens

<400> SEQUENCE: 611

Tyr Gln Gln Pro Arg Leu Leu Leu Arg
1               5

<210> SEQ ID NO 612
<211> LENGTH: 9
<212> TYPE: PRT
<213> ORGANISM: Homo sapiens

<400> SEQUENCE: 612

Asn Thr Gly Arg Leu Leu Leu Pro Pro
1               5

<210> SEQ ID NO 613
<211> LENGTH: 9
<212> TYPE: PRT
<213> ORGANISM: Homo sapiens

<400> SEQUENCE: 613

Lys Thr Gln Leu Leu Leu Pro Cys Arg
1               5

<210> SEQ ID NO 614
<211> LENGTH: 9
<212> TYPE: PRT
<213> ORGANISM: Homo sapiens

<400> SEQUENCE: 614

Arg Val Thr Gly Pro Arg Leu Leu Asp
1               5

<210> SEQ ID NO 615
<211> LENGTH: 9
<212> TYPE: PRT
<213> ORGANISM: Homo sapiens

<400> SEQUENCE: 615

Gln Gly Gly Pro Arg Leu Leu Leu Lys
1               5

<210> SEQ ID NO 616
<211> LENGTH: 9
<212> TYPE: PRT
<213> ORGANISM: Homo sapiens

<400> SEQUENCE: 616

Ser Asp Trp Arg Leu Leu Leu Pro Lys
1               5

<210> SEQ ID NO 617
<211> LENGTH: 9
<212> TYPE: PRT
<213> ORGANISM: Homo sapiens

<400> SEQUENCE: 617

Ser His Glu Leu Leu Leu Pro Cys Arg
1               5

<210> SEQ ID NO 618
<211> LENGTH: 9
<212> TYPE: PRT
<213> ORGANISM: Homo sapiens
```

<400> SEQUENCE: 618

Lys Ala Cys Gly Pro Arg Leu Leu Tyr
1               5

<210> SEQ ID NO 619
<211> LENGTH: 9
<212> TYPE: PRT
<213> ORGANISM: Homo sapiens

<400> SEQUENCE: 619

Arg Gly Pro Pro Arg Leu Leu Leu Tyr
1               5

<210> SEQ ID NO 620
<211> LENGTH: 9
<212> TYPE: PRT
<213> ORGANISM: Homo sapiens

<400> SEQUENCE: 620

Asp Pro Thr Arg Leu Leu Leu Pro Tyr
1               5

<210> SEQ ID NO 621
<211> LENGTH: 9
<212> TYPE: PRT
<213> ORGANISM: Homo sapiens

<400> SEQUENCE: 621

Pro Gly Ser Gly Pro Arg Leu Leu Ser
1               5

<210> SEQ ID NO 622
<211> LENGTH: 9
<212> TYPE: PRT
<213> ORGANISM: Homo sapiens

<400> SEQUENCE: 622

Arg Ser Gly Leu Leu Leu Pro Cys Arg
1               5

<210> SEQ ID NO 623
<211> LENGTH: 9
<212> TYPE: PRT
<213> ORGANISM: Homo sapiens

<400> SEQUENCE: 623

Ser Ser Ser Pro Arg Leu Leu Leu Pro
1               5

<210> SEQ ID NO 624
<211> LENGTH: 9
<212> TYPE: PRT
<213> ORGANISM: Homo sapiens

<400> SEQUENCE: 624

Arg Ser Leu Arg His Ser Tyr Cys Arg
1               5

<210> SEQ ID NO 625
<211> LENGTH: 9
<212> TYPE: PRT
<213> ORGANISM: Homo sapiens

<400> SEQUENCE: 625

Ser Lys Leu His Ser Tyr Cys Asn Lys
1               5

<210> SEQ ID NO 626
<211> LENGTH: 9
<212> TYPE: PRT
<213> ORGANISM: Homo sapiens

<400> SEQUENCE: 626

Gly Ala Arg Arg His Ser Tyr Cys Arg
1               5

<210> SEQ ID NO 627
<211> LENGTH: 9
<212> TYPE: PRT
<213> ORGANISM: Homo sapiens

<400> SEQUENCE: 627

Pro Leu Gly His Ser Tyr Cys Asn Arg
1               5

<210> SEQ ID NO 628
<211> LENGTH: 9
<212> TYPE: PRT
<213> ORGANISM: Homo sapiens

<400> SEQUENCE: 628

Gly Leu Thr Tyr Cys Asn Gly Ser Arg
1               5

<210> SEQ ID NO 629
<211> LENGTH: 5
<212> TYPE: PRT
<213> ORGANISM: Homo sapiens

<400> SEQUENCE: 629

Asp Phe Gly Arg Ala
1               5

<210> SEQ ID NO 630
<211> LENGTH: 5
<212> TYPE: PRT
<213> ORGANISM: Homo sapiens

<400> SEQUENCE: 630

Asp Phe Gly Arg Ala
1               5

<210> SEQ ID NO 631
<211> LENGTH: 5
<212> TYPE: PRT
<213> ORGANISM: Homo sapiens

<400> SEQUENCE: 631

Phe Gly Arg Ala Lys
1               5

<210> SEQ ID NO 632
<211> LENGTH: 5
<212> TYPE: PRT
<213> ORGANISM: Homo sapiens

<400> SEQUENCE: 632

Gly Arg Ala Lys Leu

```
1               5

<210> SEQ ID NO 633
<211> LENGTH: 5
<212> TYPE: PRT
<213> ORGANISM: Homo sapiens

<400> SEQUENCE: 633

Arg Ala Lys Leu Leu
1               5

<210> SEQ ID NO 634
<211> LENGTH: 5
<212> TYPE: PRT
<213> ORGANISM: Homo sapiens

<400> SEQUENCE: 634

Thr Asp Phe Gly Arg
1               5

<210> SEQ ID NO 635
<211> LENGTH: 5
<212> TYPE: PRT
<213> ORGANISM: Homo sapiens

<400> SEQUENCE: 635

Asp Phe Gly Arg Ala
1               5

<210> SEQ ID NO 636
<211> LENGTH: 5
<212> TYPE: PRT
<213> ORGANISM: Homo sapiens

<400> SEQUENCE: 636

Phe Gly Arg Ala Lys
1               5

<210> SEQ ID NO 637
<211> LENGTH: 5
<212> TYPE: PRT
<213> ORGANISM: Homo sapiens

<400> SEQUENCE: 637

Gly Arg Ala Lys Leu
1               5

<210> SEQ ID NO 638
<211> LENGTH: 5
<212> TYPE: PRT
<213> ORGANISM: Homo sapiens

<400> SEQUENCE: 638

Ser Gly Ile Ile Leu
1               5

<210> SEQ ID NO 639
<211> LENGTH: 5
<212> TYPE: PRT
<213> ORGANISM: Homo sapiens

<400> SEQUENCE: 639

Pro Glu Gln Pro Ser
1               5
```

<210> SEQ ID NO 640
<211> LENGTH: 5
<212> TYPE: PRT
<213> ORGANISM: Homo sapiens

<400> SEQUENCE: 640

Glu Gln Pro Ser Gly
1               5

<210> SEQ ID NO 641
<211> LENGTH: 5
<212> TYPE: PRT
<213> ORGANISM: Homo sapiens

<400> SEQUENCE: 641

Gln Pro Ser Gly Ile
1               5

<210> SEQ ID NO 642
<211> LENGTH: 5
<212> TYPE: PRT
<213> ORGANISM: Homo sapiens

<400> SEQUENCE: 642

Pro Glu Gln Pro Ser
1               5

<210> SEQ ID NO 643
<211> LENGTH: 5
<212> TYPE: PRT
<213> ORGANISM: Homo sapiens

<400> SEQUENCE: 643

Glu Gln Pro Ser Gly
1               5

<210> SEQ ID NO 644
<211> LENGTH: 5
<212> TYPE: PRT
<213> ORGANISM: Homo sapiens

<400> SEQUENCE: 644

Gly Pro Arg Leu Leu
1               5

<210> SEQ ID NO 645
<211> LENGTH: 5
<212> TYPE: PRT
<213> ORGANISM: Homo sapiens

<400> SEQUENCE: 645

Pro Arg Leu Leu Leu
1               5

<210> SEQ ID NO 646
<211> LENGTH: 5
<212> TYPE: PRT
<213> ORGANISM: Homo sapiens

<400> SEQUENCE: 646

Arg Leu Leu Leu Pro
1               5

<210> SEQ ID NO 647

```
<211> LENGTH: 5
<212> TYPE: PRT
<213> ORGANISM: Homo sapiens

<400> SEQUENCE: 647

Leu Leu Leu Pro Cys
1               5

<210> SEQ ID NO 648
<211> LENGTH: 5
<212> TYPE: PRT
<213> ORGANISM: Homo sapiens

<400> SEQUENCE: 648

Gly Pro Arg Leu Leu
1               5

<210> SEQ ID NO 649
<211> LENGTH: 5
<212> TYPE: PRT
<213> ORGANISM: Homo sapiens

<400> SEQUENCE: 649

Pro Arg Leu Leu Leu
1               5

<210> SEQ ID NO 650
<211> LENGTH: 5
<212> TYPE: PRT
<213> ORGANISM: Homo sapiens

<400> SEQUENCE: 650

Arg Leu Leu Leu Pro
1               5

<210> SEQ ID NO 651
<211> LENGTH: 5
<212> TYPE: PRT
<213> ORGANISM: Homo sapiens

<400> SEQUENCE: 651

Leu Leu Leu Pro Cys
1               5

<210> SEQ ID NO 652
<211> LENGTH: 5
<212> TYPE: PRT
<213> ORGANISM: Homo sapiens

<400> SEQUENCE: 652

Gly Pro Arg Leu Leu
1               5

<210> SEQ ID NO 653
<211> LENGTH: 5
<212> TYPE: PRT
<213> ORGANISM: Homo sapiens

<400> SEQUENCE: 653

Pro Arg Leu Leu Leu
1               5

<210> SEQ ID NO 654
<211> LENGTH: 5
<212> TYPE: PRT
```

-continued

```
<213> ORGANISM: Homo sapiens

<400> SEQUENCE: 654

Arg Leu Leu Leu Pro
1               5

<210> SEQ ID NO 655
<211> LENGTH: 5
<212> TYPE: PRT
<213> ORGANISM: Homo sapiens

<400> SEQUENCE: 655

Gly Pro Arg Leu Leu
1               5

<210> SEQ ID NO 656
<211> LENGTH: 5
<212> TYPE: PRT
<213> ORGANISM: Homo sapiens

<400> SEQUENCE: 656

Leu Leu Leu Pro Cys
1               5

<210> SEQ ID NO 657
<211> LENGTH: 5
<212> TYPE: PRT
<213> ORGANISM: Homo sapiens

<400> SEQUENCE: 657

Pro Arg Leu Leu Leu
1               5

<210> SEQ ID NO 658
<211> LENGTH: 5
<212> TYPE: PRT
<213> ORGANISM: Homo sapiens

<400> SEQUENCE: 658

Arg His Ser Tyr Cys
1               5

<210> SEQ ID NO 659
<211> LENGTH: 5
<212> TYPE: PRT
<213> ORGANISM: Homo sapiens

<400> SEQUENCE: 659

His Ser Tyr Cys Asn
1               5

<210> SEQ ID NO 660
<211> LENGTH: 5
<212> TYPE: PRT
<213> ORGANISM: Homo sapiens

<400> SEQUENCE: 660

Arg His Ser Tyr Cys
1               5

<210> SEQ ID NO 661
<211> LENGTH: 5
<212> TYPE: PRT
<213> ORGANISM: Homo sapiens
```

```
<400> SEQUENCE: 661

His Ser Tyr Cys Asn
1               5

<210> SEQ ID NO 662
<211> LENGTH: 5
<212> TYPE: PRT
<213> ORGANISM: Homo sapiens

<400> SEQUENCE: 662

Tyr Cys Asn Gly Ser
1               5

<210> SEQ ID NO 663
<211> LENGTH: 15
<212> TYPE: PRT
<213> ORGANISM: Homo sapiens

<400> SEQUENCE: 663

Leu Cys Met Gly Lys Ile Thr Asp Phe Gly Arg Ala Asn His Glu
1               5                   10                  15

<210> SEQ ID NO 664
<211> LENGTH: 15
<212> TYPE: PRT
<213> ORGANISM: Homo sapiens

<400> SEQUENCE: 664

Arg Leu Val Phe Lys Ile Thr Asp Phe Gly Arg Glu Asn Ile Met
1               5                   10                  15

<210> SEQ ID NO 665
<211> LENGTH: 15
<212> TYPE: PRT
<213> ORGANISM: Homo sapiens

<400> SEQUENCE: 665

Lys Leu Leu Leu Lys Ile Thr Asp Phe Gly Arg Gly Gln Tyr Leu
1               5                   10                  15

<210> SEQ ID NO 666
<211> LENGTH: 15
<212> TYPE: PRT
<213> ORGANISM: Homo sapiens

<400> SEQUENCE: 666

Leu Asp Phe Ile Ile Thr Asp Phe Gly Arg Ala Ser Thr Gln Thr
1               5                   10                  15

<210> SEQ ID NO 667
<211> LENGTH: 15
<212> TYPE: PRT
<213> ORGANISM: Homo sapiens

<400> SEQUENCE: 667

Pro Gly Phe Trp Ile Thr Asp Phe Gly Arg Ala Glu Leu Met Asp
1               5                   10                  15

<210> SEQ ID NO 668
<211> LENGTH: 15
<212> TYPE: PRT
<213> ORGANISM: Homo sapiens

<400> SEQUENCE: 668
```

-continued

```
Gln Thr Leu Leu Ile Thr Asp Phe Gly Arg Ala Ser Met Tyr Thr
1               5                   10                  15

<210> SEQ ID NO 669
<211> LENGTH: 15
<212> TYPE: PRT
<213> ORGANISM: Homo sapiens

<400> SEQUENCE: 669

Val Met Glu Lys Arg Ala Lys Leu Leu Gly Ala Pro Lys Tyr Ser
1               5                   10                  15

<210> SEQ ID NO 670
<211> LENGTH: 15
<212> TYPE: PRT
<213> ORGANISM: Homo sapiens

<400> SEQUENCE: 670

Pro His Leu Leu Pro Gln Pro Glu Gln Pro Ser Leu His Tyr Cys
1               5                   10                  15

<210> SEQ ID NO 671
<211> LENGTH: 15
<212> TYPE: PRT
<213> ORGANISM: Homo sapiens

<400> SEQUENCE: 671

Leu Lys Trp Phe Pro Gln Pro Glu Gln Pro Ser Ile Met Ser Phe
1               5                   10                  15

<210> SEQ ID NO 672
<211> LENGTH: 15
<212> TYPE: PRT
<213> ORGANISM: Homo sapiens

<400> SEQUENCE: 672

Trp Asn Ile Leu Pro Gln Pro Glu Gln Pro Ser Gln Ile Leu Lys
1               5                   10                  15

<210> SEQ ID NO 673
<211> LENGTH: 15
<212> TYPE: PRT
<213> ORGANISM: Homo sapiens

<400> SEQUENCE: 673

Leu Gly Ser Ala Gln Pro Glu Gln Pro Ser Gly Ser Tyr Ala Cys
1               5                   10                  15

<210> SEQ ID NO 674
<211> LENGTH: 15
<212> TYPE: PRT
<213> ORGANISM: Homo sapiens

<400> SEQUENCE: 674

Arg Leu Ile Phe Gln Pro Glu Gln Pro Ser Gly Leu Ser Ile Val
1               5                   10                  15

<210> SEQ ID NO 675
<211> LENGTH: 15
<212> TYPE: PRT
<213> ORGANISM: Homo sapiens

<400> SEQUENCE: 675

Gly Ser Leu Met Gln Pro Glu Gln Pro Ser Gly Leu Leu Phe Ser
1               5                   10                  15
```

-continued

```
<210> SEQ ID NO 676
<211> LENGTH: 15
<212> TYPE: PRT
<213> ORGANISM: Homo sapiens

<400> SEQUENCE: 676

Leu Ser Thr Leu Glu Gln Pro Ser Gly Ile Ile Ser Arg Asn Ser
1               5                   10                  15

<210> SEQ ID NO 677
<211> LENGTH: 15
<212> TYPE: PRT
<213> ORGANISM: Homo sapiens

<400> SEQUENCE: 677

His Pro Phe Trp Glu Gln Pro Ser Gly Ile Ile Gln Gln Ile Asp
1               5                   10                  15

<210> SEQ ID NO 678
<211> LENGTH: 15
<212> TYPE: PRT
<213> ORGANISM: Homo sapiens

<400> SEQUENCE: 678

Ser Tyr Leu Phe Glu Gln Pro Ser Gly Ile Ile Thr Ile Asn Ser
1               5                   10                  15

<210> SEQ ID NO 679
<211> LENGTH: 15
<212> TYPE: PRT
<213> ORGANISM: Homo sapiens

<400> SEQUENCE: 679

Phe Thr Trp Arg Pro Ser Gly Ile Ile Leu Asp Asn Ile Arg Asn
1               5                   10                  15

<210> SEQ ID NO 680
<211> LENGTH: 15
<212> TYPE: PRT
<213> ORGANISM: Homo sapiens

<400> SEQUENCE: 680

Ser Asn Pro Ala Ser Gly Ile Ile Leu Asp Tyr Leu Lys Ala Val
1               5                   10                  15

<210> SEQ ID NO 681
<211> LENGTH: 15
<212> TYPE: PRT
<213> ORGANISM: Homo sapiens

<400> SEQUENCE: 681

Phe Ser Thr Tyr Ser Gly Ile Ile Leu Asp Tyr Pro Arg His Met
1               5                   10                  15

<210> SEQ ID NO 682
<211> LENGTH: 15
<212> TYPE: PRT
<213> ORGANISM: Homo sapiens

<400> SEQUENCE: 682

Lys Leu Pro Ile Ser Gly Ile Ile Leu Asp Tyr His Val Asp Ser
1               5                   10                  15
```

<210> SEQ ID NO 683
<211> LENGTH: 15
<212> TYPE: PRT
<213> ORGANISM: Homo sapiens

<400> SEQUENCE: 683

Arg Thr Tyr Met Thr Ile Gly Pro Arg Leu Leu Ile Ala Arg Gln
1               5                   10                  15

<210> SEQ ID NO 684
<211> LENGTH: 15
<212> TYPE: PRT
<213> ORGANISM: Homo sapiens

<400> SEQUENCE: 684

Arg Leu Gly Glu Thr Ile Gly Pro Arg Leu Leu Leu Val Arg Gln
1               5                   10                  15

<210> SEQ ID NO 685
<211> LENGTH: 15
<212> TYPE: PRT
<213> ORGANISM: Homo sapiens

<400> SEQUENCE: 685

Pro Lys Glu Tyr Ile Gly Pro Arg Leu Leu Leu Thr Val Gln Thr
1               5                   10                  15

<210> SEQ ID NO 686
<211> LENGTH: 15
<212> TYPE: PRT
<213> ORGANISM: Homo sapiens

<400> SEQUENCE: 686

Asp Ser Arg Phe Ile Gly Pro Arg Leu Leu Leu Pro Ser Ala Asn
1               5                   10                  15

<210> SEQ ID NO 687
<211> LENGTH: 15
<212> TYPE: PRT
<213> ORGANISM: Homo sapiens

<400> SEQUENCE: 687

Asn Ile Leu Thr Pro Arg Leu Leu Leu Pro Cys Pro Glu Cys Glu
1               5                   10                  15

<210> SEQ ID NO 688
<211> LENGTH: 15
<212> TYPE: PRT
<213> ORGANISM: Homo sapiens

<400> SEQUENCE: 688

Asp Glu Tyr Leu Pro Arg Leu Leu Leu Pro Cys Ala Gln Tyr Asp
1               5                   10                  15

<210> SEQ ID NO 689
<211> LENGTH: 15
<212> TYPE: PRT
<213> ORGANISM: Homo sapiens

<400> SEQUENCE: 689

Tyr Glu Glu Tyr Leu Leu Leu Pro Cys Pro Met Pro Arg Thr Ala
1               5                   10                  15

<210> SEQ ID NO 690
<211> LENGTH: 15

```
<212> TYPE: PRT
<213> ORGANISM: Homo sapiens

<400> SEQUENCE: 690

Pro Arg Arg Pro Leu Leu Leu Pro Cys Pro Met Gln Thr Ala Thr
1               5                   10                  15

<210> SEQ ID NO 691
<211> LENGTH: 15
<212> TYPE: PRT
<213> ORGANISM: Homo sapiens

<400> SEQUENCE: 691

Gln Gln Val Ser Leu Leu Pro Cys Pro Met Asp Pro Glu Phe Ser
1               5                   10                  15

<210> SEQ ID NO 692
<211> LENGTH: 15
<212> TYPE: PRT
<213> ORGANISM: Homo sapiens

<400> SEQUENCE: 692

Asn Gly Ile Leu Leu Leu Pro Cys Pro Met Asp Ser Ser Glu Ser
1               5                   10                  15

<210> SEQ ID NO 693
<211> LENGTH: 15
<212> TYPE: PRT
<213> ORGANISM: Homo sapiens

<400> SEQUENCE: 693

Lys His Ser Leu Leu Leu Pro Cys Pro Met Asp Lys Val Leu Asp
1               5                   10                  15

<210> SEQ ID NO 694
<211> LENGTH: 15
<212> TYPE: PRT
<213> ORGANISM: Homo sapiens

<400> SEQUENCE: 694

Leu Cys Phe Arg Thr Arg His Ser Tyr Cys Asn Thr Arg Thr Ile
1               5                   10                  15

<210> SEQ ID NO 695
<211> LENGTH: 15
<212> TYPE: PRT
<213> ORGANISM: Homo sapiens

<400> SEQUENCE: 695

Met Ile Ala Gly His Ser Tyr Cys Asn Gly Ser Val Ala Cys Gly
1               5                   10                  15

<210> SEQ ID NO 696
<211> LENGTH: 15
<212> TYPE: PRT
<213> ORGANISM: Homo sapiens

<400> SEQUENCE: 696

His Glu Ala Met Tyr Cys Asn Gly Ser Glu Asp Ala Gln Ile Thr
1               5                   10                  15

<210> SEQ ID NO 697
<211> LENGTH: 5
<212> TYPE: PRT
<213> ORGANISM: Homo sapiens
```

```
<400> SEQUENCE: 697

Lys Ile Asp Gly Arg
1               5

<210> SEQ ID NO 698
<211> LENGTH: 5
<212> TYPE: PRT
<213> ORGANISM: Homo sapiens

<400> SEQUENCE: 698

Ile Thr Phe Arg Ala
1               5

<210> SEQ ID NO 699
<211> LENGTH: 5
<212> TYPE: PRT
<213> ORGANISM: Homo sapiens

<400> SEQUENCE: 699

Arg Ala Leu Gly Ala
1               5

<210> SEQ ID NO 700
<211> LENGTH: 5
<212> TYPE: PRT
<213> ORGANISM: Homo sapiens

<400> SEQUENCE: 700

Pro Gln Glu Pro Ser
1               5

<210> SEQ ID NO 701
<211> LENGTH: 5
<212> TYPE: PRT
<213> ORGANISM: Homo sapiens

<400> SEQUENCE: 701

Gln Pro Gln Ser Gly
1               5

<210> SEQ ID NO 702
<211> LENGTH: 5
<212> TYPE: PRT
<213> ORGANISM: Homo sapiens

<400> SEQUENCE: 702

Glu Gln Ser Ile Ile
1               5

<210> SEQ ID NO 703
<211> LENGTH: 5
<212> TYPE: PRT
<213> ORGANISM: Homo sapiens

<400> SEQUENCE: 703

Pro Ser Ile Leu Asp
1               5

<210> SEQ ID NO 704
<211> LENGTH: 5
<212> TYPE: PRT
<213> ORGANISM: Homo sapiens

<400> SEQUENCE: 704
```

Ser Gly Ile Asp Tyr
1               5

<210> SEQ ID NO 705
<211> LENGTH: 5
<212> TYPE: PRT
<213> ORGANISM: Homo sapiens

<400> SEQUENCE: 705

Thr Ile Pro Leu Leu
1               5

<210> SEQ ID NO 706
<211> LENGTH: 5
<212> TYPE: PRT
<213> ORGANISM: Homo sapiens

<400> SEQUENCE: 706

Ile Gly Arg Leu Leu
1               5

<210> SEQ ID NO 707
<211> LENGTH: 5
<212> TYPE: PRT
<213> ORGANISM: Homo sapiens

<400> SEQUENCE: 707

Pro Arg Leu Pro Cys
1               5

<210> SEQ ID NO 708
<211> LENGTH: 5
<212> TYPE: PRT
<213> ORGANISM: Homo sapiens

<400> SEQUENCE: 708

Leu Leu Pro Pro Met
1               5

<210> SEQ ID NO 709
<211> LENGTH: 5
<212> TYPE: PRT
<213> ORGANISM: Homo sapiens

<400> SEQUENCE: 709

Leu Leu Cys Met Asp
1               5

<210> SEQ ID NO 710
<211> LENGTH: 5
<212> TYPE: PRT
<213> ORGANISM: Homo sapiens

<400> SEQUENCE: 710

Thr Arg Ser Cys Asn
1               5

<210> SEQ ID NO 711
<211> LENGTH: 5
<212> TYPE: PRT
<213> ORGANISM: Homo sapiens

<400> SEQUENCE: 711

His Ser Cys Gly Ser

-continued

```
1               5

<210> SEQ ID NO 712
<211> LENGTH: 5
<212> TYPE: PRT
<213> ORGANISM: Homo sapiens

<400> SEQUENCE: 712

Tyr Cys Gly Glu Asp
1               5

<210> SEQ ID NO 713
<211> LENGTH: 9
<212> TYPE: PRT
<213> ORGANISM: Homo sapiens

<400> SEQUENCE: 713

Ile Gly Glu Tyr Ser Phe Gly Val Ser
1               5

<210> SEQ ID NO 714
<211> LENGTH: 9
<212> TYPE: PRT
<213> ORGANISM: Homo sapiens

<400> SEQUENCE: 714

Lys Ser Glu Ser Phe Gly Val Ala Arg
1               5

<210> SEQ ID NO 715
<211> LENGTH: 9
<212> TYPE: PRT
<213> ORGANISM: Homo sapiens

<400> SEQUENCE: 715

Phe Gln Ser Gly Val Ala Thr Cys Pro
1               5

<210> SEQ ID NO 716
<211> LENGTH: 9
<212> TYPE: PRT
<213> ORGANISM: Homo sapiens

<400> SEQUENCE: 716

Asp Ser Ser Val Ala Thr Cys Val Leu
1               5

<210> SEQ ID NO 717
<211> LENGTH: 9
<212> TYPE: PRT
<213> ORGANISM: Homo sapiens

<400> SEQUENCE: 717

Asp Lys Tyr Ser Phe Gly Val Ala Phe
1               5

<210> SEQ ID NO 718
<211> LENGTH: 9
<212> TYPE: PRT
<213> ORGANISM: Homo sapiens

<400> SEQUENCE: 718

Glu Arg Tyr Phe Gly Val Ala Thr Leu
1               5
```

-continued

```
<210> SEQ ID NO 719
<211> LENGTH: 9
<212> TYPE: PRT
<213> ORGANISM: Homo sapiens

<400> SEQUENCE: 719

His Lys Trp Gly Val Ala Thr Cys Trp
1               5

<210> SEQ ID NO 720
<211> LENGTH: 9
<212> TYPE: PRT
<213> ORGANISM: Homo sapiens

<400> SEQUENCE: 720

Ile Gly Arg Tyr Ser Phe Gly Val Gln
1               5

<210> SEQ ID NO 721
<211> LENGTH: 9
<212> TYPE: PRT
<213> ORGANISM: Homo sapiens

<400> SEQUENCE: 721

Glu Gln Arg Ser Phe Gly Val Ala Gly
1               5

<210> SEQ ID NO 722
<211> LENGTH: 9
<212> TYPE: PRT
<213> ORGANISM: Homo sapiens

<400> SEQUENCE: 722

Lys Gly Gln Val Ala Thr Cys Val Pro
1               5

<210> SEQ ID NO 723
<211> LENGTH: 9
<212> TYPE: PRT
<213> ORGANISM: Homo sapiens

<400> SEQUENCE: 723

Leu Asn Gly Phe Gly Val Ala Thr Arg
1               5

<210> SEQ ID NO 724
<211> LENGTH: 9
<212> TYPE: PRT
<213> ORGANISM: Homo sapiens

<400> SEQUENCE: 724

Ile Lys Asp Phe Gly Arg Leu Ala Tyr
1               5

<210> SEQ ID NO 725
<211> LENGTH: 9
<212> TYPE: PRT
<213> ORGANISM: Homo sapiens

<400> SEQUENCE: 725

Glu Tyr His Thr Asp Phe Gly Arg Leu
1               5

<210> SEQ ID NO 726
```

```
<211> LENGTH: 9
<212> TYPE: PRT
<213> ORGANISM: Homo sapiens

<400> SEQUENCE: 726

Ser Leu Lys Asp Phe Gly Arg Leu Ile
1               5

<210> SEQ ID NO 727
<211> LENGTH: 9
<212> TYPE: PRT
<213> ORGANISM: Homo sapiens

<400> SEQUENCE: 727

Asp Val Phe Gly Arg Leu Ala Lys Phe
1               5

<210> SEQ ID NO 728
<211> LENGTH: 9
<212> TYPE: PRT
<213> ORGANISM: Homo sapiens

<400> SEQUENCE: 728

Arg Leu Arg Arg Leu Ala Lys Leu Leu
1               5

<210> SEQ ID NO 729
<211> LENGTH: 9
<212> TYPE: PRT
<213> ORGANISM: Homo sapiens

<400> SEQUENCE: 729

Thr Ala Arg Asp Phe Gly Arg Leu Glu
1               5

<210> SEQ ID NO 730
<211> LENGTH: 9
<212> TYPE: PRT
<213> ORGANISM: Homo sapiens

<400> SEQUENCE: 730

Thr Asn Lys Phe Gly Arg Leu Ala Asp
1               5

<210> SEQ ID NO 731
<211> LENGTH: 9
<212> TYPE: PRT
<213> ORGANISM: Homo sapiens

<400> SEQUENCE: 731

His Gly Asn Asp Phe Gly Arg Leu Arg
1               5

<210> SEQ ID NO 732
<211> LENGTH: 9
<212> TYPE: PRT
<213> ORGANISM: Homo sapiens

<400> SEQUENCE: 732

Cys Pro Arg Phe Gly Arg Leu Ala Tyr
1               5

<210> SEQ ID NO 733
<211> LENGTH: 9
<212> TYPE: PRT
```

-continued

```
<213> ORGANISM: Homo sapiens

<400> SEQUENCE: 733

Lys Cys Ile Arg Leu Ala Lys Leu Arg
1               5

<210> SEQ ID NO 734
<211> LENGTH: 9
<212> TYPE: PRT
<213> ORGANISM: Homo sapiens

<400> SEQUENCE: 734

Arg Ser Glu Leu Ile Lys Arg Gln Leu
1               5

<210> SEQ ID NO 735
<211> LENGTH: 9
<212> TYPE: PRT
<213> ORGANISM: Homo sapiens

<400> SEQUENCE: 735

Ser Phe Ala Ile Lys Arg Gln Arg Leu
1               5

<210> SEQ ID NO 736
<211> LENGTH: 9
<212> TYPE: PRT
<213> ORGANISM: Homo sapiens

<400> SEQUENCE: 736

Pro Arg Leu Lys Arg Gln Arg Gln Ile
1               5

<210> SEQ ID NO 737
<211> LENGTH: 9
<212> TYPE: PRT
<213> ORGANISM: Homo sapiens

<400> SEQUENCE: 737

Val Ile Asn Arg Gln Arg Gln Gln Phe
1               5

<210> SEQ ID NO 738
<211> LENGTH: 9
<212> TYPE: PRT
<213> ORGANISM: Homo sapiens

<400> SEQUENCE: 738

Leu Ser Tyr Gln Arg Gln Gln Lys Phe
1               5

<210> SEQ ID NO 739
<211> LENGTH: 9
<212> TYPE: PRT
<213> ORGANISM: Homo sapiens

<400> SEQUENCE: 739

Ser Gly Lys Ile Lys Arg Gln Arg Asn
1               5

<210> SEQ ID NO 740
<211> LENGTH: 9
<212> TYPE: PRT
<213> ORGANISM: Homo sapiens
```

```
<400> SEQUENCE: 740

Thr Met Arg Arg Gln Arg Gln Gln Ser
1               5

<210> SEQ ID NO 741
<211> LENGTH: 9
<212> TYPE: PRT
<213> ORGANISM: Homo sapiens

<400> SEQUENCE: 741

Ala Val Glu Leu Ile Lys Arg Gln Tyr
1               5

<210> SEQ ID NO 742
<211> LENGTH: 9
<212> TYPE: PRT
<213> ORGANISM: Homo sapiens

<400> SEQUENCE: 742

Arg Gly Asn Thr Asp Val Gly Phe Leu
1               5

<210> SEQ ID NO 743
<211> LENGTH: 9
<212> TYPE: PRT
<213> ORGANISM: Homo sapiens

<400> SEQUENCE: 743

Tyr Gly Gln Asp Val Gly Phe Ser Gln
1               5

<210> SEQ ID NO 744
<211> LENGTH: 9
<212> TYPE: PRT
<213> ORGANISM: Homo sapiens

<400> SEQUENCE: 744

Tyr Thr Asp Val Gly Phe Ser Cys Ala
1               5

<210> SEQ ID NO 745
<211> LENGTH: 9
<212> TYPE: PRT
<213> ORGANISM: Homo sapiens

<400> SEQUENCE: 745

His Lys Leu Thr Asp Val Gly Phe Phe
1               5

<210> SEQ ID NO 746
<211> LENGTH: 9
<212> TYPE: PRT
<213> ORGANISM: Homo sapiens

<400> SEQUENCE: 746

Gln Arg Thr Asp Val Gly Phe Ser Phe
1               5

<210> SEQ ID NO 747
<211> LENGTH: 9
<212> TYPE: PRT
<213> ORGANISM: Homo sapiens

<400> SEQUENCE: 747
```

Pro Arg Tyr Gly Phe Ser Cys Thr Phe
1               5

<210> SEQ ID NO 748
<211> LENGTH: 9
<212> TYPE: PRT
<213> ORGANISM: Homo sapiens

<400> SEQUENCE: 748

Val Val Lys Thr Asp Val Gly Phe Ala
1               5

<210> SEQ ID NO 749
<211> LENGTH: 9
<212> TYPE: PRT
<213> ORGANISM: Homo sapiens

<400> SEQUENCE: 749

Ser Ile Lys Val Gly Phe Ser Cys Ser
1               5

<210> SEQ ID NO 750
<211> LENGTH: 9
<212> TYPE: PRT
<213> ORGANISM: Homo sapiens

<400> SEQUENCE: 750

Thr Ile Arg Phe Ser Cys Thr Leu Gln
1               5

<210> SEQ ID NO 751
<211> LENGTH: 9
<212> TYPE: PRT
<213> ORGANISM: Homo sapiens

<400> SEQUENCE: 751

Ile Ser Thr Phe Ser Cys Thr Leu Arg
1               5

<210> SEQ ID NO 752
<211> LENGTH: 9
<212> TYPE: PRT
<213> ORGANISM: Homo sapiens

<400> SEQUENCE: 752

Leu Leu Asp Ala Thr Glu Val Lys Pro
1               5

<210> SEQ ID NO 753
<211> LENGTH: 9
<212> TYPE: PRT
<213> ORGANISM: Homo sapiens

<400> SEQUENCE: 753

Phe Lys Cys Glu Val Lys Ser Arg Pro
1               5

<210> SEQ ID NO 754
<211> LENGTH: 9
<212> TYPE: PRT
<213> ORGANISM: Homo sapiens

<400> SEQUENCE: 754

Tyr Leu Lys Gly Leu Ala Thr Glu Trp
1               5

<210> SEQ ID NO 755
<211> LENGTH: 9
<212> TYPE: PRT
<213> ORGANISM: Homo sapiens

<400> SEQUENCE: 755

Lys Pro Pro Leu Ala Thr Glu Val Phe
1               5

<210> SEQ ID NO 756
<211> LENGTH: 9
<212> TYPE: PRT
<213> ORGANISM: Homo sapiens

<400> SEQUENCE: 756

Leu Phe Lys Ala Thr Glu Val Lys Leu
1               5

<210> SEQ ID NO 757
<211> LENGTH: 9
<212> TYPE: PRT
<213> ORGANISM: Homo sapiens

<400> SEQUENCE: 757

Leu Gln Phe Glu Val Lys Ser Arg Leu
1               5

<210> SEQ ID NO 758
<211> LENGTH: 9
<212> TYPE: PRT
<213> ORGANISM: Homo sapiens

<400> SEQUENCE: 758

Ala Val Lys Ala Thr Glu Val Lys Ala
1               5

<210> SEQ ID NO 759
<211> LENGTH: 9
<212> TYPE: PRT
<213> ORGANISM: Homo sapiens

<400> SEQUENCE: 759

Val Gly Leu Thr Glu Val Lys Ser Tyr
1               5

<210> SEQ ID NO 760
<211> LENGTH: 9
<212> TYPE: PRT
<213> ORGANISM: Homo sapiens

<400> SEQUENCE: 760

Ile Glu Ile Glu Val Lys Ser Arg Tyr
1               5

<210> SEQ ID NO 761
<211> LENGTH: 9
<212> TYPE: PRT
<213> ORGANISM: Homo sapiens

<400> SEQUENCE: 761

Ala Ser Asp Leu Ala Thr Met Val Glu
1               5

-continued

```
<210> SEQ ID NO 762
<211> LENGTH: 9
<212> TYPE: PRT
<213> ORGANISM: Homo sapiens

<400> SEQUENCE: 762

Met Ser Asn Ala Thr Met Val Lys Leu
1               5

<210> SEQ ID NO 763
<211> LENGTH: 9
<212> TYPE: PRT
<213> ORGANISM: Homo sapiens

<400> SEQUENCE: 763

Ile Ala Glu Met Val Lys Ser Arg Val
1               5

<210> SEQ ID NO 764
<211> LENGTH: 9
<212> TYPE: PRT
<213> ORGANISM: Homo sapiens

<400> SEQUENCE: 764

Lys Trp Asp Gly Leu Ala Thr Met Leu
1               5

<210> SEQ ID NO 765
<211> LENGTH: 9
<212> TYPE: PRT
<213> ORGANISM: Homo sapiens

<400> SEQUENCE: 765

Arg Met Ser Ala Thr Met Val Lys Phe
1               5

<210> SEQ ID NO 766
<211> LENGTH: 9
<212> TYPE: PRT
<213> ORGANISM: Homo sapiens

<400> SEQUENCE: 766

Ile Arg Arg Thr Met Val Lys Ser Ile
1               5

<210> SEQ ID NO 767
<211> LENGTH: 9
<212> TYPE: PRT
<213> ORGANISM: Homo sapiens

<400> SEQUENCE: 767

Val Arg Thr Met Val Lys Ser Arg Phe
1               5

<210> SEQ ID NO 768
<211> LENGTH: 9
<212> TYPE: PRT
<213> ORGANISM: Homo sapiens

<400> SEQUENCE: 768

Asn Met Lys Leu Ala Thr Met Val Gly
1               5

<210> SEQ ID NO 769
<211> LENGTH: 9
```

-continued

```
<212> TYPE: PRT
<213> ORGANISM: Homo sapiens

<400> SEQUENCE: 769

Tyr Gly Lys Ala Thr Met Val Lys Ala
1               5

<210> SEQ ID NO 770
<211> LENGTH: 9
<212> TYPE: PRT
<213> ORGANISM: Homo sapiens

<400> SEQUENCE: 770

Val Glu Leu Thr Met Val Lys Ser Tyr
1               5

<210> SEQ ID NO 771
<211> LENGTH: 9
<212> TYPE: PRT
<213> ORGANISM: Homo sapiens

<400> SEQUENCE: 771

Thr Val Ile Met Val Lys Ser Arg Arg
1               5

<210> SEQ ID NO 772
<211> LENGTH: 9
<212> TYPE: PRT
<213> ORGANISM: Homo sapiens

<400> SEQUENCE: 772

Cys Pro Glu Ile Thr Lys Glu Gln Tyr
1               5

<210> SEQ ID NO 773
<211> LENGTH: 9
<212> TYPE: PRT
<213> ORGANISM: Homo sapiens

<400> SEQUENCE: 773

Arg Gly Ile Glu Ile Thr Lys Glu Arg
1               5

<210> SEQ ID NO 774
<211> LENGTH: 9
<212> TYPE: PRT
<213> ORGANISM: Homo sapiens

<400> SEQUENCE: 774

Pro Ser Asp Met Asn Asp Ala Arg Leu
1               5

<210> SEQ ID NO 775
<211> LENGTH: 9
<212> TYPE: PRT
<213> ORGANISM: Homo sapiens

<400> SEQUENCE: 775

Tyr Ala Asp Ala Arg His His Gly Cys
1               5

<210> SEQ ID NO 776
<211> LENGTH: 9
<212> TYPE: PRT
<213> ORGANISM: Homo sapiens
```

-continued

<400> SEQUENCE: 776

Ala Pro Arg Asp Ala Arg His His Lys
1               5

<210> SEQ ID NO 777
<211> LENGTH: 9
<212> TYPE: PRT
<213> ORGANISM: Homo sapiens

<400> SEQUENCE: 777

Lys Ala Arg Ala Arg His His Gly Ala
1               5

<210> SEQ ID NO 778
<211> LENGTH: 9
<212> TYPE: PRT
<213> ORGANISM: Homo sapiens

<400> SEQUENCE: 778

Trp Lys Ile Arg His His Gly Gly Arg
1               5

<210> SEQ ID NO 779
<211> LENGTH: 9
<212> TYPE: PRT
<213> ORGANISM: Homo sapiens

<400> SEQUENCE: 779

Phe Gly Asp Lys Gly Gly Arg Thr Gly
1               5

<210> SEQ ID NO 780
<211> LENGTH: 9
<212> TYPE: PRT
<213> ORGANISM: Homo sapiens

<400> SEQUENCE: 780

Gln Gly Lys Ala Gly Lys Gly Gly Pro
1               5

<210> SEQ ID NO 781
<211> LENGTH: 9
<212> TYPE: PRT
<213> ORGANISM: Homo sapiens

<400> SEQUENCE: 781

Asp Asn Arg Lys Gly Gly Arg Thr Lys
1               5

<210> SEQ ID NO 782
<211> LENGTH: 9
<212> TYPE: PRT
<213> ORGANISM: Homo sapiens

<400> SEQUENCE: 782

Asn Asn Arg Gly Gly Arg Thr Gly Ala
1               5

<210> SEQ ID NO 783
<211> LENGTH: 9
<212> TYPE: PRT
<213> ORGANISM: Homo sapiens

<400> SEQUENCE: 783

-continued

Leu Ile Thr Ala Gly Lys Gly Gly Tyr
1               5

<210> SEQ ID NO 784
<211> LENGTH: 9
<212> TYPE: PRT
<213> ORGANISM: Homo sapiens

<400> SEQUENCE: 784

Glu His Phe Lys Gly Gly Arg Thr Tyr
1               5

<210> SEQ ID NO 785
<211> LENGTH: 9
<212> TYPE: PRT
<213> ORGANISM: Homo sapiens

<400> SEQUENCE: 785

Pro Ala Lys Ala Gly Lys Gly Gln Pro
1               5

<210> SEQ ID NO 786
<211> LENGTH: 9
<212> TYPE: PRT
<213> ORGANISM: Homo sapiens

<400> SEQUENCE: 786

Pro Asp Arg Lys Gly Gln Arg Thr Gly
1               5

<210> SEQ ID NO 787
<211> LENGTH: 9
<212> TYPE: PRT
<213> ORGANISM: Homo sapiens

<400> SEQUENCE: 787

Arg Ala Trp Gly Gln Arg Thr Gly Pro
1               5

<210> SEQ ID NO 788
<211> LENGTH: 9
<212> TYPE: PRT
<213> ORGANISM: Homo sapiens

<400> SEQUENCE: 788

Gly Val Leu Ala Gly Lys Gly Gln Tyr
1               5

<210> SEQ ID NO 789
<211> LENGTH: 9
<212> TYPE: PRT
<213> ORGANISM: Homo sapiens

<400> SEQUENCE: 789

Gln Glu Cys Lys Gly Gln Arg Thr Tyr
1               5

<210> SEQ ID NO 790
<211> LENGTH: 9
<212> TYPE: PRT
<213> ORGANISM: Homo sapiens

<400> SEQUENCE: 790

Pro Asp Lys Ser Phe Gly Val Ala Tyr

-continued

```
1               5

<210> SEQ ID NO 791
<211> LENGTH: 9
<212> TYPE: PRT
<213> ORGANISM: Homo sapiens

<400> SEQUENCE: 791

Trp Lys Thr Phe Gly Val Ala Thr Ser
1               5

<210> SEQ ID NO 792
<211> LENGTH: 9
<212> TYPE: PRT
<213> ORGANISM: Homo sapiens

<400> SEQUENCE: 792

Pro Glu Phe Gly Val Ala Thr Cys Lys
1               5

<210> SEQ ID NO 793
<211> LENGTH: 9
<212> TYPE: PRT
<213> ORGANISM: Homo sapiens

<400> SEQUENCE: 793

Phe Glu His Ser Phe Gly Val Ala Ser
1               5

<210> SEQ ID NO 794
<211> LENGTH: 9
<212> TYPE: PRT
<213> ORGANISM: Homo sapiens

<400> SEQUENCE: 794

Tyr Arg Pro Gly Val Ala Thr Cys Val
1               5

<210> SEQ ID NO 795
<211> LENGTH: 9
<212> TYPE: PRT
<213> ORGANISM: Homo sapiens

<400> SEQUENCE: 795

Gly Lys Thr Ser Phe Gly Val Ala Gly
1               5

<210> SEQ ID NO 796
<211> LENGTH: 9
<212> TYPE: PRT
<213> ORGANISM: Homo sapiens

<400> SEQUENCE: 796

Gly Lys His Phe Gly Val Ala Thr Leu
1               5

<210> SEQ ID NO 797
<211> LENGTH: 9
<212> TYPE: PRT
<213> ORGANISM: Homo sapiens

<400> SEQUENCE: 797

Arg Glu Gln Gly Val Ala Thr Cys Leu
1               5
```

-continued

```
<210> SEQ ID NO 798
<211> LENGTH: 9
<212> TYPE: PRT
<213> ORGANISM: Homo sapiens

<400> SEQUENCE: 798

Arg Gly Ser Tyr Ser Phe Gly Val Tyr
1               5

<210> SEQ ID NO 799
<211> LENGTH: 9
<212> TYPE: PRT
<213> ORGANISM: Homo sapiens

<400> SEQUENCE: 799

Gly Gly Ser Gly Val Ala Thr Cys Tyr
1               5

<210> SEQ ID NO 800
<211> LENGTH: 9
<212> TYPE: PRT
<213> ORGANISM: Homo sapiens

<400> SEQUENCE: 800

Asp Arg Leu Thr Asp Phe Gly Arg Glu
1               5

<210> SEQ ID NO 801
<211> LENGTH: 9
<212> TYPE: PRT
<213> ORGANISM: Homo sapiens

<400> SEQUENCE: 801

Tyr Glu Met Asp Phe Gly Arg Leu Tyr
1               5

<210> SEQ ID NO 802
<211> LENGTH: 9
<212> TYPE: PRT
<213> ORGANISM: Homo sapiens

<400> SEQUENCE: 802

Val Arg Gly Gly Arg Leu Ala Lys Arg
1               5

<210> SEQ ID NO 803
<211> LENGTH: 9
<212> TYPE: PRT
<213> ORGANISM: Homo sapiens

<400> SEQUENCE: 803

Phe Arg Phe Thr Asp Phe Gly Arg Thr
1               5

<210> SEQ ID NO 804
<211> LENGTH: 9
<212> TYPE: PRT
<213> ORGANISM: Homo sapiens

<400> SEQUENCE: 804

Gln Glu Leu Gly Arg Leu Ala Lys Pro
1               5

<210> SEQ ID NO 805
```

```
<211> LENGTH: 9
<212> TYPE: PRT
<213> ORGANISM: Homo sapiens

<400> SEQUENCE: 805

Lys Gln Tyr Thr Asp Phe Gly Arg Leu
1               5

<210> SEQ ID NO 806
<211> LENGTH: 9
<212> TYPE: PRT
<213> ORGANISM: Homo sapiens

<400> SEQUENCE: 806

Arg Cys Tyr Asp Phe Gly Arg Leu Trp
1               5

<210> SEQ ID NO 807
<211> LENGTH: 9
<212> TYPE: PRT
<213> ORGANISM: Homo sapiens

<400> SEQUENCE: 807

Tyr Lys Leu Gly Arg Leu Ala Lys Ile
1               5

<210> SEQ ID NO 808
<211> LENGTH: 9
<212> TYPE: PRT
<213> ORGANISM: Homo sapiens

<400> SEQUENCE: 808

Glu Asn Pro Arg Leu Ala Lys Leu Ile
1               5

<210> SEQ ID NO 809
<211> LENGTH: 9
<212> TYPE: PRT
<213> ORGANISM: Homo sapiens

<400> SEQUENCE: 809

Glu Leu Asn Thr Asp Phe Gly Arg Trp
1               5

<210> SEQ ID NO 810
<211> LENGTH: 9
<212> TYPE: PRT
<213> ORGANISM: Homo sapiens

<400> SEQUENCE: 810

Cys Ser Asn Gly Arg Leu Ala Lys Phe
1               5

<210> SEQ ID NO 811
<211> LENGTH: 9
<212> TYPE: PRT
<213> ORGANISM: Homo sapiens

<400> SEQUENCE: 811

Ile Arg Ser Leu Ile Lys Arg Gln Leu
1               5

<210> SEQ ID NO 812
<211> LENGTH: 9
<212> TYPE: PRT
```

```
<213> ORGANISM: Homo sapiens

<400> SEQUENCE: 812

Thr His Trp Gln Arg Gln Gln Lys Leu
1               5

<210> SEQ ID NO 813
<211> LENGTH: 9
<212> TYPE: PRT
<213> ORGANISM: Homo sapiens

<400> SEQUENCE: 813

Arg Cys Leu Lys Arg Gln Arg Gln Leu
1               5

<210> SEQ ID NO 814
<211> LENGTH: 9
<212> TYPE: PRT
<213> ORGANISM: Homo sapiens

<400> SEQUENCE: 814

Arg Asp Leu Gln Arg Gln Gln Lys Val
1               5

<210> SEQ ID NO 815
<211> LENGTH: 9
<212> TYPE: PRT
<213> ORGANISM: Homo sapiens

<400> SEQUENCE: 815

Ser Pro Trp Leu Ile Lys Arg Gln Ile
1               5

<210> SEQ ID NO 816
<211> LENGTH: 9
<212> TYPE: PRT
<213> ORGANISM: Homo sapiens

<400> SEQUENCE: 816

Thr Ala Ala Gln Arg Gln Gln Lys Tyr
1               5

<210> SEQ ID NO 817
<211> LENGTH: 9
<212> TYPE: PRT
<213> ORGANISM: Homo sapiens

<400> SEQUENCE: 817

Thr Lys Arg Gly Phe Ser Cys Thr Lys
1               5

<210> SEQ ID NO 818
<211> LENGTH: 9
<212> TYPE: PRT
<213> ORGANISM: Homo sapiens

<400> SEQUENCE: 818

Thr Arg Lys Asp Val Gly Phe Ser Ile
1               5

<210> SEQ ID NO 819
<211> LENGTH: 9
<212> TYPE: PRT
<213> ORGANISM: Homo sapiens
```

-continued

```
<400> SEQUENCE: 819

Leu Arg His Gly Phe Ser Cys Thr Cys
1               5

<210> SEQ ID NO 820
<211> LENGTH: 9
<212> TYPE: PRT
<213> ORGANISM: Homo sapiens

<400> SEQUENCE: 820

Gln Asp Glu Asp Val Gly Phe Ser Met
1               5

<210> SEQ ID NO 821
<211> LENGTH: 9
<212> TYPE: PRT
<213> ORGANISM: Homo sapiens

<400> SEQUENCE: 821

Gln Asn Glu Gly Phe Ser Cys Thr Ala
1               5

<210> SEQ ID NO 822
<211> LENGTH: 9
<212> TYPE: PRT
<213> ORGANISM: Homo sapiens

<400> SEQUENCE: 822

Pro Asn Gln Phe Ser Cys Thr Leu Ser
1               5

<210> SEQ ID NO 823
<211> LENGTH: 9
<212> TYPE: PRT
<213> ORGANISM: Homo sapiens

<400> SEQUENCE: 823

His Ser Lys Asp Val Gly Phe Ser Ile
1               5

<210> SEQ ID NO 824
<211> LENGTH: 9
<212> TYPE: PRT
<213> ORGANISM: Homo sapiens

<400> SEQUENCE: 824

Gly Ser Lys Gly Phe Ser Cys Thr Met
1               5

<210> SEQ ID NO 825
<211> LENGTH: 9
<212> TYPE: PRT
<213> ORGANISM: Homo sapiens

<400> SEQUENCE: 825

Asp Gln Phe Gly Leu Ala Thr Glu Lys
1               5

<210> SEQ ID NO 826
<211> LENGTH: 9
<212> TYPE: PRT
<213> ORGANISM: Homo sapiens

<400> SEQUENCE: 826
```

-continued

```
Leu Arg Asp Glu Val Lys Ser Arg Glu
1               5

<210> SEQ ID NO 827
<211> LENGTH: 9
<212> TYPE: PRT
<213> ORGANISM: Homo sapiens

<400> SEQUENCE: 827

Ile Arg Lys Gly Leu Ala Thr Glu Tyr
1               5

<210> SEQ ID NO 828
<211> LENGTH: 9
<212> TYPE: PRT
<213> ORGANISM: Homo sapiens

<400> SEQUENCE: 828

Pro Asn Val Gly Leu Ala Thr Glu Ile
1               5

<210> SEQ ID NO 829
<211> LENGTH: 9
<212> TYPE: PRT
<213> ORGANISM: Homo sapiens

<400> SEQUENCE: 829

Ala Lys Ala Ala Thr Glu Val Lys Leu
1               5

<210> SEQ ID NO 830
<211> LENGTH: 9
<212> TYPE: PRT
<213> ORGANISM: Homo sapiens

<400> SEQUENCE: 830

Pro Ser Cys Gly Leu Ala Thr Glu Met
1               5

<210> SEQ ID NO 831
<211> LENGTH: 9
<212> TYPE: PRT
<213> ORGANISM: Homo sapiens

<400> SEQUENCE: 831

Leu Ser Lys Ala Thr Glu Val Lys Leu
1               5

<210> SEQ ID NO 832
<211> LENGTH: 9
<212> TYPE: PRT
<213> ORGANISM: Homo sapiens

<400> SEQUENCE: 832

Ser Cys Ile Thr Glu Val Lys Ser Phe
1               5

<210> SEQ ID NO 833
<211> LENGTH: 9
<212> TYPE: PRT
<213> ORGANISM: Homo sapiens

<400> SEQUENCE: 833

Glu Ser Pro Glu Val Lys Ser Arg Tyr
1               5
```

```
<210> SEQ ID NO 834
<211> LENGTH: 9
<212> TYPE: PRT
<213> ORGANISM: Homo sapiens

<400> SEQUENCE: 834

Asp Lys Val Gly Leu Ala Thr Met Ala
1               5

<210> SEQ ID NO 835
<211> LENGTH: 9
<212> TYPE: PRT
<213> ORGANISM: Homo sapiens

<400> SEQUENCE: 835

Ile Arg Gly Met Val Lys Ser Arg Asn
1               5

<210> SEQ ID NO 836
<211> LENGTH: 9
<212> TYPE: PRT
<213> ORGANISM: Homo sapiens

<400> SEQUENCE: 836

Leu Arg Gln Gly Leu Ala Thr Met Gln
1               5

<210> SEQ ID NO 837
<211> LENGTH: 9
<212> TYPE: PRT
<213> ORGANISM: Homo sapiens

<400> SEQUENCE: 837

Glu Asn Pro Gly Leu Ala Thr Met Ile
1               5

<210> SEQ ID NO 838
<211> LENGTH: 9
<212> TYPE: PRT
<213> ORGANISM: Homo sapiens

<400> SEQUENCE: 838

Ser Lys Gly Ala Thr Met Val Lys Leu
1               5

<210> SEQ ID NO 839
<211> LENGTH: 9
<212> TYPE: PRT
<213> ORGANISM: Homo sapiens

<400> SEQUENCE: 839

Gly Gln Val Thr Met Val Lys Ser Ile
1               5

<210> SEQ ID NO 840
<211> LENGTH: 9
<212> TYPE: PRT
<213> ORGANISM: Homo sapiens

<400> SEQUENCE: 840

Lys Ala Lys Gly Leu Ala Thr Met Met
1               5
```

```
<210> SEQ ID NO 841
<211> LENGTH: 9
<212> TYPE: PRT
<213> ORGANISM: Homo sapiens

<400> SEQUENCE: 841

Arg Gly Asp Ala Thr Met Val Lys Ile
1               5

<210> SEQ ID NO 842
<211> LENGTH: 9
<212> TYPE: PRT
<213> ORGANISM: Homo sapiens

<400> SEQUENCE: 842

Val Gly Cys Thr Met Val Lys Ser Met
1               5

<210> SEQ ID NO 843
<211> LENGTH: 9
<212> TYPE: PRT
<213> ORGANISM: Homo sapiens

<400> SEQUENCE: 843

Thr Ile Thr Met Val Lys Ser Arg Trp
1               5

<210> SEQ ID NO 844
<211> LENGTH: 9
<212> TYPE: PRT
<213> ORGANISM: Homo sapiens

<400> SEQUENCE: 844

Lys Lys Ala Glu Ile Thr Lys Glu Ser
1               5

<210> SEQ ID NO 845
<211> LENGTH: 9
<212> TYPE: PRT
<213> ORGANISM: Homo sapiens

<400> SEQUENCE: 845

Met Arg Pro Thr Lys Glu Gln Glu Gln
1               5

<210> SEQ ID NO 846
<211> LENGTH: 9
<212> TYPE: PRT
<213> ORGANISM: Homo sapiens

<400> SEQUENCE: 846

Ala Asp Leu Ser Glu Ile Thr Lys Val
1               5

<210> SEQ ID NO 847
<211> LENGTH: 9
<212> TYPE: PRT
<213> ORGANISM: Homo sapiens

<400> SEQUENCE: 847

Asn Lys Leu Ile Thr Lys Glu Gln Leu
1               5

<210> SEQ ID NO 848
<211> LENGTH: 9
```

```
<212> TYPE: PRT
<213> ORGANISM: Homo sapiens

<400> SEQUENCE: 848

Leu Arg Val Asn Asp Ala Arg His Ile
1               5

<210> SEQ ID NO 849
<211> LENGTH: 9
<212> TYPE: PRT
<213> ORGANISM: Homo sapiens

<400> SEQUENCE: 849

Leu Lys Pro Arg His His Gly Gly Asn
1               5

<210> SEQ ID NO 850
<211> LENGTH: 9
<212> TYPE: PRT
<213> ORGANISM: Homo sapiens

<400> SEQUENCE: 850

Ile Arg Met Asp Ala Arg His His Val
1               5

<210> SEQ ID NO 851
<211> LENGTH: 9
<212> TYPE: PRT
<213> ORGANISM: Homo sapiens

<400> SEQUENCE: 851

Pro Glu Trp Ala Arg His His Gly Trp
1               5

<210> SEQ ID NO 852
<211> LENGTH: 9
<212> TYPE: PRT
<213> ORGANISM: Homo sapiens

<400> SEQUENCE: 852

Ser Gln Ala Arg His His Gly Gly Cys
1               5

<210> SEQ ID NO 853
<211> LENGTH: 9
<212> TYPE: PRT
<213> ORGANISM: Homo sapiens

<400> SEQUENCE: 853

Ile Glu Gln Asn Asp Ala Arg His Phe
1               5

<210> SEQ ID NO 854
<211> LENGTH: 9
<212> TYPE: PRT
<213> ORGANISM: Homo sapiens

<400> SEQUENCE: 854

Phe Gly His Arg His His Gly Gly Arg
1               5

<210> SEQ ID NO 855
<211> LENGTH: 9
<212> TYPE: PRT
<213> ORGANISM: Homo sapiens
```

-continued

```
<400> SEQUENCE: 855

Lys Gln Leu Ala Gly Lys Gly Gly Pro
1               5

<210> SEQ ID NO 856
<211> LENGTH: 9
<212> TYPE: PRT
<213> ORGANISM: Homo sapiens

<400> SEQUENCE: 856

Arg Glu Trp Gly Arg Thr Gly Val Glu
1               5

<210> SEQ ID NO 857
<211> LENGTH: 9
<212> TYPE: PRT
<213> ORGANISM: Homo sapiens

<400> SEQUENCE: 857

Val His Cys Ala Gly Lys Gly Gly Leu
1               5

<210> SEQ ID NO 858
<211> LENGTH: 9
<212> TYPE: PRT
<213> ORGANISM: Homo sapiens

<400> SEQUENCE: 858

Met Cys Trp Gly Lys Gly Gly Arg Ala
1               5

<210> SEQ ID NO 859
<211> LENGTH: 9
<212> TYPE: PRT
<213> ORGANISM: Homo sapiens

<400> SEQUENCE: 859

Ala Arg Gln Gly Arg Thr Gly Val Ser
1               5

<210> SEQ ID NO 860
<211> LENGTH: 9
<212> TYPE: PRT
<213> ORGANISM: Homo sapiens

<400> SEQUENCE: 860

Lys Thr Trp Lys Gly Gly Arg Thr Leu
1               5

<210> SEQ ID NO 861
<211> LENGTH: 9
<212> TYPE: PRT
<213> ORGANISM: Homo sapiens

<400> SEQUENCE: 861

Phe Lys Cys Gly Arg Thr Gly Val Leu
1               5

<210> SEQ ID NO 862
<211> LENGTH: 9
<212> TYPE: PRT
<213> ORGANISM: Homo sapiens

<400> SEQUENCE: 862
```

-continued

```
Asn Ile Thr Ala Gly Lys Gly Gly Trp
1               5

<210> SEQ ID NO 863
<211> LENGTH: 9
<212> TYPE: PRT
<213> ORGANISM: Homo sapiens

<400> SEQUENCE: 863

Leu Ser His Lys Gly Gly Arg Thr Arg
1               5

<210> SEQ ID NO 864
<211> LENGTH: 9
<212> TYPE: PRT
<213> ORGANISM: Homo sapiens

<400> SEQUENCE: 864

Gly Gly Pro Gly Gly Arg Thr Gly Met
1               5

<210> SEQ ID NO 865
<211> LENGTH: 9
<212> TYPE: PRT
<213> ORGANISM: Homo sapiens

<400> SEQUENCE: 865

Asp Arg Thr Ala Gly Lys Gly Gln Glu
1               5

<210> SEQ ID NO 866
<211> LENGTH: 9
<212> TYPE: PRT
<213> ORGANISM: Homo sapiens

<400> SEQUENCE: 866

Leu Arg Lys Ala Gly Lys Gly Gln Pro
1               5

<210> SEQ ID NO 867
<211> LENGTH: 9
<212> TYPE: PRT
<213> ORGANISM: Homo sapiens

<400> SEQUENCE: 867

Leu Arg Thr Gln Arg Thr Gly Val Pro
1               5

<210> SEQ ID NO 868
<211> LENGTH: 9
<212> TYPE: PRT
<213> ORGANISM: Homo sapiens

<400> SEQUENCE: 868

Gly Met Phe Lys Gly Gln Arg Thr Leu
1               5

<210> SEQ ID NO 869
<211> LENGTH: 9
<212> TYPE: PRT
<213> ORGANISM: Homo sapiens

<400> SEQUENCE: 869

Pro Asp Leu Gln Arg Thr Gly Val Leu
```

```
1               5
```

<210> SEQ ID NO 870
<211> LENGTH: 9
<212> TYPE: PRT
<213> ORGANISM: Homo sapiens

<400> SEQUENCE: 870

```
Gly Asp Phe Ala Gly Lys Gly Gln Phe
1               5
```

<210> SEQ ID NO 871
<211> LENGTH: 9
<212> TYPE: PRT
<213> ORGANISM: Homo sapiens

<400> SEQUENCE: 871

```
Gln Ala Asn Lys Gly Gln Arg Thr Leu
1               5
```

<210> SEQ ID NO 872
<211> LENGTH: 9
<212> TYPE: PRT
<213> ORGANISM: Homo sapiens

<400> SEQUENCE: 872

```
Glu Gly Met Gly Gln Arg Thr Gly Leu
1               5
```

<210> SEQ ID NO 873
<211> LENGTH: 15
<212> TYPE: PRT
<213> ORGANISM: Homo sapiens

<400> SEQUENCE: 873

```
Ser Ser Asp Ala Gly Lys Tyr Ser Phe Gly Val Leu Arg Leu Met
1               5                   10                  15
```

<210> SEQ ID NO 874
<211> LENGTH: 15
<212> TYPE: PRT
<213> ORGANISM: Homo sapiens

<400> SEQUENCE: 874

```
Gly Glu Gln Gln Lys Tyr Ser Phe Gly Val Ala Gln Asn Trp Cys
1               5                   10                  15
```

<210> SEQ ID NO 875
<211> LENGTH: 15
<212> TYPE: PRT
<213> ORGANISM: Homo sapiens

<400> SEQUENCE: 875

```
Arg Ala Glu Pro Ser Phe Gly Val Ala Thr Cys Gly His Phe Asn
1               5                   10                  15
```

<210> SEQ ID NO 876
<211> LENGTH: 15
<212> TYPE: PRT
<213> ORGANISM: Homo sapiens

<400> SEQUENCE: 876

```
Ala Ile Ser Lys Gly Val Ala Thr Cys Val Lys Gly Lys Phe Val
1               5                   10                  15
```

-continued

```
<210> SEQ ID NO 877
<211> LENGTH: 15
<212> TYPE: PRT
<213> ORGANISM: Homo sapiens

<400> SEQUENCE: 877

Met Asn Cys Asn Val Ala Thr Cys Val Lys Lys Ala Cys Val Phe
1               5                   10                  15

<210> SEQ ID NO 878
<211> LENGTH: 15
<212> TYPE: PRT
<213> ORGANISM: Homo sapiens

<400> SEQUENCE: 878

Leu Asp Leu Leu Gly Lys Tyr Ser Phe Gly Val Ser Ala Pro Gly
1               5                   10                  15

<210> SEQ ID NO 879
<211> LENGTH: 15
<212> TYPE: PRT
<213> ORGANISM: Homo sapiens

<400> SEQUENCE: 879

Val Val Asn Arg Gly Val Ala Thr Cys Val Lys Ala Val Asn Glu
1               5                   10                  15

<210> SEQ ID NO 880
<211> LENGTH: 15
<212> TYPE: PRT
<213> ORGANISM: Homo sapiens

<400> SEQUENCE: 880

Leu Phe Gln Lys Val Ala Thr Cys Val Lys Lys Ala Glu Ser Ser
1               5                   10                  15

<210> SEQ ID NO 881
<211> LENGTH: 15
<212> TYPE: PRT
<213> ORGANISM: Homo sapiens

<400> SEQUENCE: 881

Arg Cys His Phe Gly Val Ala Thr Cys Val Lys Thr Met Asp Phe
1               5                   10                  15

<210> SEQ ID NO 882
<211> LENGTH: 15
<212> TYPE: PRT
<213> ORGANISM: Homo sapiens

<400> SEQUENCE: 882

Ile Arg Arg His Ser Phe Gly Val Ala Thr Cys Glu Leu Val Cys
1               5                   10                  15

<210> SEQ ID NO 883
<211> LENGTH: 15
<212> TYPE: PRT
<213> ORGANISM: Homo sapiens

<400> SEQUENCE: 883

His Ser Asp His Gly Val Ala Thr Cys Val Lys Pro Met Tyr Thr
1               5                   10                  15

<210> SEQ ID NO 884
```

-continued

<211> LENGTH: 15
<212> TYPE: PRT
<213> ORGANISM: Homo sapiens

<400> SEQUENCE: 884

Leu Ser Thr Pro Ile Thr Asp Phe Gly Arg Leu Ala Gly His Ala
1               5                   10                  15

<210> SEQ ID NO 885
<211> LENGTH: 15
<212> TYPE: PRT
<213> ORGANISM: Homo sapiens

<400> SEQUENCE: 885

Phe Asp Gln Lys Gly Arg Leu Ala Lys Leu Leu Thr Trp Ile Cys
1               5                   10                  15

<210> SEQ ID NO 886
<211> LENGTH: 15
<212> TYPE: PRT
<213> ORGANISM: Homo sapiens

<400> SEQUENCE: 886

Phe Val Ile Trp Lys Ile Thr Asp Phe Gly Arg Val Lys Tyr Asn
1               5                   10                  15

<210> SEQ ID NO 887
<211> LENGTH: 15
<212> TYPE: PRT
<213> ORGANISM: Homo sapiens

<400> SEQUENCE: 887

Ile Val Ser Trp Ile Thr Asp Phe Gly Arg Leu Trp Lys Arg Asn
1               5                   10                  15

<210> SEQ ID NO 888
<211> LENGTH: 15
<212> TYPE: PRT
<213> ORGANISM: Homo sapiens

<400> SEQUENCE: 888

Thr Leu Leu Met Asp Phe Gly Arg Leu Ala Lys Arg Thr Met Lys
1               5                   10                  15

<210> SEQ ID NO 889
<211> LENGTH: 15
<212> TYPE: PRT
<213> ORGANISM: Homo sapiens

<400> SEQUENCE: 889

Ser Glu Met Phe Gly Arg Leu Ala Lys Leu Leu Glu Tyr Ala Ile
1               5                   10                  15

<210> SEQ ID NO 890
<211> LENGTH: 15
<212> TYPE: PRT
<213> ORGANISM: Homo sapiens

<400> SEQUENCE: 890

Ser Gln Glu Ile Arg Leu Ala Lys Leu Leu Gly Tyr Arg Ser Arg
1               5                   10                  15

<210> SEQ ID NO 891
<211> LENGTH: 15
<212> TYPE: PRT

-continued

```
<213> ORGANISM: Homo sapiens

<400> SEQUENCE: 891

Ser Ala Tyr Glu Lys Ile Thr Asp Phe Gly Arg Lys Ile Val Ile
1               5                   10                  15

<210> SEQ ID NO 892
<211> LENGTH: 15
<212> TYPE: PRT
<213> ORGANISM: Homo sapiens

<400> SEQUENCE: 892

Leu Gly Tyr Glu Ile Thr Asp Phe Gly Arg Leu Arg Val Gly Tyr
1               5                   10                  15

<210> SEQ ID NO 893
<211> LENGTH: 15
<212> TYPE: PRT
<213> ORGANISM: Homo sapiens

<400> SEQUENCE: 893

Asn Lys Ile Phe Asp Phe Gly Arg Leu Ala Lys Arg Leu Ile Ile
1               5                   10                  15

<210> SEQ ID NO 894
<211> LENGTH: 15
<212> TYPE: PRT
<213> ORGANISM: Homo sapiens

<400> SEQUENCE: 894

Leu Asn Leu Leu Ile Lys Arg Gln Arg Gln Gln Pro Pro Asn Cys
1               5                   10                  15

<210> SEQ ID NO 895
<211> LENGTH: 15
<212> TYPE: PRT
<213> ORGANISM: Homo sapiens

<400> SEQUENCE: 895

Leu Gly Val His Gly Ile Leu Ile Lys Arg Gln Ala Cys His Cys
1               5                   10                  15

<210> SEQ ID NO 896
<211> LENGTH: 15
<212> TYPE: PRT
<213> ORGANISM: Homo sapiens

<400> SEQUENCE: 896

Tyr Met Cys Leu Ile Leu Ile Lys Arg Gln Arg Leu Thr Asn Arg
1               5                   10                  15

<210> SEQ ID NO 897
<211> LENGTH: 15
<212> TYPE: PRT
<213> ORGANISM: Homo sapiens

<400> SEQUENCE: 897

Phe Ala Leu Phe Ile Lys Arg Gln Arg Gln Gln Ser Gln Cys Trp
1               5                   10                  15

<210> SEQ ID NO 898
<211> LENGTH: 15
<212> TYPE: PRT
<213> ORGANISM: Homo sapiens
```

<400> SEQUENCE: 898

Leu Ile Val Trp Gln Arg Gln Gln Lys Ile Arg Ala Leu Thr Glu
1               5                   10                  15

<210> SEQ ID NO 899
<211> LENGTH: 15
<212> TYPE: PRT
<213> ORGANISM: Homo sapiens

<400> SEQUENCE: 899

Asp Ala Trp Tyr Ile Lys Arg Gln Arg Gln Gln Arg Leu Thr Cys
1               5                   10                  15

<210> SEQ ID NO 900
<211> LENGTH: 15
<212> TYPE: PRT
<213> ORGANISM: Homo sapiens

<400> SEQUENCE: 900

Pro Gly Leu Asp Arg Gln Arg Gln Gln Lys Ile Ile Val Gln Asp
1               5                   10                  15

<210> SEQ ID NO 901
<211> LENGTH: 15
<212> TYPE: PRT
<213> ORGANISM: Homo sapiens

<400> SEQUENCE: 901

Gly Phe Lys Thr Gln Arg Gln Gln Lys Ile Arg Val Phe Leu Glu
1               5                   10                  15

<210> SEQ ID NO 902
<211> LENGTH: 15
<212> TYPE: PRT
<213> ORGANISM: Homo sapiens

<400> SEQUENCE: 902

Gly Val Asp Val Leu Ser Thr Asp Val Gly Phe Gln Asp Ile Cys
1               5                   10                  15

<210> SEQ ID NO 903
<211> LENGTH: 15
<212> TYPE: PRT
<213> ORGANISM: Homo sapiens

<400> SEQUENCE: 903

Pro Gly Thr Ser Ser Thr Asp Val Gly Phe Ser Gly Glu Phe His
1               5                   10                  15

<210> SEQ ID NO 904
<211> LENGTH: 15
<212> TYPE: PRT
<213> ORGANISM: Homo sapiens

<400> SEQUENCE: 904

Ser Glu Asn Tyr Asp Val Gly Phe Ser Cys Thr Tyr Asp Leu Val
1               5                   10                  15

<210> SEQ ID NO 905
<211> LENGTH: 15
<212> TYPE: PRT
<213> ORGANISM: Homo sapiens

<400> SEQUENCE: 905

```
Gly Phe Gly Asn Gly Phe Ser Cys Thr Leu Val Gln His Asp Thr
1               5                   10                  15

<210> SEQ ID NO 906
<211> LENGTH: 15
<212> TYPE: PRT
<213> ORGANISM: Homo sapiens

<400> SEQUENCE: 906

Leu Ala Leu Gln Leu Ser Thr Asp Val Gly Phe Ser Ala Pro Ser
1               5                   10                  15

<210> SEQ ID NO 907
<211> LENGTH: 15
<212> TYPE: PRT
<213> ORGANISM: Homo sapiens

<400> SEQUENCE: 907

Ser Asn Ile Ser Ser Thr Asp Val Gly Phe Ser Pro Leu Ala Val
1               5                   10                  15

<210> SEQ ID NO 908
<211> LENGTH: 15
<212> TYPE: PRT
<213> ORGANISM: Homo sapiens

<400> SEQUENCE: 908

Ser Ala Thr Val Asp Val Gly Phe Ser Cys Thr Asp His Leu Thr
1               5                   10                  15

<210> SEQ ID NO 909
<211> LENGTH: 15
<212> TYPE: PRT
<213> ORGANISM: Homo sapiens

<400> SEQUENCE: 909

Ala Glu Ile Leu Gly Phe Ser Cys Thr Leu Val Ala Thr Arg Ser
1               5                   10                  15

<210> SEQ ID NO 910
<211> LENGTH: 15
<212> TYPE: PRT
<213> ORGANISM: Homo sapiens

<400> SEQUENCE: 910

Asp His Phe Phe Leu Ser Thr Asp Val Gly Phe Arg Ile Glu Arg
1               5                   10                  15

<210> SEQ ID NO 911
<211> LENGTH: 15
<212> TYPE: PRT
<213> ORGANISM: Homo sapiens

<400> SEQUENCE: 911

Leu Met Arg Ile Ser Thr Asp Val Gly Phe Ser Val Lys Val Cys
1               5                   10                  15

<210> SEQ ID NO 912
<211> LENGTH: 15
<212> TYPE: PRT
<213> ORGANISM: Homo sapiens

<400> SEQUENCE: 912

Leu Ser Arg Met Phe Ser Cys Thr Leu Val Cys Gln Ser Gly His
1               5                   10                  15
```

<210> SEQ ID NO 913
<211> LENGTH: 15
<212> TYPE: PRT
<213> ORGANISM: Homo sapiens

<400> SEQUENCE: 913

Ser Ser Trp Glu Leu Ser Thr Asp Val Gly Phe Tyr Ser Glu Ile
1               5                   10                  15

<210> SEQ ID NO 914
<211> LENGTH: 15
<212> TYPE: PRT
<213> ORGANISM: Homo sapiens

<400> SEQUENCE: 914

Ser Thr Leu Tyr Ser Thr Asp Val Gly Phe Ser Tyr Ile Thr Gly
1               5                   10                  15

<210> SEQ ID NO 915
<211> LENGTH: 15
<212> TYPE: PRT
<213> ORGANISM: Homo sapiens

<400> SEQUENCE: 915

Ile Glu Arg Lys Gly Phe Ser Cys Thr Leu Val Thr Met Ile Gln
1               5                   10                  15

<210> SEQ ID NO 916
<211> LENGTH: 15
<212> TYPE: PRT
<213> ORGANISM: Homo sapiens

<400> SEQUENCE: 916

Ala Asn Lys Lys Glu Val Lys Ser Arg Trp Ser Ala Gln Leu Cys
1               5                   10                  15

<210> SEQ ID NO 917
<211> LENGTH: 15
<212> TYPE: PRT
<213> ORGANISM: Homo sapiens

<400> SEQUENCE: 917

Leu Cys Lys Ser Leu Ala Thr Glu Val Lys Ser Pro Phe Lys Gln
1               5                   10                  15

<210> SEQ ID NO 918
<211> LENGTH: 15
<212> TYPE: PRT
<213> ORGANISM: Homo sapiens

<400> SEQUENCE: 918

Phe Asn Leu Leu Thr Glu Val Lys Ser Arg Trp Pro Tyr Cys Asp
1               5                   10                  15

<210> SEQ ID NO 919
<211> LENGTH: 15
<212> TYPE: PRT
<213> ORGANISM: Homo sapiens

<400> SEQUENCE: 919

Ala Gln Leu Pro Glu Val Lys Ser Arg Trp Ser Thr Asp Trp Glu
1               5                   10                  15

-continued

```
<210> SEQ ID NO 920
<211> LENGTH: 15
<212> TYPE: PRT
<213> ORGANISM: Homo sapiens

<400> SEQUENCE: 920

Ser Val Leu Arg Asp Phe Gly Leu Ala Thr Glu Leu Tyr Lys Ile
1               5                   10                  15

<210> SEQ ID NO 921
<211> LENGTH: 15
<212> TYPE: PRT
<213> ORGANISM: Homo sapiens

<400> SEQUENCE: 921

Gly Met Arg Tyr Phe Gly Leu Ala Thr Glu Val Pro Ala Ser Met
1               5                   10                  15

<210> SEQ ID NO 922
<211> LENGTH: 15
<212> TYPE: PRT
<213> ORGANISM: Homo sapiens

<400> SEQUENCE: 922

Cys Pro Phe Cys Thr Glu Val Lys Ser Arg Trp Phe Leu Leu Lys
1               5                   10                  15

<210> SEQ ID NO 923
<211> LENGTH: 15
<212> TYPE: PRT
<213> ORGANISM: Homo sapiens

<400> SEQUENCE: 923

Pro Arg His Arg Phe Gly Leu Ala Thr Met Val Cys Cys Thr Gly
1               5                   10                  15

<210> SEQ ID NO 924
<211> LENGTH: 15
<212> TYPE: PRT
<213> ORGANISM: Homo sapiens

<400> SEQUENCE: 924

Asp Cys Gln Asp Leu Ala Thr Met Val Lys Ser Val Cys Ser Ser
1               5                   10                  15

<210> SEQ ID NO 925
<211> LENGTH: 15
<212> TYPE: PRT
<213> ORGANISM: Homo sapiens

<400> SEQUENCE: 925

Phe Arg Lys Thr Met Val Lys Ser Arg Trp Ser Arg Cys Leu Cys
1               5                   10                  15

<210> SEQ ID NO 926
<211> LENGTH: 15
<212> TYPE: PRT
<213> ORGANISM: Homo sapiens

<400> SEQUENCE: 926

Leu Asn Pro Thr Leu Ala Thr Met Val Lys Ser Leu Glu Glu Ser
1               5                   10                  15

<210> SEQ ID NO 927
<211> LENGTH: 15
```

<212> TYPE: PRT
<213> ORGANISM: Homo sapiens

<400> SEQUENCE: 927

Leu Ala Leu Leu Met Val Lys Ser Arg Trp Ser Thr Gly Glu Val
1               5                   10                  15

<210> SEQ ID NO 928
<211> LENGTH: 15
<212> TYPE: PRT
<213> ORGANISM: Homo sapiens

<400> SEQUENCE: 928

Asn Tyr Gly Val Asp Phe Gly Leu Ala Thr Met Leu Thr His His
1               5                   10                  15

<210> SEQ ID NO 929
<211> LENGTH: 15
<212> TYPE: PRT
<213> ORGANISM: Homo sapiens

<400> SEQUENCE: 929

Lys Tyr Ile Ser Phe Gly Leu Ala Thr Met Val Lys Asn Val Asp
1               5                   10                  15

<210> SEQ ID NO 930
<211> LENGTH: 15
<212> TYPE: PRT
<213> ORGANISM: Homo sapiens

<400> SEQUENCE: 930

Val Cys Glu Ile Leu Ala Thr Met Val Lys Ser Tyr Arg Leu Asp
1               5                   10                  15

<210> SEQ ID NO 931
<211> LENGTH: 15
<212> TYPE: PRT
<213> ORGANISM: Homo sapiens

<400> SEQUENCE: 931

Leu Asn Glu Leu Thr Met Val Lys Ser Arg Trp Leu Pro Leu Lys
1               5                   10                  15

<210> SEQ ID NO 932
<211> LENGTH: 15
<212> TYPE: PRT
<213> ORGANISM: Homo sapiens

<400> SEQUENCE: 932

Asp Gly Glu Asn Glu Ile Thr Lys Glu Gln Glu Gln Cys Leu Glu
1               5                   10                  15

<210> SEQ ID NO 933
<211> LENGTH: 15
<212> TYPE: PRT
<213> ORGANISM: Homo sapiens

<400> SEQUENCE: 933

Leu Tyr Phe Ser Leu Ser Glu Ile Thr Lys Glu Leu Gly Gln Cys
1               5                   10                  15

<210> SEQ ID NO 934
<211> LENGTH: 15
<212> TYPE: PRT
<213> ORGANISM: Homo sapiens -continued

<400> SEQUENCE: 934

Leu Cys Leu Gly Lys Glu Gln Glu Lys Asp Phe Val Ala Arg Ala
1               5                   10                  15

<210> SEQ ID NO 935
<211> LENGTH: 15
<212> TYPE: PRT
<213> ORGANISM: Homo sapiens

<400> SEQUENCE: 935

Phe Ile Leu Leu Glu Ile Thr Lys Glu Gln Glu Arg Val Tyr Cys
1               5                   10                  15

<210> SEQ ID NO 936
<211> LENGTH: 15
<212> TYPE: PRT
<213> ORGANISM: Homo sapiens

<400> SEQUENCE: 936

Ser Tyr Trp Gln Thr Lys Glu Gln Glu Lys Asp Arg Leu Val Thr
1               5                   10                  15

<210> SEQ ID NO 937
<211> LENGTH: 15
<212> TYPE: PRT
<213> ORGANISM: Homo sapiens

<400> SEQUENCE: 937

Lys Asn Leu Asp Lys Glu Gln Glu Lys Asp Phe Ile Ile Ile Ile
1               5                   10                  15

<210> SEQ ID NO 938
<211> LENGTH: 15
<212> TYPE: PRT
<213> ORGANISM: Homo sapiens

<400> SEQUENCE: 938

Leu Asp Leu Thr Arg His His Gly Gly Trp Thr Ala Ser Ile Asp
1               5                   10                  15

<210> SEQ ID NO 939
<211> LENGTH: 15
<212> TYPE: PRT
<213> ORGANISM: Homo sapiens

<400> SEQUENCE: 939

Asp Phe Asn Glu Lys Gln Met Asn Asp Ala Arg Tyr Ile Ile Glu
1               5                   10                  15

<210> SEQ ID NO 940
<211> LENGTH: 15
<212> TYPE: PRT
<213> ORGANISM: Homo sapiens

<400> SEQUENCE: 940

Cys Pro Val Val Gln Met Asn Asp Ala Arg His Gln Leu Ile Val
1               5                   10                  15

<210> SEQ ID NO 941
<211> LENGTH: 15
<212> TYPE: PRT
<213> ORGANISM: Homo sapiens

<400> SEQUENCE: 941

-continued

```
Lys Lys Tyr Leu Asn Asp Ala Arg His His Gly Ile Ile Leu Val
1               5                   10                  15

<210> SEQ ID NO 942
<211> LENGTH: 15
<212> TYPE: PRT
<213> ORGANISM: Homo sapiens

<400> SEQUENCE: 942

Gly Gln Leu Arg Cys Lys Ala Gly Lys Gly Gly Tyr Arg Pro Asn
1               5                   10                  15

<210> SEQ ID NO 943
<211> LENGTH: 15
<212> TYPE: PRT
<213> ORGANISM: Homo sapiens

<400> SEQUENCE: 943

Leu Glu Glu Asn Gly Lys Gly Gly Arg Thr Gly Pro Ile Asn Cys
1               5                   10                  15

<210> SEQ ID NO 944
<211> LENGTH: 15
<212> TYPE: PRT
<213> ORGANISM: Homo sapiens

<400> SEQUENCE: 944

Asn Lys Glu Phe Gly Gly Arg Thr Gly Val Met Trp Cys Ile Ile
1               5                   10                  15

<210> SEQ ID NO 945
<211> LENGTH: 15
<212> TYPE: PRT
<213> ORGANISM: Homo sapiens

<400> SEQUENCE: 945

Ser Asn Gln Asp Gly Arg Thr Gly Val Met Ile Met Glu Ile Asp
1               5                   10                  15

<210> SEQ ID NO 946
<211> LENGTH: 15
<212> TYPE: PRT
<213> ORGANISM: Homo sapiens

<400> SEQUENCE: 946

Ile Cys Leu Leu Cys Lys Ala Gly Lys Gly Gly Ser Ser Glu Ser
1               5                   10                  15

<210> SEQ ID NO 947
<211> LENGTH: 15
<212> TYPE: PRT
<213> ORGANISM: Homo sapiens

<400> SEQUENCE: 947

Leu Val Ala Gln Gly Lys Gly Gly Arg Thr Gly Leu Pro Ile Gly
1               5                   10                  15

<210> SEQ ID NO 948
<211> LENGTH: 15
<212> TYPE: PRT
<213> ORGANISM: Homo sapiens

<400> SEQUENCE: 948

Leu Pro Ala Tyr Gly Gly Arg Thr Gly Val Met Ser Tyr Glu Gly
```

-continued

```
1               5               10              15

<210> SEQ ID NO 949
<211> LENGTH: 15
<212> TYPE: PRT
<213> ORGANISM: Homo sapiens

<400> SEQUENCE: 949

Thr Asn Asn Pro Cys Lys Ala Gly Lys Gly Gln Phe Glu Val Trp
1               5               10              15

<210> SEQ ID NO 950
<211> LENGTH: 15
<212> TYPE: PRT
<213> ORGANISM: Homo sapiens

<400> SEQUENCE: 950

Gln Phe Glu Lys Gly Lys Gly Gln Arg Thr Gly Gly His Val Met
1               5               10              15

<210> SEQ ID NO 951
<211> LENGTH: 15
<212> TYPE: PRT
<213> ORGANISM: Homo sapiens

<400> SEQUENCE: 951

Ala Glu Leu Ala Gly Gln Arg Thr Gly Val Met Ala Cys Tyr Asp
1               5               10              15

<210> SEQ ID NO 952
<211> LENGTH: 15
<212> TYPE: PRT
<213> ORGANISM: Homo sapiens

<400> SEQUENCE: 952

Ser Gln Arg Leu Gln Arg Thr Gly Val Met Ile Pro Cys Phe Ile
1               5               10              15

<210> SEQ ID NO 953
<211> LENGTH: 15
<212> TYPE: PRT
<213> ORGANISM: Homo sapiens

<400> SEQUENCE: 953

Leu Val Pro Thr Gly Lys Gly Gln Arg Thr Gly Ala Tyr Tyr Ser
1               5               10              15

<210> SEQ ID NO 954
<211> LENGTH: 15
<212> TYPE: PRT
<213> ORGANISM: Homo sapiens

<400> SEQUENCE: 954

Ser Cys Ile Phe Lys Ala Gly Lys Gly Gln Arg Pro His Ile Thr
1               5               10              15

<210> SEQ ID NO 955
<211> LENGTH: 15
<212> TYPE: PRT
<213> ORGANISM: Homo sapiens

<400> SEQUENCE: 955

Phe Gln Arg Pro Gly Gln Arg Thr Gly Val Met Cys Met Gly Met
1               5               10              15
```

-continued

```
<210> SEQ ID NO 956
<211> LENGTH: 15
<212> TYPE: PRT
<213> ORGANISM: Homo sapiens

<400> SEQUENCE: 956

Leu Thr Gln Asp Gln Arg Thr Gly Val Met Ile Tyr Asp Phe Cys
1               5                   10                  15

<210> SEQ ID NO 957
<211> LENGTH: 9
<212> TYPE: PRT
<213> ORGANISM: Homo sapiens

<400> SEQUENCE: 957

Leu Ala Asp Lys Lys Gly Asn Tyr Val
1               5

<210> SEQ ID NO 958
<211> LENGTH: 9
<212> TYPE: PRT
<213> ORGANISM: Homo sapiens

<400> SEQUENCE: 958

Lys Ala Ser Glu Lys Lys Gly Asn Tyr
1               5

<210> SEQ ID NO 959
<211> LENGTH: 9
<212> TYPE: PRT
<213> ORGANISM: Homo sapiens

<400> SEQUENCE: 959

Asp Gly Asp Gly Asn Tyr Val Val Ser
1               5

<210> SEQ ID NO 960
<211> LENGTH: 9
<212> TYPE: PRT
<213> ORGANISM: Homo sapiens

<400> SEQUENCE: 960

Lys Leu Ala Glu Lys Lys Gly Asn Val
1               5

<210> SEQ ID NO 961
<211> LENGTH: 9
<212> TYPE: PRT
<213> ORGANISM: Homo sapiens

<400> SEQUENCE: 961

Gln Tyr Thr Lys Lys Gly Asn Tyr Phe
1               5

<210> SEQ ID NO 962
<211> LENGTH: 9
<212> TYPE: PRT
<213> ORGANISM: Homo sapiens

<400> SEQUENCE: 962

Lys Tyr Thr Lys Gly Asn Tyr Val Trp
1               5

<210> SEQ ID NO 963
```

```
<211> LENGTH: 9
<212> TYPE: PRT
<213> ORGANISM: Homo sapiens

<400> SEQUENCE: 963

Glu Ser Asp Lys Gly Asn Tyr Val Cys
1               5

<210> SEQ ID NO 964
<211> LENGTH: 9
<212> TYPE: PRT
<213> ORGANISM: Homo sapiens

<400> SEQUENCE: 964

Ala Pro Gly Glu Glu Lys Lys Gly Gly
1               5

<210> SEQ ID NO 965
<211> LENGTH: 9
<212> TYPE: PRT
<213> ORGANISM: Homo sapiens

<400> SEQUENCE: 965

Pro Pro Asp Lys Gly Asn Tyr Val Ala
1               5

<210> SEQ ID NO 966
<211> LENGTH: 9
<212> TYPE: PRT
<213> ORGANISM: Homo sapiens

<400> SEQUENCE: 966

Leu Leu Arg Glu Glu Lys Lys Gly Phe
1               5

<210> SEQ ID NO 967
<211> LENGTH: 9
<212> TYPE: PRT
<213> ORGANISM: Homo sapiens

<400> SEQUENCE: 967

Phe Ala Met Glu Lys Lys Gly Asn Tyr
1               5

<210> SEQ ID NO 968
<211> LENGTH: 9
<212> TYPE: PRT
<213> ORGANISM: Homo sapiens

<400> SEQUENCE: 968

Glu Cys Arg Lys Gly Asn Tyr Val Glu
1               5

<210> SEQ ID NO 969
<211> LENGTH: 9
<212> TYPE: PRT
<213> ORGANISM: Homo sapiens

<400> SEQUENCE: 969

Pro Cys Gln Lys Lys Gly Asn Tyr Val
1               5

<210> SEQ ID NO 970
<211> LENGTH: 9
<212> TYPE: PRT
```

-continued

```
<213> ORGANISM: Homo sapiens

<400> SEQUENCE: 970

Leu Gly Asp Glu Lys Lys Gly Asn Phe
1               5

<210> SEQ ID NO 971
<211> LENGTH: 9
<212> TYPE: PRT
<213> ORGANISM: Homo sapiens

<400> SEQUENCE: 971

Pro Ala Ser Glu Glu Lys Lys Gly Phe
1               5

<210> SEQ ID NO 972
<211> LENGTH: 9
<212> TYPE: PRT
<213> ORGANISM: Homo sapiens

<400> SEQUENCE: 972

Ile Arg Gln Lys Gly Asn Tyr Val Ser
1               5

<210> SEQ ID NO 973
<211> LENGTH: 9
<212> TYPE: PRT
<213> ORGANISM: Homo sapiens

<400> SEQUENCE: 973

Leu Trp Ser Glu Lys Lys Gly Asn Gly
1               5

<210> SEQ ID NO 974
<211> LENGTH: 9
<212> TYPE: PRT
<213> ORGANISM: Homo sapiens

<400> SEQUENCE: 974

Thr Lys Ser Lys Lys Gly Asn Tyr Arg
1               5

<210> SEQ ID NO 975
<211> LENGTH: 9
<212> TYPE: PRT
<213> ORGANISM: Homo sapiens

<400> SEQUENCE: 975

Ile Arg Arg Gly Asn Tyr Val Val Ser
1               5

<210> SEQ ID NO 976
<211> LENGTH: 9
<212> TYPE: PRT
<213> ORGANISM: Homo sapiens

<400> SEQUENCE: 976

Leu Lys Glu Glu Glu Lys Lys Gly Asp
1               5

<210> SEQ ID NO 977
<211> LENGTH: 9
<212> TYPE: PRT
<213> ORGANISM: Homo sapiens
```

-continued

```
<400> SEQUENCE: 977

Arg Ala Glu Gly Asn Tyr Val Val Arg
1               5

<210> SEQ ID NO 978
<211> LENGTH: 9
<212> TYPE: PRT
<213> ORGANISM: Homo sapiens

<400> SEQUENCE: 978

Met Gly Glu Lys Lys Gly Asn Tyr Asp
1               5

<210> SEQ ID NO 979
<211> LENGTH: 9
<212> TYPE: PRT
<213> ORGANISM: Homo sapiens

<400> SEQUENCE: 979

Thr Ala Asp Glu Lys Lys Gly Asn Phe
1               5

<210> SEQ ID NO 980
<211> LENGTH: 9
<212> TYPE: PRT
<213> ORGANISM: Homo sapiens

<400> SEQUENCE: 980

Arg Leu Lys Glu Lys Lys Gly Asn Val
1               5

<210> SEQ ID NO 981
<211> LENGTH: 9
<212> TYPE: PRT
<213> ORGANISM: Homo sapiens

<400> SEQUENCE: 981

Gln Leu Pro Lys Lys Gly Asn Tyr Ile
1               5

<210> SEQ ID NO 982
<211> LENGTH: 9
<212> TYPE: PRT
<213> ORGANISM: Homo sapiens

<400> SEQUENCE: 982

Thr Lys Gly Lys Gly Asn Tyr Val Ile
1               5

<210> SEQ ID NO 983
<211> LENGTH: 9
<212> TYPE: PRT
<213> ORGANISM: Homo sapiens

<400> SEQUENCE: 983

Glu Val Ser Lys Gly Asn Tyr Val Ala
1               5

<210> SEQ ID NO 984
<211> LENGTH: 9
<212> TYPE: PRT
<213> ORGANISM: Homo sapiens

<400> SEQUENCE: 984
```

-continued

```
Asn Val Arg Lys Gly Asn Tyr Val Ala
1               5

<210> SEQ ID NO 985
<211> LENGTH: 9
<212> TYPE: PRT
<213> ORGANISM: Homo sapiens

<400> SEQUENCE: 985

Arg Thr Gln Glu Glu Lys Lys Gly Ile
1               5

<210> SEQ ID NO 986
<211> LENGTH: 9
<212> TYPE: PRT
<213> ORGANISM: Homo sapiens

<400> SEQUENCE: 986

Gln Ser Cys Glu Lys Lys Gly Asn Trp
1               5

<210> SEQ ID NO 987
<211> LENGTH: 9
<212> TYPE: PRT
<213> ORGANISM: Homo sapiens

<400> SEQUENCE: 987

Phe Pro Met Glu Glu Lys Lys Gly Arg
1               5

<210> SEQ ID NO 988
<211> LENGTH: 9
<212> TYPE: PRT
<213> ORGANISM: Homo sapiens

<400> SEQUENCE: 988

Ser Glu Glu Lys Lys Gly Asn Tyr Gln
1               5

<210> SEQ ID NO 989
<211> LENGTH: 9
<212> TYPE: PRT
<213> ORGANISM: Homo sapiens

<400> SEQUENCE: 989

Leu Glu Leu Lys Gly Asn Tyr Val Pro
1               5

<210> SEQ ID NO 990
<211> LENGTH: 9
<212> TYPE: PRT
<213> ORGANISM: Homo sapiens

<400> SEQUENCE: 990

Glu Gly Pro Glu Glu Lys Lys Gly Tyr
1               5

<210> SEQ ID NO 991
<211> LENGTH: 9
<212> TYPE: PRT
<213> ORGANISM: Homo sapiens

<400> SEQUENCE: 991

Ile Ser Lys Glu Lys Lys Gly Asn Phe
1               5
```

-continued

```
<210> SEQ ID NO 992
<211> LENGTH: 9
<212> TYPE: PRT
<213> ORGANISM: Homo sapiens

<400> SEQUENCE: 992

Glu His Met Lys Gly Asn Tyr Val Gly
1               5

<210> SEQ ID NO 993
<211> LENGTH: 9
<212> TYPE: PRT
<213> ORGANISM: Homo sapiens

<400> SEQUENCE: 993

Arg Glu Leu Glu Lys Lys Gly Asn Ala
1               5

<210> SEQ ID NO 994
<211> LENGTH: 9
<212> TYPE: PRT
<213> ORGANISM: Homo sapiens

<400> SEQUENCE: 994

Ala Glu His Gly Asn Tyr Val Val Thr
1               5

<210> SEQ ID NO 995
<211> LENGTH: 9
<212> TYPE: PRT
<213> ORGANISM: Homo sapiens

<400> SEQUENCE: 995

Thr Arg Val Lys Lys Gly Asn Tyr Ser
1               5

<210> SEQ ID NO 996
<211> LENGTH: 9
<212> TYPE: PRT
<213> ORGANISM: Homo sapiens

<400> SEQUENCE: 996

Trp Lys Glu Glu Glu Lys Lys Gly Arg
1               5

<210> SEQ ID NO 997
<211> LENGTH: 15
<212> TYPE: PRT
<213> ORGANISM: Homo sapiens

<400> SEQUENCE: 997

Phe Lys Arg Glu Leu Met Asn Leu Pro Gln Gln Cys Asn Phe Arg
1               5                  10                  15

<210> SEQ ID NO 998
<211> LENGTH: 15
<212> TYPE: PRT
<213> ORGANISM: Homo sapiens

<400> SEQUENCE: 998

Gln Phe Lys Arg Glu Leu Met Asn Leu Pro Gln Gln Cys Asn Phe
1               5                  10                  15
```

```
<210> SEQ ID NO 999
<211> LENGTH: 15
<212> TYPE: PRT
<213> ORGANISM: Homo sapiens

<400> SEQUENCE: 999

Gln Gln Phe Lys Arg Glu Leu Met Asn Leu Pro Gln Gln Cys Asn
1               5                   10                  15

<210> SEQ ID NO 1000
<211> LENGTH: 15
<212> TYPE: PRT
<213> ORGANISM: Homo sapiens

<400> SEQUENCE: 1000

Glu Gln His Ile Met Gln Arg Ile Met Gly Glu Gln Glu Gln Tyr
1               5                   10                  15

<210> SEQ ID NO 1001
<211> LENGTH: 15
<212> TYPE: PRT
<213> ORGANISM: Homo sapiens

<400> SEQUENCE: 1001

Gln Phe Lys Arg Glu Leu Met Asn Leu Pro Gln Gln Cys Asn Phe
1               5                   10                  15

<210> SEQ ID NO 1002
<211> LENGTH: 15
<212> TYPE: PRT
<213> ORGANISM: Homo sapiens

<400> SEQUENCE: 1002

Asn Thr Gln Arg Cys Met Cys Glu Ala Leu Gln Gln Ile Met Glu
1               5                   10                  15

<210> SEQ ID NO 1003
<211> LENGTH: 15
<212> TYPE: PRT
<213> ORGANISM: Homo sapiens

<400> SEQUENCE: 1003

Gln Gln Phe Lys Arg Glu Leu Met Asn Leu Pro Gln Gln Cys Asn
1               5                   10                  15

<210> SEQ ID NO 1004
<211> LENGTH: 15
<212> TYPE: PRT
<213> ORGANISM: Homo sapiens

<400> SEQUENCE: 1004

Phe Lys Arg Glu Leu Met Asn Leu Pro Gln Gln Cys Asn Phe Arg
1               5                   10                  15

<210> SEQ ID NO 1005
<211> LENGTH: 15
<212> TYPE: PRT
<213> ORGANISM: Homo sapiens

<400> SEQUENCE: 1005

Gln Phe Lys Arg Glu Leu Met Asn Leu Pro Gln Gln Cys Asn Phe
1               5                   10                  15

<210> SEQ ID NO 1006
<211> LENGTH: 15
```

```
<212> TYPE: PRT
<213> ORGANISM: Homo sapiens

<400> SEQUENCE: 1006

Lys Pro Cys Glu Gln His Ile Met Gln Arg Ile Met Gly Glu Gln
1               5                   10                  15

<210> SEQ ID NO 1007
<211> LENGTH: 15
<212> TYPE: PRT
<213> ORGANISM: Homo sapiens

<400> SEQUENCE: 1007

Glu Gln His Ile Met Gln Arg Ile Met Gly Glu Gln Glu Gln Tyr
1               5                   10                  15

<210> SEQ ID NO 1008
<211> LENGTH: 15
<212> TYPE: PRT
<213> ORGANISM: Homo sapiens

<400> SEQUENCE: 1008

Cys Glu Gln His Ile Met Gln Arg Ile Met Gly Glu Gln Glu Gln
1               5                   10                  15

<210> SEQ ID NO 1009
<211> LENGTH: 15
<212> TYPE: PRT
<213> ORGANISM: Homo sapiens

<400> SEQUENCE: 1009

Pro Cys Glu Gln His Ile Met Gln Arg Ile Met Gly Glu Gln Glu
1               5                   10                  15

<210> SEQ ID NO 1010
<211> LENGTH: 15
<212> TYPE: PRT
<213> ORGANISM: Homo sapiens

<400> SEQUENCE: 1010

Lys Pro Cys Glu Gln His Ile Met Gln Arg Ile Met Gly Glu Gln
1               5                   10                  15

<210> SEQ ID NO 1011
<211> LENGTH: 15
<212> TYPE: PRT
<213> ORGANISM: Homo sapiens

<400> SEQUENCE: 1011

Met Val Gln Gln Phe Lys Arg Glu Leu Met Asn Leu Pro Gln Gln
1               5                   10                  15

<210> SEQ ID NO 1012
<211> LENGTH: 15
<212> TYPE: PRT
<213> ORGANISM: Homo sapiens

<400> SEQUENCE: 1012

Gln Phe Lys Arg Glu Leu Met Asn Leu Pro Gln Gln Cys Asn Phe
1               5                   10                  15

<210> SEQ ID NO 1013
<211> LENGTH: 15
<212> TYPE: PRT
<213> ORGANISM: Homo sapiens
```

-continued

```
<400> SEQUENCE: 1013

Cys Glu Gln His Ile Met Gln Arg Ile Met Gly Glu Gln Glu Gln
1               5                   10                  15

<210> SEQ ID NO 1014
<211> LENGTH: 15
<212> TYPE: PRT
<213> ORGANISM: Homo sapiens

<400> SEQUENCE: 1014

Lys Pro Cys Glu Gln His Ile Met Gln Arg Ile Met Gly Glu Gln
1               5                   10                  15

<210> SEQ ID NO 1015
<211> LENGTH: 15
<212> TYPE: PRT
<213> ORGANISM: Homo sapiens

<400> SEQUENCE: 1015

Pro Cys Glu Gln His Ile Met Gln Arg Ile Met Gly Glu Gln Glu
1               5                   10                  15

<210> SEQ ID NO 1016
<211> LENGTH: 15
<212> TYPE: PRT
<213> ORGANISM: Homo sapiens

<400> SEQUENCE: 1016

Leu Asn Arg Leu Leu Met Asn Leu Pro Gln Gln Ala Thr Leu Ile
1               5                   10                  15

<210> SEQ ID NO 1017
<211> LENGTH: 15
<212> TYPE: PRT
<213> ORGANISM: Homo sapiens

<400> SEQUENCE: 1017

Ile Arg Gln Leu Glu Leu Met Asn Leu Pro Gln Ile Tyr Leu Asn
1               5                   10                  15

<210> SEQ ID NO 1018
<211> LENGTH: 15
<212> TYPE: PRT
<213> ORGANISM: Homo sapiens

<400> SEQUENCE: 1018

Met Ile Arg Leu Arg Glu Leu Met Asn Leu Pro Val Ala Arg Cys
1               5                   10                  15

<210> SEQ ID NO 1019
<211> LENGTH: 15
<212> TYPE: PRT
<213> ORGANISM: Homo sapiens

<400> SEQUENCE: 1019

Val Gln Ala Met Met Gln Arg Ile Met Gly Glu Leu Leu Leu Glu
1               5                   10                  15

<210> SEQ ID NO 1020
<211> LENGTH: 15
<212> TYPE: PRT
<213> ORGANISM: Homo sapiens

<400> SEQUENCE: 1020
```

Arg Gln Met Gln Glu Leu Met Asn Leu Pro Gln Leu Ile Leu Ile
1               5                   10                  15

<210> SEQ ID NO 1021
<211> LENGTH: 15
<212> TYPE: PRT
<213> ORGANISM: Homo sapiens

<400> SEQUENCE: 1021

Met Gln Phe Met Cys Met Cys Glu Ala Leu Gln Ala Leu Leu Val
1               5                   10                  15

<210> SEQ ID NO 1022
<211> LENGTH: 15
<212> TYPE: PRT
<213> ORGANISM: Homo sapiens

<400> SEQUENCE: 1022

Pro Met Leu Leu Arg Glu Leu Met Asn Leu Pro Arg Thr Arg Arg
1               5                   10                  15

<210> SEQ ID NO 1023
<211> LENGTH: 15
<212> TYPE: PRT
<213> ORGANISM: Homo sapiens

<400> SEQUENCE: 1023

Leu Ile Leu Leu Leu Met Asn Leu Pro Gln Gln Asn Thr Val Asn
1               5                   10                  15

<210> SEQ ID NO 1024
<211> LENGTH: 15
<212> TYPE: PRT
<213> ORGANISM: Homo sapiens

<400> SEQUENCE: 1024

Phe Leu Ile Phe Glu Leu Met Asn Leu Pro Gln Met Arg Asn Ile
1               5                   10                  15

<210> SEQ ID NO 1025
<211> LENGTH: 15
<212> TYPE: PRT
<213> ORGANISM: Homo sapiens

<400> SEQUENCE: 1025

Ile Met Phe Leu Gln His Ile Met Gln Arg Ile Glu Leu Gln Tyr
1               5                   10                  15

<210> SEQ ID NO 1026
<211> LENGTH: 15
<212> TYPE: PRT
<213> ORGANISM: Homo sapiens

<400> SEQUENCE: 1026

Leu Arg Met Leu Met Gln Arg Ile Met Gly Glu Asn Gln Arg Val
1               5                   10                  15

<210> SEQ ID NO 1027
<211> LENGTH: 15
<212> TYPE: PRT
<213> ORGANISM: Homo sapiens

<400> SEQUENCE: 1027

Arg Glu Leu Gln Ile Met Gln Arg Ile Met Gly Ala Val Leu Cys

-continued

```
1               5                10               15

<210> SEQ ID NO 1028
<211> LENGTH: 15
<212> TYPE: PRT
<213> ORGANISM: Homo sapiens

<400> SEQUENCE: 1028

Leu His Gln Arg His Ile Met Gln Arg Ile Met Ala Gln Val Phe
1               5                10               15

<210> SEQ ID NO 1029
<211> LENGTH: 15
<212> TYPE: PRT
<213> ORGANISM: Homo sapiens

<400> SEQUENCE: 1029

Leu Gln Val Asp Gln His Ile Met Gln Arg Ile Ser Cys Leu Met
1               5                10               15

<210> SEQ ID NO 1030
<211> LENGTH: 15
<212> TYPE: PRT
<213> ORGANISM: Homo sapiens

<400> SEQUENCE: 1030

Asn Ile Ile Leu Phe Lys Arg Glu Leu Met Asn Met His Gln Cys
1               5                10               15

<210> SEQ ID NO 1031
<211> LENGTH: 15
<212> TYPE: PRT
<213> ORGANISM: Homo sapiens

<400> SEQUENCE: 1031

Cys Cys Val Gln Glu Leu Met Asn Leu Pro Gln Arg Cys Ala Ala
1               5                10               15

<210> SEQ ID NO 1032
<211> LENGTH: 15
<212> TYPE: PRT
<213> ORGANISM: Homo sapiens

<400> SEQUENCE: 1032

Met Ile Met Met Ile Met Gln Arg Ile Met Gly Ser Val Cys Gly
1               5                10               15

<210> SEQ ID NO 1033
<211> LENGTH: 15
<212> TYPE: PRT
<213> ORGANISM: Homo sapiens

<400> SEQUENCE: 1033

Gly Cys Ala Cys Gln His Ile Met Gln Arg Ile Pro Cys Ala Arg
1               5                10               15

<210> SEQ ID NO 1034
<211> LENGTH: 15
<212> TYPE: PRT
<213> ORGANISM: Homo sapiens

<400> SEQUENCE: 1034

Cys Cys Ser Ile His Ile Met Gln Arg Ile Met Ala Leu Ala Asp
1               5                10               15
```

<210> SEQ ID NO 1035
<211> LENGTH: 5
<212> TYPE: PRT
<213> ORGANISM: Homo sapiens

<400> SEQUENCE: 1035

Leu Met Leu Gln Gln
1               5

<210> SEQ ID NO 1036
<211> LENGTH: 5
<212> TYPE: PRT
<213> ORGANISM: Homo sapiens

<400> SEQUENCE: 1036

Glu Leu Asn Pro Gln
1               5

<210> SEQ ID NO 1037
<211> LENGTH: 5
<212> TYPE: PRT
<213> ORGANISM: Homo sapiens

<400> SEQUENCE: 1037

Arg Glu Met Leu Pro
1               5

<210> SEQ ID NO 1038
<211> LENGTH: 5
<212> TYPE: PRT
<213> ORGANISM: Homo sapiens

<400> SEQUENCE: 1038

Met Gln Ile Gly Glu
1               5

<210> SEQ ID NO 1039
<211> LENGTH: 5
<212> TYPE: PRT
<213> ORGANISM: Homo sapiens

<400> SEQUENCE: 1039

Glu Leu Asn Pro Gln
1               5

<210> SEQ ID NO 1040
<211> LENGTH: 5
<212> TYPE: PRT
<213> ORGANISM: Homo sapiens

<400> SEQUENCE: 1040

Cys Met Glu Leu Gln
1               5

<210> SEQ ID NO 1041
<211> LENGTH: 5
<212> TYPE: PRT
<213> ORGANISM: Homo sapiens

<400> SEQUENCE: 1041

Arg Glu Met Leu Pro
1               5

<210> SEQ ID NO 1042

```
<211> LENGTH: 5
<212> TYPE: PRT
<213> ORGANISM: Homo sapiens

<400> SEQUENCE: 1042

Leu Met Leu Gln Gln
1               5

<210> SEQ ID NO 1043
<211> LENGTH: 5
<212> TYPE: PRT
<213> ORGANISM: Homo sapiens

<400> SEQUENCE: 1043

Glu Leu Asn Pro Gln
1               5

<210> SEQ ID NO 1044
<211> LENGTH: 5
<212> TYPE: PRT
<213> ORGANISM: Homo sapiens

<400> SEQUENCE: 1044

Gln His Met Arg Ile
1               5

<210> SEQ ID NO 1045
<211> LENGTH: 5
<212> TYPE: PRT
<213> ORGANISM: Homo sapiens

<400> SEQUENCE: 1045

Met Gln Ile Gly Glu
1               5

<210> SEQ ID NO 1046
<211> LENGTH: 5
<212> TYPE: PRT
<213> ORGANISM: Homo sapiens

<400> SEQUENCE: 1046

Ile Met Arg Met Gly
1               5

<210> SEQ ID NO 1047
<211> LENGTH: 5
<212> TYPE: PRT
<213> ORGANISM: Homo sapiens

<400> SEQUENCE: 1047

His Ile Gln Ile Met
1               5

<210> SEQ ID NO 1048
<211> LENGTH: 5
<212> TYPE: PRT
<213> ORGANISM: Homo sapiens

<400> SEQUENCE: 1048

Gln His Met Arg Ile
1               5

<210> SEQ ID NO 1049
<211> LENGTH: 5
<212> TYPE: PRT
```

```
<213> ORGANISM: Homo sapiens

<400> SEQUENCE: 1049

Phe Lys Glu Met Asn
1               5

<210> SEQ ID NO 1050
<211> LENGTH: 5
<212> TYPE: PRT
<213> ORGANISM: Homo sapiens

<400> SEQUENCE: 1050

Glu Leu Asn Pro Gln
1               5

<210> SEQ ID NO 1051
<211> LENGTH: 5
<212> TYPE: PRT
<213> ORGANISM: Homo sapiens

<400> SEQUENCE: 1051

Ile Met Arg Met Gly
1               5

<210> SEQ ID NO 1052
<211> LENGTH: 5
<212> TYPE: PRT
<213> ORGANISM: Homo sapiens

<400> SEQUENCE: 1052

Gln His Met Arg Ile
1               5

<210> SEQ ID NO 1053
<211> LENGTH: 5
<212> TYPE: PRT
<213> ORGANISM: Homo sapiens

<400> SEQUENCE: 1053

His Ile Gln Ile Met
1               5

<210> SEQ ID NO 1054
<211> LENGTH: 15
<212> TYPE: PRT
<213> ORGANISM: Homo sapiens
<220> FEATURE:
<221> NAME/KEY: misc_feature
<222> LOCATION: (11)..(11)
<223> OTHER INFORMATION: Xaa can be any naturally occurring amino acid

<400> SEQUENCE: 1054

Lys Ile His Ala Arg Glu Ile Phe Asp Ser Xaa Gly Asn Pro Thr
1               5                   10                  15

<210> SEQ ID NO 1055
<211> LENGTH: 15
<212> TYPE: PRT
<213> ORGANISM: Homo sapiens
<220> FEATURE:
<221> NAME/KEY: misc_feature
<222> LOCATION: (8)..(8)
<223> OTHER INFORMATION: Xaa can be any naturally occurring amino acid

<400> SEQUENCE: 1055

Ala Arg Glu Ile Phe Asp Ser Xaa Gly Asn Pro Thr Val Glu Val
```

-continued

```
1               5               10              15

<210> SEQ ID NO 1056
<211> LENGTH: 15
<212> TYPE: PRT
<213> ORGANISM: Homo sapiens
<220> FEATURE:
<221> NAME/KEY: misc_feature
<222> LOCATION: (8)..(8)
<223> OTHER INFORMATION: Xaa can be any naturally occurring amino acid

<400> SEQUENCE: 1056

Ala Arg Glu Ile Phe Asp Ser Xaa Gly Asn Pro Thr Val Glu Val
1               5               10              15

<210> SEQ ID NO 1057
<211> LENGTH: 15
<212> TYPE: PRT
<213> ORGANISM: Homo sapiens
<220> FEATURE:
<221> NAME/KEY: misc_feature
<222> LOCATION: (8)..(8)
<223> OTHER INFORMATION: Xaa can be any naturally occurring amino acid

<400> SEQUENCE: 1057

Phe Thr Ser Lys Gly Leu Phe Xaa Ala Ala Val Pro Ser Gly Ala
1               5               10              15

<210> SEQ ID NO 1058
<211> LENGTH: 15
<212> TYPE: PRT
<213> ORGANISM: Homo sapiens
<220> FEATURE:
<221> NAME/KEY: misc_feature
<222> LOCATION: (6)..(6)
<223> OTHER INFORMATION: Xaa can be any naturally occurring amino acid

<400> SEQUENCE: 1058

Ser Lys Gly Leu Phe Xaa Ala Ala Val Pro Ser Gly Ala Ser Thr
1               5               10              15

<210> SEQ ID NO 1059
<211> LENGTH: 15
<212> TYPE: PRT
<213> ORGANISM: Homo sapiens
<220> FEATURE:
<221> NAME/KEY: misc_feature
<222> LOCATION: (5)..(5)
<223> OTHER INFORMATION: Xaa can be any naturally occurring amino acid

<400> SEQUENCE: 1059

Lys Gly Leu Phe Xaa Ala Ala Val Pro Ser Gly Ala Ser Thr Gly
1               5               10              15

<210> SEQ ID NO 1060
<211> LENGTH: 15
<212> TYPE: PRT
<213> ORGANISM: Homo sapiens
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
```

```
<400> SEQUENCE: 1060

Pro Gly Gly Val Tyr Ala Thr Xaa Ser Ser Ala Val Xaa Leu Xaa
1               5                   10                  15

<210> SEQ ID NO 1061
<211> LENGTH: 15
<212> TYPE: PRT
<213> ORGANISM: Homo sapiens
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 1061

Val Tyr Ala Thr Xaa Ser Ser Ala Val Xaa Leu Xaa Ser Ser Val
1               5                   10                  15

<210> SEQ ID NO 1062
<211> LENGTH: 15
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 1062

Xaa Ser Ser Ala Val Xaa Leu Xaa Ser Ser Val Pro Gly Val Arg
1               5                   10                  15

<210> SEQ ID NO 1063
<211> LENGTH: 15
<212> TYPE: PRT
<213> ORGANISM: Homo sapiens
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 1063

Ser Ser Ala Val Xaa Leu Xaa Ser Ser Val Pro Gly Val Arg Leu
1               5                   10                  15

<210> SEQ ID NO 1064
<211> LENGTH: 15
<212> TYPE: PRT
<213> ORGANISM: Homo sapiens
<220> FEATURE:
<221> NAME/KEY: misc_feature
<222> LOCATION: (4)..(4)
```

```
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 1064

Ser Ala Val Xaa Leu Xaa Ser Ser Val Pro Gly Val Arg Leu Leu
1               5                   10                  15

<210> SEQ ID NO 1065
<211> LENGTH: 15
<212> TYPE: PRT
<213> ORGANISM: Homo sapiens
<220> FEATURE:
<221> NAME/KEY: misc_feature
<222> LOCATION: (11)..(11)
<223> OTHER INFORMATION: Xaa can be any naturally occurring amino acid

<400> SEQUENCE: 1065

Pro Leu Pro Asn Phe Ser Ser Leu Asn Leu Xaa Glu Thr Asn Leu
1               5                   10                  15

<210> SEQ ID NO 1066
<211> LENGTH: 15
<212> TYPE: PRT
<213> ORGANISM: Homo sapiens
<220> FEATURE:
<221> NAME/KEY: misc_feature
<222> LOCATION: (8)..(8)
<223> OTHER INFORMATION: Xaa can be any naturally occurring amino acid

<400> SEQUENCE: 1066

Asn Phe Ser Ser Leu Asn Leu Xaa Glu Thr Asn Leu Asp Ser Leu
1               5                   10                  15

<210> SEQ ID NO 1067
<211> LENGTH: 15
<212> TYPE: PRT
<213> ORGANISM: Homo sapiens
<220> FEATURE:
<221> NAME/KEY: misc_feature
<222> LOCATION: (6)..(6)
<223> OTHER INFORMATION: Xaa can be any naturally occurring amino acid

<400> SEQUENCE: 1067

Ser Ser Leu Asn Leu Xaa Glu Thr Asn Leu Asp Ser Leu Pro Leu
1               5                   10                  15

<210> SEQ ID NO 1068
<211> LENGTH: 15
<212> TYPE: PRT
<213> ORGANISM: Homo sapiens
<220> FEATURE:
<221> NAME/KEY: misc_feature
<222> LOCATION: (11)..(11)
<223> OTHER INFORMATION: Xaa can be any naturally occurring amino acid

<400> SEQUENCE: 1068

Pro Leu Ile Phe Arg Glu Ile Phe Asp Ser Xaa Gly Val Gln Ile
1               5                   10                  15

<210> SEQ ID NO 1069
<211> LENGTH: 15
<212> TYPE: PRT
<213> ORGANISM: Homo sapiens
<220> FEATURE:
<221> NAME/KEY: misc_feature
<222> LOCATION: (8)..(8)
```

-continued

<223> OTHER INFORMATION: Xaa can be any naturally occurring amino acid

<400> SEQUENCE: 1069

Lys Leu Ile Phe Phe Asp Ser Xaa Gly Asn Pro Thr Ala Asp Met
1               5                   10                  15

<210> SEQ ID NO 1070
<211> LENGTH: 15
<212> TYPE: PRT
<213> ORGANISM: Homo sapiens
<220> FEATURE:
<221> NAME/KEY: misc_feature
<222> LOCATION: (8)..(8)
<223> OTHER INFORMATION: Xaa can be any naturally occurring amino acid

<400> SEQUENCE: 1070

Asp Phe Asn Phe Phe Asp Ser Xaa Gly Asn Pro Ser Ala Ser Leu
1               5                   10                  15

<210> SEQ ID NO 1071
<211> LENGTH: 15
<212> TYPE: PRT
<213> ORGANISM: Homo sapiens
<220> FEATURE:
<221> NAME/KEY: misc_feature
<222> LOCATION: (8)..(8)
<223> OTHER INFORMATION: Xaa can be any naturally occurring amino acid

<400> SEQUENCE: 1071

Gln Leu Leu Phe Gly Leu Phe Xaa Ala Ala Val Leu Thr Lys His
1               5                   10                  15

<210> SEQ ID NO 1072
<211> LENGTH: 15
<212> TYPE: PRT
<213> ORGANISM: Homo sapiens
<220> FEATURE:
<221> NAME/KEY: misc_feature
<222> LOCATION: (6)..(6)
<223> OTHER INFORMATION: Xaa can be any naturally occurring amino acid

<400> SEQUENCE: 1072

Ala Leu Gln Tyr Phe Xaa Ala Ala Val Pro Ser Ser Gly Leu Met
1               5                   10                  15

<210> SEQ ID NO 1073
<211> LENGTH: 15
<212> TYPE: PRT
<213> ORGANISM: Homo sapiens
<220> FEATURE:
<221> NAME/KEY: misc_feature
<222> LOCATION: (5)..(5)
<223> OTHER INFORMATION: Xaa can be any naturally occurring amino acid

<400> SEQUENCE: 1073

Val Ile Ile Phe Xaa Ala Ala Val Pro Ser Gly Gly Gly Leu Ile
1               5                   10                  15

<210> SEQ ID NO 1074
<211> LENGTH: 15
<212> TYPE: PRT
<213> ORGANISM: Homo sapiens
<220> FEATURE:
<221> NAME/KEY: misc_feature
<222> LOCATION: (8)..(8)
<223> OTHER INFORMATION: Xaa can be any naturally occurring amino acid

<400> SEQUENCE: 1074

```
Lys Gln Gln Tyr Tyr Ala Thr Xaa Ser Ser Ala Gly Ser Leu Phe
1               5                   10                  15
```

<210> SEQ ID NO 1075
<211> LENGTH: 15
<212> TYPE: PRT
<213> ORGANISM: Homo sapiens
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 1075

```
Asn Ala Phe Phe Xaa Ser Ser Ala Val Xaa Leu Gly Leu Ser Thr
1               5                   10                  15
```

<210> SEQ ID NO 1076
<211> LENGTH: 15
<212> TYPE: PRT
<213> ORGANISM: Homo sapiens
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 1076

```
Arg Ala Ile Leu Val Xaa Leu Xaa Ser Ser Val Lys Ala Gln Ile
1               5                   10                  15
```

<210> SEQ ID NO 1077
<211> LENGTH: 15
<212> TYPE: PRT
<213> ORGANISM: Homo sapiens
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 1077

```
Glu Met Leu Trp Xaa Leu Xaa Ser Ser Val Pro Gly Thr Gln Asp
1               5                   10                  15
```

<210> SEQ ID NO 1078
<211> LENGTH: 15
<212> TYPE: PRT
<213> ORGANISM: Homo sapiens
<220> FEATURE:
<221> NAME/KEY: misc_feature
<222> LOCATION: (6)..(6)
<223> OTHER INFORMATION: Xaa can be any naturally occurring amino acid

<400> SEQUENCE: 1078

```
Thr Leu Glu Trp Leu Xaa Ser Ser Val Pro Gly Ser Gly Leu Pro
1               5                   10                  15
```

<210> SEQ ID NO 1079
<211> LENGTH: 15
<212> TYPE: PRT

<213> ORGANISM: Homo sapiens
<220> FEATURE:
<221> NAME/KEY: misc_feature
<222> LOCATION: (11)..(11)
<223> OTHER INFORMATION: Xaa can be any naturally occurring amino acid

<400> SEQUENCE: 1079

Pro Phe Tyr Val Phe Ser Ser Leu Asn Leu Xaa Asn Asn Val Ala
1               5                   10                  15

<210> SEQ ID NO 1080
<211> LENGTH: 15
<212> TYPE: PRT
<213> ORGANISM: Homo sapiens
<220> FEATURE:
<221> NAME/KEY: misc_feature
<222> LOCATION: (8)..(8)
<223> OTHER INFORMATION: Xaa can be any naturally occurring amino acid

<400> SEQUENCE: 1080

Gln Leu Ile Trp Leu Asn Leu Xaa Glu Thr Asn Ile Gln Thr Ala
1               5                   10                  15

<210> SEQ ID NO 1081
<211> LENGTH: 15
<212> TYPE: PRT
<213> ORGANISM: Homo sapiens
<220> FEATURE:
<221> NAME/KEY: misc_feature
<222> LOCATION: (6)..(6)
<223> OTHER INFORMATION: Xaa can be any naturally occurring amino acid

<400> SEQUENCE: 1081

Tyr Gln Ile Leu Leu Xaa Glu Thr Asn Leu Asp Asp Ala Pro Met
1               5                   10                  15

<210> SEQ ID NO 1082
<211> LENGTH: 5
<212> TYPE: PRT
<213> ORGANISM: Homo sapiens
<220> FEATURE:
<221> NAME/KEY: misc_feature
<222> LOCATION: (5)..(5)
<223> OTHER INFORMATION: Xaa can be any naturally occurring amino acid

<400> SEQUENCE: 1082

Arg Glu Phe Ser Xaa
1               5

<210> SEQ ID NO 1083
<211> LENGTH: 5
<212> TYPE: PRT
<213> ORGANISM: Homo sapiens
<220> FEATURE:
<221> NAME/KEY: misc_feature
<222> LOCATION: (3)..(3)
<223> OTHER INFORMATION: Xaa can be any naturally occurring amino acid

<400> SEQUENCE: 1083

Phe Asp Xaa Asn Pro
1               5

<210> SEQ ID NO 1084
<211> LENGTH: 5
<212> TYPE: PRT
<213> ORGANISM: Homo sapiens
<220> FEATURE:
<221> NAME/KEY: misc_feature
<222> LOCATION: (3)..(3)

<223> OTHER INFORMATION: Xaa can be any naturally occurring amino acid

<400> SEQUENCE: 1084

Phe Asp Xaa Asn Pro
1               5

<210> SEQ ID NO 1085
<211> LENGTH: 5
<212> TYPE: PRT
<213> ORGANISM: Homo sapiens
<220> FEATURE:
<221> NAME/KEY: misc_feature
<222> LOCATION: (3)..(3)
<223> OTHER INFORMATION: Xaa can be any naturally occurring amino acid

<400> SEQUENCE: 1085

Gly Leu Xaa Ala Val
1               5

<210> SEQ ID NO 1086
<211> LENGTH: 5
<212> TYPE: PRT
<213> ORGANISM: Homo sapiens
<220> FEATURE:
<221> NAME/KEY: misc_feature
<222> LOCATION: (2)..(2)
<223> OTHER INFORMATION: Xaa can be any naturally occurring amino acid

<400> SEQUENCE: 1086

Phe Xaa Ala Pro Ser
1               5

<210> SEQ ID NO 1087
<211> LENGTH: 5
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid

<400> SEQUENCE: 1087

Xaa Ala Val Ser Gly
1               5

<210> SEQ ID NO 1088
<211> LENGTH: 5
<212> TYPE: PRT
<213> ORGANISM: Homo sapiens
<220> FEATURE:
<221> NAME/KEY: misc_feature
<222> LOCATION: (3)..(3)
<223> OTHER INFORMATION: Xaa can be any naturally occurring amino acid

<400> SEQUENCE: 1088

Tyr Ala Xaa Ser Ala
1               5

<210> SEQ ID NO 1089
<211> LENGTH: 5
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(4)

<223> OTHER INFORMATION: Xaa can be any naturally occurring amino acid

<400> SEQUENCE: 1089

Xaa Ser Ala Xaa Leu
1               5

<210> SEQ ID NO 1090
<211> LENGTH: 5
<212> TYPE: PRT
<213> ORGANISM: Homo sapiens
<220> FEATURE:
<221> NAME/KEY: misc_feature
<222> LOCATION: (2)..(3)
<223> OTHER INFORMATION: Xaa can be any naturally occurring amino acid

<400> SEQUENCE: 1090

Val Xaa Xaa Ser Val
1               5

<210> SEQ ID NO 1091
<211> LENGTH: 5
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid

<400> SEQUENCE: 1091

Xaa Leu Ser Val Pro
1               5

<210> SEQ ID NO 1092
<211> LENGTH: 5
<212> TYPE: PRT
<213> ORGANISM: Homo sapiens
<220> FEATURE:
<221> NAME/KEY: misc_feature
<222> LOCATION: (2)..(2)
<223> OTHER INFORMATION: Xaa can be any naturally occurring amino acid

<400> SEQUENCE: 1092

Leu Xaa Ser Pro Gly
1               5

<210> SEQ ID NO 1093
<211> LENGTH: 5
<212> TYPE: PRT
<213> ORGANISM: Homo sapiens
<220> FEATURE:
<221> NAME/KEY: misc_feature
<222> LOCATION: (5)..(5)
<223> OTHER INFORMATION: Xaa can be any naturally occurring amino acid

<400> SEQUENCE: 1093

Phe Ser Leu Leu Xaa
1               5

<210> SEQ ID NO 1094
<211> LENGTH: 5
<212> TYPE: PRT
<213> ORGANISM: Homo sapiens
<220> FEATURE:
<221> NAME/KEY: misc_feature
<222> LOCATION: (3)..(3)
<223> OTHER INFORMATION: Xaa can be any naturally occurring amino acid

<400> SEQUENCE: 1094

-continued

```
Leu Asn Xaa Thr Asn
1               5

<210> SEQ ID NO 1095
<211> LENGTH: 5
<212> TYPE: PRT
<213> ORGANISM: Homo sapiens
<220> FEATURE:
<221> NAME/KEY: misc_feature
<222> LOCATION: (2)..(2)
<223> OTHER INFORMATION: Xaa can be any naturally occurring amino acid

<400> SEQUENCE: 1095

Leu Xaa Thr Leu Asp
1               5
```

NEOANTIGEN IMMUNOTHERAPIES

CROSS-REFERENCE TO RELATED APPLICATIONS

The present application claims the benefit of U.S. Prov. Appl. 62/983,197 filed Feb. 28, 2020 and U.S. Prov. Appl. 62/859,962, filed Jun. 11, 2019, each of which are incorporated by reference herein in their entireties.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 165,000 Byte ASCII (Text) file named "37855-203_ST25," created on Jun. 11, 2020.

FIELD OF THE INVENTION

This invention provides a method for maximizing the immune response to mutated tumor specific proteins, either by means of stimulation of dendritic cells or T cells in vitro followed by administration of these cells to a patient, or by means of administration of a neoantigen vaccine in which de novo peptides, or their encoding nucleic acids, have been designed to ensure an appropriate level of binding affinity to a particular cancer patient's MHC alleles. In addition it provides for enhancing B cell responses to tumors with exposed B cell epitopes. A further application of the present invention is to provide for the design of peptides to modulate the T cell immune response in immunopathologies other than solid tumors.

BACKGROUND OF THE INVENTION

Immunology is based on self-non-self discrimination. Most pathogens contain molecular signatures that can be recognized by the host and trigger immune responses. Unlike pathogens, these molecular signatures are not generally expressed by tumor cells, making them more difficult to be distinguished from normal cells. However, T cells can recognize tumor antigens expressed by tumor cells. A class of tumor antigens, named tumor-associated antigens, is expressed in some normal tissues at low levels but is over-expressed in malignant cells. Many of the tumor-associated antigens have been identified as the targets of tumor-reactive T cells, isolated from tumor infiltrating lymphocytes (TILs), from draining lymph nodes or from peripheral blood. However, expression of these antigens in normal cells can trigger central and peripheral tolerance mechanisms that lead to the selection of T cells with low-affinity T cell receptors (TCR). Conversely, attempts to target tumor-associated antigens with high-affinity TCRs can lead to severe toxicities due to normal tissue destruction.

Another class of tumor antigens is tumor-specific neoantigens, which arise via mutations that alter amino acid coding sequences (non-synonymous somatic mutations). Some of these mutated peptides can be expressed, processed and presented on the cell surface, and subsequently recognized by T cells. Because normal tissues do not possess these somatic mutations, neoantigen-specific T cells are not subject to central and peripheral tolerance, and also lack the ability to induce normal tissue destruction. As a result, neoantigens are targets for T cell-based cancer immunotherapy.

In some instances tumor mutations may change the B cell epitopes in a tumor protein and create new epitope targets for antibody mediated therapy. Furthermore, changes in T cell neoantigens may alter T cell help to B cell epitopes.

In immunopathologies other than solid tumors, including but not limited to autoimmunity, allergies and inflammation, an excessive immune response by T cells may drive the pathology. In such a situation the provision of a very high affinity MHC binding peptide may allow dampening of the T cell response by causing specific clones to become exhausted and anergic. As this is a clonal specific intervention, the design of peptides which can bring about such modulation may be specific to the individual subject.

SUMMARY OF THE INVENTION

This invention provides a method for maximizing the immune response to mutated tumor specific proteins, either by means of stimulation of dendritic cells or T cells in vitro followed by administration of these cells to a patient, or by means of administration of a neoantigen vaccine in which de novo peptides, or their encoding nucleic acids, have been designed to ensure an appropriate level of binding affinity to a particular cancer patient's MHC alleles. In addition, it provides for enhancing B cell responses to tumors with exposed B cell epitopes.

In some preferred embodiments, the present invention provides methods for treating cancer in a subject comprising designing a group of one or more tumor-specific T-cell stimulating peptides, or nucleic acids encoding T cell stimulating peptides, which have a desired predicted binding affinity for the MHC alleles of the subject, comprising the following steps: obtaining a biopsy of the subject's tumor; sequencing proteins in said biopsy and identifying the mutated amino acids in said proteins and the peptide comprising each said mutated amino acids; determining T cell exposed motifs which comprise mutated amino acids in each of the proteins; determining the predicted binding affinity to the subject's MHC alleles of peptides which comprises each said T cell exposed motif, or a subset thereof; generating an array of alternative peptides not present in the tumor, wherein each peptide in the array comprises the amino acids of one of said T cell exposed motifs, and in which the amino acids not within the T cell exposed motif are substituted to change the predicted MHC binding affinity; selecting a group of one or more selected peptides from said array of alternative peptides which have a desired predicted binding affinity for one or more of the subject's MHC alleles; and synthesizing said group of one or more selected peptides, or nucleic acids encoding the selected peptides. In some preferred embodiments, the group of one or more selected peptides, or nucleic acids encoding the peptides, stimulate a tumor-specific T cell response in said subject upon administration. In some preferred embodiments, the group of one or more selected peptides, or nucleic acids encoding the peptides, are administered to said subject to stimulate a tumor-specific T cell response.

In some preferred embodiments, the MHC alleles are MHC type I and said T cell response is a CD8+ response. In some preferred embodiments, the MHC alleles are MHC type II and said T cell response is a CD4+ response. In some preferred embodiments, the selected peptides are 9 or 10 amino acids long. In some preferred embodiments, the selected peptides are 13-20 amino acids long.

In some preferred embodiments, the group of one or more selected peptides comprises at least 5 unique peptides not present in the proteins sequenced in the tumor. In some preferred embodiments, the group of one or more selected peptides comprises at least 20 unique peptides not present in the proteins sequenced in the tumor. In some preferred embodiments, the group of one or more selected peptides comprises at least 60 peptides not present in the proteins sequenced in the tumor.

In some preferred embodiments, the group of one or more selected peptides comprises more than 5 different T cell exposed motifs identified in the tumor. In some preferred embodiments, the group of one or more selected peptides comprises more than 10 different T cell exposed motifs identified in the tumor. In some preferred embodiments, the group of one or more selected peptides comprises more than 50 distinct T cell exposed motifs identified in the tumor. In some preferred embodiments, the group of one or more selected peptides comprises peptides each of which binds to one of at least 2 MHC alleles carried by said subject. In some preferred embodiments, the group of one or more selected peptides comprises peptides each of which binds to one of at least 4 MHC alleles carried by said subject.

In some preferred embodiments, the desired predicted binding affinity exceeds 85% of the binding affinity of all peptides in the tumor protein that comprises the mutated amino acid. In some preferred embodiments, the desired predicted binding affinity exceeds 95% of the binding affinity of all peptides in the tumor protein that comprises the mutated amino acid. In some preferred embodiments, the desired predicted binding affinity exceeds 99% of the binding affinity of all peptides in the tumor protein that comprises the mutated amino acid.

In some preferred embodiments, the desired predicted binding affinity is less than 20 nanomolar. In some preferred embodiments, the desired predicted binding affinity is less than 50 nanomolar. In some preferred embodiments, the desired predicted binding affinity is less than 100 nanomolar. In some preferred embodiments, the desired predicted binding affinity is less than 500 nanomolar.

In some preferred embodiments, the group of one or more selected peptides includes only peptides which are soluble in a desired solvent.

In some preferred embodiments, the proteins in the subject's biopsy comprise mutations that are unique to that subject. In some preferred embodiments, the group of one or more selected peptides, or nucleic acids encoding the peptides are unique to the subject. In some preferred embodiments, the proteins in the subject's biopsy comprise mutations that are found in a multiplicity of cancers affecting a multiplicity of subjects. In some preferred embodiments, the group of one or more selected peptides, or nucleic acids encoding the peptides are applicable to multiple subjects of shared MHC alleles.

In some preferred embodiments, the mutated amino acids comprise a substituted amino acid. In some preferred embodiments, the mutated amino acids comprise the product of insertion or deletion of one or more amino acids. In some preferred embodiments, the mutated amino acids comprise a new sequence that is the product of an in-frame nucleotide mutation. In some preferred embodiments, the mutated amino acids comprise a new sequence that is the product of a fusion of two gene. In some preferred embodiments, the protein sequencing is derived from a whole genome sequence. In some preferred embodiments, the MHC alleles of said subject are also determined from the whole genome sequence. In some preferred embodiments, the HLA alleles are determined by comparison of the sequence of chromosome 6 with a HLA sequence database.

In some preferred embodiments, each of said one or more selected peptides are linked by a linker to a fusion partner. In some preferred embodiments, the a multiplicity of said one or more selected peptides are linked by a linker to a fusion partner. In some preferred embodiments, the fusion partner is selected from the group consisting of a multimer of hydrophobic amino acids, or an unnatural hydrophobic amino acid, and a lipid core peptide system. In some preferred embodiments, the fusion partner facilitates nanoparticle formation. In some preferred embodiments, the fusion partner is selected from the group consisting of an immunoglobulin, Fc portion of an immunoglobulin, and fragment of an immunoglobulin. In some preferred embodiments, the linker is a cleavable linker. In some preferred embodiments, the linker is selected from the group consisting of linkers comprising one or more lysines, linkers comprising one or more arginines, and a cathepsin cleavable linker.

In some preferred embodiments, the group of one or more selected peptides, or nucleic acids encoding the peptides, are prescribed for an identified individual patient. In some preferred embodiments, the group of one or more selected peptides, or nucleic acids encoding the peptides, are formulated by a compounding pharmacy.

In some preferred embodiments, the peptides are selected from the group consisting of SEQ ID NO: 1-244 and combinations thereof.

In some preferred embodiments, where the peptides comprise a deletion, the deletion is the deletion in EGFRviii. In some preferred embodiments, the array of alternative peptides spans the deletion of exons 2-7 in EGFRviii. In some preferred embodiments, the peptides comprise the T cell exposed motifs from the group EEKKG (SEQ ID NO: 252), EKKGN (SEQ ID NO: 246), KKGNY (SEQ ID NO: 245), KGNYV (SEQ ID NO: 250), GNYVV (SEQ ID NO: 247). In some preferred embodiments, the array of alternative peptides comprise any of the peptides of SEQ 245-284. In other embodiments said dendritic cells are contacted with autologous T cells from the subject or donor T cells, and the T cells, or clonal populations arising from them, are then subsequently administered to the subject. In yet other preferred embodiments, the selected peptide and the MHC which binds it is engineered into a T cell and said T cell grown to provide an expanded clone which is subsequently administered to a subject.

In some preferred embodiments, the group of one or more selected peptides is provided to stimulate T cells in vitro which are subsequently administered to a subject. In some preferred embodiments, the group of one or more selected peptides, or the nucleic acids that encode them, is provided to contact dendritic cells in vitro, and the dendritic cells are subsequently administered to a subject.

In some preferred embodiments, the group of one or more selected peptides is administered to a subject as a vaccine.

In some preferred embodiments, the peptides in said group of one or more selected peptides are each encoded in nucleic acid which is administered to a subject as a vaccine. In some preferred embodiments, the nucleic acid is RNA. In some preferred embodiments, the nucleic acid is DNA.

In some preferred embodiments, the foregoing methods further comprise down-selecting the group of tumor-specific T-cell stimulating peptides on an allele-specific basis to remove those which have low probability of being accessible to T cell targeting in the subject, comprising: evaluating the predicted binding affinity to each of the subject's MHC alleles of the peptide which comprises each said T cell exposed motif in the mutated protein; determining if said predicted binding affinity is in the lower 50% of binding affinity for that MHC allele relative to predicted binding of other peptides in the same protein; and removing from the group of one or more selected peptides those peptides with low probability of being accessible to T cell targeting for that specific allele-T cell exposed motif combination.

In some preferred embodiments, the present invention provides a diagnostic test comprising peptides identified according to the foregoing methods.

In some preferred embodiments, the present invention provides a vaccination regimen comprising administering a group of peptides, or nucleic acids encoding the same peptides, or fusions selected according to the methods described above to a subject with cancer. In some preferred embodiments, the group of peptides, or nucleic acids encoding the same peptides, is divided into subgroups and each subgroup administered at a different timepoint. In some preferred embodiments, the subgroups of peptides, or nucleic acids encoding the same peptides, are selected so that each subgroup comprises peptides which collectively binds to a multiplicity of different MHC alleles, and include a multiplicity of different T cell exposed motif targets. In some preferred embodiments, the peptides included in said subgroups of peptides, or nucleic acids encoding the same peptides, are prioritized according to the frequency classification in the human proteome of the T cell exposed motif which each peptide comprises. In some preferred embodiments, the vaccination is accompanied by administration of an immunotherapy intervention. In some preferred embodiments, the immunotherapy intervention is a checkpoint inhibitor immunotherapeutic. In some preferred embodiments, the vaccination is followed by administration of an immunotherapy intervention. In some preferred embodiments, the immunotherapy intervention is a checkpoint inhibitor immunotherapeutic. In some preferred embodiments, the vaccination by each subgroup of peptides is followed by administration of an immunotherapy intervention. In some preferred embodiments, the immunotherapy intervention is a checkpoint inhibitor immunotherapeutic.

In some preferred embodiments, the present invention provides vaccines for administration to a subject with cancer comprising a group of peptides, or nucleic acids encoding the same peptides, or fusions selected according to the methods described above. In some preferred embodiments, the group of peptides or nucleic acids encoding the same peptides, is selected to stimulate T cells that target mutations unique to the particular subject. In some preferred embodiments, the group of peptides or nucleic acids encoding the same peptides, is selected to stimulate T cells that target mutations shared among a multiplicity of cancers. In some preferred embodiments, the group of peptides or nucleic acids encoding the same peptides, comprises both peptides selected to stimulate T cells that target mutations unique to the particular subject and those selected to stimulate T cells that target mutations shared among a multiplicity of cancers. In some preferred embodiments, the vaccine is administered to a subject parenterally. In some preferred embodiments, the vaccine is administered to a subject intradermally. In some preferred embodiments, the vaccine is administered by microneedle array. In some preferred embodiments, the vaccine comprises an adjuvant. In some preferred embodiments, the vaccine is accompanied by the application of a local pro-inflammatory agent. In some preferred embodiments, the vaccine also comprises peptides which occur naturally in the tumor protein. In some preferred embodiments, the vaccine also comprises one or more peptides which comprise a B cell epitope.

In some preferred embodiments, the present invention provides arrays of peptides comprising peptides selected by the methods described above to have a desired MHC binding affinity to stimulate T cells targeting mutated T cell exposed motifs shared by more than one cancer. In some preferred embodiments, the array of peptides includes peptides which are designed to stimulate T cells in multiple individuals carrying MHC of one or more specific HLA alleles. In some preferred embodiments, the desired binding affinity of each peptide is less than 20 nanomolar. In some preferred embodiments, the desired binding affinity of each peptide is less than 50 nanomolar. In some preferred embodiments, the desired binding affinity of each peptide is less than 100 nanomolar. In some preferred embodiments, the desired binding affinity of each peptide is less than 500 nanomolar. In some preferred embodiments, the mutated T cell exposed motifs are shared by 3 or more cancer types. In some preferred embodiments, the mutated T cell exposed motifs are shared by cancers affecting 3 or more tissue types. In some preferred embodiments, the mutated T cell exposed motifs are drawn from 5 or more proteins. In some preferred embodiments, the mutated T cell exposed motifs are drawn from 10 or more proteins. In some preferred embodiments, the array comprises any of the peptides of SEQ 1-244. In some preferred embodiments, where the peptides comprise a deletion, the deletion is the deletion in EGFRviii. In some preferred embodiments, the array of alternative peptides spans the deletion of exons 2-7 in EGFRviii. In some preferred embodiments, the peptides comprise the T cell exposed motifs from the group EEKKG (SEQ ID NO: 252), EKKGN (SEQ ID NO: 246), KKGNY (SEQ ID NO: 245), KGNYV (SEQ ID NO: 250), GNYVV (SEQ ID NO: 247). In some preferred embodiments, the array of alternative peptides comprise any of the peptides of SEQ 245-284. In some preferred embodiments, the array also comprises peptides which occur naturally in the tumor protein. In some preferred embodiments, the array also comprises one or more peptides which comprise a B cell epitope.

In some preferred embodiments, the present invention provides methods for designing a group of one or more of tumor-specific T-cell stimulating peptides for a particular subject with cancer, and identifying potential adverse targets of the T cells in the self-proteome of that subject, comprising: obtaining a biopsy of the subject's tumor; sequencing proteins in said biopsy and identifying the mutated amino acids in said proteins from said tumor; determining the T cell exposed motifs which comprise mutated amino acids in one or more proteins and which are selected as potential neoantigen targets; identifying those proteins in the normal human proteome which carry the same T cell exposed motifs; determining the predicted binding affinity of the subject's MHC alleles for the peptide which carries each T cell exposed motif in a protein of the normal human proteome; based on its MHC binding affinity, determining the probability that a T cell exposed motif would be presented and exposed to T cells in its natural context in the normal human proteome in this subject; listing the human proteome proteins which share T cell exposed motifs with said potential neoantigen targets and wherein the T cell exposed motif in the normal human proteome protein is are predicted to be exposed to T cells in the particular subject; and identifying those proteins in said listing which are a potential source of adverse effects. In some preferred embodiments, the subject's MHC alleles are MHC I. In some preferred embodiments, the subject's MHC alleles are MHC II. In some preferred embodiments, the predicted binding affinity of the subject's MHC alleles for the peptide which carries each T cell exposed motif in a protein of the normal human proteome is above 100 nm. In some preferred embodiments, the predicted binding affinity of the subject's MHC alleles for the peptide which carries each T cell exposed motif in a protein of the normal human proteome is in the highest 15% of peptides in that protein. In some preferred embodiments, the methods further comprise providing said listing to an oncologist to conduct a risk-benefit analysis of the use of said neoantigens in said subject.

In some preferred embodiments, the present invention provides methods for treating an immunopathology in a subject, comprising designing a group of one or more T-cell epitope peptides, or nucleic acids encoding T cell epitope peptides, which have a desired predicted binding affinity for MHC alleles of the subject, comprising the following steps: identifying a protein of interest comprising an epitope of interest that is causing the immunopathological T cell response; obtaining the sequence for said protein of interest and identifying the peptide comprising the epitope of interest; determining T cell exposed motifs in said epitope of interest; determining the predicted binding affinity to the subject's MHC alleles of peptides which comprise each said T cell exposed motif, or a subset thereof; generating an array of alternative peptides not present in the natural protein sequence, wherein each peptide in the array comprises the amino acids of one of said T cell exposed motifs, and in which one or more of the amino acids not within the T cell exposed motif are substituted to change the predicted MHC binding affinity; selecting a group of one or more selected peptides from said array of alternative peptides which have a desired predicted binding affinity for one or more of the subject's MHC alleles; synthesizing said group of one or more selected peptides, or nucleic acids encoding the selected peptides; and administering said group of one or more selected peptides, or nucleic acids encoding the selected peptides, to the subject.

In some preferred embodiments, the MHC alleles are MHC type I and said T cell response is a CD8+ response. In some preferred embodiments, the MHC alleles are MHC type II and said T cell response is a CD4+ response. In some preferred embodiments, the selected peptides are 9 or 10 amino acids long. In some preferred embodiments, the selected peptides are 13-20 amino acids long. In some preferred embodiments, the group of one or more selected peptides comprises at least 3 unique peptides not present in the original protein of interest in the subject. In some preferred embodiments, the group of one or more selected peptides comprises more than one different T cell exposed motifs. In some preferred embodiments, the group of one or more selected peptides comprises peptides each of which binds to more than one MHC alleles carried by said subject.

In some preferred embodiments, the desired predicted binding affinity exceeds 99% of the binding affinity of all peptides in the protein of interest that comprises the T cell epitope of interest. In some preferred embodiments, the desired predicted binding affinity is less than 500 nanomolar. In some preferred embodiments, the desired predicted binding affinity is less than 100 nanomolar. In some preferred embodiments, the desired predicted binding affinity is less than 50 nanomolar. In some preferred embodiments, the desired predicted binding affinity is less than 20 nanomolar.

In some preferred embodiments, the group of one or more selected peptides includes only peptides which are soluble in a desired solvent. In some preferred embodiments, the group of one or more selected peptides, or nucleic acids encoding the peptides are unique to the subject. In some preferred embodiments, the group of one or more selected peptides, or nucleic acids encoding the peptides are applicable to multiple subjects of shared MHC alleles.

In some preferred embodiments, each of said one or more selected peptides are linked by a linker to a fusion partner. In some preferred embodiments, the fusion partner is selected from the group consisting of a multimer of hydrophobic amino acids, or an unnatural hydrophobic amino acid, and a lipid core peptide system. In some preferred embodiments, the fusion partner facilitates nanoparticle formation. In some preferred embodiments, the fusion partner is selected from the group consisting of an immunoglobulin, Fc portion of an immunoglobulin and a fragment of an immunoglobulin. In some preferred embodiments, the linker is a cleavable linker.

In some preferred embodiments, the group of one or more selected peptides, or nucleic acids encoding the peptides, are prescribed for an identified individual patient. In some preferred embodiments, the group of one or more selected peptides, or nucleic acids encoding the peptides, are formulated by a compounding pharmacy.

In some preferred embodiments, the selected peptides are administered to the subject parenterally. In some preferred embodiments, the selected peptides are administered to the subject intradermally. In some preferred embodiments, the selected peptides are administered to the subject orally. In some preferred embodiments, the selected peptides are administered to the subject by microneedle array. In some preferred embodiments, the subject is afflicted by an allergy. In some preferred embodiments, the subject is afflicted by an autoimmune disease. In some preferred embodiments, the immunopathology arises as an adverse immune response to a biopharmaceutical protein.

In some preferred embodiments, the selected peptides comprise one or more of the peptides in Table 27 or nucleic acids encoding these peptides. In some preferred embodiments, the selected peptides comprise one or more of the peptides in Table 28 or nucleic acids encoding these peptides.

DEFINITIONS

Figure 1:
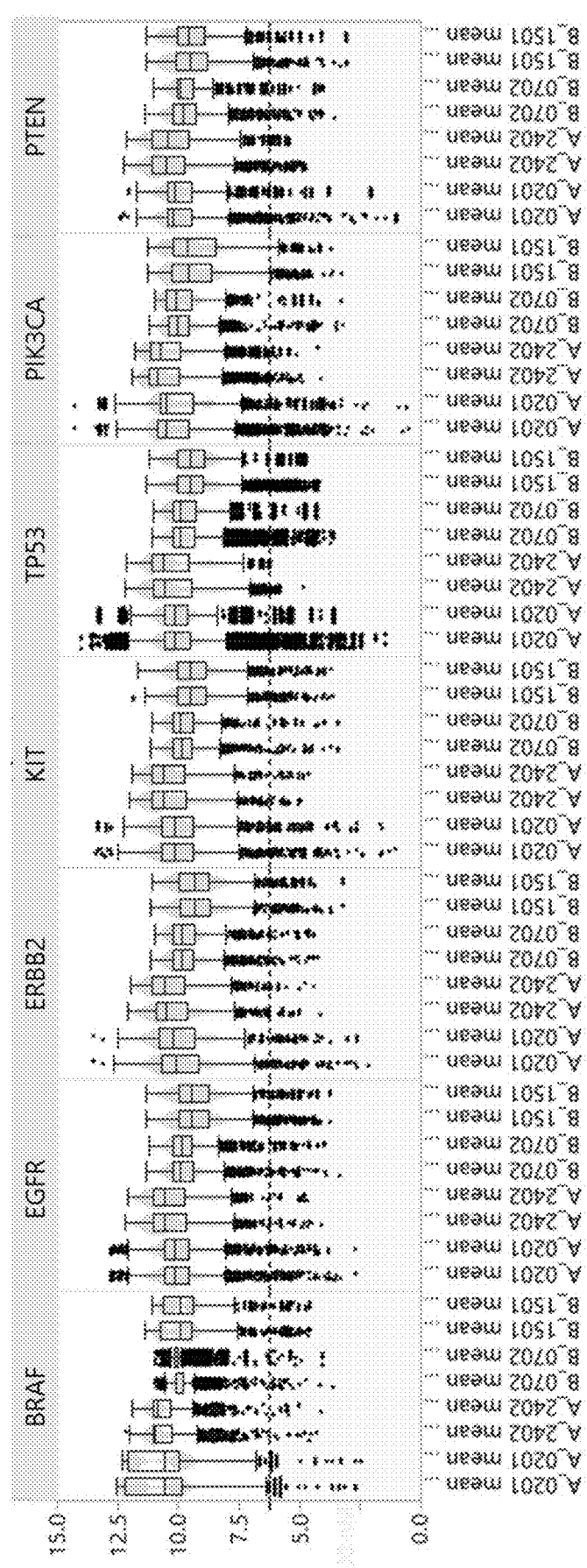
FIG. 1: Predicted binding affinity with mutant amino acid in T cell exposed motif I positions of wild type (wt) and mutant homologs of 7 tumor specific proteins. Predicted affinity (Y-axis=LN $IC_{50}$) for 4 MHC I alleles of wild type vs multiple different mutant TCEM I for 7 different proteins commonly mutated in different cancers. The dashed line is at 500 nM, a value commonly used to predict T cell responses. The boxplot is a Tukey outlier type where the box represents the 25 and 75 percentile and the whiskers correspond to 1.5×interquartile range. The yellow shaded area comprises peptides with the highest affinity and for any of the alleles corresponds to approximately 1% of the total TCEM and are all outliers. Overall, the MHC I binding affinity of the peptides containing the TCEM is very low; a median of 10 implies a value of about 22 uM (micromolar), more than 40×lower than the 500 nM (nanomolar) that is the consensus T cell stimulatory level. In addition, there is no statistical difference between the wt and mutant TCEM-containing peptides as is shown graphically by the boxplots and the datapoint scatter.

As used herein, the term "genome" refers to the genetic material (e.g., chromosomes) of an organism or a host cell.

As used herein, the term "proteome" refers to the entire set of proteins expressed by a genome, cell, tissue or organism. A "partial proteome" refers to a subset the entire set of proteins expressed by a genome, cell, tissue or organism. Examples of "partial proteomes" include, but are not limited to, transmembrane proteins, secreted proteins, and proteins with a membrane motif. Human proteome refers to all the proteins comprised in a human being. Multiple such sets of proteins have been sequenced and are accessible at the InterPro international repository (www.ebi-.ac.uk/interpro). Human proteome is also understood to include those proteins and antigens thereof which may be over-expressed in certain pathologies, or expressed in a different isoforms in certain pathologies. Hence, as used herein, tumor associated antigens are considered part of the human proteome. "Proteome" may also be used to describe a large compilation or collection of proteins, such as all the proteins in an immunoglobulin collection or a T cell receptor repertoire, or the proteins which comprise a collection such as the allergome, such that the collection is a proteome which may be subject to analysis. All the proteins in a bacteria or other microorganism are considered its proteome.

As used herein, the terms "protein," "polypeptide," and "peptide" refer to a molecule comprising amino acids joined via peptide bonds. In general "peptide" is used to refer to a sequence of 40 or less amino acids and "polypeptide" is used to refer to a sequence of greater than 40 amino acids.

As used herein, the term, "synthetic polypeptide," "synthetic peptide" and "synthetic protein" refer to peptides, polypeptides, and proteins that are produced by a recombinant process (i.e., expression of exogenous nucleic acid encoding the peptide, polypeptide or protein in an organism, host cell, or cell-free system) or by chemical synthesis.

As used herein, the term "protein of interest" refers to a protein encoded by a nucleic acid of interest. It may be applied to any protein to which further analysis is applied or the properties of which are tested or examined. Similarly, as used herein, "target protein" may be used to describe a protein of interest that is subject to further analysis.

As used herein "peptidase" refers to an enzyme which cleaves a protein or peptide. The term peptidase may be used interchangeably with protease, proteinases, oligopeptidases, and proteolytic enzymes. Peptidases may be endopeptidases (endoproteases), or exopeptidases (exoproteases). The the term peptidase would also include the proteasome which is a complex organelle containing different subunits each having a different type of characteristic scissile bond cleavage specificity. Similarly the term peptidase inhibitor may be used interchangeably with protease inhibitor or inhibitor of any of the other alternate terms for peptidase.

As used herein, the term "exopeptidase" refers to a peptidase that requires a free N-terminal amino group, C-terminal carboxyl group or both, and hydrolyses a bond not more than three residues from the terminus. The exo-peptidases are further divided into aminopeptidases, car-boxypeptidases, dipeptidyl-peptidases, peptidyl-dipepti-dases, tripeptidyl-peptidases and dipeptidases.

As used herein, the term "endopeptidase" refers to a peptidase that hydrolyses internal, alpha-peptide bonds in a polypeptide chain, tending to act away from the N-terminus or C-terminus. Examples of endopeptidases are chy-motrypsin, pepsin, papain and cathepsins. A very few endo-peptidases act a fixed distance from one terminus of the substrate, an example being mitochondrial intermediate pep-tidase. Some endopeptidases act only on substrates smaller than proteins, and these are termed oligopeptidases. An example of an oligopeptidase is thimet oligopeptidase. Endopeptidases initiate the digestion of food proteins, gen-erating new N- and C-termini that are substrates for the exopeptidases that complete the process. Endopeptidases also process proteins by limited proteolysis. Examples are the removal of signal peptides from secreted proteins (e.g. signal peptidase I,) and the maturation of precursor proteins (e.g. enteropeptidase, furin,). In the nomenclature of the Nomenclature Committee of the International Union of Biochemistry and Molecular Biology (NC-IUBMB) endo-peptidases are allocated to sub-subclasses EC 3.4.21, EC 3.4.22, EC 3.4.23, EC 3.4.24 and EC 3.4.25 for serine-, cysteine-, aspartic-, metallo- and threonine-type endopepti-dases, respectively. Endopeptidases of particular interest are the cathepsins, and especially cathepsin B, L and S known to be active in antigen presenting cells.

As used herein, the term "immunogen" refers to a mol-ecule which stimulates a response from the adaptive immune system, which may include responses drawn from the group comprising an antibody response, a cytotoxic T cell response, a T helper response, and a T cell memory. An immunogen may stimulate an upregulation of the immune response with a resultant inflammatory response, or may result in down regulation or immunosuppression. Thus the T-cell response may be a T regulatory response. An immu-nogen also may stimulate a B-cell response and lead to an increase in antibody titer. Another term used herein to describe a molecule or combination of molecules which stimulate an immune response is "antigen".

As used herein, the term "native" (or wild type) when used in reference to a protein refers to proteins encoded by the genome of a cell, tissue, or organism, other than one manipulated to produce synthetic proteins.

As used herein the term "epitope" refers to a peptide sequence which elicits an immune response, from either T cells or B cells or antibody. As used herein, the term "B-cell epitope" refers to a polypeptide sequence that is recognized and bound by a B-cell receptor. A B-cell epitope may be a linear peptide or may comprise several discontinuous sequences which together are folded to form a structural epitope. Such component sequences which together make up a B-cell epitope are referred to herein as B-cell epitope sequences. Hence, a B-cell epitope may comprise one or more B-cell epitope sequences. Hence, a B cell epitope may comprise one or more B-cell epitope sequences. A linear B-cell epitope may comprise as few as 2-4 amino acids or more amino acids.

"B cell core peptides" or "core pentamer" when used herein refers to the central 5 amino acid peptide in a predicted B cell epitope sequence. Said B cell epitope may be evaluated by predicting the binding of across a series of 9-mer windows, the core pentamer then is the central pentamer of the 9-mer window As used herein, the term "predicted B-cell epitope" refers to a polypeptide sequence that is predicted to bind to a B-cell receptor by a computer program, for example, as described in PCT PCT US2011/029192, PCT US2012/055038, US2014/014523, and PCT US2015/039969, each of which is incorporated herein by reference, and in addition by Bepipred (Larsen, et al., Immunome Research 2:2, 2006.) and others as referenced by Larsen et al (ibid) (Hopp T et al PNAS 78:3824-3828, 1981; Parker J et al, Biochem. 25:5425-5432, 1986). A predicted B-cell epitope may refer to the identification of B-cell epitope sequences forming part of a structural B-cell epitope or to a complete B-cell epitope.

As used herein, the term "T-cell epitope" refers to a polypeptide sequence which when bound to a major histocompatibility protein molecule provides a configuration recognized by a T-cell receptor. Typically, T-cell epitopes are presented bound to a MHC molecule on the surface of an antigen-presenting cell.

As used herein, the term "predicted T-cell epitope" refers to a polypeptide sequence that is predicted to bind to a major histocompatibility protein molecule by the neural network algorithms described herein, by other computerized methods, or as determined experimentally. As used herein, the term "major histocompatibility complex (MHC)" refers to the MHC Class I and MHC Class II genes and the proteins encoded thereby. Molecules of the MHC bind small peptides and present them on the surface of cells for recognition by T-cell receptor-bearing T-cells. The MHC is both polygenic (there are several MHC class I and MHC class II genes) and polyallelic or polymorphic (there are multiple alleles of each gene). The terms MHC-I, MHC-II, MHC-1 and MHC-2 are variously used herein to indicate these classes of molecules. Included are both classical and nonclassical MHC molecules. An MHC molecule is made up of multiple chains (alpha and beta chains) which associate to form a molecule. The MHC molecule contains a cleft or groove which forms a binding site for peptides. Peptides bound in the cleft or groove may then be presented to T-cell receptors. The term "MHC binding region" refers to the groove region of the MHC molecule where peptide binding occurs.

As used herein, a "MHC II binding groove" refers to the structure of an MHC molecule that binds to a peptide. The peptide that binds to the MHC II binding groove may be from about 11 amino acids to about 23 amino acids in length, but typically comprises a 15-mer. The amino acid positions in the peptide that binds to the groove are numbered based on a central core of 9 amino acids numbered 1-9, and positions outside the 9 amino acid core numbered as negative (N terminal) or positive (C terminal). Hence, in a 15mer the amino acid binding positions are numbered from −3 to +3 or as follows: −3, −2, −1, 1, 2, 3, 4, 5, 6, 7, 8, 9, +1, +2, +3.

As used herein, the term "haplotype" refers to the HLA alleles found on one chromosome and the proteins encoded thereby. Haplotype may also refer to the allele present at any one locus within the MHC. Each class of MHC-Is represented by several loci: e.g., HLA-A (Human Leukocyte Antigen-A), HLA-B, HLA-C, HLA-E, HLA-F, HLA-G, HLA-H, HLA-J, HLA-K, HLA-L, HLA-P and HLA-V for class I and HLA-DRA, HLA-DRB1-9, HLA-, HLA-DQA1, HLA-DQB1, HLA-DPA1, HLA-DPB1, HLA-DMA, HLA-DMB, HLA-DOA, and HLA-DOB for class II. The terms "HLA allele" and "MHC allele" are used interchangeably herein. HLA alleles are listed at hla.alleles.org/nomenclature/naming.html, which is incorporated herein by reference.

The MI-ICs exhibit extreme polymorphism: within the human population there are, at each genetic locus, a great number of haplotypes comprising distinct alleles—the IMGT/HLA database release (February 2010) lists 948 class I and 633 class II molecules, many of which are represented at high frequency (>1%). MHC alleles may differ by as many as 30-aa substitutions. Different polymorphic MHC alleles, of both class I and class II, have different peptide specificities: each allele encodes proteins that bind peptides exhibiting particular sequence patterns.

The naming of new HLA genes and allele sequences and their quality control is the responsibility of the WHO Nomenclature Committee for Factors of the HLA System, which first met in 1968, and laid down the criteria for successive meetings. This committee meets regularly to discuss issues of nomenclature and has published 19 major reports documenting firstly the HLA antigens and more recently the genes and alleles. The standardization of HLA antigenic specifications has been controlled by the exchange of typing reagents and cells in the International Histocompatibility Workshops. The IMGT/HLA Database collects both new and confirmatory sequences, which are then expertly analyzed and curated before been named by the Nomenclature Committee. The resulting sequences are then included in the tools and files made available from both the IMGT/HLA Database and at hla.alleles.org.

Each HLA allele name has a unique number corresponding to up to four sets of digits separated by colons. See e.g., hla.alleles.org/nomenclature/naming.html which provides a description of standard HLA nomenclature and Marsh et al., Nomenclature for Factors of the HLA System, 2010 Tissue Antigens 2010 75:291-455. HLA-DRB1*13:01 and HLA-DRB1*13:01:01:02 are examples of standard HLA nomenclature. The length of the allele designation is dependent on the sequence of the allele and that of its nearest relative. All alleles receive at least a four digit name, which corresponds to the first two sets of digits, longer names are only assigned when necessary.

The digits before the first colon describe the type, which often corresponds to the serological antigen carried by an allele, The next set of digits are used to list the subtypes, numbers being assigned in the order in which DNA sequences have been determined. Alleles whose numbers differ in the two sets of digits must differ in one or more nucleotide substitutions that change the amino acid sequence of the encoded protein. Alleles that differ only by synonymous nucleotide substitutions (also called silent or non-coding substitutions) within the coding sequence are distinguished by the use of the third set of digits. Alleles that only differ by sequence polymorphisms in the introns or in the 5' or 3' untranslated regions that flank the exons and introns are distinguished by the use of the fourth set of digits. In addition to the unique allele number there are additional optional suffixes that may be added to an allele to indicate its expression status. Alleles that have been shown not to be expressed, 'Null' alleles have been given the suffix 'N'. Those alleles which have been shown to be alternatively expressed may have the suffix 'L', 'S', 'C', 'A' or 'Q'. The suffix 'L' is used to indicate an allele which has been shown to have 'Low' cell surface expression when compared to normal levels. The 'S' suffix is used to denote an allele specifying a protein which is expressed as a soluble 'Secreted' molecule but is not present on the cell surface. A 'C' suffix to indicate an allele product which is present in the 'Cytoplasm' but not on the cell surface. An 'A' suffix to indicate 'Aberrant' expression where there is some doubt as to whether a protein is expressed. A 'Q' suffix when the expression of an allele is 'Questionable' given that the mutation seen in the allele has previously been shown to affect normal expression levels.

In some instances, the HLA designations used herein may differ from the standard HLA nomenclature just described due to limitations in entering characters in the databases described herein. As an example, DRB1_0104, DRB1*0104, and DRB1-0104 are equivalent to the standard nomenclature of DRB1*01:04. In most instances, the asterisk is replaced with an underscore or dash and the semicolon between the two digit sets is omitted.

As used herein, the term "polypeptide sequence that binds to at least one major histocompatibility complex (MHC) binding region" refers to a polypeptide sequence that is recognized and bound by one or more particular MHC binding regions as predicted by the neural network algorithms described herein or as determined experimentally.

As used herein the terms "canonical" and "non-canonical" are used to refer to the orientation of an amino acid sequence. Canonical refers to an amino acid sequence presented or read in the N terminal to C terminal order; non-canonical is used to describe an amino acid sequence presented in the inverted or C terminal to N terminal order.

As used herein, the term "allergen" refers to an antigenic substance capable of producing immediate hypersensitivity and includes both synthetic as well as natural immunostimulant peptides and proteins. Allergen includes but is not limited to any protein or peptide catalogued in the Structural Database of Allergenic Proteins database http://fermi.utmb.edu/SDAP/index.html As used herein, the term "transmembrane protein" refers to proteins that span a biological membrane. There are two basic types of transmembrane proteins. Alpha-helical proteins are present in the inner membranes of bacterial cells or the plasma membrane of eukaryotes, and sometimes in the outer membranes. Beta-barrel proteins are found only in outer membranes of Gram-negative bacteria, cell wall of Gram-positive bacteria, and outer membranes of mitochondria and chloroplasts.

As used herein, the term "affinity" refers to a measure of the strength of binding between two members of a binding pair, for example, an antibody and an epitope and an epitope and a MHC-I or II haplotype. $K_d$ is the dissociation constant and has units of molarity. The affinity constant is the inverse of the dissociation constant. An affinity constant is sometimes used as a generic term to describe this chemical entity. It is a direct measure of the energy of binding. The natural logarithm of K is linearly related to the Gibbs free energy of binding through the equation $\Delta G_0 = -RT\, LN(K)$ where R=gas constant and temperature is in degrees Kelvin. Affinity may be determined experimentally, for example by surface plasmon resonance (SPR) using commercially available Biacore SPR units (GE Healthcare) or in silico by methods such as those described herein in detail. Affinity may also be expressed as the ic50 or inhibitory concentration 50, that concentration at which 50% of the peptide is displaced. Likewise ln(ic50) refers to the natural log of the ic50.

The term "$K_{off}$", as used herein, is intended to refer to the off rate constant, for example, for dissociation of an antibody from the antibody/antigen complex, or for dissociation of an epitope from an MHC haplotype.

The term "$K_d$", as used herein, is intended to refer to the dissociation constant (the reciprocal of the affinity constant "Ka"), for example, for a particular antibody-antigen interaction or interaction between an epitope and an MHC haplotype.

As used herein, the terms "strong binder" and "strong binding" and "High binder" and "high binding" or "high affinity" refer to a binding pair or describe a binding pair that have an affinity of greater than $2 \times 10^7 M^{-1}$ (equivalent to a dissociation constant of 50 nM Kd)

As used herein, the term "moderate binder" and "moderate binding" and "moderate affinity" refer to a binding pair or describe a binding pair that have an affinity of from $2 \times 10^7 M^{-1}$ to $2 \times 10^6 M^{-1}$.

As used herein, the terms "weak binder" and "weak binding" and "low affinity" refer to a binding pair or describe a binding pair that have an affinity of less than $2 \times 10^6 M^{-1}$ (equivalent to a dissociation constant of 500 nM Kd)

Binding affinity may also be expressed by the standard deviation from the mean binding found in the peptides making up a protein. Hence a binding affinity may be expressed as "$-1\sigma$" or $<-1\sigma$, where this refers to a binding affinity of 1 or more standard deviations below the mean. A common mathematical transformation used in statistical analysis is a process called standardization wherein the distribution is transformed from its standard units to standard deviation units where the distribution has a mean of zero and a variance (and standard deviation) of 1. Because each protein comprises unique distributions for the different MHC alleles standardization of the affinity data to zero mean and unit variance provides a numerical scale where different alleles and different proteins can be compared. Analysis of a wide range of experimental results suggest that a criterion of standard deviation units can be used to discriminate between potential immunological responses and non-responses. An affinity of 1 standard deviation below the mean was found to be a useful threshold in this regard and thus approximately 15% (16.2% to be exact) of the peptides found in any protein will fall into this category.

The terms "specific binding" or "specifically binding" when used in reference to the interaction of an antibody and a protein or peptide or an epitope and an MHC haplotype means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabeled A) in a reaction containing labeled "A" and the antibody will reduce the amount of labeled A bound to the antibody.

As used herein, the term "antigen binding protein" refers to proteins that bind to a specific antigen. "Antigen binding proteins" include, but are not limited to, immunoglobulins, including polyclonal, monoclonal, chimeric, single chain, and humanized antibodies, Fab fragments, F(ab')2 fragments, and Fab expression libraries. Various procedures known in the art are used for the production of polyclonal antibodies. For the production of antibody, various host animals can be immunized by injection with the peptide corresponding to the desired epitope including but not limited to rabbits, mice, rats, sheep, goats, etc.

"Adjuvant" as used herein encompasses various adjuvants that are used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, squalene, squalene emulsions, liposomes, imiquimod, keyhole limpet hemocyanins, dinitrophenol, and potentially useful human adjuvants such as BCG (Bacille Calmette-Guerin) and *Corynebacterium parvum*. In other embodiments a cytokine may be co-administered, including but not limited to interferon gamma or stimulators thereof, interleukin 12, or granulocyte stimulating factor. In other embodiments the peptides or their encoding nucleic acids may be co-administered with a local inflammatory agent, either chemical or physical. Examples include, but are not limited to, heat, infrared light, proinflammatory drugs, including but not limited to imiquimod.

As used herein "immunoglobulin" means the distinct antibody molecule secreted by a clonal line of B cells; hence when the term "100 immunoglobulins" is used it conveys the distinct products of 100 different B-cell clones and their lineages.

As used herein, the terms "computer memory" and "computer memory device" refer to any storage media readable by a computer processor. Examples of computer memory include, but are not limited to, RAM, ROM, computer chips, digital video disc (DVDs), compact discs (CDs), hard disk drives (HDD), and magnetic tape.

As used herein, the term "computer readable medium" refers to any device or system for storing and providing information (e.g., data and instructions) to a computer processor. Examples of computer readable media include, but are not limited to, DVDs, CDs, hard disk drives, magnetic tape and servers for streaming media over networks.

As used herein, the terms "processor" and "central processing unit" or "CPU" are used interchangeably and refer to a device that is able to read a program from a computer memory (e.g., ROM or other computer memory) and perform a set of steps according to the program.

As used herein, the term "support vector machine" refers to a set of related supervised learning methods used for classification and regression. Given a set of training examples, each marked as belonging to one of two categories, an SVM training algorithm builds a model that predicts whether a new example falls into one category or the other.

As used herein, the term "classifier" when used in relation to statistical processes refers to processes such as neural nets and support vector machines.

As used herein "neural net", which is used interchangeably with "neural network" and sometimes abbreviated as NN, refers to various configurations of classifiers used in machine learning, including multilayered perceptrons with one or more hidden layer, support vector machines and dynamic Bayesian networks. These methods share in common the ability to be trained, the quality of their training evaluated, and their ability to make either categorical classifications of non numeric data or to generate equations for predictions of continuous numbers in a regression mode. Perceptron as used herein is a classifier which maps its input x to an output value which is a function of x, or a graphical representation thereof.

As used herein, the term "principal component analysis", or as abbreviated "PCA", refers to a mathematical process which reduces the dimensionality of a set of data (Wold, S., Sjorstrom, M., and Eriksson, L., Chemometrics and Intelligent Laboratory Systems 2001. 58: 109-130.; Multivariate and Megavariate Data Analysis Basic Principles and Applications (Parts I&II) by L. Eriksson, E. Johansson, N. Kettaneh-Wold, and J. Trygg, 2006 $2^{nd}$ Edit. Umetrics Academy). Derivation of principal components is a linear transformation that locates directions of maximum variance in the original input data, and rotates the data along these axes. For n original variables, n principal components are formed as follows: The first principal component is the linear combination of the standardized original variables that has the greatest possible variance. Each subsequent principal component is the linear combination of the standardized original variables that has the greatest possible variance and is uncorrelated with all previously defined components. Further, the principal components are scale-independent in that they can be developed from different types of measurements. The application of PCA generates numerical coefficients (descriptors). The coefficients are effectively proxy variables whose numerical values are seen to be related to underlying physical properties of the molecules. A description of the application of PCA to generate descriptors of amino acids and by combination thereof peptides is provided in PCT US2011/029192 incorporated herein by reference in its entirety. Unlike neural nets PCA do not have any predictive capability. PCA is deductive not inductive.

As used herein, the term "vector" when used in relation to a computer algorithm or the present invention, refers to the mathematical properties of the amino acid sequence.

As used herein, the term "vector," when used in relation to recombinant DNA technology, refers to any genetic element, such as a plasmid, phage, transposon, cosmid, chromosome, retrovirus, virion, etc., which is capable of replication when associated with the proper control elements and which can transfer gene sequences between cells. Thus, the term includes cloning and expression vehicles, as well as viral vectors. "Viral vector" as used herein includes but is not limited to adenoviral vectors, adeno-associated viral vectors, lentiviral vectors, retroviral vectors, poliovirus vectors, measles virus vectors, flavivirus vectors, poxvirus vectors, and other viral vectors which may be used to deliver a peptide or nucleic acid sequence to a host cell.

As used herein, the term "host cell" refers to any eukaryotic cell (e.g., mammalian cells, avian cells, amphibian cells, plant cells, fish cells, insect cells, yeast cells), and bacteria cells, and the like, whether located in vitro or in vivo (e.g., in a transgenic organism).

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro, including oocytes and embryos.

The term "isolated" when used in relation to a nucleic acid, as in "an isolated oligonucleotide" refers to a nucleic acid sequence that is identified and separated from at least one contaminant nucleic acid with which it is ordinarily associated in its natural source. Isolated nucleic acids are nucleic acids present in a form or setting that is different from that in which they are found in nature. In contrast, non-isolated nucleic acids are nucleic acids such as DNA and RNA that are found in the state in which they exist in nature.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

A "subject" is an animal such as vertebrate, preferably a mammal such as a human, a bird, or a fish. Mammals are understood to include, but are not limited to, murines, simians, humans, bovines, ovines, cervids, equines, porcines, canines, felines etc.).

An "effective amount" is an amount sufficient to effect beneficial or desired results. An effective amount can be administered in one or more administrations.

As used herein, the term "purified" or "to purify" refers to the removal of undesired components from a sample. As used herein, the term "substantially purified" refers to molecules, either nucleic or amino acid sequences, that are removed from their natural environment, isolated or separated, and are at least 60% free, preferably 75% free, and most preferably 90% free from other components with which they are naturally associated. An "isolated polynucleotide" is therefore a substantially purified polynucleotide.

As used herein "Complementarity Determining Regions" (CDRs) are those parts of the immunoglobulin variable chains which determine how these molecules bind to their specific antigen. Each immunoglobulin variable region typically comprises three CDRs and these are the most highly variable regions of the molecule. T cell receptors also comprise similar CDRs and the term CDR may be applied to T cell receptors.

As used herein, the term "motif" refers to a characteristic sequence of amino acids forming a distinctive pattern.

The term "Groove Exposed Motif" (GEM) as used herein refers to a subset of amino acids within a peptide that binds to an MHC molecule; the GEM comprises those amino acids which are turned inward towards the groove formed by the MHC molecule and which play a significant role in determining the binding affinity. In the case of human MHC-I the GEM amino acids are typically (1,2,3,9). In the case of MHC-II molecules two formats of GEM are most common comprising amino acids (−3,2, −1,1,4,6, 9, +1, +2, +3) and (−3, 2, 1, 2, 4, 6, 9, +1, +2, +3) based on a 15-mer peptide with a central core of 9 amino acids numbered 1-9 and positions outside the core numbered as negative (N terminal) or positive (C terminal).

"Immunoglobulin germline" is used herein to refer to the variable region sequences encoded in the inherited germline genes and which have not yet undergone any somatic hypermutation. Each individual carries and expresses multiple copies of germline genes for the variable regions of heavy and light chains. These undergo somatic hypermutation during affinity maturation. Information on the germline sequences of immunoglobulins is collated and referenced by www.imgt.org [1]. "Germline family" as used herein refers to the 7 main gene groups, catalogued at IMGT, which share similarity in their sequences and which are further subdivided into subfamilies.

"Affinity maturation" is the molecular evolution that occurs during somatic hypermutation during which unique variable region sequences generated that are the best at targeting and neutralizing and antigen become clonally expanded and dominate the responding cell populations.

"Germline motif" as used herein describes the amino acid subsets that are found in germline immunoglobulins. Germline motifs comprise both GEM and TCEM motifs found in the variable regions of immunoglobulins which have not yet undergone somatic hypermutation.

"Immunopathology" when used herein describes an abnormality of the immune system. An immunopathology may affect B-cells and their lineage causing qualitative or quantitative changes in the production of immunoglobulins. Immunopathologies may alternatively affect T-cells and result in abnormal T-cell responses. Immunopathologies may also affect the antigen presenting cells. Immunopathologies may be the result of neoplasias of the cells of the immune system. Immunopathology is also used to describe diseases mediated by the immune system such as autoimmune diseases. Illustrative examples of immunopathologies include, but are not limited to, B-cell lymphoma, T-cell lymphomas, Systemic Lupus Erythematosus (SLE), allergies, hypersensitivities, immunodeficiency syndromes, radiation exposure or chronic fatigue syndrome.

"pMHC" Is used to describe a complex of a peptide bound to an MHC molecule. In many instances a peptide bound to an MHC-I will be a 9-mer or 10-mer however other sizes of 7-11 amino acids may be thus bound. Similarly MHC-II molecules may form pMHC complexes with peptides of 15 amino acids or with peptides of other sizes from 11-23 amino acids. The term pMHC is thus understood to include any short peptide bound to a corresponding MHC.

"Somatic hypermutation" (SHM), as used herein refers to the process by which variability in the immunoglobulin variable region is generated during the proliferation of individual B-cells responding to an immune stimulus. SHM occurs in the complementarity determining regions.

"T-cell exposed motif" (also where abbreviated TCEM), as used herein, refers to the sub set of amino acids in a peptide bound in a MHC molecule which are directed outwards and exposed to a T-cell binding to the pMHC complex. A T-cell binds to a complex molecular space-shape made up of the outer surface MHC of the particular HLA allele and the exposed amino acids of the peptide bound within the MHC. Hence any T-cell recognizes a space shape or receptor which is specific to the combination of HLA and peptide. The amino acids which comprise the TCEM in an MHC-I binding peptide typically comprise positions 4, 5, 6, 7, 8 of a 9-mer. The amino acids which comprise the TCEM in an MHC-II binding peptide typically comprise 2, 3, 5, 7, 8 or −1, 3, 5, 7, 8 based on a 15-mer peptide with a central core of 9 amino acids numbered 1-9 and positions outside the core numbered as negative (N terminal) or positive (C terminal). As indicated under pMHC, the peptide bound to a MHC may be of other lengths and thus the numbering system here is considered a non-exclusive example of the instances of 9-mer and 15 mer peptides.

As used herein "histotope" refers to the outward facing surface of the MHC molecules which surrounds the T cell exposed motif and in combination with the T cell exposed motif serves as the binding surface for the T cell receptor.

As used herein the T cell receptor refers to the molecules exposed on the surface of a T cell which engage the histotope of the MHC and the T cell exposed motif of a peptide bound in said MHC. The T cell receptor comprises two protein chains, known as the alpha and beta chain in 95% of human T cells and as the delta and gamma chains in the remaining 5% of human T cells. Each chain comprises a variable region and a constant region. Each variable region comprises three complementarity determining regions or CDRs "Regulatory T-cell" or "Treg" as used herein, refers to a T-cell which has an immunosuppressive or down-regulatory function. Regulatory T-cells were formerly known as suppressor T-cells. Regulatory T-cells come in many forms but typically are characterized by expression CD4+, CD25, and Foxp3. Tregs are involved in shutting down immune responses after they have successfully eliminated invading organisms, and also in preventing immune responses to self-antigens or autoimmunity.

"uTOPE™ analysis" as used herein refers to the computer assisted processes for predicting binding of peptides to MHC and predicting cathepsin cleavage, described in PCT US2011/029192, PCT US2012/055038, and US2014/01452, each of which is incorporated herein by reference in its entirety.

"Framework region" as used herein refers to the amino acid sequences within an immunoglobulin variable region which do not undergo somatic hypermutation.

"Isotype" as used herein refers to the related proteins of particular gene family. Immunoglobulin isotype refers to the distinct forms of heavy and light chains in the immunoglobulins. In heavy chains there are five heavy chain isotypes (alpha, delta, gamma, epsilon, and mu, leading to the formation of IgA, IgD, IgG, IgE and IgM respectively) and light chains have two isotypes (kappa and lambda). Isotype when applied to immunoglobulins herein is used interchangeably with immunoglobulin "class".

"Isoform" as used herein refers to different forms of a protein which differ in a small number of amino acids. The isoform may be a full length protein (i.e., by reference to a reference wild-type protein or isoform) or a modified form of a partial protein, i.e., be shorter in length than a reference wild-type protein or isoform.

"Class switch recombination" (CSR) as used herein refers to the change from one isotype of immunoglobulin to another in an activated B cell, wherein the constant region associated with a specific variable region is changed, typically from IgM to IgG or other isotypes.

"Immunostimulation" as used herein refers to the signaling that leads to activation of an immune response, whether said immune response is characterized by a recruitment of cells or the release of cytokines which lead to suppression of the immune response. Thus, immunostimulation refers to both upregulation or down regulation.

"Up-regulation" as used herein refers to an immunostimulation which leads to cytokine release and cell recruitment tending to eliminate a non self or exogenous epitope. Such responses include recruitment of T cells, including effectors such as cytotoxic T cells, and inflammation. In an adverse reaction upregulation may be directed to a self-epitope.

"Down regulation" as used herein refers to an immunostimulation which leads to cytokine release that tends to dampen or eliminate a cell response. In some instances such elimination may include apoptosis of the responding T cells.

"Frequency class" or "frequency classification" as used herein is used to describe logarithmic based bins or subsets of amino acid motifs or cells. When applied to the counts of TCEM motifs found in a given dataset of peptides a logarithmic (log base 2) frequency categorization scheme was developed to describe the distribution of motifs in a dataset. As the cellular interactions between T-cells and antigen presenting cells displaying the motifs in MHC molecules on their surfaces are the ultimate result of the molecular interactions, using a log base 2 system implies that each adjacent frequency class would double or halve the cellular interactions with that motif. Thus, using such a frequency categorization scheme makes it possible to characterize subtle differences in motif usage as well as providing a comprehensible way of visualizing the cellular interaction dynamics with the different motifs. Hence a Frequency Class 2, or FC 2 means 1 in 4, a Frequency class 10 or FC 10 means 1 in $2^{10}$ or 1 in 1024. In other embodiments the frequency classification of the TCEM motif in the reference dataset is described by the quantile score of the TCEM in the reference dataset. Quantile scores are used, but is not limited to, applications where the reference dataset is the human proteome or a microbial proteome. "Frequency class" or "frequency classification" may also be applied to cellular clonotypic frequency where it refers to subgroups or bins defined by logarithmic based groupings, whether log base 2 or another selected log base.

A "rare TCEM" as used herein is one which is completely missing in the human proteome or present in up to only five instances in the human proteome.

"IGHV" as used herein is an abbreviation for immunoglobulin heavy chain variable regions.

"IGLV" as used herein is an abbreviation for immunoglobulin light chain variable regions "Adverse immune response" as used herein may refer to (a) the induction of immunosuppression when the appropriate response is an active immune response to eliminate a pathogen or tumor or (b) the induction of an upregulated active immune response to a self-antigen or (c) an excessive up-regulation unbalanced by any suppression, as may occur for instance in an allergic response.

"Clonotype" as used herein refers to the cell lineage arising from one unique cell. In the particular case of a B cell clonotype it refers to a clonal population of B cells that produces a unique sequence of IGV. The number of B cells that express that sequence varies from singletons to thousands in the repertoire of an individual. In the case of a T cell it refers to a cell lineage which expresses a particular TCR. A clonotype of cancer cells all arise from one cell and carry a particular mutation or mutations or the derivates thereof. The above are examples of clonotypes of cells and should not be considered limiting.

As used herein "epitope mimic" or "TCEM mimic" is used to describe a peptide which has an identical or overlapping TCEM, but may have a different GEM. Such a mimic occurring in one protein may induce an immune response directed towards another protein which carries the same TCEM motif. This may give rise to autoimmunity or inappropriate responses to the second protein.

"Cytokine" as used herein refers to a protein which is active in cell signaling and may include, among other examples, chemokines, interferons, interleukins, lymphokines, granulocyte colony-stimulating factor tumor necrosis factor and programmed death proteins.

As used herein "oncoprotein" means a protein encoded by an oncogene which can cause the transformation of a cell into a tumor cell if introduced into it. Examples of oncoproteins include but are not limited to the early proteins of papillomaviruses, polyomaviruses, adenoviruses and herpesviruses, however oncoproteins are not necessarily of viral origin.

"MHC subunit chain" as used herein refers to the alpha and beta subunits of MHC molecules. A MHC II molecule is made up of an alpha chain which is constant among each of the DR, DP, and DQ variants and a beta chain which varies by allele. The MHC I molecule is made up of a constant beta macroglobulin and a variable MHC A, B or C chain.

As used here in "virome" comprises the viruses present in a human subject, latently chronically or during acute infection, or a sub set thereof made up of viruses of a particular taxonomic group or of the viruses located in a particular tissue or organ.

"Immunoglobulinome" as used herein refers to the total complement of immunoglobulins produced and carried by any one subject.

As used herein "allergome" refers to all proteins which may give rise to allergies. This includes proteins recorded in allergen datasets such as that represented at www.allergome.com, http://www.allergenonline.org/, http://comparedatabase.org/www.allergen.org as well as included in Uniprot, Swiss prot, etc.

As used herein the term "repertoire" is used to describe a collection of molecules or cells making up a functional unit or whole. Thus, as one non limiting example, the entirely of the B cells or T cells in a subject comprise its repertoire of B cells or T cells. The entirety of all immunoglobulins expressed by said B cells are its immunoglobulinome or the repertoire of immunoglobulins. A collection of proteins or cell clonotypes which make up a tissue sample, an individual subject or a microorganism may be referred to as a repertoire.

As used herein "mutated amino acid" refers to the appearance of an amino acid in a protein that is the result of a nucleotide change, a missense mutation, or an insertion or deletion or fusion.

"Splice variant" as used herein refers to different proteins that are expressed from one gene as the result of inclusion or exclusion of particular exons of a gene in the final, processed messenger RNA produced from that gene or that is the result of cutting and re-annealing of RNA or DNA.

"TRAV" as used herein refers to the T cell receptor alpha variable region family or allele subgroups and "TRBV" refers to T cell receptor beta variable region family or allele subgroups as described in IMGT http://imgt.org/IMGTrepertoire/Proteins/index.php#C http://imglorg/IMGTrepertoire/Proteins/taballeles/human/TRA/TRAV/ Hu_TRAVall.html TRAV comprises at least 41 subgroups, with some having sub-subgroups. TRBV comprises at least 30 subgroups. Most combinations of alpha and beta variable region subgroups are encountered. "hTRAV" refers to human TRAV.

As used here in a "receptor bearing cell" is any cell which carries a ligand binding recognition motif on its surface. In some particular instances a receptor bearing cell is a B cell and its surface receptor comprises an immunoglobulin variable region, said immunoglobulin variable region comprising both heavy and light chains which make up said receptor. In other particular instances a receptor bearing cell may be a T cell which bears a receptor made up of both alpha and beta chains or both delta and gamma chains. Other examples of a receptor bearing cell include cells which carry other ligands such as, in one particular non limiting example, a programmed death protein of which there are multiple isoforms.

As used herein the term "bin" refers to a quantitative grouping and a "logarithmic bin" is used to describe a grouping according to the logarithm of the quantity.

As used herein "immunotherapy intervention" is used to describe any deliberate modification of the immune system including but not limited to through the administration of therapeutic drugs or biopharmaceuticals, radiation, T cell therapy, application of engineered T cells, which may include T cells linked to cytotoxic, chemotherapeutic or radiosensitive moieties, checkpoint inhibitor administration, cytokine or recombinant cytokine or cytokine enhancer, including but not limited to a IL-15 agonist, microbiome manipulation, vaccination, B or T cell depletion or ablation, or surgical intervention to remove any immune related tissues.

As used herein "immunomodulatory intervention" refers to any medical or nutritional treatment or prophylaxis administered with the intent of changing the immune response or the balance of immune responsive cells. Such an intervention may be delivered parenterally or orally or via inhalation. Such intervention may include, but is not limited to, a vaccine including both prophylactic and therapeutic vaccines, a biopharmaceutical, which may be from the group comprising an immunoglobulin or part thereof, a T cell stimulator, checkpoint inhibitor, or suppressor, an adjuvant, a cytokine, a cytotoxin, receptor binder, an enhancer of NK (natural killer) cells, an interleukin including but not limited to variants of IL15, superagonists, and a nutritional or dietary supplement. The intervention may also include radiation or chemotherapy to ablate a target group of cells. The impact on the immune response may be to stimulate or to down regulate.

"Checkpoint inhibitor" or "checkpoint blockade" as used herein refers to a type of drug that blocks certain proteins made by some types of immune system cells, such as T cells, and some cancer cells. These proteins help keep immune responses in check and can keep T cells from killing cancer cells. When these proteins are blocked, the "brakes" on the immune system are released and T cells are able to kill cancer cells better. Examples of checkpoint proteins found on T cells or cancer cells include, but are not limited to, PD-1/PD-L1 and CTLA-4/B7-1/B7-2.

As used herein the "cluster of differentiation" proteins refers to cell surface molecules providing targets for immunophenotyping of cells. The cluster of differentiation is also known as cluster of designation or classification determinant and may be abbreviated as CD. Examples of CD proteins include those listed at https://www.uniprot.org/docs/cdlist As used herein "microbiome" refers to the constellation of commensal microorganisms found within the human or other host body, inhabiting sites such as the gastrointestine, skin the urogenital tract, the oral cavity, the upper respiratory tract. While most frequently referring to bacteria, the microbiome also may include the viruses in these sites, referred to as the "virome", or commensal fungi.

As used herein "tumor associated mutations" refers to all nucleotide or amino acid mutations detected in a tumor. In some cases the tumor associated mutations are commonly found within many patients with a particular tumor type. In other cases tumor associated mutations may be unique to a specific patient. In other instances different patients may carry different tumor associated mutations are in the same protein.

"Pattern" as used herein means a characteristic or consistent distribution of data points.

As used herein a "frequency pattern" is a data set that displays the frequency of TCEMs in a repertoire of proteins from a proteome associated with an individual subject as compared to the frequency of those TCEMs in a reference database. Particular TCEMs, or groups of TCEMs, within the subject's repertoire may occur at the same, lower or higher frequencies than the corresponding TCEMs in the reference database. The frequency pattern allows identification and categorization of unique TCEMs and/or patterns of TCEMs (i.e., unique features of unique TCEM features). The term "frequency pattern" as used herein is also used to describe the distribution of cellular clonotypes within a repertoire of cells from an individual subject, as compared to the frequency of the cellular clonotypes in a reference database. Particular clonotypes, or groups of clonotypes, within the subject's repertoire may occur at the same, lower or higher frequencies than the corresponding cellular clonotypes in the reference database. The frequency pattern allows identification and categorization of unique patterns of clonotypes. In some embodiments, a "frequency class" or "frequency classification" is assigned to a TCEM motif or to a cellular clonotype based on its frequency as described elsewhere herein.

As used herein "clonotype" is a line of cells derived from a committed or fully differentiated progenitor. In the case of T cells and somatic cells other than B cells, a clonotype of cells has a common genotype, i.e. comprises a common nucleotide sequence. Clonotypes with different nucleotide sequences may express a protein of identical amino acid sequence as a result of different codon utilization. Hence multiple genotypes may lead to a shared phenotype among such clonotypes. In B cells, somatic mutation results in a differentiated cell line comprising a nucleotide sequence that expresses antibodies of one isotype and variable region sequence; this is a B cell clonotype.

As used herein "clonotypic diversity" refers to the distribution of the total number of cells in a repertoire among all unique clonotypes in a repertoire. Hence, if a repertoire has 1 million cells, but these comprise 400,000 of clonotype 1 and 600,000 of clonotype 2, the repertoire has a low clonotypic diversity. If the 1 million cells are distributed as 10 each of 100,000 unique clonotypes the repertoire has a high clonotypic diversity.

As used herein "many to one" describes a relationship in which one protein or peptide sequence is encoded be many different synonymous nucleotide sequences.

As used herein "presentome" refers to the peptides bound in MHC and presented on the surface of antigen presented cells. Mass spectroscopy detects some but not all peptides which are part of the presentome.

"Neoantigen" as used herein refers to a novel epitope motif or antigen created as the result of introduction of a mutation into an amino acid sequence. Thus, a neoantigen differentiates a wildtype protein from its mutant-bearing tumor protein homolog, when such mutant is presented to T cells or B cells.

"Tumor specific antigen" or "tumor specific epitope" is used herein to designate an epitope or antigen that differentiates a mutated tumor protein from its unmutated wildtype homologue. Thus, a neoantigen is one type of tumor specific antigen.

As used herein "driver" mutations are those which arise very early in tumorogeneis and are causally associated with the early steps of cell dysregulation. Driver mutations are shared by all clonal offspring arising from the initial tumor cells and offer some additional fitness benefit to the clonal line within its microenvironment. In contrast passenger mutations are those somatic mutations which arise during the differentiation of the tumor and which offer no particular benefit of fitness to the cell. Passengers may serve as biomarkers on tumor cells and may enable some immune evasion. Passenger mutations may differ at different time points in its development and among different parts of a tumor or among metastases. "Driver and passenger" are terms largely interchangeable with "trunk and branch" mutations.

"Bespoke peptides" or "bespoke vaccine" as used herein refers to a peptide or neoantigen or a combination of peptides, or nucleic acid encoding peptides, that are tailored or personalized specifically for an individual patient, taking into account that patient's HLA alleles and mutations.

As used herein "TCGA" refers to The Cancer Genome Atlas (https://www.cancer.gov/about-nci/organization/ccg/research/structural-genomics/tcga)

As used herein a "polyhydrophobic amino acid" refers to a short chain of natural amino acids which are hydrophobic. Examples include, but are not limited to, leucines, isoleucines or tryptophans where these are assembled in multimers of 5-15 repeats of any one such amino acid. As a non-limiting example, a poly leucine comprising 8 leucines would be an example of a polyhydrophobic amino acid.

A "lipid core peptide system", as used herein, refers to subunit vaccine comprising a lipoamino acid (LAA) moiety which allows the stimulation of immune activity. A combination of T cell stimulating epitopes or T and B cell stimulating, epitopes are linked to a LAA. Multiple different constructs can be created with of different spatial orientation or LAA lengths (e.g. C12 2-amino-D,L-dodecanoic acid or C16, 2-amino-D,L-hexadecanoic acid,). When dissolved in a standard phosphate buffer LCP particles form and the particles facilitate uptake by antigen presenting cells. Different LAA chain lengths lead to different particle sizes.

As used herein, the term "cleavage site octomer" refers to the 8 amino acids located four each side of the bond at which a peptidase cleaves an amino acid sequence. Cleavage site octomer is abbreviated as CSO. "Cathepsin cleavage site octomer" is used herein where the peptidase is a cathepsin.

As used herein "compounding pharmacy" has the meaning defined in sections 503A and 503B of the Federal Food, Drug, and Cosmetic Act As used herein, a "BAM" file is a compressed binary version of a Sequence Alignment File "SAM" file wherein the all nucleotides are aligned to a reference genome. A "BAM slice" is a subset of the entire genome defined by genome coordinates. The HLA locus is located on Chromosome 6. In one particular instance a BAM slice is defined to contain just the HLA locus.

"Immunopathology" when used herein describes an abnormality of the immune system. An immunopathology may affect B-cells and their lineage causing qualitative or quantitative changes in the production of immunoglobulins. Immunopathologies may alternatively affect T-cells and result in abnormal T-cell responses. Immunopathologies may also affect the antigen presenting cells. Immunopathologies may be the result of neoplasias of the cells of the immune system. Immunopathology is also used to describe diseases mediated by the immune system such as autoimmune diseases. Representative autoimmune diseases include, but are not limited to rheumatoid arthritis, diabetes type I and type II, Ankylosing Spondylitis, Atopic allergy, Atopic Dermatitis, Autoimmune cardiomyopathy, Autoimmune enteropathy, Autoimmune hemolytic anemia, Autoimmune hepatitis, Autoimmune inner ear disease, Autoimmune lymphoproliferative syndrome, Autoimmune peripheral neuropathy, Autoimmune pancreatitis, Autoimmune polyendocrine syndrome, Autoimmune progesterone dermatitis, Autoimmune thrombocytopenic purpura, Autoimmune uveitis, Bullous Pemphigoid, Castleman's disease, Celiac disease, Cogan syndrome, Cold agglutinin disease, Crohns Disease, Dermatomyositis, Eosinophilic fasciitis, Gastrointestinal pemphigoid, Goodpasture's syndrome, Graves' disease, Guillain-Barré syndrome, Anti-ganglioside Hashimoto's encephalitis, Hashimoto's thyroiditis, Systemic Lupus erythematosus, Miller-Fisher syndrome, Mixed Connective Tissue Disease, Myasthenia gravis, Narcolepsy, Pemphigus vulgaris, Polymyositis, Primary biliary cirrhosis, Psoriasis, Psoriatic Arthritis, Relapsing polychondritis, Sjögren's syndrome, Temporal arteritis, Ulcerative Colitis, Vasculitis, and Wegener's granulomatosis.

"Antigen presenting cell" as used herein refers to cells which are capable of presentation of peptides to T cells bound to MHC molecules. This includes but is not limited to the so called "professional" antigen presenting cells comprising but not limited to dendritic cells, B cells, and macrophages, but also the so called non-professional antigen presenting cells which carry MHC molecules.

DESCRIPTION OF THE INVENTION

Cancer has been described as a personal disease. This is true at many different levels. First, mutations arise that cause disrupted metabolic pathways resulting in ongoing proliferation, evasion of growth suppressors, cellular replicative immortality, resistance to cell death and dysregulation of cell energetics, with associated angiogenesis and metastasis [2]. Each tumor comprises multiple genomic mutations. Some are silent mutations (synonymous) which do not change amino acid coding; others result in amino acid changes. Each tumor has a unique combination and number of mutated proteins. In many cases mutations are stochastic and thus unique to the individual. However, some proteins are more prone to mutations than others and have particular locations at which such mutations are more likely to occur. An initial mutation (trunk mutation or driver mutation) may be followed by many more mutations, all stochastic (branch or passenger mutations). Thus, the initial genomic aberration is personal, the combination of unique tumor proteins is personal, and various therapeutic interventions may be prescribed based on this pattern. Each cell comprising a mutated protein is then subject to surveillance by the immune system, which may result in elimination of the cancer cell, or its escape through immune evasion or by inducing anergy or immune suppression [3]. As the immune surveillance depends on an individual patient's combination of HLA alleles, this is also personal. And the presence of cognate T cells which can participate in the process of immune surveillance is determined by the individual's prior immune exposure and T cell repertoire. So this too is personal. Our findings show that mutations present in tumor proteins by the time of clinical diagnosis have developed several means of camouflage from immune surveillance and elimination, and that strategies to overcome such camouflage must be employed to achieve effective immunotherapy. The present invention provides such strategies by devising means to expose and present the tumor specific peptides to T cell recognition and effective elimination by T cells and by utilizing the B cell epitopes also exposed.

This invention provides a method for maximizing the immune response to mutated tumor specific proteins, either by means of stimulation of dendritic cells or T cells in vitro followed by administration of these cells to a patient, or by means of administration of a neoantigen vaccine in which de novo peptides, or their encoding nucleic acids, have been designed to ensure an appropriate level of binding affinity to a particular cancer patient's MHC alleles. Neoantigen selection from mutated tumor proteins is often limited by poor binding to a patient's MHC alleles. This invention overcomes this limitation by providing methods to design novel peptides, not found in the tumor protein, which bind a patient's alleles with a desired binding affinity while still retaining the tumor-specific T cell exposed motif needed to stimulate T cells cognate for the tumor mutation. The invention also provides methods to analyze tumor T cell exposed motifs and identify matches in the human proteome which will be presented by the MHC of the particular subject. It thus enables an informed choice of neoantigens based on risk-benefit analysis of off-target binding. The invention provides methods to design personalized neoantigen peptides for a particular patient based on that patient's alleles and unique mutations and to group these peptides into a vaccination regimen. It also provides methods to design an array of peptides suitable for targeting the mutations common to many tumor proteins and cancer types.

Methods for precisely predicting MHC binding, identifying and analyzing T cell exposed motifs and generating peptides with altered binding affinity are provided in the following co-pending applications, all of which are incorporated herein by reference in their entirety: PCT US2011/029192, PCT US2012/055038, US2014/014523, PCT US2015/039969, PCT US2017/021781, US Publ. No. 20130330335, US Publ. No. 20160132631, US Publ. No. 20170039314, US Publ. No 20170161430 and US Publ. No. 20190070255.

The present invention provides a method for maximizing the number of opportunities to mount a cytotoxic T cell attack on a tumor which carries mutated proteins. In one embodiment the invention provides a method for generating a peptide or an array of peptides that carry the same T cell exposed motifs that are found in the tumor specific proteins, but wherein said peptide or peptides in the array are not present in the tumor, but rather are created by substitution of flanking amino acids to optimize the binding affinity of said peptides to the alleles of a particular tumor-bearing subject. Further embodiments of the invention then enable the selection of a group of peptides so created, which when synthesized, are capable of stimulating tumor specific T cells of the tumor-bearing subject. In particular embodiments these peptides may be encoded in nucleic acid sequences, which may be RNA or DNA. In some embodiments the peptides in the array generated are of 9 or 10 amino acids long. In such embodiments the T cell response stimulated is as the result of binding to MHC I molecules and the response by CD8+ T cells. In other embodiments the peptides in the array generated are 15 amino acids long. In such embodiments the T cell response stimulated is as the result of binding to MHC II molecules and the response by CD4+ T cells. In yet other instances the peptides may be longer, up to about 35 amino acids. In yet other embodiments the T cell response stimulated is as the result of both CD8+ and CD4+ responses.

In particular embodiments a single peptide capable of stimulating tumor specific T cells of the tumor-bearing subject may be selected. In other instances, up to 5 peptides maybe selected. In another desired embodiment a group of selected peptides in the array capable of stimulating tumor specific T cells of the tumor-bearing subject comprises at least 5 unique peptides not found in the tumor; in other embodiments the array encompasses at least 20 unique peptides, while in further embodiments the array has more than 60 unique peptides not found in the tumor. Each peptide carries a T cell exposed motif that is shared with the tumor protein at a position that includes the mutated amino acid in the T cell exposed motif. In some embodiments the group of peptides has at least 5 different T cell exposed motifs; in other embodiments the group of selected peptides comprises at least 10 different T cell exposed motifs. In yet other embodiments the group of selected peptides comprises at least 50 different T cell exposed motifs. In some particular embodiments the flanking amino acids of the peptides are selected so each peptide group has peptides collectively predicted to bind to at least 2 different MHC alleles carried by the tumor bearing subject. In other embodiments the flanking amino acids of the peptides are selected so each peptide group has peptides collectively predicted to bind to at least 4 different MHC alleles carried by the tumor bearing subject. In some embodiments a group of peptides created by substitution of the flanking amino acids of one or more T cell exposed motif to optimize binding to MHC allele of an individual subject may be combined in an array with naturally occurring neoepitope peptides.

The signal strength stimulating T cells as the result of presentation of peptides to T cells depends in part on the affinity of the peptide to the MHC. In some cases a very high affinity may be sought; in others a moderately high affinity. It is therefore useful to be able to select peptides of a desired affinity, but which are still present the same T cell exposed motif. In one embodiment of the invention therefore, the invention enables the selection of peptides that bind better than 99% of other peptides in the mutant protein; in other embodiments the invention enables selection of peptides binding better than 95% of other peptides in the mutant protein, while in further instances selection of peptides with a binding affinity of about 85% or better is enabled. Described in a different way, in one embodiment the invention enables selection of peptides which are predicted to bind at concentrations of less than 20 nanomolar, and in other embodiments at less than 50 nanomolar, less than 200 nanomolar or at less than 500 nanomolar concentrations. In some particular embodiments, the peptides in the group of T cell stimulating peptides are selected to include only peptides soluble in aqueous solutions; in yet other embodiments the peptides may be soluble in other solvents, including but not limited to, dimethyl sulphoxide.

The invention addresses both tumor specific mutations which are personal to a specific cancer patient and also those mutations which appear repeatedly in the same protein in cancers of different types in different subjects. In one embodiment, therefore, the invention embodies a method to create a group of peptides, not found in the original mutated protein, which are capable of stimulating T cells specific to the individual tumor-bearing subject and which target the mutations in proteins unique to those in the tumor of that subject. Such a group of peptides is selected to bind to MHC alleles carried by that subject. In yet other embodiments however, the present invention enables selection of a group of peptides that will elicit T cells to respond to mutations that are found in multiple cancers, including cancers arising from different tissues. Such an array of peptides is selected based on the presence of T cell exposed motifs that match those in commonly mutated proteins but also on their binding to any of an extended list of alleles that may be carried by any cancer patient who has a cancer with the common mutation. In one particular embodiment, the sequences of peptides suitable to stimulate T cells targeting common mutations in BRAF, EGFR, ERBB2, PTEN and PIK3CA for individuals carrying any one of 8 MHC I or 4 MHC II alleles are provided.

The T cell stimulating peptides described and selected in this invention may be deployed in several ways. In some embodiments they can be used in vitro to prime dendritic cells which upon administration to the tumor-bearing subject will stimulate T cells. In other embodiments the peptides may be used in vitro to stimulate T cells, whether said T cells are from the tumor bearing subject or from an allele matched donor. The stimulated T cells are then administered to the subject. In preferred embodiments the groups of T cell stimulating peptides designed and selected by the methods of the invention are used as a vaccine administered to the tumor bearing subject. In some embodiments, instead of applying the peptides as a vaccine, nucleic acids encoding the peptides are administered to the subject, wherein said nucleic acids may be RNA or DNA.

The goal of the invention is to provide peptides to stimulate T cells which will target the mutant protein displaying the same T cell exposed motifs. For this to happen the peptides from the mutant protein in the tumor need to be naturally presented at some level by the MHC alleles of the subject. Therefore, another embodiment of the present invention provides for selection of peptides from the initial array which have a sufficient binding affinity to the subject's MHC alleles to allow some presentation. In particular, therefore, the selection of peptides is down-selected to remove targets which are in the lower 50% of probability of presentation by the subject's MHC, i.e. those with less than the mean binding affinity for the protein from which their T cell exposed motif is derived.

Having identified an array of T cell stimulating peptides which are suitable to target the mutated tumor protein in the particular tumor-bearing subject of known MHC alleles, the present invention then embodies the design of a vaccination regimen. In one such embodiment the group of selected peptides is administered at one time. In an alternate embodiment the group of peptides may be divided into multiple subgroups which are administered at different time points. In one embodiment the invention provides for organizing the subgroups to ensure that several T cell exposed motifs are targeted in each subgroup and that the peptides depend on several different alleles for presentation. As motifs which are rare in the human proteome may offer an advantage in stimulating T cells and specifically targeting a tumor, one embodiment provides for prioritizing the peptide subgroup composition according to the frequency classification of the T cell exposed motif that each peptide carries relative to its frequency in the human proteome or human immunoglobulinome. In a preferred embodiment, the rare motifs are included in the early subgroups.

Checkpoint inhibitor drugs prevent or delay the termination of T cell responses. In some embodiments the present invention provides for the administration of a checkpoint inhibitor with the vaccine or, in a preferred embodiment, following a peptide vaccine as described herein, or nucleic acid vaccine encoding peptides. As another embodiment, when the vaccine is administered in multiple subgroups of peptides over time the checkpoint inhibitor may be reapplied after each or some of the subgroups of peptides. Furthermore, there are other immunomodulatory interventions which extend the T cell responses, including but not limited to NK cells, IL-15, and other superagonists. In a further embodiment the present invention provides for the administration of other immunotherapeutic interventions intended to extend or enhance T cell responses with the vaccine or, in a preferred embodiment, following the vaccine.

In embodiments of this invention, a vaccine is provided comprising peptides which carry T cell exposed motifs found in the tumor, but in which flanking amino acids have been interchanged to change the binding of the peptide to optimize to a desired binding to the subject's MHC alleles. In some embodiments said vaccine is delivered to the subject parenterally, in other embodiments delivery is intradermal or transdermal. In the case of transdermal vaccination one preferred embodiment provides for delivery of peptides in a microneedle array. Said microneedle array may be configured to deliver multiple different peptides or nucleotide sequences encoding different peptides in the same array, In some embodiments, vaccination is accompanied by an adjuvant. In some embodiments an adjuvant is incorporated into the solution comprising the neoantigen peptides. When vaccine is delivered transdermally, a particular embodiment is to accompany delivery by a local proinflammatory agent, whether physical, such as, but not limited to, heat, infrared light or friction, or by administration of a proinflammatory drug or cream.

As the present invention identifies T cell stimulating peptides carrying T cell exposed motifs found in multiple cancers and provides suitable binding peptides to deliver such T cell motifs to subjects of different MHC alleles, an embodiment of the invention is to provide an array of peptides, which offer combinations of T cell exposed motifs and binding affinities, for a range of common cancer mutations and for many different alleles. Such an array, in one embodiment, provides peptides with a binding affinity of less than 20 nanomolar, in another less than 50 nanomolar, in another embodiment less than 100 nanomolar and in yet another less than 500 nanomolar concentrations. In yet others the array comprises peptides which individually have binding affinities of between 20 and 500 nanomolar. Said peptide array in one embodiment comprises T cell motifs shared by at least 3 cancers, and in another embodiment comprises T cell exposed motifs carried by cancers affecting more than three tissue types. One embodiment provides an array that encompasses the mutations commonly found in 5 proteins, while in another embodiment the array includes mutations commonly found in 10 proteins that are shared in more than one cancer type. In a particular embodiment, the array includes peptides that include T cell exposed motifs found in the proteins BRAF, EGFR, ERBB2, PTEN and PIK3CA and embodies peptides suitable to administer to individuals carrying any one of 8 MHC I or 4 MHC II particular alleles, in particular embodying sequences for such proteins. In yet other embodiments further peptide arrays are designed to be suitable to administer to individuals with yet other MHC alleles or combinations thereof. In addition to amino acid substitutions found in multiple cancers, there are also insertions and deletions that are common to many cancers, and also gene fusions which generate common junction sites in the resultant protein products. In another embodiment, therefore, the invention provides a method for designing an array of peptides which enable tumor-specific targeting of the junction sites created by insertions, deletions and fusions. In one particular embodiment the invention provides specific peptides which may be used to target EGFRviii, a common oncogenic deletion mutant of epidermal growth factor receptor found in multiple cancers.

In further embodiments a B cell epitope peptide may be administered in conjunction with a T cell stimulating peptide. In some embodiments said B cell epitope may be a separate peptide or alternatively it may be in the same peptide as that designed to stimulate the T cells, or otherwise operably linked via a linker. In some embodiments a modified T cell stimulating peptide is designed to provide stronger T cell help to a B cell epitope through modified binding. Given the polyspecificity of T cell receptor binding, the occurrence of off-target binding of T cells stimulated to respond to a tumor specific mutation is of concern as a source of potential adverse reactions. Therefore, in one embodiment the present invention provides a method to identify potential unintended targets in the human proteome and to determine if such potential collateral targets are of concern for the particular subject according to the MHC alleles said subject carries. The application of this embodiment provides a list of the proteins in the human proteome which may be inadvertently targeted by CD8+ or CD4+ T cells stimulated by the peptide arrays selected for T cell targeting of the tumor and with sufficient binding affinity to MHC alleles of the particular subject to stimulate T cells. In one embodiment said list is flagged to identify proteins of particular concern because they have a critical function or are non-redundant and the list is provided to the oncologist to enable an informed risk benefit analysis.

Determination of the subject's HLA alleles are a necessary prerequisite to designing a peptide of suitable HLA binding affinity for that individual. Therefore, in some embodiments the HLA alleles of the subject are determined from the whole exome sequence which is also used to determine the tumor mutations.

The peptides designed to stimulate an immune response of the subject may be administered as a peptide composition or a nucleic acid composition encoding said peptide or peptides. In yet another embodiment the selected designed peptides may be delivered in a nanoparticular formulation. In some particular embodiments one or more selected designed peptides may be fused to a fusion partner by means of a linker. In some embodiments said linker is cleavable. The fusion partner is selected from the group comprising polyhydrophobic acids or unnatural amino acids or a lipid core system to enhance nanoparticle formation and favor uptake by antigen presenting cells. In some embodiments the fusion partner may also be an immunoglobulin or an immunoglobulin Fc region or other immunoglobulin fragment which facilitates uptake by antigen presenting cells.

The T cell stimulating peptides designed and selected to provide binding for the individual subject MHC alleles and specific to the tumor mutations of that subject are highly personal. In some embodiments, therefore, the particular sequence specification of such peptides are included in a prescription written for that particular patient. In some embodiments the peptides in the prescription may be formulated by a compounding pharmacy.

Personalized Cancer Vaccines

There is increasing evidence that a variety of T cell immunotherapies can be successful in halting the progression of cancer [4]. Whereas in early days of cancer immunotherapy, the focus was on tumor-associated antigens as targets of both antibodies and T cell based therapies, current focus is now towards proteins comprising specific mutations in cancer cells, so called tumor-specific antigens or tumor neoantigens [5-8]. The fundamental goal in identifying and targeting mutations specific to the tumor is to differentiate normal from tumor tissue and hence eliminate tumor cells while leaving normal cells unharmed. A second current focus, and often combined strategy, is the application of checkpoint inhibitors and other immunomodulatory interventions to unleash T cell responses.

Tumor specific antigens comprise both those common to many cancers, and those which are unique to any single patient and which may change over the life of a tumor. Generally, the higher the mutational load, the more infiltrating T cells and the more inflamed a tumor, the greater probability of a check-point inhibitor leading to a successful T cell driven elimination of the tumor cells. Mutational load tends to differ between cancer types; some such as melanoma and colorectal cancers have a high mutational frequency. Others such as glioblastoma are notoriously low in mutational numbers.

Several recent publications have reported promising, but mixed, results in the development of personalized vaccines for melanoma [9, 10], lung cancer [11] and glioblastoma [12, 13]. These have employed from 1 to 20 different neoantigens. Increasing the number of neoepitopes incorporated in a vaccine allows for a multipronged attack on the tumor using multiple alleles and multiple antigens derived from different proteins. Mutations continue to arise in tumors as they develop, with antigens gained or lost in the process. There may also be heterogeneity of mutations within a tumor and the mutational landscape may not be fully reflected in the sequencing of a biopsy. Hence a high number of cytotoxic "hits" is desirable rather than depending on only one or two antigen targets [8]. A goal of the present invention is to maximize the number of tumor specific epitopes which can be targeted by T cells responding to peptides presented by a particular patient's alleles.

The goal of T cell immunotherapy has been primarily to activate CD8+ cytotoxic T cells which will target tumor cells, but also to stimulate CD4+T helper cells to enhance CD8+ responses. Stimulation of CD4+T helper cells may also enhance B cell responses. Selection of peptides for use as neoepitopes has followed several paths. As a starting point, given the diversity of the human genome, it is desirable to compare sequences of proteins in tumor biopsies with a normal tissue from the same patient [14]. However, reference human genomes are frequently used as comparators to determine mutation sites. Practitioners have then used several approaches to select peptides for use, or for encoding in RNA or DNA for administration. In some instances peptides have been selected based on mass spectroscopy [15, 16]; in yet others predictive algorithms, most often NetMHC Pan [17], was used to select peptides [9, 10, 13]. In one instance, both approaches were reported, but in this particular case none of the mutated peptides were detected by mass spectroscopy [12].

Checkpoint inhibitors are not always predictable in their efficacy; despite remarkable benefits to some patients, the percentage of patients who benefit is still low, on average about 20%. There is an effort to define better biomarkers to predict the outcome of checkpoint inhibitor therapy [18-20]. Furthermore, a wide variety of adverse off-target effects have been reported following checkpoint inhibitor treatment [21]. The issue underlying both problems is that checkpoint inhibitors are indiscriminate and will unleash whatever T cells the patient has at the time of administration, whether or not they are targeting the tumor or self-antigens. Combination of neoantigen vaccination with checkpoint inhibitor blockade has been shown to elicit T cells specific of the neoantigens [22] and has been combined with neoantigen vaccines in several of the above referenced studies. Thus, one goal of the present invention is to maximize the number of tumor-targeting T cells which are dis-inhibited by checkpoint inhibitor adminsitration, while also focusing on those T cells which do not target critical self-antigens. This has the potential to greatly increase the efficacy of checkpoint blockade therapy. Other immunomodulatory interventions have been designed to extend T cell responses, including but not limited to NK cells, IL-15, and other superagonists. In a further embodiment the present invention provides for the administration of such other immunotherapeutic interventions intended to extend T cell responses with the vaccine or, in a preferred embodiment, following the vaccine.

Neoepitope vaccines also inevitably give rise to some off-target autoimmunity due to T cell polyspecificity among proteins with shared T cell exposed motifs. The neoepitope vaccine studies cited above have not addressed this potential adverse effect. In a progressing cancer there is necessarily a risk-benefit choice between eliminating the tumor and the effect of the off-target responses. In the present invention we describe how tumor neoantigens can be pre-screened for potential self-protein cross reactivity in a particular patient, based on that patient's alleles. This allows for an informed choice of which neoantigens are beneficial for targeting the tumor while also minimizing adverse effects.

There is therefore a need to facilitate the selection of peptides suitable for use in neoantigen vaccines and to maximize the number and immunogenicity of peptides that are applied. This can then also be used to enhance the benefits of checkpoint inhibitor blockade.

Common Cancer Associated Driver Mutations

Mutations in cancers include those which are unique to a specific patient. Some are patient specific driver mutations, arising as the root cause of cell dysregulation. Others arise as branch or passenger mutations, which are sequelae to an earlier trunk or driver mutation. Such mutations may continue to evolve throughout the tumor progression. There are also a number of mutations which are found commonly at the same positions in the same proteins, some of which occur repeatedly across many cancer types [23-27]. The Cancer Genome Atlas documents many proteins which are found to share mutations across multiple cancer types (https://www.cancer.gov/about-nci/organization/ccg/research/structural-genomics/tcga). Some of these are simple amino acid substitutions arising from single nucleotide mutations; others involve amino acid duplications. In other cases, the mutations give rise to insertions and deletions (indels) and missense sequences. Where these mutations are shared across many cancers, a set of peptides can be designed for each patient HLA allele which will allow stimulation of T cells to specifically target tumor cells with cytotoxic T cells and/or T helper cells. In Example 7, provided below, therefore, we describe the approach to development of a set of "ready to go" neoantigens which have broad applicability across many cancers and for patients with defined common mutations and known HLA typing. In some embodiments, such "multicancer" neoantigens may be combined with a set of "bespoke" personalized neoantigens. In the case of indels and missense mutations, when these result in an in-frame downstream sequence they provide a target-rich sequence, but every patient is unique and so selection of vaccine peptides for these must be handled as a personalized design effort. In some embodiments consistent indels are found repeatedly in many cancers. In one particular example EGFR (Epidermal growth factor receptor) has two well documented oncogenic deletions, known as EGFRvii and EGFRviii. In EGFRviii, the most common deletion, In EGFRviii exons 2 and 7 are deleted leading to removal of amino acids 6-273 of the mature protein; a glycine is inserted in the bridge and the downstream sequence remains in frame. An effort was made to use a peptide spanning the deletion junction as a vaccine. This peptide, comprising 14 amino acids comprises a B cell epitope and was viewed as a way of inducing antibody dependent cytotoxicity when combined with a linked adjuvant [28]. In Example 8 we provide an approach to increasing the potential number of HLA alleles that could benefit from a peptide spanning the deletion junction in EGFRviii, and hence provide an example of an array of peptides which could be used for T cell stimulation to target this mutated EGFR.

In some preferred embodiments, mutated proteins in biopsy samples are identified by sequencing the genome, proteome or transcriptome of cells from the biopsy. The present invention is not limited to any particular method of obtaining sequences of mutated in a biopsy. A variety of sequencing methods are readily available to those of ordinary skill in the art.

In some preferred embodiments, the present invention utilizes nucleic acid sequencing techniques. The nucleic acid sequences are preferably converted in silico to protein sequences from the identification of mutated amino acids and peptides comprising the mutated amino acids.

In some embodiments, the sequencing is Second Generation (a.k.a. Next Generation or Next-Gen), Third Generation (a.k.a. Next-Next-Gen), or Fourth Generation (a.k.a. N3-Gen) sequencing technology including, but not limited to, pyrosequencing, sequencing-by-ligation, single molecule sequencing, sequence-by-synthesis (SBS), semiconductor sequencing, massive parallel clonal, massive parallel single molecule SBS, massive parallel single molecule real-time, massive parallel single molecule real-time nanopore technology, etc. Morozova and Marra provide a review of some such technologies in Genomics, 92: 255 (2008), herein incorporated by reference in its entirety. Those of ordinary skill in the art will recognize that because RNA is less stable in the cell and more prone to nuclease attack experimentally RNA is usually reverse transcribed to DNA before sequencing.

DNA sequencing techniques include fluorescence-based sequencing methodologies (See, e.g., Birren et al., Genome Analysis: Analyzing DNA, 1, Cold Spring Harbor, N.Y.; herein incorporated by reference in its entirety). In some embodiments, the sequencing is automated sequencing. In some embodiments, the sequencing is parallel sequencing of partitioned amplicons (PCT Publication No: WO2006084132 to Kevin McKernan et al., herein incorporated by reference in its entirety). In some embodiments, the sequencing is DNA sequencing by parallel oligonucleotide extension (See, e.g., U.S. Pat. No. 5,750,341 to Macevicz et al., and U.S. Pat. No. 6,306,597 to Macevicz et al., both of which are herein incorporated by reference in their entireties). Additional examples of sequencing techniques include the Church polony technology (Mitra et al., 2003, Analytical Biochemistry 320, 55-65; Shendure et al., 2005 Science 309, 1728-1732; U.S. Pat. Nos. 6,432,360, 6,485,944, 6,511,803; herein incorporated by reference in their entireties), the 454 picotiter pyrosequencing technology (Margulies et al., 2005 Nature 437, 376-380; US 20050130173; herein incorporated by reference in their entireties), the Solexa single base addition technology (Bennett et al., 2005, Pharmacogenomics, 6, 373-382; U.S. Pat. Nos. 6,787,308; 6,833,246; herein incorporated by reference in their entireties), the Lynx massively parallel signature sequencing technology (Brenner et al. (2000). Nat. Biotechnol. 18:630-634; U.S. Pat. Nos. 5,695,934; 5,714,330; herein incorporated by reference in their entireties), and the Adessi PCR colony technology (Adessi et al. (2000). Nucleic Acid Res. 28, E87; WO 00018957; herein incorporated by reference in its entirety).

Next-generation sequencing (NGS) methods share the common feature of massively parallel, high-throughput strategies, with the goal of lower costs in comparison to older sequencing methods (see, e.g., Voelkerding et al., *Clinical Chem.*, 55: 641-658, 2009; MacLean et al., *Nature Rev. Microbiol.*, 7: 287-296; each herein incorporated by reference in their entirety). NGS methods can be broadly divided into those that typically use template amplification and those that do not. Amplification-requiring methods include pyrosequencing commercialized by Roche as the 454 technology platforms (e.g., GS 20 and GS FLX), Life Technologies/Ion Torrent, the Solexa platform commercialized by Illumina, GnuBio, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, and emerging platforms commercialized by VisiGen, Oxford Nanopore Technologies Ltd., and Pacific Biosciences, respectively.

In pyrosequencing (Voelkerding et al., *Clinical Chem.*, 55: 641-658, 2009; MacLean et al., *Nature Rev. Microbiol.*, 7: 287-296; U.S. Pat. Nos. 6,210,891; 6,258,568; each herein incorporated by reference in its entirety), template DNA is fragmented, end-repaired, ligated to adaptors, and clonally amplified in-situ by capturing single template molecules with beads bearing oligonucleotides complementary to the adaptors. Each bead bearing a single template type is compartmentalized into a water-in-oil microvesicle, and the template is clonally amplified using a technique referred to as emulsion PCR. The emulsion is disrupted after amplification and beads are deposited into individual wells of a picotitre plate functioning as a flow cell during the sequencing reactions. Ordered, iterative introduction of each of the four dNTP reagents occurs in the flow cell in the presence of sequencing enzymes and luminescent reporter such as luciferase. In the event that an appropriate dNTP is added to the 3' end of the sequencing primer, the resulting production of ATP causes a burst of luminescence within the well, which is recorded using a CCD camera. It is possible to achieve read lengths greater than or equal to 400 bases, and $10^6$ sequence reads can be achieved, resulting in up to 500 million base pairs (Mb) of sequence.

In the Solexa/Illumina platform (Voelkerding et al., *Clinical Chem.*, 55: 641-658, 2009; MacLean et al., *Nature Rev. Microbiol.*, 7: 287-296; U.S. Pat. Nos. 6,833,246; 7,115,400; 6,969,488; each herein incorporated by reference in its entirety), sequencing data are produced in the form of shorter-length reads. In this method, single-stranded fragmented DNA is end-repaired to generate 5'-phosphorylated blunt ends, followed by Klenow-mediated addition of a single A base to the 3' end of the fragments. A-addition facilitates addition of T-overhang adaptor oligonucleotides, which are subsequently used to capture the template-adaptor molecules on the surface of a flow cell that is studded with oligonucleotide anchors. The anchor is used as a PCR primer, but because of the length of the template and its proximity to other nearby anchor oligonucleotides, extension by PCR results in the "arching over" of the molecule to hybridize with an adjacent anchor oligonucleotide to form a bridge structure on the surface of the flow cell. These loops of DNA are denatured and cleaved. Forward strands are then sequenced with reversible dye terminators. The sequence of incorporated nucleotides is determined by detection of post-incorporation fluorescence, with each fluor and block removed prior to the next cycle of dNTP addition. Sequence read length ranges from 36 nucleotides to over 250 nucleotides, with overall output exceeding 1 billion nucleotide pairs per analytical run.

Sequencing nucleic acid molecules using SOLiD technology (Voelkerding et al., *Clinical Chem.*, 55: 641-658, 2009; MacLean et al., *Nature Rev. Microbiol.*, 7: 287-296; U.S. Pat. Nos. 5,912,148; 6,130,073; each herein incorporated by reference in their entirety) also involves fragmentation of the template, ligation to oligonucleotide adaptors, attachment to beads, and clonal amplification by emulsion PCR. Following this, beads bearing template are immobilized on a derivatized surface of a glass flow-cell, and a primer complementary to the adaptor oligonucleotide is annealed. However, rather than utilizing this primer for 3' extension, it is instead used to provide a 5' phosphate group for ligation to interrogation probes containing two probe-specific bases followed by 6 degenerate bases and one of four fluorescent labels. In the SOLiD system, interrogation probes have 16 possible combinations of the two bases at the 3' end of each probe, and one of four fluors at the 5' end. Fluor color, and thus identity of each probe, corresponds to specified color-space coding schemes. Multiple rounds (usually 7) of probe annealing, ligation, and fluor detection are followed by denaturation, and then a second round of sequencing using a primer that is offset by one base relative to the initial primer. In this manner, the template sequence can be computationally re-constructed, and template bases are interrogated twice, resulting in increased accuracy. Sequence read length averages 35 nucleotides, and overall output exceeds 4 billion bases per sequencing run.

In certain embodiments, sequencing is nanopore sequencing (see, e.g., Astier et al., J. Am. Chem. Soc. 2006 Feb. 8; 128(5):1705-10, herein incorporated by reference). The theory behind nanopore sequencing has to do with what occurs when a nanopore is immersed in a conducting fluid and a potential (voltage) is applied across it. Under these conditions a slight electric current due to conduction of ions through the nanopore can be observed, and the amount of current is exceedingly sensitive to the size of the nanopore. As each base of a nucleic acid passes through the nanopore, this causes a change in the magnitude of the current through the nanopore that is distinct for each of the four bases, thereby allowing the sequence of the DNA molecule to be determined.

In certain embodiments, sequencing is HeliScope by Helicos BioSciences (Voelkerding et al., *Clinical Chem.*, 55: 641-658, 2009; MacLean et al., *Nature Rev. Microbiol.*, 7: 287-296; U.S. Pat. Nos. 7,169,560; 7,282,337; 7,482,120; 7,501,245; 6,818,395; 6,911,345; 7,501,245; each herein incorporated by reference in their entirety). Template DNA is fragmented and polyadenylated at the 3' end, with the final adenosine bearing a fluorescent label. Denatured polyadenylated template fragments are ligated to poly(dT) oligonucleotides on the surface of a flow cell. Initial physical locations of captured template molecules are recorded by a CCD camera, and then label is cleaved and washed away. Sequencing is achieved by addition of polymerase and serial addition of fluorescently-labeled dNTP reagents. Incorporation events result in fluor signal corresponding to the dNTP, and signal is captured by a CCD camera before each round of dNTP addition. Sequence read length ranges from 25-50 nucleotides, with overall output exceeding 1 billion nucleotide pairs per analytical run.

The Ion Torrent technology is a method of DNA sequencing based on the detection of hydrogen ions that are released during the polymerization of DNA (see, e.g., Science 327 (5970): 1190 (2010); U.S. Pat. Appl. Pub. Nos. 20090026082, 20090127589, 20100301398, 20100197507, 20100188073, and 20100137143, incorporated by reference in their entireties for all purposes). A microwell contains a template DNA strand to be sequenced. Beneath the layer of microwells is a hypersensitive ISFET ion sensor. All layers are contained within a CMOS semiconductor chip, similar to that used in the electronics industry. When a dNTP is incorporated into the growing complementary strand a hydrogen ion is released, which triggers a hypersensitive ion sensor. If homopolymer repeats are present in the template sequence, multiple dNTP molecules will be incorporated in a single cycle. This leads to a corresponding number of released hydrogens and a proportionally higher electronic signal. This technology differs from other sequencing technologies in that no modified nucleotides or optics are used. The per-base accuracy of the Ion Torrent sequencer is ~99.6% for 50 base reads, with ~100 Mb to 100 Gb generated per run. The read-length is 100-300 base pairs. The accuracy for homopolymer repeats of 5 repeats in length is ~98%. The benefits of ion semiconductor sequencing are rapid sequencing speed and low upfront and operating costs.

In some embodiments, sequencing is the technique developed by Stratos Genomics, Inc. and involves the use of Xpandomers. This sequencing process typically includes providing a daughter strand produced by a template-directed synthesis. The daughter strand generally includes a plurality of subunits coupled in a sequence corresponding to a contiguous nucleotide sequence of all or a portion of a target nucleic acid in which the individual subunits comprise a tether, at least one probe or nucleobase residue, and at least one selectively cleavable bond. The selectively cleavable bond(s) is/are cleaved to yield an Xpandomer of a length longer than the plurality of the subunits of the daughter strand. The Xpandomer typically includes the tethers and reporter elements for parsing genetic information in a sequence corresponding to the contiguous nucleotide sequence of all or a portion of the target nucleic acid. Reporter elements of the Xpandomer are then detected. Additional details relating to Xpandomer-based approaches are described in, for example, U.S. Pat. Pub No. 20090035777, entitled "High Throughput Nucleic Acid Sequencing by Expansion," filed Jun. 19, 2008, which is incorporated herein in its entirety. Other emerging single molecule sequencing methods include real-time sequencing by synthesis using a VisiGen platform (Voelkerding et al., *Clinical Chem.*, 55: 641-58, 2009; U.S. Pat. No. 7,329,492; U.S. patent application Ser. No. 11/671,956; U.S. patent application Ser. No. 11/781,166; each herein incorporated by reference in their entirety) in which immobilized, primed DNA template is subjected to strand extension using a fluorescently-modified polymerase and florescent acceptor molecules, resulting in detectible fluorescence resonance energy transfer (FRET) upon nucleotide addition.

In other preferred embodiments, the present invention utilizes protein sequencing techniques. In some embodiments, proteins my be sequenced by Edman degradation. See, e.g., Edman and Begg (1967). "A protein sequenator". Eur. J. Biochem. 1 (1): 80-91; Alterman and Hunziker (2011) Amino Acid Analysis: Methods and Protocols. Humana Press. ISBN 978-1-61779-444-5. In other embodiments, mass spectrometry techniques are utilized to sequence proteins. See, e.g., Shevchenko et al., (2006) "In-gel digestion for mass spectrometric characterization of proteins and proteomes". Nature Protocols. 1 (6): 2856-60; Gundry et al., (2009) "Preparation of proteins and peptides for mass spectrometry analysis in a bottom-up proteomics workflow" Current Protocols in Molecular Biology. Chapter 10: Unit10.25.

Considerations in Selection of Tumor Specific Antigens

T Cell Exposed Motifs

The goal of stimulating a cytotoxic T cell response to a tumor is to specifically and differentially destroy the tumor cells while leaving normal cells intact. It follows that to drive a T cell response specific to the cancer, the T cell receptor must recognize an epitope unique to the tumor. Thus, the mutated amino acid must be located in the exposed pentameric motif exposed to the T cell receptor. When a mutated amino acid is located in a pocket or groove exposed motif, it may or may not affect binding affinity, but it is hidden from the T cell receptor and cannot elicit tumor-specific T cell responses. In some instances, the natural binding affinity of the mutated peptide and its neighboring peptides in the affected protein may give rise to better binding in positions which do not expose the mutated amino acid. In some cases, so-called neoepitope peptides have been selected which do not, in fact, differentiate tumor and normal T cell exposed motifs [11, 29]. In the present invention we seek to maximize use of the T cell exposed motifs containing mutant amino acids, and hence focus the T cell response on these differentiating epitopes, and likewise subsequent expansion of this response as the result of administration of checkpoint inhibitors.

Peptide Binding Affinity

Many investigators have considered how to identify peptides in mutated tumor proteins which bind to a patient's MHC alleles. Some have employed mass spectrometry to identify the "presentome" of peptides bound and presented to T cells [15]. However, this has the bias of identifying very high affinity peptides. In some cases, the peptides containing mutant amino acids were never detected by mass spectroscopy [12].

It is not clear that the highest binding peptides are those which will actually generate the best cytotoxic T cell response. Indeed, evidence in other settings suggests that this is not the case and that an intermediate binding affinity may be most effective in stimulating a T cell response and good memory T cells [30]. Low affinity peptides may initiate a CD8+ response but this is not sustained [31]. Furthermore, also drawing on experience in an anti-microbial setting, an active interferon gamma response is also needed to trigger the development of T memory cells [32]. Strength of T cell receptor-pMHC binding may be a factor in determining whether the T cell response to a tumor leads to T cell exhaustion and tolerance [3].

Figure 2:
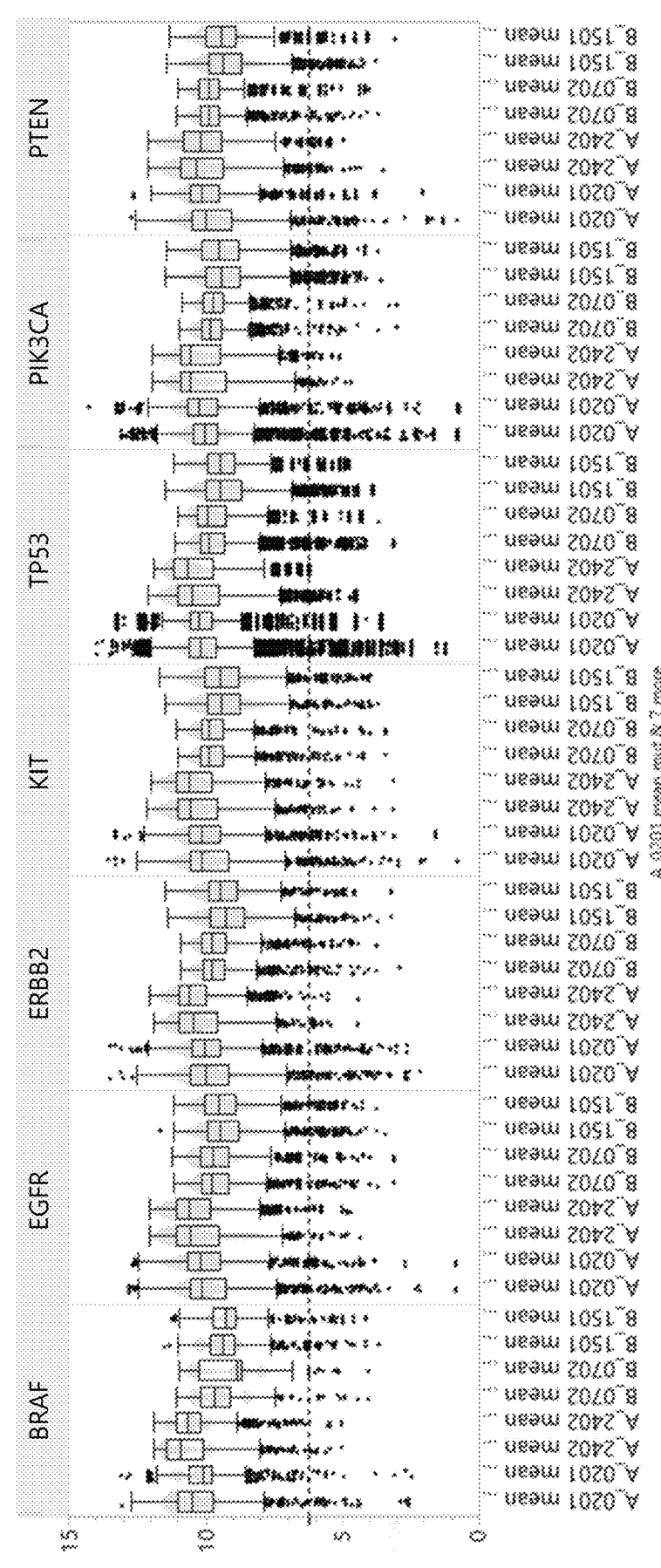
FIG. 2: Predicted binding affinity with mutant amino acid in groove exposed motif (GEM I) positions of wild type and multiple different mutant homologs of 7 tumor specific proteins. Predicted affinity (Y-axis=LN $IC_{50}$) for 4 MHC I alleles of wt vs mutant TCEM I for 7 different proteins commonly mutated in different cancers. The dashed line is at 500 nM, a value commonly used to predict T cell responses. The boxplot is a Tukey outlier type where the box represents the 25 and 75 percentile and the whiskers correspond to 1.5×interquartile range. The yellow shaded area comprises peptides with the highest affinity and for any of the alleles corresponds to approximately 1% of the total TCEM and are all outliers. Overall, the MHC I binding affinity of the peptides containing the TCEM is very low; a median of 10 implies a value of about 22 uM, more than 40×lower than the 500 nM that is the consensus T cell stimulatory level. In addition, there is no statistical difference between the wt and mutant TCEM-containing peptides as is shown graphically by the boxplots and the datapoint scatter.
Figure 11:
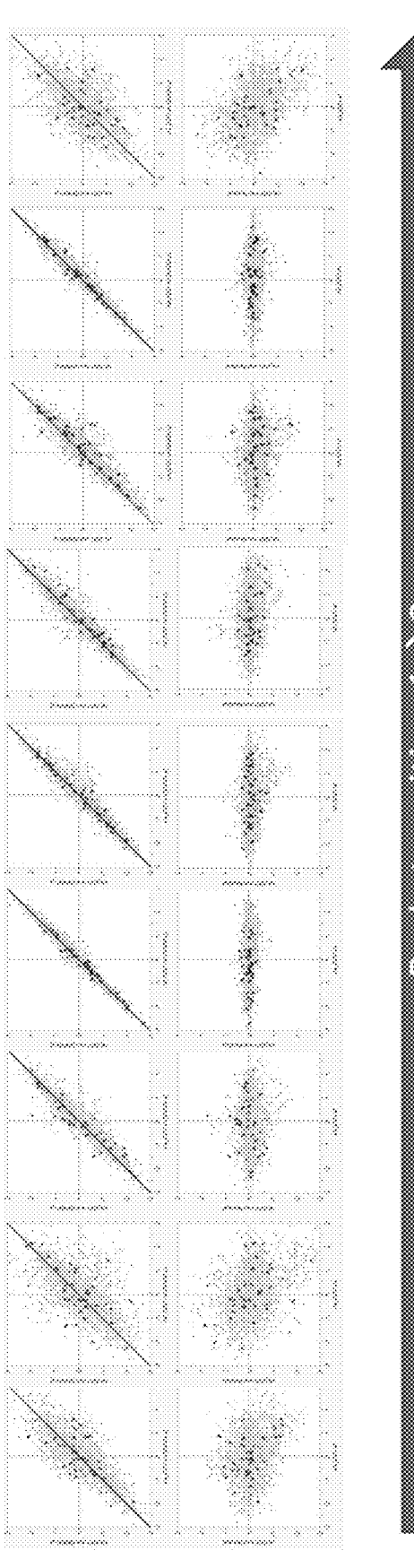
FIG. 11: Comparative predicted binding of the mutated region for one of the pairs of HLA A alleles in 60 cases. The plots combines all the data for one of the two A alleles for 60 cases (30 GBM plus 30 LUSC) and compares the binding of the native peptide to the mutated peptide with the mutant amino acid at the substituted position. All binding predictions have been standardized within protein to a zero mean unit variance distribution. The regression line is forced to a have an intercept of zero and a slope of one and essentially represents a null hypothesis that there is no difference in the binding between the wild type and mutated peptides. Squares are the oncogene mutants and triangles the tumor suppressor mutants on the background of all passenger mutants. Amino acid side chains in pocket positions 1,2,3 and 9, the GEM, are in combination bind to the side chains of the peptide in the pocket and are effectively responsible for the binding affinity. The amino acid side chains of pocket position 4,5,6,7,8, the TCEM, protrude from the surface of the histotope and interact with the T cell receptor.

Analysis of the predicted MHC binding of peptides comprising mutations among proteins documented in the TCGA shows no statistical difference in overall predicted binding affinity between mutant and wildtype homolog (FIGS. 1 and 2). However, for TCEM I there is a significant impact when the mutant amino acid lies in positions 2 or 9 of a 9mer (FIG. 11). Overall, based on analysis of proteins with mutations recorded in TCGA, the MHC I binding affinity of the peptides containing the T cell exposed motif which become mutated is very low; about 22 uM, which is more than 40×lower than the 500 nanoM that is the consensus T cell stimulatory level. This indicates that such peptides are overall not highly likely to naturally elicit an effective and sustained cytotoxic T cell response and memory.

In one embodiment, the present invention enables the design of peptides presenting the T cell exposed motif of interest with a range of MHC binding affinities, allowing for selection of very high affinity binders or intermediate binding affinity to the alleles of a particular patient with the goal of stimulating and effective cytotoxic response.

Frequency Characteristics of Peptides Generated by Mutations in Cancer

Figure 3:
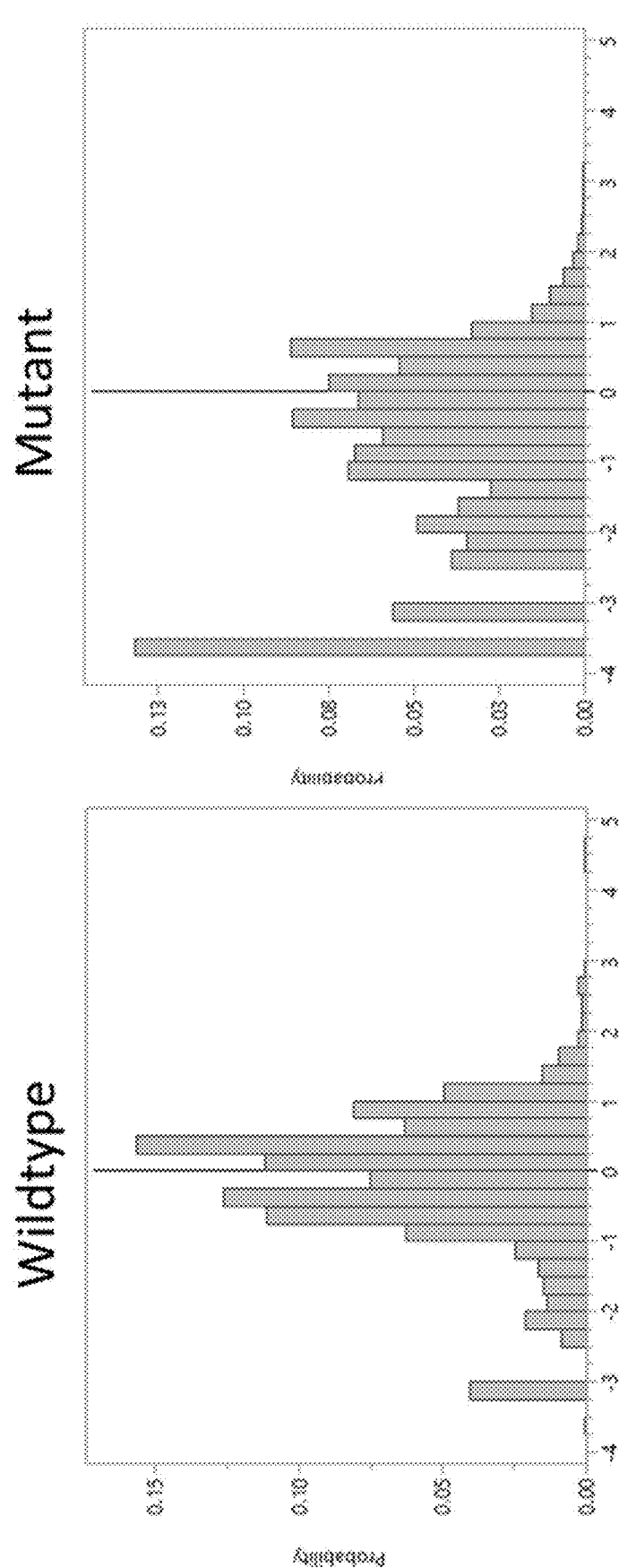
FIG. 3: Distribution histograms of TCEM I frequency for the 37,622 different TCEM peptides mutants (top panel) and wt motifs (bottom panel) in seven proteins of interest as listed in FIGS. 1 and 2. The base frequency of the TCEM in the proteome was log 2 basis. This frequency was standardized to a zero mean unit variance distribution with a Johnson Sl distribution function. The wt distribution shows that the mean is shifted slightly negative from zero mean of the full proteome but the standard deviation is very nearly 1.0 (unit variance). Thus, the it is inferred that the wt TCEM frequency is a relatively random selection from the proteome unit variance distribution. The histogram bar at the far left of the top panel is a coded frequency for TCEM completely absent from the human proteome. This pattern of TCEM generation by mutation shows the stochastic mutation process inserts amino acids into protein sequences that are either much more rare or in many cases (14% overall), completely absent in normal protein sequences in the proteome.
Figures 12A, 12B:
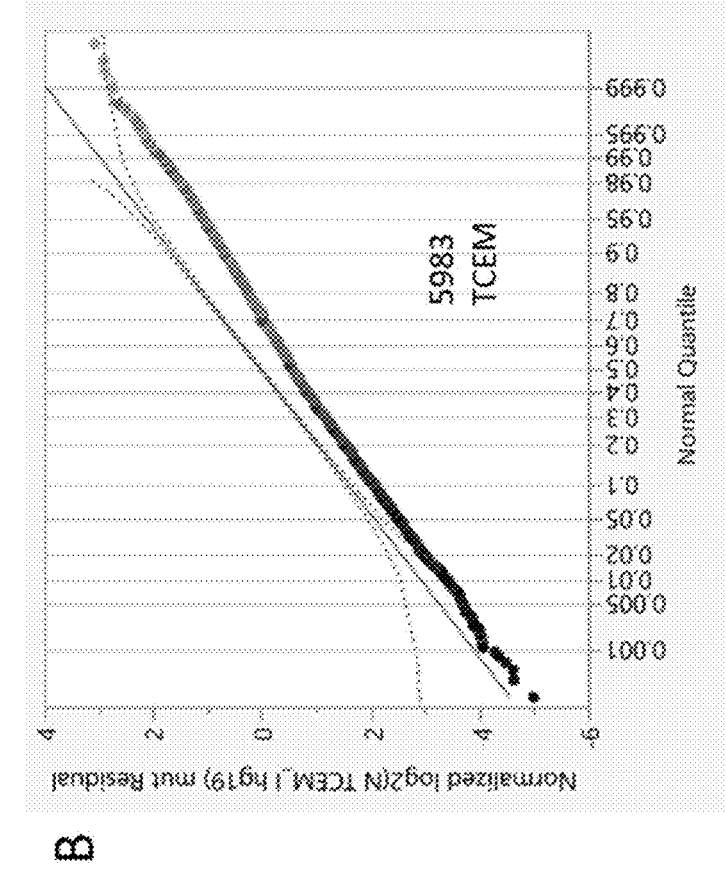
FIG. 12A-B: In 30 cases of GBM mutations in tumor proteins create rarer TCEM I motifs. A. Plot of mutant (y axis) compared to wild type (x axis) TCEM I motif frequency compared to the frequency of the motif in the human proteome. Negative numbers are less common in the proteome and values of −3 are absent completely from the proteome. Motifs are colored according to frequency with darker indicative of rarer motifs. B. The regression line is forced to a line with an intercept of zero and slope of one between the mutant and wild type sequences (i.e.=null hypothesis). The residuals all fall outside the low confidence limit on the quantile plot indicating a consistent difference between the mutant and wild type with the mutant carrying less common motifs.

Comparison of the frequency distribution of the T cell exposed motifs in peptides comprising mutations (for TCEM I cognate for MHC I molecules), among those documented in the TCGA, reveals that those comprising mutated amino acids are motifs that occur less commonly in the human proteome than their wildtype homologues (FIGS. 3 and 12). Overall the mutant peptides are biased towards those that are rare or even completely absent in the human proteome; the comparator here being all T cell exposed motif in all peptides of all isoforms of human proteins, approximately 88,000 proteins. The mutational event that inserts a new amino acid in the T cell exposed motif consistently produces T cell exposed motif that are much more rare as compared to the wildtype T cell exposed motif.

Figure 4:
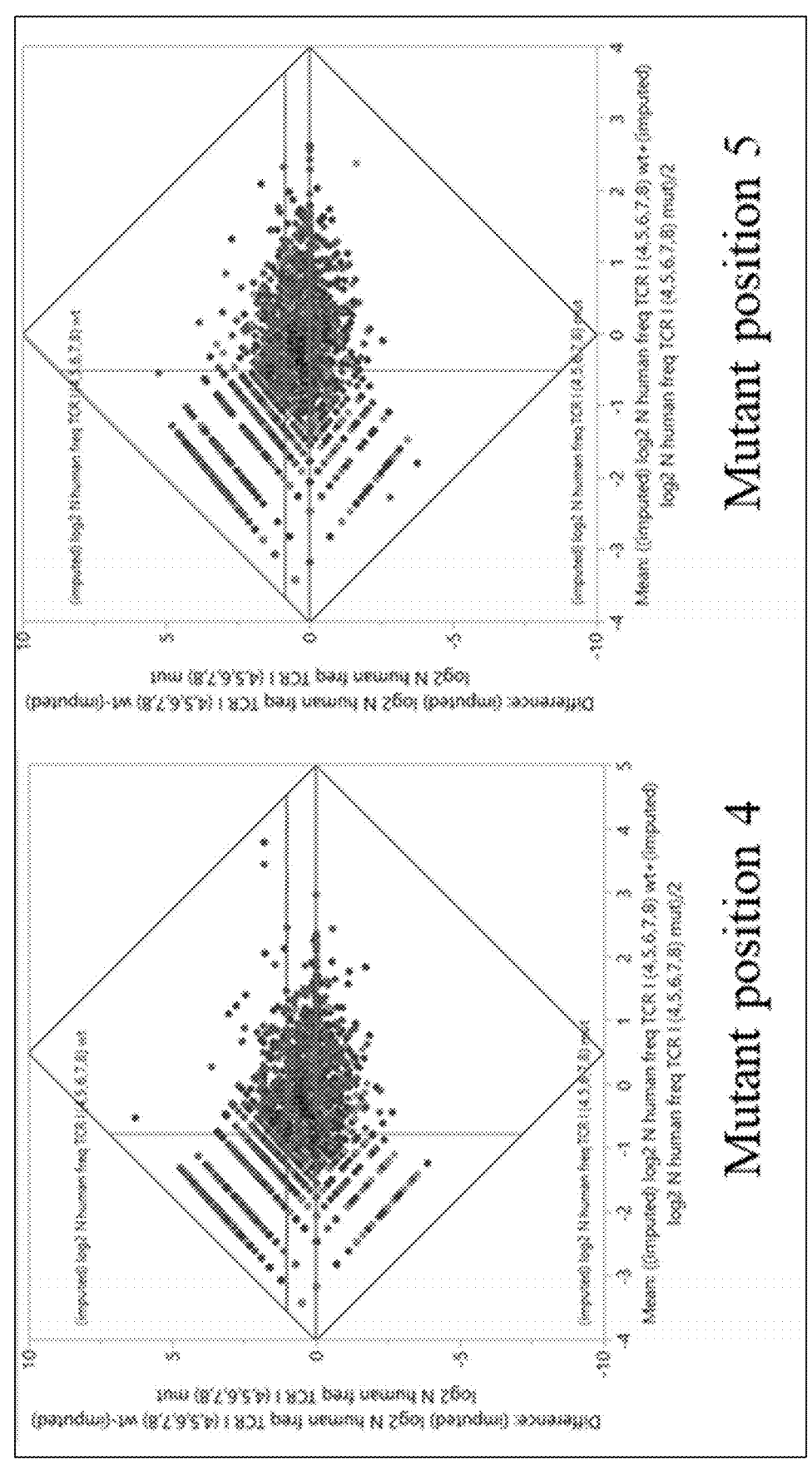
FIG. 4: Paired comparison of the human proteome TCEM I frequency of wild type and 37,621 mutated peptides of 5 different proteins commonly mutated in different cancers. The base frequency of the TCEM in the proteome was log 2 basis. This frequency was standardized with a Johnson Sl distribution function and thus the units of both the X-axis and Y-axis are standard deviations. The graphs are the paired differences (wt− mut) (Y-axis) by the paired means (wt+ mut)/2 (X-axis). The paired t-test results are for all three alternative hypotheses. The matched responses for each protein is a simple version of repeated measures analysis. The frequency of the wt TCEM in the proteome is about 1 standard deviation greater overall than the mutants. Thus, a mutational event that inserts a new amino acid in the TCEM consistently produces TCEM that are much more rare as compared to the wt TCEM
Figure 4:
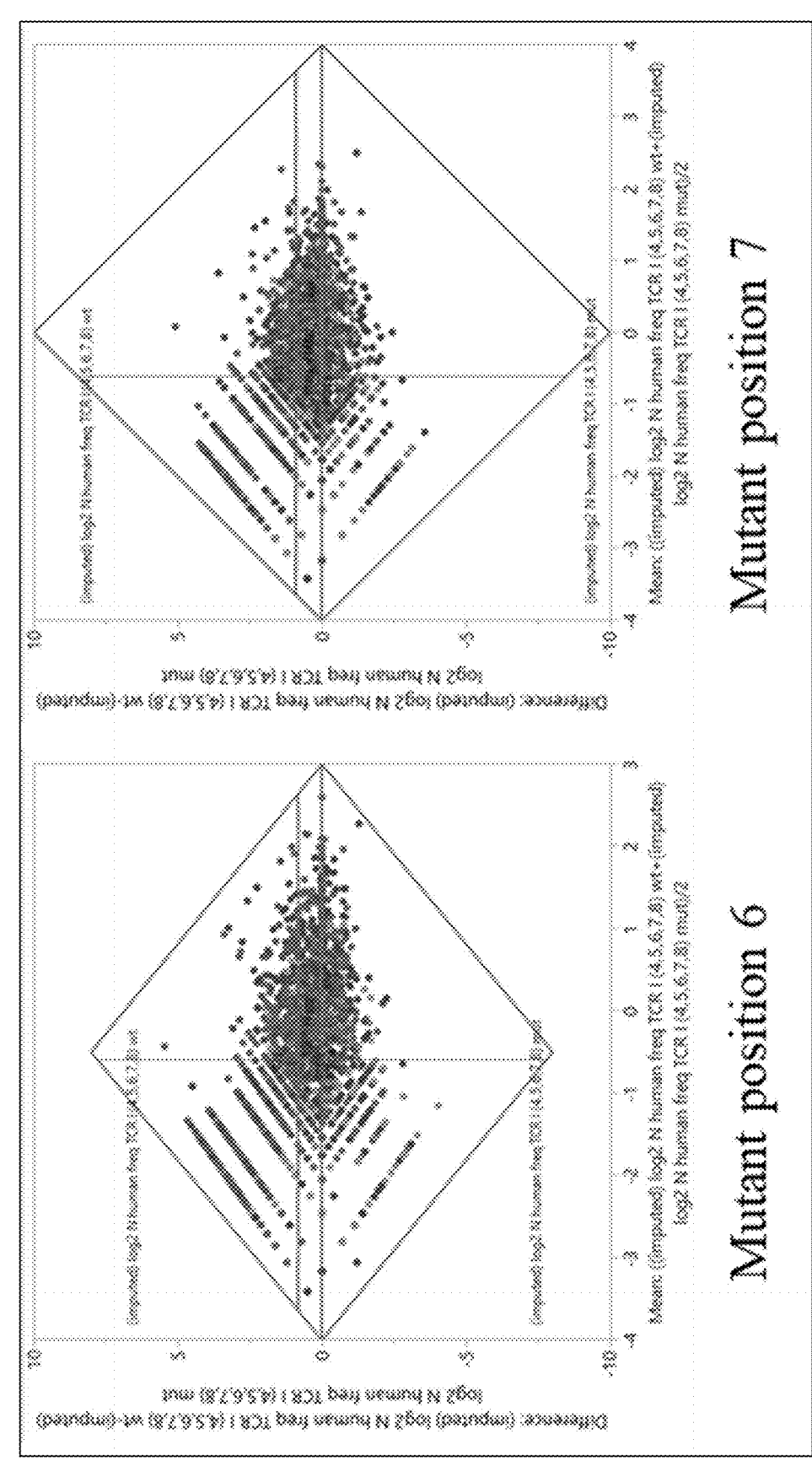
Figure 4:
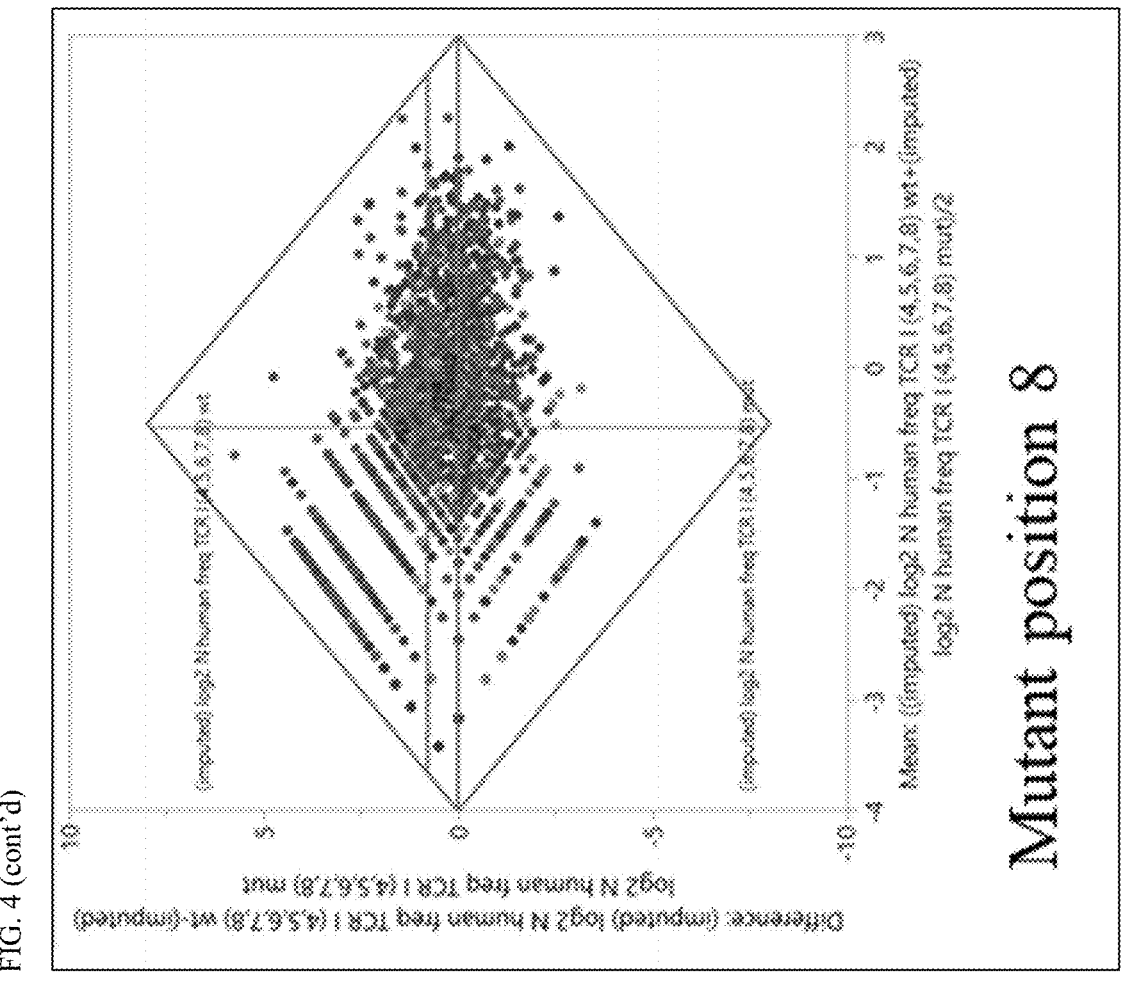

Considering 7 proteins which are commonly mutated in 32 common types of cancer (BRAF, EGFR, ERBB2, KIT, P53, PK3CA and PTEM), the T cell exposed motif frequency category is a standard deviation unit lower (less common) than the wildtype, regardless of the position in the T cell exposed motif at which the mutation occurs (FIG. 4). This Figure shows the stochastic mutation process inserts amino acids into protein sequences that are either much more rare, or in some cases (14% overall), completely absent in normal protein sequences in the human proteome.

It was also noted that when the frequency category of the T cell exposed motif comprising mutated acids in tumors are compared to the frequency of occurrence in the human immunoglobulinome, they correspond on average to the immunoglobulin frequency category FC20; indicating that on average the T cell exposed motif amino acid motifs would be found in 1 in $2^{20}$ immunoglobulin variable regions (less than 1 in a million B cell clonal lines). This is 1000 fold below the mean frequency in immunoglobulin variable regions; another indicator that tumor T cell exposed motif are uncommon and that there may be a low frequency of cognate T cells.

Cross Presentation of MHC I and II Binding Peptides

While the primary focus is on stimulating a cytotoxic T cell response, driven by CD8+ T cells, such a response is enhanced and helped by the simultaneous stimulation of a CD4+T helper response. This may be particularly important to the development of a population of memory T cells which can ensure ongoing surveillance and elimination of cancer cells. In some instances, a naturally occurring T helper response may be driven from the native mutated protein. In the present invention we also describe how a tumor specific T helper response can be stimulated by peptides designed to have a high binding affinity to the patient's MHC II alleles and to target T cell exposed motifs which comprise the mutated amino acid. Therefore, in one embodiment the invention provides for designing 15mer peptides by maintaining the TCEM II and varying the flanking sequences.

Maximizing Targeting of Mutations and Stimulation of Cytotoxic T Cell Responses

The combination of these factors: low binding affinity of mutated peptides and rare T cell exposed motif category reduces the chance of a strong natural cytotoxic response. Mutations detected in proteins in tumor biopsies are the "surviving mutations" which have escaped immune surveillance and have not been effectively eliminated after they occur, and so continue to be propagated in the tumor. In one embodiment, the present invention reverses this balance and provides strongly binding peptides which comprise the rare T cell exposed motif and are thus likely to elicit a strong cytotoxic response. Each of the peptides is designed to provide such conditions for a specific patient allele. If a patient is homozygous for any one of their MHC loci, this is detrimental as it limits the number of T cell clones which can be stimulated by the tumor mutations, likely reducing the chances of tumor elimination. Some cancer patients are further handicapped in stimulating the development of effective cytotoxic T cell responses to tumors due to low numbers of mutations.

In some embodiments, therefore, the present invention provides methods to maximize the utilization of available tumor specific antigens to generate effective cytotoxic T cell response that can bring about elimination of the tumor cells. This is achieved by identifying the T cell exposed motif containing the mutant amino acids and generating an array of peptides which combine these T cell exposed motifs with an array of different flanking amino acids of varying predicted binding affinity to enable selection of appropriate high binding peptides. In the case of TCEM I located in a 9-mer comprising 5 exposed amino acids flanked by 4 groove exposed amino acids, for each T cell exposed motif there is a maximum of $20^4$ or 160,000 possible variant amino acid combinations in the groove exposed position. In some embodiments, an array of 1000 peptides is created by random amino acid substitution in the groove exposed positions, in other embodiments an array of 10,000 peptides is likewise created, and in further embodiments a 50,000 peptide array is created. In the case of TCEM II to create peptides binding differentially to MHC II, we consider a 15 mer in which exposed positions 2, 3, 5, 7, 8 or −1, 3, 5, 7, 8 are kept constant, as all other amino acids in the peptide that are presumed to be involved in the binding affinity are changed by random substitution to create arrays of 1000, 5,000 or 10,000 peptides. In both cases the array sizes cited here are examples that are considered non limiting.

In each case, both MHC I and MHC II, the TCEM is maintained identical to the mutated peptides in the native mutated protein and all TCEM which comprise a mutated amino acid are selected as the basis for generation of binding variants.

In further steps embodied in this invention, the initial array of peptides generated by amino acid substitution is then filtered to remove any duplicate peptides, and in some preferred embodiments peptides predicted to be of low solubility are removed by assigning a score to the polarity of their constituent amino acids. The peptides are then selected to be suitable for the specific patient and his/her combination of MHC I and MHC II alleles. In preferred embodiments all alleles are typed, including MHC I A, MHC I B, MHC I C, and MHC II DRB, DP and DQ loci. In one embodiment, the predicted affinity of the peptides in the native mutant protein is reviewed to determine the probability that a particular peptide would be bound by one or more of the patient's MHC alleles, albeit with a low affinity, and hence presented for T cell recognition. As the goal is to stimulate or "train" T cells to target the specific mutated T cell exposed motifs (TCEM) in the tumor, these must be exposed to T cell recognition to enable targeting of tumor cells. In one embodiment we identify each of the TCEM-allele combinations in each native mutant protein which binds with an affinity greater than the mean for the comprising protein. Such TCEM are targetable by T cells which are also specific to that MHC allele histotope. TCEM-allele combinations which have a predicted binding affinity above the mean are set aside as unlikely to ever be presented. For this subset of "presentable" TCEM-allele combinations, we then assess the array of randomly generated peptides, filtered for binding and solubility, and identify a peptide for each TCEM-allele combination with a desired predicted binding affinity. In some embodiments, the peptide with maximum predicted binding affinity for each allele may be chosen. This may be a peptide that binds at 2.5 or 3 or more standard deviation units below the mean for peptides in the protein (ie higher affinity). Such a high binding peptide would be comparable to those detected as part of the presentome by mass spectroscopy and equivalent to approximately <20 nM to 100 nM, depending on the protein context. In preferred embodiments, peptides are chosen with high, but not excessive predicted binding affinity, keeping in mind the probability that this may be more likely to stimulate an effective cytotoxic response and memory and mitigate against T cell exhaustion. Such a binding affinity may be from 1-2 standard deviation units below the mean for peptides in the protein, typically equivalent to 100-500 nM. Overall, the invention embodies the ability to select for a desired binding affinity and can be considered "tunable" to that selected binding affinity for each patient allele.

Given that each mutated protein has 5 possible TCEM I and TCEM II which exposed the mutated amino acid, in a patient who, for example, has 6 known MHC I alleles and 4 known MHC II alleles, there is a maximum of 30 possible high binding peptides for CD8+ stimulation and 20 for CD4+ stimulation for every known mutated protein. This may be reduced, sometimes by half, due to filtering of non-presented TCEM but still offers a vastly greater number of ways to stimulate T cells which will target the TCEM of interest that depending on natural binding peptides. Simply put, if a binding peptide does not exist, we will create one and if a poor binder is found the affinity is improved by modification of the MHC groove exposed amino acids. The novel peptide thus created will stimulate T cells bearing TCR specific to the tumor.

In some embodiments the novel peptides are used in vitro to stimulate dendritic cells or T cells. In some embodiments such cells are of autologous source, in yet other embodiments they are obtained from allele-matched donors. Stimulated cells are then administered to the cancer patient to passively provide an active T cell population or to provide dendritic cells presenting the TCEM of interest which can stimulate T cells in the patient. In yet other embodiments the peptides are used as components of a peptide vaccine. In yet other embodiments the peptides are applied as a fusion with antibody sequences. In further embodiments the peptides may be encoded in RNA or DNA for administration.

In some embodiments, the frequency classification of the TCEM in the human proteome is noted. In further embodiments the frequency classification of the TCEM in the human immunoglobulinome is noted. In both cases this is achieved by reference to a precomputed reference database comprising over 88,000 human proteins including multiple isoforms and over 35 million unique human immunoglobulin variable regions. Based on this, in some embodiments peptides comprising rare TCEM are identified for priority use.

In desired embodiments, therefore, the process described above yields a unique array of peptides for a particular patient, enabling stimulation of T cells targeting the maximum possible TCEM specific to that patient's tumor-specific mutations and mutated proteins, by presentation of peptides of selected binding affinity in each of the known alleles the patient carries, and said peptides further selected to be soluble. This is a panel of peptides which can then be deployed to stimulate T cells in vivo and in vitro by application in a number of different formats.

TCEMs comprise 5 amino acids, or $20^5 = 3.2$ million possible configurations. T cell receptor polyspecificity is well recognized [33]. Any neoantigen carries with it the risk of generating an off-target T cell targeting of a self-protein with potential adverse consequences, which may be magnified by immunodulatory interventions such as checkpoint inhibitors.. Prior developers of neoantigen vaccines have not addressed this aspect. In a further embodiment of the present invention therefore, TCEM are identified which comprise mutated amino acids and which are bound and presented in the patient's alleles, and are therefore identified as candidates for targeting with T cells stimulated by highly bound peptides. The stimulation of T cells targeting these peptides, when enhanced by high binding affinity neoantigens and potentially further boosted by a checkpoint inhibitor blockade could potentially give rise to self-protein targeting. In one embodiment, therefore, a "call list" of such TCEM is cross-correlated with the reference data set of the human proteome to identify all human proteins carrying said TCEM. These proteins are reviewed to determine the predicted binding affinity of the peptide in which the TCEM occurs for each of the patient's known alleles. If the human proteome carries that TCEM and the patient alleles would bind the contextual peptide at a moderate or high affinity (which may be considered to be an affinity at less than 1 standard deviation below the mean for the comprising protein, although this range is not considered limiting) then the protein carrying the TCEM is added to an advisory list. In preferred embodiments the protein is identified by its Uniprot identifier or identifiers linking it to other reference databases. In preferred embodiments the advisory list is reviewed to further identify proteins where deficiencies or blockades are associated with known pathologies, and to identify proteins which are of critical function and non-redundant. Such proteins may not be suitable for inclusion in a neoantigen vaccine and may be added to a caution list. However, the advisory and caution lists only identify potential sources of adverse reactions and must be weighed against the progression and severity of the cancer. Given the degree of inherent polyspecificity, the advisory list is typically quite extensive. Many proteins are shielded by anatomic or cellular location, some may be considered redundant, or may be considered an acceptable tradeoff to overcoming cancer. However, this embodiment allows an informed decision to be made regarding possible adverse effects in neoantigen selection.

As further illustrated in the Examples, this invention may be applied in two ways, to design and apply bespoke neoantigen vaccines for individual patients and to provide ready-to-go multi-cancer neoantigen arrays for neoantigens found commonly in many cancers.

Bespoke Design of Neoantigen Vaccines

In a preferred embodiment the present invention allows the rapid design of a personalized immunotherapeutic intervention designed for each cancer patient based on their HLA alleles and particular set of mutations. In some applications of this embodiment the mutations are unique to one patient. This intervention becomes feasible as soon as sequencing of a tumor biopsy and HLA typing is available and can be rapidly computed. In some embodiments the process of sequencing a biopsy may be repeated several times in the course of treatment and the selection of peptides updated based on detection of new mutations. In some preferred embodiments the invention provides an immunotherapy solution for patients who have few proteins with known mutations, for example, but not limited to, glioblastoma patients, who would otherwise be limited to only one neoantigen per protein and possibly no neoantigens with appropriate HLA binding. The preferred embodiment of the present invention is to provide the maximum number of T cell stimulating peptides which will result in targeting of every possible TCEM in which the mutant amino acid occurs and by utilizing every possible HLA. In a further embodiment of the invention the peptides are down-selected to those which will target TCEM presented in vivo and those which are less likely to cause adverse targeting of other human proteins. In an extension of this preferred embodiment, the selected stimulatory peptides may be grouped to provide a series of vaccinations or treatments which allow the utilization of all available alleles the patient carries, while not causing competition for peptide presentation in any one group of peptides.

In some embodiments the selected peptides are applied to dendritic cells in vitro which are then administered to the patient to stimulate T cells. In yet other embodiments the selected peptides are applied in vitro to stimulate a population of T cells which are administered to the patient. In yet other embodiments the peptides, or nucleic acids encoding them are administered directly to the patient in one or more groups spaced over time.

Neoantigen Array for Common Mutations in Multiple Cancers

Recognizing that many cancers share common mutations in certain proteins, an embodiment of the present invention provides an array of pre-computed and designed peptides which will provide high affinity binding peptides, or nucleic acids that encode them, for said common mutations in commonly mutated proteins shared by many cancers. In preferred embodiments, the proteins with common mutations which are pre-computed and have designed peptides include but are not limited to those shown in Table1 or isoforms thereof.

TABLE 1

Examples of proteins with mutations shared across cancer types

| Gene ID | Protein name |
|---------|--------------|
| AKT1 | RAC-alpha serine/threonine-protein kinase |
| BRAF | Serine/threonine-protein kinase B-raf |
| CASP8 | Caspase-8 |
| CDH1 | CDH1 protein |

TABLE 1-continued

Examples of proteins with mutations shared across cancer types

| Gene ID | Protein name |
|---------|--------------|
| CDKN2A | Cyclin-dependent kinase inhibitor 2A |
| CHEK2 | Serine/threonine-protein kinase Chk2 |
| CTNNB1 | Catenin beta-1 |
| DDX3X | ATP-dependent RNA helicase DDX3X |
| DICER1 | DICER variant 1 |
| EGFR | Epidermal growth factor receptor |
| EP300 | Histone acetyltransferase p300 |
| ERBB2 | Receptor tyrosine-protein kinase erbB-2 |
| ERBB3 | Receptor tyrosine-protein kinase erbB-3 |
| ERBB4 | Receptor tyrosine-protein kinase erbB-4 |
| FBXW7 | F-box/WD repeat-containing protein 7 |
| FGFR2 | Fibroblast growth factor receptor 2 |
| FGFR3 | Fibroblast growth factor receptor 3 |
| FLT3 | Receptor-type tyrosine-protein kinase FLT3 |
| GNA11 | Guanine nucleotide-binding protein subunit alpha-11 |
| GNAQ | Guanine nucleotide-binding protein G(q) subunit alpha |
| HRAS | GTPase HRas |
| IDH1 | Isocitrate dehydrogenase [NADP] 1 |
| IDH2 | Isocitrate dehydrogenase [NADP] 2 |
| KEAP1 | Kelch-like ECH-associated protein 1 |
| KIT | Mast/stem cell growth factor receptor Kit |
| KMT2C | Histone-lysine N-methyltransferase 2C |
| KRAS | GTPase KRas |
| MAP2K1 | MAP kinase |
| MET | Hepatocyte growth factor receptor |
| MTOR | Serine/threonine-protein kinase mTOR |
| NFE2L2 | Nuclear factor erythroid 2-related factor 2 |
| NOTCH1 | NOTCH1 protein |
| NRAS | GTPase NRas |
| PIK3CA | Phosphatidylinositol 4,5-bisphosphate 3-kinase catalytic subunit alpha isoform |
| PIK3R1 | Phosphatidylinositol 3-kinase regulatory subunit alph |
| PPP2R1A | Serine/threonine-protein phosphatase 2A 65 kDa regulatory subunit A alpha isoform |
| PTPN11 | Tyrosine-protein phosphatase non-receptor type 11 |
| RAC1 | Ras-related C3 botulinum toxin substrate 1 |
| RASA1 | Ras GTPase-activating protein 1 |
| RB1 | RB1 protein |
| RHEB | GTP-binding protein Rheb |
| RHOA | Transforming protein RhoA |
| RRAS2 | Ras-related protein R-Ras2 |
| RUNX1 | Runt-related transcription factor 1 |
| SETD2 | Histone-lysine N-methyltransferase SETD2 |
| SF3B1 | Splicing factor 3B subunit 1 |
| SMAD2 | Mothers against decapentaplegic homolog 2 |
| SMAD4 | Mothers against decapentaplegic homolog 4 |
| SPOP | Speckle-type POZ protein |
| TGFBR2 | TGF-beta receptor type-2 |
| TP53 | TP 53 |
| VHL | von Hippel-Lindau disease tumor suppressor |
| ZFP36L2 | mRNA decay activator protein ZFP36L2 |

In some proteins, and in the particular case of EGFR, in addition to the common amino acid substitution mutations, insertion-deletions are also common in many types of cancer. In a further embodiment of the invention, we therefore also provide a method of selecting an array of peptides which can serve as tumor specific T cell stimulating peptides for these common deletions. The is an approach which can be applied wherever a deletion creates a novel amino acid motif and thus the example for EGFR is not considered limiting.

In preferred embodiments one or more said pre-computed and designed high affinity peptide from common mutated proteins are applied in the treatment of cancers, including but not limited to adrenocortical carcinoma, bladder urothelial carcinoma, breast adenocarcinoma, cervical squamous cell carcinoma, cholangiocarcinoma, colon carcinoma, lymphoid neoplasm diffuse large b-cell lymphoma, esophageal carcinoma, glioblastoma multiforme, head and neck squamous cell carcinoma, kidney chromophobe, kidney renal clear cell carcinoma, kidney renal papillary cell carcinoma, acute myeloid leukemia, chronic myelogenous leukemia, brain lower grade glioma, liver hepatocellular carcinoma, lung adenocarcinoma, lung squamous cell carcinoma, mesothelioma, ovarian serous carcinoma, pancreatic adenocarcinoma, pheochromocytoma and paraganglioma, prostate adenocarcinoma, rectal carcinoma, sarcoma, skin cutaneous melanoma, stomach adenocarcinoma, testicular germ cell tumors, thyroid carcinoma, thymoma, uterine corpus endometrial carcinoma, uterine carcinosarcoma, uveal melanoma. In preferred embodiments said precomputed and designed peptides included in the array are designed to have high binding for any one of the following alleles A_0101, A_0201, A_0202, A_0203, A_0206, A_0211, A_0212, A_0216, A_0217, A_0219, A_0250, A_0301, A_0801, A_1101, A_2301, A_2402, A_2403, A_2501, A_2601, A_2602, A_2603, A_2902, A_3001, A_3002, A_3101, A_3201, A_3301, A_6801, A_6802, A_6901, A_8001, B_0702, B_0801, B_0802, B_0803, B_1501, B_1502, B_1503, B_1509, B_1517, B_1542, B_1801, B_2703, B_2705, B_3501, B_3801, B_3901, B_4001, B_4002, B_4402, B_4403, B_4501, B_4506, B_4601, B_4801, B_5101, B_5301, B_5401, B_5701, B_5801, B_7301, B_8301, C_0303, C_0401, C_0501, C_0602, C_0702, C_1203, C_1402, C_1502, DPA1_0103-DPB1_0201, DPA1_0201-DPB1_0101, DPA1_0201-DPB1_0501, DPA1_0301-DPB1_0401, DPA1_0301-DPB1_0402, DPB1_0101, DPB1_0201, DPB1_0301, DPB1_0401, DPB1_0402, DPB1_0501, DPB1_1401, DPB1_2001, DQA1_0101-DQB1_0501, DQA1_0102-DQB1_0501, DQA1_0102-DQB1_0502, DQA1_0102-DQB1_0602, DQA1_0103-DQB1_0603, DQA1_0104-DQB1_0503, DQA1_0201-DQB1_0202, DQA1_0201-DQB1_0301, DQA1_0201-DQB1_0303, DQA1_0201-DQB1_0402, DQA1_0301-DQB1_0302, DQA1_0303-DQB1_0402, DQA1_0401-DQB1_0402, DQA1_0501-DQB1_0201, DQA1_0501-DQB1_0301, DQA1_0501-DQB1_0302, DQA1_0501-DQB1_0303, DQA1_0501-DQB1_0402, DQA1_0601-DQB1_0402, DQB1_0201-, DQB1_0202-, DQB1_0301-, DQB1_0302-, DQB1_0402-, DQB1_0501-, DQB1_0502-, DQB1_0503-, DQB1_0602-, DRB1_0101, DRB1_0101 C30S mutant, DRB1_0301, DRB1_0401, DRB1_0404, DRB1_0405, DRB1_0701, DRB1_0801, DRB1_0802, DRB1_0901, DRB1_1001, DRB1_1101, DRB1_1201, DRB1_1301, DRB1_1302, DRB1_1454, DRB1_1501, DRB1_1602, DRB3_0101, DRB3_0202, DRB3_0301, DRB4_0101, DRB4_0103, DRB5_0101. Additional alleles may be added to this list as training sets become available and thus this allele list is not considered limiting. In preferred embodiments, as soon as a patient is identified as carrying a common mutation in a tumor, and his or her HLA typing is known, one or more peptides from the pre-computed ready-to-go array is selected and used in vitro to provide dendritic cells that stimulate T cells on administration to the patient, stimulate T cells which are administered to the patient, or is administered as a component of a peptide vaccination regimen or vaccination with nucleic acids encoding said peptides. In a further embodiment the TCEM matches which can give rise to off-target cytotoxic effects are also precomputed for all potential allele binding situations, enabling risk analysis of peptide use for each patient based on their allele combination.

Neoantigen Based Interventions Combined with Additional Immunotherapies

Application of the bespoke and multi-cancer designed peptides described in the prior sections may, in some embodiments, be combined with other cancer immunotherapies. In some embodiments the peptides or their encoding nucleic acids may be used in vitro to prime dendritic cells or stimulate T cells, or as vaccines in conjunction with drugs targeting upregulated cancer-expressed proteins, biopharmaceuticals binding to tumors, CAR T therapies, radiotherapy, chemotherapy and other clinical interventions. In preferred embodiments said combined chemotherapy should not lead to lymphodepletion. In one particular embodiment the application of the designed peptides or encoding nucleic acids to stimulate dendritic cells or T cells administered to the patient may be combined with a check point inhibitor blockade. In other preferred embodiments, the methods of the present invention comprise administering an immune checkpoint inhibitor to a subject following administration of a multi peptide vaccine or nucleic acid vaccine encoding said peptides. Checkpoint inhibitors act by blocking the inhibition of T cell responses or blocking the termination of a T cell response, thereby unleashing continuing T cell actions. The present invention is applied to ensure that the appropriate tumor targeting T cells are present prior to administration of such a check point blockade. In preferred embodiments, therefore, the peptides designed by the present invention are applied prior to a checkpoint blockade. Suitable checkpoint inhibitors include, but are not limited to, antigen binding proteins that inhibit immune checkpoints, for example by PD-1, PD-L1 or CTLA-4. Suitable checkpoint inhibitors include, but are not limited to, Pembrolizumab, Nivolumab, Ipilimumab, Atezolizumab, Durvalumab, REGN2810 (Anti-PD-1), BMS-936558 (Anti-PD-1), SHR1210 (Anti-PD-1), KNO35 (Anti-PD-L1), IBI308 (Anti-PD-1), PDR001 (Anti-PD-1), BGB-A317 (Anti-PD-1), BCD-100 (Anti-PD-1), and JS001 (Anti-PD-1). Other immunomodulatory interventions having the effect of enhancing or extending cellular immune function include but are not limited to ALT-803 and N-803 (IL-15), and haNK, tank and other NK cells.

Utilization of Designed Peptides

In some embodiments the present invention will yield an array of many peptides suitable for enhancing the CD8+ response of a particular patient to his/her mutated tumor proteins and a list of many peptides suitable for enhancing a CD4+ helper response to these proteins. In some particular embodiments the number of peptides designed to bind MHC and stimulate T cells in a particular patient may be up to 5, in others it is about 20, in yet others it is over 100 and in yet others over 200 peptides. In some embodiments said peptide array will include those which bind to 1 allele, 2 alleles or up to 6 MHC I alleles and others which bind 1, 2 or up to 6 MHC II alleles. In order to optimize the application of said peptides and maximize the use of binding alleles while minimizing competition for binding at any single administration, a further embodiment of the present invention is to prioritize and group the peptides for sequential administration. In a preferred embodiment the peptides may be grouped into subgroups of about 5, in other embodiments subgroups of about 10 are preferred, and in yet other embodiments subgroups of about 20 are preferred and in further embodiments larger groups are preferred. Said subgroups may combine both MHC I and MHC II binding peptides. Some peptides may be repeated in several subgroups. In some embodiments where vaccination regimens comprise sequential administration of a subset of selected peptides, each peptide administration may be followed by check point inhibitor treatment. In some embodiments, consideration is given to whether particular TCEM encompassed in the peptides in each group are rare or common TCEM in the human proteome or immunoglobulinome. In some preferred embodiments priority is given to inclusion of peptides that comprise rare TCEM. In each instance where a peptide is mentioned above, this may also refer to the application of a nucleic acid encoding said peptide. In preferred embodiments peptides that have TCEM matches in certain human proteins are excluded from consideration, where stimulating a T cell response which may target said human proteins may result in an adverse effect. In yet another embodiment, where transcription levels of the mutated proteins in a tumor are known, peptides may be prioritized based on their transcription level to increase the chance of successful targeting of tumor cells.

Many Delivery Formulations

Many delivery formulations have been proposed for neoepitope vaccines, including but not limited to, peptide vaccines, antibody-antigen fusion proteins, DNA or RNA encoding antigens, particulate vaccines. Neoantigens have been administered directly to subjects or have served to prime dendritic cells or stimulate T cells in vitro for administration of such cells to the subject. The dendritic cells or T cells have included those of autologous or of donor origin. Any of these delivery formulations may be used for delivery of peptides designed by the present invention.

In some embodiments of the present invention the peptides, or their encoding nucleic acids, designed to bind to the patient alleles and stimulate T cells that are specific for tumor TCEM may be administered parenterally. In yet other embodiments the peptides or their encoding nucleic acids may be delivered intradermally or subcutaneously. In some embodiments intradermal administration may be achieved by needle injection. In preferred embodiments intradermal administration may be provided by micro needle patch or array. In yet further embodiments said microneedle patch or array may deliver multiple different peptides or encoding nucleic acids thereof.

In some embodiments the designed peptides or their encoding nucleic acids may be delivered with an adjuvant. Various adjuvants are used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, squalene, squalene emulsions, liposomes, imiquimod, keyhole limpet hemocyanins, dinitrophenol, and potentially useful human adjuvants such as BCG (Bacille Calmette-Guerin) and *Corynebacterium parvum*. In other embodiments a cytokine may be co-administered, including but not limited to interferon gamma or stimulators thereof, interleukin 12, or granulocyte stimulating factor. In other embodiments the peptides or their encoding nucleic acids may be co-administered with a local inflammatory agent, either chemical or physical. Examples include, but are not limited to, heat, infrared light, proinflammatory drugs, including but not limited to imiquimod.

In some embodiments the designed peptides may be administered as a fusion to a moiety which favors formation of nanoparticles. Examples of such moieties include but are not limited to leucine multimers (polyleucine), unnatural hydrophobic amino acids, or liposomes. The peptide of interest may be attached to its fusion partner by a linker. In some instances the linker is cleavable. Said cleavable linker may be one or more lysine or arginine residues, or a cathepsin cleavable linker.

Having knowledge of the patient's HLA alleles is a prerequisite to designing a bespoke peptide vaccine. Several approaches to HLA typing may be employed, including PCR, and such testing is widely available. As the patient tumor sequencing is often conducted in association with whole genome sequencing of normal and tumor tissue, the HLA can be derived from the whole genome sequence at the same time by analysis of chromosome 6 using the appropriate BAM slice of_chromosome 6 derived from the whole exome sequence.

Bespoke vaccines, designed based on the mutations and HLA of an individual cancer patient are distinctly personal. The particular combination of peptides and the modifications to said peptides to ensure MHC binding and exposure of a particular T cell exposed motif are only suitable for that one individual. As such, the combination of peptides maybe determined and selected in consultation with the patient's clinician and prescribed for that patient. In some embodiments, therefore, this may enable preparation of a bespoke vaccine by an entity functioning as a compounding pharmacy.

Treatment of Other Immunopathologies

Modified epitopes can also play a role in modulation of other immunopathologies, outside the field of oncology. This includes, but is not limited to, applications in autoimmune diseases, allergies and inflammation where the problem is not an insufficient T cell stimulation, but rather an overexuberant response. Provision of a very high affinity binding peptide can serve to exhaust or diminish the T cell response to the particular T cell exposed motif in question and thereby diminish CD4 T cell help or a CD8 cytotoxic response and ameliorate the pathogenesis of the disease. In each case the peptides are customized to ensure binding appropriate the HLA alleles of the individual patient.

Autoimmune diseases in which such an approach may be useful include, but are not limited to rheumatoid arthritis, diabetes type I and type II, Ankylosing Spondylitis, Atopic allergy, Atopic Dermatitis, Autoimmune cardiomyopathy, Autoimmune enteropathy, Autoimmune hemolytic anemia, Autoimmune hepatitis, Autoimmune inner ear disease, Autoimmune lymphoproliferative syndrome, Autoimmune peripheral neuropathy, Autoimmune pancreatitis, Autoimmune polyendocrine syndrome, Autoimmune progesterone dermatitis, Autoimmune thrombocytopenic purpura, Autoimmune uveitis, Bullous Pemphigoid, Castleman's disease, Celiac disease, Cogan syndrome, Cold agglutinin disease, Crohns Disease, Dermatomyositis, Eosinophilic fasciitis, Gastrointestinal pemphigoid, Goodpasture's syndrome, Graves' disease, Guillain-Barré syndrome, Anti-ganglioside Hashimoto's encephalitis, Hashimoto's thyroiditis, Systemic Lupus erythematosus, Miller-Fisher syndrome, Mixed Connective Tissue Disease, Myasthenia gravis, Narcolepsy, Pemphigus vulgaris, Polymyositis, Primary biliary cirrhosis, Psoriasis, Psoriatic Arthritis, Relapsing polychondritis, Sjögren's syndrome, Temporal arteritis, Ulcerative Colitis, Vasculitis, and Wegener's granulomatosis. Allergic responses which may benefit from immunomodulation by design of personal peptides of modified binding include but are not limited to allergies to plant, animal, insect, arachnoid materials and other environmental materials comprising allergen epitopes. Allergies may result form airborne or gastrointestinal exposure or from skin contact.

In some instances, an immunopathology can arise as the result of an adverse response to a therapeutic agent administered to a subject. In some cases said therapeutic is a biopharmaceutical protein.

In each case an individual subject afflicted by an autoimmune disease or allergen may be typed as to their HLA alleles and a peptide array designed specifically for that person to provide peptides that exhaust the T cell response. Examples of such customized peptides are shown in Example 12.

EXAMPLES

Example 1: Selection of Mutant Peptides and Generation of Better Binding Peptides The development of vaccines and stimulants for dendritic cells and T cells in vitro to comprise multiple peptides with a selected desired affinity for the patient's alleles builds on methods previously described to precisely predict MHC binding, identify and analyze T cell exposed motifs and generate peptides with altered binding affinity (See PCT Appl. US14/41523, PCT Appl. US15/39969, and PCT Appl US17/21781, all of which are incorporated herein by reference in their entirety).

Identification of Relevant Peptide Positions.

In order for a T cell to differentially target a tumor cell expressing a mutated protein, the mutated amino acid has to be located in a position "visible" or exposed to the T cell receptor and not hidden in the pocket or groove exposed positions that determine binding. A first step in designing a multi peptide vaccine or stimulant panel is therefore to identify those peptide positions which expose the mutated amino acid. For MHC I this means the mutant amino acid must be at positions 4,5,6, 7 or 8 of a 9-mer peptide and for MHC II at positions 2, 3, 5, 7, 8 of the 9-mer core of a 15 mer. This identifies TCEM IIA; TCEM IIB positions are at −1, 3, 5, 7, 8. We first calculated the predicted binding affinity of all sequential peptide positions in the mutant protein and then selected those peptides with relevant TCEM comprising mutated amino acids.

A T cell is only able to target a TCEM if that motif is presented in the host from the naturally occurring mutant peptide. Mutant TCEM that lie in peptides that are extremely unlikely to ever be presented are thus poor targets. We therefore filtered the TCEM to identify those which have some likelihood of exposure in the host, limiting to those whose predicted binding affinity is greater than the mean for the protein. This is not an absolute requirement but maximizes the potential for a successful targeting.

For each of the selected peptides comprising a mutant TCEM, a bank of peptides was generated by randomly varying the flanking amino acids, and recalculating the new binding affinity for each allele of interest. For a 9-mer with a pentamer exposed TCEM, this implies up to 160,000 ($20^4$) different peptides could be generated, each with a different binding affinity. For practical purposes a bank of 1000 or up to 10,000 peptides is usually sufficient to provide peptides within the range of binding affinity desired. For MHC II we opted to vary only those amino acids outside the core 9 mer peptide comprising the TCEM, as the intercalated amino acids which are in pocket (groove exposed) positions affect binding but may also influence the positioning of the exposed amino acids.

A further practical consideration is solubility of the peptide. A score was generated based on the polarity of the constituent amino acids and only peptides likely to be soluble were put forward as candidates. Sufficient peptides can be generated to prevent this from becoming a limitation.

For a group of 5 proteins each with one mutation and a patient with 4 known alleles therefore a maximum number of allele TCEM combinations is 5 TCEM×5 proteins×4 alleles or 100 possible ways to stimulate T cells which will uniquely target those proteins. This is reduced by the TCEM of low probability of natural presentation.

Example 2: Selection of Personalized Simulated Peptides

The process described in Example 1 generates a selection of peptides of different binding affinity for each combination of mutant-containing-TCEM and patient allele. Peptides are then selected which have a desired predicted binding affinity. We have discussed the relevance of binding affinity on T cell phenotype in the Description above. As peptides of many different binding affinities are provided the desired affinity may be selected. In the subsequent examples we have opted to focus on peptides with predicted binding affinity at about 2 standard deviations below the mean of the protein, placing them at about the $95^{th}$ percentile; i.e. the top 5% binders, but not higher, because conceivably very high affinity peptide could lead to immunosuppression or exhaustion. We have shown the number of peptides available at this level and in some cases at 3 SD or greater (very high binders).

Utilization of the available peptides may depend on the intended use as a neoepitope vaccine or in vitro stimulant of dendritic cells and T cells to be administered to the patient.

Peptides may be selected to use in groups that target the maximum number of combinations of allele and TCEM in any one application. One desired aspect is to ensure not all peptides administered at any one time as a multi-neoepitope vaccine target the same allele, thus competing with each other for space in MHC and presentation. When dendritic cells and T cells are targeted in vitro it may be desirable to provide as many combinations as possible.

Example 3: Reference to Human Proteome to Identify Potential Adverse Reactions To identify potential off target effects of the T cells stimulated by the peptides designed to generate targeting of cancer mutations, we compare the TCEM with those in the human proteome to identify relevant matches. The entire human proteome, comprising over 88,000 proteins (including all known isoforms of each protein), was pre-analyzed to determine the binding affinity of each peptide in each protein for all MHC alleles. The TCEM comprised in the peptides selected for each cancer patient, selected as described in Example 1 are assembled into a "call list". The human proteome reference database is searched for all TCEM on the patient call list; a subset of proteins with matching TCEM is assembled. The peptides in this subset which contain the TCEM on the call list are then examined to determine if the TCEM would be likely to be presented in the MHC corresponding to that patient's alleles. If the proteome peptide comprising the TCEM of interest is predicted to bind to any one of the patient's known alleles with an affinity<1 SD below the mean for the protein, the protein is included in an advisory list. The list is curated to remove duplicates and references to any protein fragments catalogued in UniProt (www.uniprot.org). Individual proteins may be reviewed in UniProt and elsewhere to determine if there is evidence of pathologies arising from deficiencies or mutations in the protein. Instances in which a protein of immediate concern is targeted are flagged with a "caution" and excluded from the proposed peptides encoded in a vaccine or in vitro cell stimulation. Examples include, but are not limited to, coagulation factors, neurotransmitters, complement, other proteins with known essential and non-redundant functions. Decision on off-targeting of proteins in the advisory list may be based on a risk-benefit analysis of the patient's condition but access to such a list allows the oncologist to make an informed decision. The most complete typing of a patient's alleles enables a more complete assessment of potential off-targets. Notably, as the relevance of each target will depend on its presentation as a result of the MHC binding of the peptide in which the TCEM occurs, identifying the potential off-target impacts is as personalized as the design of the peptide array for that cancer patient. Specific examples of such advisory and caution proteins are shown in Example 4 below.

Example 4: Application of Personalized Multiplex Vaccine or In Vitro T Cell and Dendritic Cell Stimulants in a Glioblastoma Patient In this Example and the two following Examples 5 and 6 we illustrate the design of a personalized array of peptides to stimulate cancer specific cytotoxic T cells for patients with three different types of cancer: glioblastoma, melanoma and small cell lung cancer. Such peptides may be used to stimulate dendritic cells or T cells in vitro for subsequent administration to the patient, or may form the basis for a personalized vaccine. Said vaccine may be administered by any one of many delivery vehicles. The peptides may be encoded as DNA or RNA for delivery. The peptides may be used alone or expressed as a fusion to an antibody or partial immunoglobulin molecule. Peptides or nucleic acids encoding them may be injected intradermally or parenterally or may be applied in a transdermal microneedle array. The peptides or nucleic acids may be delivered with an adjuvant, cytokine, chemokine or with a physical stimulus of inflammation. In addition, each peptide or nucleic acid administration to stimulate the tumor specific T cells may be accompanied with or followed by a check point inhibitor drug. In each case, to the extent possible based on allele typing, we identify potential off target effects.

Glioblastoma Patient Personalized Peptide Neoepitope Array

Patient X, diagnosed with glioblastoma, has 10 proteins with identified mutations and is MHC typed as A0301, B3501, B_4402 and C0401 for MHC I, and DRB1_0401 and DRB 1_0701. The proteins and mutations are shown in Table 2. While mutations identified in a tumor biopsy were demonstrated by comparison with contemporaneous normal tissue (PBMCs), complete sequencing was not available from the normal patient tissue, so a reference sequence was used as the basis for whole protein peptide affinity predictions.

TABLE 2

| Protein and mutations for Patient X | | |
|---|---|---|
| Protein | Reference gi | Amino acid Mutation |
| Angiomotin isoform 1 | 166064029 | P415L |
| ATP-dependent RNA helicase DDX3X isoform 2 | 301171467 | E481K |
| Coiled-coil domain-containing protein 50 long isoform | 41281911 | Q122P |
| Dipeptidyl peptidase 4 | 18765694 | K56M |
| Kelch-like ECH-associated protein 1 | 22027642 | R614W |
| Kinesin heavy chain isoform 5C | 4758650 | E492K |
| Nephrocystin-4 isoform a | 23510323 | S43P |
| Peroxisomal acyl-coenzyme A oxidase 1 isoform a | 30089972 | P126L |
| Phosphatidylinositol 3 | 73765544 | K6E |
| Symplekin H | 124028529 | P1069S |

Tumor Specific MHC I Binding Targets to Generate CD8 T Cells.

Table 3 summarizes for MHC I alleles that 200 TCEM allele combinations are available for potential targeting in this patient and shows the process of down selection to those TCEM likely to be accessible to T cells as a result of natural presentation and down-selected for other reasons. It determines that if binding affinity of ~2 SD is used, a panel of 1000 simulated peptides for each TCEM allele combination generates 88 distinct T cell targets for which T cell stimulating peptides have been identified. If a higher affinity of <3 SD is preferred this number is reduced to 56 peptides or their encoding nucleotides.

TABLE 3

| Potential TCEM allele combinations and filtration to actual available | | | | | | |
|---|---|---|---|---|---|---|
| Patient X | | | | | | |
| Proteins with identified mutations | 10 | | | | | |
| TCEM with mutations | 50 for 4 alleles = 200 MHC I and 100 MHC II | | | | | |
| Patient MHC Alleles | A0301 | B3501 | B4402 | C0401 | DRB0401 | DRB0701 |
| TCEM naturally presented for allele | 24 | 24 | 25 | 29 | 28 | 24 |
| Mutated proteins in which natural presentation occurs | 10 | 10 | 10 | 10 | 9 | 8 |
| Proteins omitted as no natural presentation | 0 | 0 | 0 | 0 | 1 | 2 |
| Unique peptides simulated with any binding | 20915 | 24731 | 21780 | 25752 | 39818 | 39344 |
| Subset for which TCEM is naturally presented | 10738 | 13016 | 13255 | 16781 | 15904 | 15916 |
| Filtered by polarity score <1 indicating solubility | 7765 | 9207 | 8232 | 13337 | 11986 | 11563 |
| Peptides selected in binding window <−1.75 > −2.25 SD | 948 | 545 | 667 | 294 | 1061 | 356 |

TABLE 3-continued

| Potential TCEM allele combinations and filtration to actual available | | | | | | |
|---|---|---|---|---|---|---|
| Peptides selected in binding window <3.0 SD | 129 | 11 | 375 | 145 | 8 | 5 |
| Represent TCEM allele combos <−1.75 > −2.25 SD | 24 | 21 | 25 | 26 | 24 | 22 |
| Represent TCEM allele combos <3.0 | 18 | 6 | 24 | 13 | 1 | 5 |
| Removed due to immediate off target caution; or high frequency Fc | 1 | 3 | 2 | 2 | 0 | 0 |
| Net TCEM allele combos available <−1.75 > −2.25 SD | 23 | 18 | 23 | 24 | 24 | 22 |
| Net TCEM allele combos available <3.0 SD | 17 | 6 | 22 | 11 | 1 | 5 |
| Potential vaccine peptides per patient for all mutated proteins | MHC I | <−1.75 > −2.25 | 88 | MHC II | <−1.75 > −2.25 | 46 |
| | | <3.0 | 56 | | <3.0 | 6 |

Binding shown in standard deviation units

Table 4 shows example peptides and their predicted binding affinity for each of the MHC I TCEM allele combinations and shows those combinations for which presentation in the native mutant protein is not likely. Table 4 also shows TCEM removed from consideration due to an immediate caution of off target responses. These are further explained in Table 6. Table 5 shows how the peptides identified in Table 4 could be grouped into arrays of 10 for sequential application to maximize utilization of alleles and minimize competition for binding sites at any one time. Table 7 provides details of the concerns for potential adverse reactions arising from targeting for the immediate caution proteins with matching and presented TCEM I For MHC II Table 8 shows example peptides and their predicted binding affinity for each of the MHC IIA TCEM allele combinations designed to stimulate CD4 stimulation and shows those combinations for which presentation in the native mutant protein is not likely. One protein, the ATP-dependent RNA helicase DDX3X, is not represented in the simulated peptide list as it would be expected to have very poor binding in the peptides overlapping the mutated amino acid. However, it would be expected to benefit from T cell help from a very close downstream set of peptides (index positions 481-493) which have high predicted binding for the alleles of interest and would be naturally presented in the mutated protein. Table 9 shows how the peptides identified in Table 7 could be grouped into arrays for sequential application to maximize utilization of alleles and minimize competition for binding sites at any one time. Table 10 shows the advisory list of potential off target binding for the selected TCEM and patient X MHC II alleles. A set of the peptides designed were administered intradermally to Patient X and subsequent Elispots detected responses to groups of peptides.

TABLE 4

TCEM Allele combinations and selected peptides for each designed to stimulate CD8 T cells in Patient X

| Protein curation and reference sequence | aa Mut | position | TCEM 1 | SEQ ID NO: | A0301 Simulated | A0301 | B3501 Simulated | B3501 | B4402 Simulated | B4402 | C0401 Simulated | C0401 | Caution |
|---|---|---|---|---|---|---|---|---|---|---|---|---|---|
| kelch-like ECH-associated protein 1 Homo sapiens gi:22027642 | W | 607 | ~~~MEPCW~ | 285 | KITMEPCWP (SEQ ID NO: 335) | -1.80 | no | | no | | no | | |
| | W | 608 | ~~~EPCWK~ | 286 | AGKEPCWKP (SEQ ID NO: 336) | -1.91 | HGVEPCWKI (SEQ ID NO: 357) | -1.95 | ASLEPCWKH (SEQ ID NO: 377) | -1.93 | no | | |
| | W | 609 | ~~~PCWKQ~ | 287 | no | | MKGPCWKQF (SEQ ID NO: 358) | -2.04 | VESPCWKQS (SEQ ID NO: 378) | -1.76 | LLRPCWKQA (SEQ ID NO: 400) | -1.79 | |
| | W | 610 | ~~~CWKQI~ | 288 | LAACWKQIK (SEQ ID NO: 337) | -2.00 | No | | IERCWKQIE (SEQ ID NO: 379) | -1.95 | no | | |
| | W | 611 | ~~~WKQID~ | 289 | no | | RPSWKQIDF (SEQ ID NO: 359) | -1.88 | CERWKQIDD (SEQ ID NO: 380) | -1.99 | PFDWKQIDP (SEQ ID NO: 401) | -1.97 | |
| dipeptidyl peptidase 4 Homo sapiens gi:1876 5694 | M | 49 | ~~~TYRLM~ | 290 | no | | FKNTYRLML (SEQ ID NO: 360) | -1.97 | TETTYRLMV (SEQ ID NO: 381) | -2.00 | No | | |
| | M | 50 | ~~~YRLML~ | 291 | LDPYRLMLK (SEQ ID NO: 338) | -2.19 | No | | no | | No | | |
| | M | 51 | ~~~RLMLY~ | 292 | no | | No | | no | | SKIRLMLYS (SEQ ID NO: 402) | -1.82 | |
| | M | 52 | ~~~LMLYS~ | 293 | no | | No | | REELMLYSQ (SEQ ID NO: 382) | -2.04 | RRYLMLYSK (SEQ ID NO: 403) | -1.92 | |
| | M | 53 | ~~~MLYSL~ | 294 | TQSMLYSLK (SEQ ID NO: 339) | -1.96 | RPRMLYSLM (SEQ ID NO: 361) | -1.55 | IERMLYSLR (SEQ ID NO: 383) | -1.96 | KKLMLYSLK (SEQ ID NO: 404) | -1.35 | |
| peroxisomal acyl-coenzyme A oxidase 1 isoform a gi:30089972 | L | 119 | ~~~RFFML~ | 295 | no | | No | | No | | SABRFFMLK (SEQ ID NO: 405) | -1.82 | |
| | L | 120 | ~~~FFMLA~ | 296 | DDRFFMLAK (SEQ ID NO: 340) | -2.05 | KSEFFMLAR (SEQ ID NO: 362) | -1.15 | EEQFMLAQ (SEQ ID NO: 384) | -2.19 | DRRFFMLAK (SEQ ID NO: 406) | -1.83 | |
| | L | 121 | ~~~FMLAW~ | 297 | no | | No | | AEKFMLAWE (SEQ ID NO: 385) | -1.91 | no | | |
| | L | 122 | ~~~MLAWN~ | 298 | EPSMLAWNK (SEQ ID NO: 341) | -1.88 | QARMLAWNY (SEQ ID NO: 363) | -2.36 | SGPMLAWNR (SEQ ID NO: 386) | -2.00 | PGSMLAWNK (SEQ ID NO: 407) | -1.63 | |
| | L | 123 | ~~~LAWNL~ | 299 | SGRLAWNLP (SEQ ID NO: 342) | -2.04 | RQELAWNLW (SEQ ID NO: 364) | -1.64 | TEVLAWNLK (SEQ ID NO: 387) | -1.98 | no | | |

TABLE 4 -continued

TCEM Allele combinations and selected peptides for each designed to stimulate CD8 T cells in Patient X

| Protein curation and reference sequence | aa Mut | position | TCEM 1 | SEQ ID NO: | A0301 Simulated | A0301 | B3501 Simulated | B3501 | B4402 Simulated | B4402 | C0401 Simulated | C0401 | Caution |
|---|---|---|---|---|---|---|---|---|---|---|---|---|---|
| angiomotin isoform 1 Homo sapiens gi:166064029 | L | 408 | ~~~PRAQL~ | 300 | RFVPRAQLP (SEQ ID NO: 343) | -2.06 | No | | EEVPRAQLP (SEQ ID NO: 388) | -1.94 | KLKPRAQLL (SEQ ID NO: 408) | -1.90 | |
| | L | 409 | ~~~RAQLS~ | 301 | no | | No | | DCSRAQLSA (SEQ ID NO: 389) | -1.91 | LELRAQLSS (SEQ ID NO: 409) | -1.98 | |
| | L | 410 | ~~~AQLSS~ | 302 | no | | Caution | | no | | caution | | #1 |
| | L | 411 | ~~~QLSSA~ | 303 | no | | No | | no | | SLRQLSSAL (SEQ ID NO: 410) | -1.86 | |
| | L | 412 | ~~~LSSAS~ | 304 | EGRLSSASK (SEQ ID NO: 344) | -1.76 | KNVLSSASW (SEQ ID NO: 365) | -2.02 | no | | no | | |
| coiled-coil domain-containing protein 50 long isoform Homo sapiens gi:41281911 | P | 115 | ~~~EKELP~ | 305 | KGSEKELPQ (SEQ ID NO: 345) | -2.03 | DAEEKELPY (SEQ ID NO: 366) | -2.14 | no | | APFEKELPR (SEQ ID NO: 411) | -1.82 | |
| | P | 116 | ~~~KELPE~ | 306 | no | | caution | | GHFELPEEM (SEQ ID NO: 390) | -2.02 | no | | #2 |
| | P | 117 | ~~~ELPQQ~ | 307 | yes | | no | | No | | no | | |
| | P | 118 | ~~~LPEEK~ | 308 | no | | no | | | | WLQLPEEKW (SEQ ID NO: 412) | -1.95 | |
| | P | 119 | ~~~PEEKK~ | 309 | GGYPEEKKP (SEQ ID NO: 346) | -1.82 | DLIPEEKKF (SEQ ID NO: 367) | -1.96 | VELPEEKKS (SEQ ID NO: 391) | -2.01 | QCLPEEKKS (SEQ ID NO: 413) | -1.80 | |
| kinesin heavy chain isoform 5C gi:4758650 | K | 485 | ~~~LQALK~ | 310 | caution | | No | | Caution | | caution | | #3 |
| | K | 486 | ~~~QALKE~ | 311 | no | | VLRQALKEF (SEQ ID NO: 368) | -1.99 | FESQALKEV (SEQ ID NO: 392) | -2.02 | no | | |
| | K | 487 | ~~~ALKEL~ | 312 | no | | VGDALKELM (SEQ ID NO: 369) | -1.90 | PEKALKELQ (SEQ ID NO: 393) | -1.91 | no | | |
| | K | 488 | ~~~LKELA~ | 313 | VEFLKERLAR (SEQ ID NO: 347) | -1.95 | KSQLKELAY (SEQ ID NO: 370) | -1.99 | QCELKELAT (SEQ ID NO: 394) | -1.90 | YQMLKELAT (SEQ ID NO: 414) | -1.97 | |
| | K | 489 | ~~~KELAV~ | 314 | YVRKELAVQ (SEQ ID NO: 348) | -1.98 | WPSKELAVR (SEQ ID NO: 371) | -1.94 | no | | no | | |
| symplekin Homo sapiens gi:124028529 | S | 1062 | ~~~FDKCS~ | 315 | KCFFDKCSD (SEQ ID NO: 349) | -1.77 | No | | LCLFDKCSS (SEQ ID NO: 395) | -1.80 | QWRFDKCSQ (SEQ ID NO: 415) | -1.88 | |
| | S | 1063 | ~~~DKCSE~ | 316 | VCFDKCSEQ (SEQ ID NO: 350) | -1.87 | No | | no | | LQHDKCSE (SEQ ID NO: 416) | -1.94 | |

TABLE 4 -continued

TCEM Allele combinations and selected peptides for each designed to stimulate CD8 T cells in Patient X

| Protein curation and reference sequence | aa Mut | position | TCEM 1 | SEQ ID NO: | A0301 Simulated | A0301 | B3501 Simulated | B3501 | B4402 Simulated | B4402 | C0401 Simulated | C0401 | Caution |
|---|---|---|---|---|---|---|---|---|---|---|---|---|---|
| | S | 1064 | ~~~KCSL~ | 317 | DVMKCSELP (SEQ ID NO: 351) | -2.14 | RSNKCSELY (SEQ ID NO: 372) | -1.96 | no | | LKFKCSELA (SEQ ID NO: 417) | -1.80 | |
| | S | 1065 | ~~~CSELR~ | 318 | no | | No | | LEECSELRT (SEQ ID NO: 396) | -1.84 | no | | |
| | S | 1066 | ~~~SELRE~ | 319 | no | | Caution | | caution | | no | | #4 |
| ATP-dependent RNA helicase DDX3X isoform 2 Homo sapiens Gi: 301171467 | K | 474 | ~~~QRDRK~ | 320 | no | | No | | no | | VILQRDRKK (SEQ ID NO: 418) | -1.46 | |
| | K | 475 | ~~~RDRKE~ | 321 | no | | No | | no | | no | | |
| | K | 476 | ~~~DRKEA~ | 322 | no | | No | | no | | FDWDRKEAG (SEQ ID NO: 419) | -1.88 | |
| | K | 477 | ~~~RKEAL~ | 323 | no | | No | | no | | no | | |
| | K | 478 | ~~~KEALH~ | 324 | KPYKEALHP (SEQ ID NO: 352) | -1.90 | No | | no | | AYDKEALHL (SEQ ID NO: 420) | -1.90 | |
| phosphatidyli-nositol 3 gi:73765544 | E | 14 | ~~~TAIIE~ | 325 | no | | No | | REATAIIEE (SEQ ID NO: 397) | -1.92 | AAVTAIIEK (SEQ ID NO: 421) | -1.76 | |
| | E | 15 | ~~~AIIEE~ | 326 | no | | No | | no | | no | | |
| | E | 16 | ~~~IIEEI~ | 327 | KCKEEIVSP (SEQ ID NO: 353) | -2.00 | LAEIIEEIH (SEQ ID NO: 373) | -1.87 | EEHIIEEID (SEQ ID NO: 398) | -1.94 | no | | |
| | E | 17 | ~~~IEEIV~ | 328 | no | | KGEIEEIVY (SEQ ID NO: 374) | -2.07 | no | | PTCIEEIVK (SEQ ID NO: 422) | -1.96 | |
| | E | 18 | ~~~EEIVS~ | 329 | DAWEEIVSY (SEQ ID NO: 354) | -1.86 | LGSEEIVSR (SEQ ID NO: 375) | -1.75 | no | | RRFEEIVSD (SEQ ID NO: 423) | -1.93 | |
| nephrocys-tin-4 isoform a gi:23510323 | P | 36 | ~~~PWKEP~ | 330 | no | | No | | no | | no | | |
| | P | 37 | ~~~WKEPT~ | 331 | no | | No | | no | | STCWKEPTK (SEQ ID NO: 424) | -1.97 | |
| | P | 38 | ~~~KEPTA~ | 332 | MYLKEPTAK (SEQ ID NO: 355) | -1.93 | LPSKEPTAA (SEQ ID NO: 376) | -1.78 | no | | AMKKEPTAL (SEQ ID NO: 425) | -1.83 | |

TABLE 4 -continued

| | | | | | | | | | |
|---|---|---|---|---|---|---|---|---|---|
| TCEM Allele combinations and selected peptides for each designed to stimulate CD8 T cells in Patient X | | | | | | | | | |
| Protein curation and reference sequence | aa Mut | position | TCEM 1 | SEQ ID NO: | A0301 Simulated | B3501 Simulated | B4402 Simulated | C0401 Simulated | C0401 Caution |
| P | 39 | ~~EPTAF~ | | 333 | no | No | no | IYREPTAFS (SEQ ID NO: 426) no | -1.88 |
| P | 40 | ~~PTAFQQ | | 334 | IVRPTAFQQ (SEQ ID NO: 356) | -2.20 NSAPTAFQF (SEQ ID NO: 377) | -1.92 VERPTAFQG (SEQ ID NO: 399) | -1.96 no | |

1 Cautions: 1: Complement factor H; 2: Choline O-acetyltransferase; 3: 5-hydroxytryptamine receptor 1D; 4: DNA mismatch repair protein Msh2

2 Several peptides were included at the highest binding affinity possible; but fall below the desired/selected window: RPRNILYSLM (SEQ ID NO: 361), KKLMLYSLK (SEQ ID NO: 404), KSEFFMLAR (SEQ ID NO: 362), DRRFFMLAK (SEQ ID NO: 363), QARNILAWNY (SEQ ID NO: 406), PGSMLAWNK (SEQ ID NO: 407), RQELAWNLM (SEQ ID NO: 364), VILQRDRKK (SEQ ID NO: 418)

3 No indicates TCEM which would not be presented in vivo in the natural mutated protein and thus never exposed as targets Binding shown in standard deviation units

TABLE 5

Recommended grouping for application of MHC I peptides or nucleotides encoding the same to Patient X

| Series | Peptide | SEQ ID NO: | Allele | Protein Target | position | TCEM | SEQ ID NO: | Fc | Human Freq# |
|---|---|---|---|---|---|---|---|---|---|
| 1 | PEKALKELQ | 393 | B4402 | kinesin heavy chain isoform 5C | 487 | ~~~ALKEL~ | 312 | 14 | 1.68 |
| | RFVPRAQLP | 343 | A0301 | angiomotin isoform 1 | 408 | ~~~PRAQL~ | 300 | 21 | 0.35 |
| | VILQRDRKK | 418 | C0401 | ATP-dependent RNA helicase DDX3X isoform 2 | 474 | ~~~QRDRK~ | 320 | 22 | -1.36 |
| | FKNTYRLML | 360 | B3501 | dipeptidyl peptidase 4 | 49 | ~~~TYRLM~ | 290 | 23 | -3.66 |
| | KTFMEPCWP | 335 | A0301 | kelch-like ECH-associated protein 1 | 607 | ~~~MEPCW~ | 285 | 23 | -3.66 |
| | STCWKEPTK | 424 | C0401 | nephrocystin-4 isoform a | 37 | ~~~WKEPT~ | 331 | 23 | -3.16 |
| | EPSMLAWNK | 341 | A0301 | peroxisomal acyl-coenzyme A oxidase 1 isoform a | 122 | ~~~MLAWN~ | 298 | 23 | -3.66 |
| | KGEIEEIVY | 374 | B3501 | phosphatidylinositol 3 | 17 | ~~~IEEIV~ | 328 | 23 | -0.47 |
| | KCFFDKCSD | 349 | A0301 | symplekin | 1062 | ~~~FDKCS~ | 315 | 24 | -3.16 |
| | GHFELPEEM | 390 | B4402 | coiled-coil domain-containing protein 50 long isoform | 117 | ~~~ELPEE~ | 307 | 21 | 1.17 |
| 2 | YVRKELAVQ | 348 | A0301 | kinesin heavy chain isoform 5C | 489 | ~~~KELAV~ | 314 | 16 | 0.15 |
| | EEVPRAQLP | 388 | B4402 | angiomotin isoform 1 | 408 | ~~~PRAQL~ | 300 | 21 | 0.35 |
| | KPYKEALHP | 352 | A0301 | ATP-dependent RNA helicase DDX3X isoform 2 | 478 | ~~~KEALH~ | 324 | 20 | -0.61 |
| | DAEKELPY | 366 | B3501 | coiled-coil domain-containing protein 50 long isoform | 115 | ~~~EKELP~ | 305 | 22 | 0.65 |
| | TETTYRLMV | 381 | B4402 | dipeptidyl peptidase 4 | 49 | ~~~TYRLM~ | 290 | 23 | -3.66 |
| | RPSWKQIDF | 359 | B3501 | kelch-like ECH -associated protein 1 | 611 | ~~~WKQID~ | 289 | 24 | -3.66 |
| | IYREPTAFS | 426 | C0401 | nephrocystin-4 isoform a | 39 | ~~~EPTAF~ | 333 | 22 | -0.77 |
| | QARMLAWNY | 363 | B3501 | peroxisomal acyl-coenzyme A oxidase 1 isoform a | 122 | ~~~MLAWN~ | 298 | 23 | -3.66 |
| | PTCIEEIVK | 422 | C0401 | phosphatidylinositol 3 | 17 | ~~~IEEIV~ | 328 | 23 | -0.47 |
| | LCLFDKCSS | 395 | B4402 | symplekin | 1062 | ~~~FDKCS~ | 315 | 24 | -3.16 |
| 3 | HGVEPCWKI | 357 | B3501 | kelch-like ECH-associated protein 1 | 608 | ~~~EPCWK~ | 286 | 24 | -0.96 |
| | KLKPRAQLL | 408 | C0401 | angiomotin isoform 1 | 408 | ~~~PRAQL~ | 300 | 21 | 0.35 |
| | AYDKEALHL | 420 | C0401 | ATP-dependent RNA helicase DDX3X isoform 2 | 478 | ~~~KEALH~ | 324 | 20 | -0.61 |
| | REELMLYSQ | 382 | B4402 | dipeptidyl peptidase 4 | 52 | ~~~LMLYS~ | 293 | 18 | -2.45 |
| | MKGPCWKQF | 358 | B3501 | kelch-like ECH-associated protein 1 | 609 | ~~~PCWKQ~ | 287 | 24 | -3.66 |
| | VEFLKELAR | 347 | A0301 | kinesin heavy chain isoform 5C | 488 | ~~~LKELA~ | 313 | 21 | 1.13 |
| | IVRPTAFQQ | 356 | A0301 | nephrocystin-4 isoform a | 40 | ~~~PTAFQ~ | 334 | 22 | 0.29 |
| | SGPMLAWNR | 386 | B4402 | peroxisomal acyl-coenzyme A oxidase 1 isoform a | 122 | ~~~MLAWN~ | 298 | 23 | -3.66 |
| | REATAIIEE | 397 | B4402 | phosphatidylinositol 3 | 14 | ~~~TAIIE~ | 325 | 20 | -0.20 |
| | QWRFDKCSQ | 415 | C0401 | symplekin | 1062 | ~~~FDKCS~ | 315 | 24 | -3.16 |
| 4 | TEVLAWNLK | 387 | B4402 | peroxisomal acyl-coenzyme A oxidase 1 isoform a | 123 | ~~~LAWNL~ | 299 | 23 | -1.08 |
| | ASLEPCWKH | 427 | B4402 | kelch-like ECH-associated protein 1 | 608 | ~~~EPCWK~ | 286 | 24 | -0.96 |
| | KGSEKELPQ | 345 | A0301 | coiled-coil domain-containing protein 50 long isoform | 115 | ~~~EKELP~ | 305 | 22 | 0.65 |
| | LDPYRLMLK | 338 | A0301 | dipeptidyl peptidase 4 | 50 | ~~~YRLML~ | 291 | 23 | -0.61 |
| | SLRQLSSAL | 410 | C0401 | angiomotin isoform 1 | 411 | ~~~QLSSA~ | 303 | 18 | 1.43 |
| | FDWDRKEAG | 419 | C0401 | ATP-dependent RNA helicase DDX3X isoform 2 476 | 476 | ~~~DRKEA~ | 322 | 22 | -0.20 |

TABLE 5 -continued

Recommended grouping for application of MHC I peptides or nucleotides encoding the same to Patient X

| Series | Peptide | SEQ ID NO: | Allele | Protein Target | position | TCEM | SEQ ID NO: | Fc | Human Freq# |
|---|---|---|---|---|---|---|---|---|---|
| | CERWKQIDD | 380 | B4402 | kelch-like ECH-associated protein 1 | 611 | ~~WKQID~ | 289 | 24 | -3.66 |
| | KSQLKELAY | 370 | B3501 | kinesin heavy chain isoform 5C | 488 | ~~LKELA~ | 313 | 21 | 1.13 |
| | NSAPTAFQF | 377 | B3501 | nephrocystin-4 isoform a | 40 | ~~PTAFQ~ | 334 | 22 | 0.29 |
| | AAVTAIIEK | 421 | C0401 | phosphatidylinositol 3 | 14 | ~~TAIIE~ | 325 | 20 | -0.20 |
| | VCFDKCSEQ | 350 | A0301 | symplekin | 1063 | ~~DKCSE~ | 316 | 23 | -1.21 |
| 5 | PGSMLAWNK | 407 | C0401 | peroxisomal acyl-coenzyme A oxidase 1 isoform a | 122 | ~~MLAWN~ | 298 | 23 | -3.66 |
| | RQELAWNLW | 364 | B3501 | peroxisomal acyl-coenzyme A oxidase 1 isoform a | 123 | ~~LAWNL~ | 299 | 23 | -1.08 |
| | RRFEEIVSD | 423 | C0401 | phosphatidylinositol 3 | 18 | ~~EEIVS~ | 329 | 21 | 0.47 |
| | DCSRAQLSA | 389 | B4402 | angiomotin isoform 1 | 409 | ~~RAQLS~ | 301 | 17 | 0.15 |
| | TQSMLYSLK | 339 | A0301 | dipeptidyl peptidase 4 | 53 | ~~MLYSL~ | 294 | 20 | -1.54 |
| | VESPCWKQS | 378 | B4402 | kelch-like ECH-associated protein 1 | 609 | ~~PCWKQ~ | 287 | 24 | -3.66 |
| | QCELKELAT | 394 | B4402 | kinesin heavy chain isoform 5C | 488 | ~~LKELA~ | 313 | 21 | 1.13 |
| | DDRFFMLAK | 340 | A0301 | peroxisomal acyl-coenzyme A oxidase 1 isoform a | 120 | ~~FFMLA~ | 296 | 24 | -3.16 |
| | KCKEEIVSP | 353 | A0301 | phosphatidylinositol 3 | 16 | ~~IIEET~ | 327 | 22 | 0.32 |
| | LQHDKCSEK | 416 | C0401 | symplekin | 1063 | ~~DKCSE~ | 316 | 23 | -1.21 |
| | DLIPEEKKF | 367 | B3501 | coiled-coil domain-containing protein 50 long isoform | 119 | ~~PEEKK~ | 309 | 23 | 1.53 |
| 6 | AEKFMLAWE | 385 | B4402 | peroxisomal acyl-coenzyme A oxidase 1 isoform a | 121 | ~~FMLAW~ | 297 | 24 | -0.86 |
| | LELRAQLSS | 409 | C0401 | angiomotin isoform 1 | 409 | ~~RAQLS~ | 301 | 17 | 0.15 |
| | GGYPEEKKP | 346 | A0301 | coiled-coil domain-containing protein 50 long isoform | 119 | ~~PEEKK~ | 309 | 23 | 1.53 |
| | RPRMLYSLM | 361 | B3501 | dipeptidyl peptidase 4 | 53 | ~~MLYSL~ | 294 | 20 | -1.54 |
| | PFDWKQIDP | 401 | C0401 | kelch-like ECH-associated protein 1 | 611 | ~~WKQID~ | 289 | 24 | -3.66 |
| | YQMLKELAP | 414 | C0401 | kinesin heavy chain isoform 5C | 488 | ~~LKELA~ | 313 | 21 | 1.13 |
| | MYLKEPTAK | 355 | A0301 | nephrocystin-4 isoform a | 38 | ~~KEPTA~ | 332 | 19 | -0.69 |
| | KSEFFMLAR | 362 | B3501 | peroxisomal acyl-coenzyme A oxidase 1 isoform a | 120 | ~~FFMLA~ | 296 | 24 | -3.16 |
| | LAEIIEEIH | 373 | B3501 | phosphatidylinositol 3 | 16 | ~~IIEEI~ | 327 | 22 | 0.32 |
| | LEECSELRT | 396 | B4402 | symplekin | 1065 | ~~CSELR~ | 318 | 16 | -0.25 |
| 7 | AGKEPCWKP | 336 | A0301 | kelch-like ECH-associated protein 1 | 608 | ~~EPCWK~ | 286 | 24 | -0.96 |
| | RRYIMLYSK | 403 | C0401 | dipeptidyl peptidase 4 | 52 | ~~LMLYS~ | 293 | 18 | -2.45 |
| | EGRLSSASK | 344 | A0301 | angiomotin isoform 1 | 412 | ~~LSSAS~ | 304 | 13 | 2.11 |
| | IERMLYSLR | 383 | B4402 | dipeptidyl peptidase 4 | 53 | ~~MLYSL~ | 294 | 20 | -1.54 |
| | LLRPCWKQA | 400 | C0401 | kelch-like ECH-associated protein 1 | 609 | ~~PCWKQ~ | 287 | 24 | -3.66 |
| | VLRQALKEF | 368 | B3501 | kine sin heavy chain isoform 5C | 486 | ~~QALKE~ | 311 | 21 | 1.61 |
| | LPSKEPTAA | 376 | B3501 | nephrocystin-4 isoform a | 38 | ~~KEPTA~ | 332 | 19 | -0.69 |

TABLE 5 -continued

Recommended grouping for application of MHC I peptides or nucleotides encoding the same to Patient X

| Series | Peptide | SEQ ID NO: | Allele | Protein Target | position | TCEM | SEQ ID NO: | Fc | Human Freq# |
|---|---|---|---|---|---|---|---|---|---|
| 8 | EEQFFMLAQ | 384 | B4402 | peroxisomal acyl-coenzyme A oxidase 1 isoform a | 120 | ~~~FFMLA~ | 296 | 24 | -3.16 |
| | EEHIIEEID | 398 | B4402 | phosphatidylinositol 3 | 16 | ~~~IIEEI~ | 327 | 22 | 0.32 |
| | DVMKC SELP | 351 | A0301 | symplekin | 1064 | ~~~KCSEL~ | 317 | 16 | 0.08 |
| | APFEKELPR | 411 | C0401 | coiled-coil domain-containing protein 50 long isoform | 115 | ~~EKELP~ | 305 | 22 | 0.65 |
| | WLQLPEEKW | 428 | C0401 | coiled-coil domain-containing protein 50 long isoform | 118 | ~~LPEEK~ | 308 | 22 | 1.02 |
| | KNVL SSASW | 365 | B3501 | angiomotin isoform 1 | 412 | ~~~LSSAS~ | 304 | 13 | 2.11 |
| | VELPEEKKS | 391 | B4402 | coiled-coil domain-containing protein 50 long isoform | 119 | ~~~PEEKK~ | 309 | 23 | 1.53 |
| | KKLMLYSLK | 404 | C0401 | dipeptidyl peptidase 4 | 53 | ~~~MLYSL~ | 294 | 20 | -1.54 |
| | LAACWKQIK | 337 | A0301 | kelch-like ECH-associated protein 1 | 610 | ~~~CWKQI~ | 288 | 24 | -2.04 |
| | FESQALKEV | 392 | B4402 | kinesin heavy chain isoform 5C | 486 | ~~~QALKE~ | 311 | 21 | 1.61 |
| | AMKKEPTAL | 425 | C0401 | nephrocystin-4 isoform a | 38 | ~~~KEPTA~ | 332 | 19 | -0.69 |
| | DRRPFMLAK | 406 | C0401 | peroxisomal acyl-coenzyme A oxidase 1 isoform a | 120 | ~~~FFMLA~ | 296 | 24 | -3.16 |
| | DAWEEIVSY | 354 | A0301 | phosphatidylinositol 3 | 18 | ~~~EEIVS~ | 329 | 21 | 0.47 |
| | RSNKCSELY | 372 | B3501 | symplekin | 1064 | ~~~KCSEL~ | 317 | 16 | 0.08 |
| 9 | WPSKELAVR | 371 | B3501 | kinesin heavy chain isoform 5C | 489 | ~~KELAV~ | 314 | 16 | 0.15 |
| | SGRLAWNLP | 342 | A0301 | peroxisomal acyl-coenzyme A oxidase 1 isoform a | 123 | ~~LAWNL~ | 299 | 23 | -1.08 |
| | VERPTAFQG | 399 | B4402 | nephrocystin-4 isoform a | 40 | ~~PTAFQ~ | 334 | 22 | 0.29 |
| | QCLPEEKKS | 413 | C0401 | coiled-coil domain-containing protein 50 long isoform | 119 | ~~PEEKK~ | 309 | 23 | 1.53 |
| | SKIRLMLYS | 402 | C0401 | dipeptidyl peptidase 4 | 51 | ~~~RLMLY~ | 292 | 22 | -1.21 |
| | IERCWKQIE | 379 | B4402 | kelch-like ECH-associated protein 1 | 610 | ~~~CWKQI~ | 288 | 24 | -2.04 |
| | VGDALKELM | 369 | B3501 | kinesin heavy chain isoform 5C | 487 | ~~~ALKEL~ | 312 | 14 | 1.68 |
| | SAERFFMLK | 405 | C0401 | peroxisomal acyl-coenzyme A oxidase 1 isoform a | 119 | ~~~RFFML~ | 295 | 22 | -2.04 |
| | LGSEEIVSR | 375 | B3501 | phosphatidylinositol 3 | 18 | ~~~EEIVS~ | 329 | 21 | 0.47 |
| | LKFKCSELA | 417 | C0401 | symplekin | 1064 | ~~~KCSEL~ | 317 | 16 | 0.08 |

Human Frequency based on a zero mean unit variance transformation of the TCEM I frequencies in the human proteome

TABLE 6

Patient X Advisory list of potential off-target binding of T cells matched to
tumor specific sites for MHC I.

| TCEM core | SEQ ID NO: | Human proteome target | UniProt identifier | Advisory vs Immediate caution |
|---|---|---|---|---|
| LQALK | 310 | 5-hydroxytryptamine receptor 1D | 5HT1D_HUMAN | Immediate caution |
| SELRE | 319 | Acid-sensing ion channel 4 | ASIC4_HUMAN | |
| ELPEE | 307 | ADAMTS-like protein 3 | ATL3_HUMAN | |
| KCSEL | 317 | A-kinase anchor protein 9 | AKAP9_HUMAN | |
| TAIIE | 325 | Amyotrophic lateral sclerosis 2 chromosomal region candidate gene 12 protein | AL2SB_HUMAN | |
| ALKEL | 312 | Ankyrin repeat | ASZ1_HUMAN | |
| ELPEE | 307 | Arsenite methyltransferase | AS3MT_HUMAN | |
| LQALK | 310 | Arylsulfatase A | ARSA_HUMAN | |
| RAQLS | 301 | ATP-binding cassette sub-family A member 2 | ABCA2_HUMAN | |
| ELPEE | 307 | ATP-dependent RNA helicase DDX39A | DX39A_HUMAN | |
| LSSAS | 304 | Bromodomain adjacent to zinc finger domain protein 1A | BAZ1A_HUMAN | |
| ALKEL | 312 | Butyrophilin subfamily 2 member A1 | BT2A1_HUMAN | |
| EKELP | 305 | C2 calcium-dependent domain-containing protein 4C | C2C4C_HUMAN | |
| QLSSA | 303 | C6orf182 protein | Q6P2R3_HUMAN | |
| LQALK | 310 | Calcium-activated chloride channel regulator 2 | CLCA2_HUMAN | |
| QLSSA | 303 | Centrosomal protein CEP57L1 | CE57L_HUMAN | |
| ALKEL | 312 | Centrosomal protein of 120 kDa | CE120_HUMAN | |
| KELPE | 306 | Choline O-acetyltransferase | CLAT_HUMAN | Immediate caution |
| QALKE | 311 | Cleavage and polyadenylation specific factor 3-like | C9IYS7_HUMAN | |
| KCSEL | 317 | Coiled-coil domain-containing protein 150 | CC150_HUMAN | |
| AQLSS | 302 | Complement factor H | CFAH_HUMAN | Immediate caution |
| IEEIV | 328 | Conserved oligomeric Golgi complex subunit 5 | COGS_HUMAN | |
| QLSSA | 303 | Cyclic AMP-responsive element-binding protein 5 | CREB5_HUMAN | |
| QALKE | 311 | Cytochrome c oxidase subunit 4 isoform 2 | COX42_HUMAN | |
| QALKE | 311 | DEAD (Asp-Glu-Ala-Asp) box polypeptide 56 | G3V0G3_HUMAN | |
| KELPE | 306 | Decorin | PGS2_HUMAN | |
| ELPEE | 307 | Disks large-associated protein 3 | DLGP3_HUMAN | |
| SELRE | 319 | DNA mismatch repair protein Msh2 | MSH2_HUMAN | Immediate caution |
| IIEEI | 327 | DNA nucleotidylexotransferase | TDT_HUMAN | |
| ALKEL | 312 | DNA-binding protein SATB2 | SATB2_HUMAN | |
| PRAQL | 300 | Down syndrome cell adhesion molecule | DSCAM_HUMAN | |
| KELAV | 314 | Dynein heavy chain 8 | DYH8_HUMAN | |
| QALKE | 311 | E1A-binding protein p400 | EP400_HUMAN | |

TABLE 6 -continued

Patient X Advisory list of potential off-target binding of T cells matched to
tumor specific sites for MHC I.

| TCEM core | SEQ ID NO: | Human proteome target | UniProt identifier | Advisory vs Immediate caution |
|---|---|---|---|---|
| QLSSA | 303 | E3 ubiquitin-protein ligase E3D | UBE3D_HUMAN | |
| EEIVS | 329 | E3 ubiquitin-protein ligase RFWD2 | RFWD2_HUMAN | |
| ALKEL | 312 | EH domain-containing protein 2 | EHD2_HUMAN | |
| QALKE | 311 | EP400 N-terminal-like protein | E400N_HUMAN | |
| EEIVS | 329 | Epidermal growth factor-like protein 6 | EGFL6_HUMAN | |
| ELPEE | 307 | Exonuclease 3'-5' domain-containing protein 1 | EXD1_HUMAN | |
| SELRE | 319 | Fanconi anemia group D2 protein | FACD2_HUMAN | |
| ELPEE | 307 | F-box only protein 42 | FBX42_HUMAN | |
| ALKEL | 312 | Fer-1-like protein 6 | FR1L6_HUMAN | |
| QALKE | 311 | FERM domain-containing protein 4A | FRM4A_HUMAN | |
| QALKE | 311 | Filamin-A-interacting protein 1 | FLIP1_HUMAN | |
| RAQLS | 301 | G patch domain-containing protein 1 | GPTC1_HUMAN | |
| RAQLS | 301 | Golgin subfamily A member 2 | GOGA2_HUMAN | |
| QALKE | 311 | Heat shock 70 kDa protein 12A | HS12A_HUMAN | |
| ALKEL | 312 | Homeobox protein SIX4 | SIX4_HUMAN | |
| LKELA | 313 | Homeodomain-interacting protein kinase 4 | HIPK4_HUMAN | |
| ALKEL | 312 | Insulin receptor substrate 2 | IRS2_HUMAN | |
| KELAV | 314 | Insulin-like growth factor-binding protein 2 | IBP2_HUMAN | |
| QALKE | 311 | Integrator complex subunit 11 | INT11_HUMAN | |
| ELPEE | 307 | Integrin alpha-L | ITAL_HUMAN | |
| SELRE | 319 | JmjC domain-containing protein 7 | JMJD7_HUMAN | |
| LSSAS | 304 | Kinesin-like protein KIF7 | KIF7_HUMAN | |
| QALKE | 311 | Leucine-rich repeat and IQ domain-containing protein 4 | LRIQ4_HUMAN | |
| ALKEL | 312 | Leucine-rich repeat-containing protein 18 | LRC18_HUMAN | |
| LKELA | 313 | Leucine-rich repeat-containing protein 7 | LRRC7_HUMAN | |
| EEIVS | 329 | Leucine-rich repeat-containing protein 8C | LRC8C_HUMAN | |
| IEEIV | 328 | Leucine-rich repeat-containing protein 8C | LRC8C_HUMAN | |
| ALKEL | 312 | Low-density lipoprotein receptor-related protein 8 | LRP8_HUMAN | |
| ALKEL | 312 | Meiosis-specific nuclear structural protein 1 | MNS1_HUMAN | |
| IIEEI | 327 | Metal transporter CNNM1 | CNNM1_HUMAN | |
| ALKEL | 312 | Mitogen-activated protein kinase kinase kinase 4 | M3K4_HUMAN | |
| SELRE | 319 | Mixed lineage kinase domain-like protein | MLKL_HUMAN | |
| LSSAS | 304 | Mucin-16 | MUC16_HUMAN | |
| EEIVS | 329 | NACHT | NALP9_HUMAN | |
| LSSAS | 304 | Neurobeachin-like protein 1 | NBEL1_HUMAN | |
| SELRE | 319 | Neuron navigator 3 | NAV3_HUMAN | |

TABLE 6 -continued

Patient X Advisory list of potential off-target binding of T cells matched to
tumor specific sites for MHC I.

| TCEM core | SEQ ID NO: | Human proteome target | UniProt identifier | Advisory vs Immediate caution |
|---|---|---|---|---|
| KELPE | 306 | Niban-like protein 2 | MOQZV9_HUMAN | |
| KELPE | 306 | Niban-like protein 2 | MOQZV9_HUMAN | |
| LMLYS | 293 | Nodal homolog | NODAL_HUMAN | |
| LSSAS | 304 | Olfactory receptor 14A16 | O14AG_HUMAN | |
| ALKEL | 312 | Origin recognition complex subunit 4 | ORC4_HUMAN | |
| QALKE | 311 | Peroxisomal 2 | H7C078_HUMAN | |
| LSSAS | 304 | PERQ amino acid-rich with GYF domain-containing protein 1 | PERQ1_HUMAN | |
| LKELA | 313 | PH and SEC7 domain-containing protein 1 | PSD1_HUMAN | |
| LAWNL | 299 | Placenta-specific protein 9 | PLAC9_HUMAN | |
| AQLSS | 302 | Pleckstrin homology domain-containing family H member 1 | PKHH1_HUMAN | |
| ALKEL | 312 | Polycystic kidney disease protein 1-like 3 | PK1L3_HUMAN | |
| QALKE | 311 | Probable ATP-dependent RNA helicase DDX56 | DDX56_HUMAN | |
| KELPE | 306 | Probable ATP-dependent RNA helicase DHX37 | DHX37_HUMAN | |
| SELRE | 319 | Probable C-mannosyltransfemse DPY19L3 | D19L3_HUMAN | |
| ALKEL | 312 | Probable phospholipid-transporting ATPase IK | AT8B3_HUMAN | |
| KELPE | 306 | Programmed cell death 6-interacting protein | PDC61_HUMAN | |
| SELRE | 319 | Pro-interleukin-16 | IL16_HUMAN | |
| PTAFQ | 334 | Protein bassoon | BSN_HUMAN | |
| AQLSS | 302 | Protein dopey-1 | DOP1_HUMAN | |
| ELPEE | 307 | Protein FAM178B | F178B_HUMAN | |
| RAQLS | 301 | Protein FAM189A1 | F1891_HUMAN | |
| EPTAF | 333 | Protein-tyrosine kinase 2-beta | FAK2_HUMAN | |
| KCSEL | 317 | P-selectin | LYAM3_HUMAN | |
| EKELP | 305 | Putative ankyrin repeat domain-containing protein 31 | ANR31_HUMAN | |
| PRAQL | 300 | Putative uncharacterized protein CXorf49 | CX049_HUMAN | |
| ELPEE | 307 | Ras-associating and dilute domain-containing protein | RADIL_HUMAN | |
| SELRE | 319 | Ras-related protein Rab-43 | RAB43_HUMAN | |
| ELPEE | 307 | Regulatory solute carrier protein family 1 member 1 | RSCA1_HUMAN | |
| ALKEL | 312 | Regulatory solute carrier protein family 1 member 1 | RSCA1_HUMAN | |
| AQLSS | 302 | Rho GTPase-activating protein 40 | RHG40_HUMAN | |
| IIEEI | 327 | RING finger protein 17 | RNF17_HUMAN | |
| LSSAS | 304 | Rotatin | RTTN_HUMAN | |
| ELPEE | 307 | Sarcalumenin | I3L4D6_HUMAN | |
| LKELA | 313 | Schlafen-like protein 1 | SLNL1_HUMAN | |

TABLE 6 -continued

Patient X Advisory list of potential off-target binding of T cells matched to tumor specific sites for MHC I.

| TCEM core | SEQ ID NO: | Human proteome target | UniProt identifier | Advisory vs Immediate caution |
|---|---|---|---|---|
| ELPEE | 307 | Solute carrier family 26 member 10 | E9PIH7_HUMAN | |
| LSSAS | 304 | Sorting nexin-5 | U3KQP5_HUMAN | |
| ALKEL | 312 | Spectrin beta chain | SPTN4_HUMAN | |
| ALKEL | 312 | Spectrin beta chain | MOQZQ3_HUMAN | |
| LQALK | 310 | Spermatogenesis-associated protein 31E1 | S31E1_HUMAN | |
| PRAQL | 300 | Sulfide quinone oxidoreductase | SQRD_HUMAN | |
| ELPEE | 307 | Syndecan-3 | SDC3_HUMAN | |
| QALKE | 311 | Threonine--tRNA ligase | U3KQG0_HUMAN | |
| QALKE | 311 | Threonine--tRNA ligase | SYTM_HUMAN | |
| LSSAS | 304 | TNF receptor-associated factor 1 | TRAF1_HUMAN | |
| AQLSS | 302 | Transcription factor Spl | SP1_HUMAN | |
| SELRE | 319 | Tudor domain-containing protein 7 | TDRD7_HUMAN | |
| AQLSS | 302 | Uncharacterized protein C16orf59 | CP059_HUMAN | |
| KELPE | 306 | Vitamin D-binding protein | D6RBJ7_HUMAN | |
| EKELP | 305 | Zinc finger and SCAN domain-containing protein 25 | ZSC25_HUMAN | |
| PEEKK | 309 | Zinc finger C3H1 domain-containing protein | ZC3H1_HUMAN | |
| LSSAS | 304 | Zinc finger protein 184 | ZN184_HUMAN | |
| LSSAS | 304 | Zinc finger protein 469 | ZN469_HUMAN | |
| ELPEE | 307 | Zinc finger protein 541 | ZN541_HUMAN | |
| ELPEE | 307 | Zinc finger protein castor homolog 1 | CASZ1_HUMAN | |

TABLE 7

Caution list for Patient X MHC I TCEM

| TCEM core | SEQ ID NO: | Protein sharing TCEM bound by patient alleles | UniProt Identifier | Basis for caution: Potential adverse effects described in Uniprot (abbreviated) |
|---|---|---|---|---|
| LQALK | 310 | 5-hydroxytryptamine receptor 1D | 5HT1D_HUMAN | G-protein coupled receptor for 5-hydroxytryptamine (serotonin). Also functions as a receptor for ergot alkaloid derivatives, various anxiolytic and antidepressant drugs and other psychoactive substances. Regulates the release of 5-hydroxytryptamine in the brain, and thereby affects neural activity. May also play a role in regulating the release of other neurotransmitters. May play a role in vasoconstriction. No documented pathology from deficiency. |
| KELPE | 306 | Choline O-acetyltransferase | CLAT_HUMAN | Myasthenic syndrome, congenital, 6, presynaptic (CMS6) Catalyzes the reversible synthesis of acetylcholine (ACh) from acetyl CoA and choline at cholinergic synapses The disease is caused by mutations affecting this gene. A form of congenital myasthenic syndrome, a group of disorders characterized |

TABLE 7-continued

| Caution list for Patient X MHC I TCEM | | | | |
|---|---|---|---|---|
| TCEM core | SEQ ID NO: | Protein sharing TCEM bound by patient alleles | UniProt Identifier | Basis for caution: Potential adverse effects described in Uniprot (abbreviated) |
| | | | | by failure of neuromuscular transmission, including pre-synaptic, synaptic, and post-synaptic disorders that are not of autoimmune origin. |
| AQLSS | 302 | Complement factor H | CFAH_HUMAN | Basal laminar drusen (BLD): Glycoprotein that plays an essential role in maintaining a well-balanced immune response by modulating complement activation. Acts as a soluble inhibitor of complement. The gene represented in this entry is involved in disease pathogenesis. Drusen are extracellular deposits that accumulate below the retinal pigment epithelium on Bruch membrane. Complement factor H deficiency (CFHD): A disorder that can manifest as several different phenotypes, including asymptomatic, recurrent bacterial infections, and renal failure. It is associated with a number of renal diseases with variable clinical presentation and progression, including membranoproliferative glomerulonephritis and atypical hemolytic uremic syndrome. |
| SELRE | 319 | DNA mismatch repair protein Msh2 | MSH2_HUMAN | Hereditary non-polyposis colorectal cancer 1 (HNPCC1): Component of the post-replicative DNA mismatch repair system (MMR) Associated with an autosomal dominant disease associated with marked increase in cancer susceptibility. HNPCC is reported to be the most common form of inherited colorectal cancer in the Western world. |

TABLE 8

TCEM Allele combinations and selected peptides for each designed to stimulate
CD4 T cells in Patient X

| Protein curation and reference sequence | aa Mut | position | TCEM IIA | SEQ ID NO: | DRB0401 Simulated | SEQ ID NO: | DRB0401 Predicted Affinity | DRB0701 Simulated | SEQ ID NO: | DRB0701 Predicted Affinity |
|---|---|---|---|---|---|---|---|---|---|---|
| kelch-like ECH- | W | 609 | CW~Q~DQ | 429 | MLMWCWKQIDQNHQY | 465 | -1.85 | no | | |
| associated protein 1 | W | 610 | WK~I~QQ | 430 | no | | | ISRLWKQIDQQYIIA | 493 | -1.93 |
| gi:22027642 | | | | | | | | | | |
| dipeptidyl | M | 46 | KN~Y~LM | 431 | QIIYKNTYRLMLDGL | 466 | -1.49 | HRIFKNTYRLMVLLH | 494 | -1.95 |
| peptidase 4 | M | 47 | NT~R~ML | 432 | QIWSNTYRLMLTTVG | 467 | -1.51 | no | | |
| gi:18765694 | M | 49 | YR~M~YS | 433 | DSLGYRLMLYSDQGD | 468 | -2.03 | FAFRYRLMLYSKQEF | 495 | -1.95 |
| | M | 51 | LM~Y~LR | 434 | TLPHLMLYSLRSENG | 469 | -1.87 | MQPQLMLYSLRIDKV | 496 | -1.85 |
| | M | 52 | ML~S~RW | 435 | RKIHMLYSLRWGLAQ | 470 | -2.11 | RQRQMLYSLRWVDRF | 497 | -1.75 |
| peroxisomal acyl- | L | 116 | QE~F~ML | 436 | no | | | RQIRQERFFMLQRYF | 498 | -1.63 |
| coenzyme A | L | 117 | ER~F~LA | 437 | no | | | KMLEERFFMLAKLYP | 499 | -1.88 |
| oxidase 1 isoform a | L | 119 | FF~L~WN | 438 | RDIQFFMLAWNHQDL | 471 | -1.98 | RPQFFFMLAWNNRLR | 500 | -2.03 |
| gi:30089972 | L | 121 | ML~W~LE | 439 | SYTFMLAWNLESDTE | 472 | -1.92 | QVSHMLAWNLEFIQE | 501 | -1.99 |
| | L | 122 | LA~N~EI | 440 | SYMRLAWNLEISSEI | 473 | -1.85 | RRWLLAWNLEICDLD | 502 | -1.99 |
| angiomotin | L | 406 | MP~A~LS | 441 | LPLLMPRAQLSQSQD | 474 | -1.91 | no | | |
| isoform 1 | L | 408 | RA~L~SA | 442 | QRFQRAQLSSAATPL | 475 | -1.78 | GVYLRAQLSSAPIPA | 503 | -2.01 |
| gi:166064029 | L | 410 | QL~S~SY | 443 | DQMWQLSSASYLDTT | 476 | -1.91 | FEFLQLSSASYAHCR | 504 | -1.94 |
| | L | 411 | LS~A~YQ | 444 | PALILSSASYQNSLP | 477 | -1.97 | KFLHLSSASYQWRIM | 505 | -2.03 |
| coiled-coil domain- | P | 112 | LQ~K~LP | 445 | TLLILQEKELPALNT | 478 | -1.91 | no | | |
| containing protein | P | 113 | QE~E~PE | 446 | YSMWQEKELPELSYS | 479 | -1.19 | no | | |
| 50 long isoform | P | 115 | KE~P~EK | 447 | AYLFKELPEEKDDDK | 480 | -2.04 | no | | |
| gi:41281911 | P | 117 | LP~E~KR | 448 | PKLFLPEEKKRPQLP | 481 | -2.11 | no | | |
| | P | 118 | PE~K~RK | 449 | LFHYPEEKKRKNLRK | 482 | -1.09 | no | | |

TABLE 8 -continued

TCEM Allele combinations and selected peptides for each designed to stimulate
CD4 T cells in Patient X

| Protein curation and reference sequence | aa Mut | position | TCEM IIA | SEQ ID NO: | DRB0401 Simulated | SEQ ID NO: | DRB0401 Predicted Affinity | DRB0701 Simulated | SEQ ID NO: | DRB0701 Predicted Affinity |
|---|---|---|---|---|---|---|---|---|---|---|
| kinesin heavy chain | K | 482 | EV~Q~LK | 450 | SLNLEVLQALKGTGL | 483 | -1.93 | PTLPEVLQALKAMLE | 506 | -2.09 |
| isoform 5C | K | 483 | VL~A~KE | 451 | no | | | RMPLVLQALKEVRSI | 507 | -2.12 |
| gi:4758650 | K | 485 | QA~K~LA | 452 | FSRWQALKELALARP | 484 | -1.99 | KSLFQALKELALNPV | 508 | -2.02 |
| | K | 487 | LK~L~VN | 453 | FLNILKELAVNLTQD | 485 | -1.83 | HEKMLKELAVNPNFL | 509 | -2.07 |
| | K | 488 | KE~A~NY | 454 | SIQWKELAVNYYKKE | 486 | -1.90 | ELWYKELAVNYWRLP | 510 | -1.97 |
| symplekin gi: | S | 1062 | DK~S~LR | 455 | FILLDKCSELRADTP | 487 | -1.86 | no | | |
| 124028529 | S | 1065 | SE~R~PL | 456 | no | | | HELWSELREPLLLIS | 511 | -2.09 |
| phosphatidylinositol | E | 12 | MT~I~EE | 457 | ALKMMTAIIEELSPS | 488 | -2.01 | RYLTMTAIIEEYDVL | 512 | -1.81 |
| 3 | E | 14 | AI~E~IV | 458 | ARFFAIIEEIVQEAE | 489 | -1.79 | no | | |
| gi:73765544 | E | 16 | IE~I~SR | 459 | MWLRIEEIVSRNSDL | 490 | -1.81 | no | | |
| | E | 17 | EE~V~RN | 460 | PDLWEEIVSRNLQLA | 491 | -1.82 | no | | |
| nephrocystin-4 | P | 34 | QP~K~PT | 461 | no | | | SLNVQPWKEPTLVIM | 513 | -2.00 |
| isoform a | P | 36 | WK~P~AF | 462 | no | | | DKFRWKEPTAFFKVC | 514 | -1.91 |
| gi:23510323 | P | 38 | EP~A~QC | 463 | no | | | LKKQEPTAFQCLLII | 515 | -1.64 |
| | P | 39 | PT~F~CV | 464 | DFYVPTAFQCVPKTQ | 492 | -1.90 | KPLYPTAFQCVPYQM | 516 | -1.91 |

"No" indicates TCEM which would not be presented in vivo in the natural mutated protein and thus never exposed as targets
No immediate cautions were detected in the MHC II call list

TABLE 9

Recommended grouping for application of MHC II peptides or nucleotides
encoding the same to Patient X

| Sub groups | Peptide | SEQ ID NO: | Allele | Protein Target | position | TCEM | SEQ ID NO: | Fc | Human Freq |
|---|---|---|---|---|---|---|---|---|---|
| 1 | QRFQRAQLSSAATPL | 475 | DRB0401 | angiomotin isoform 1 | 408 | RA~L~SA | 442 | 18 | 0.99 |
| | AYLFKELPEEKDDDK | 480 | DRB0401 | coiled-coil domain-containing protein | 115 | KE~P~EK | | 23 | -0.06 |
| | RQRQMLYSLRWVDRF | 497 | DRB0701 | dipeptidyl peptidase 4 | 52 | ML~S~RW | 447 | 24 | -1.54 |
| | ISRLWKQIDQQYIIA | 493 | DRB0701 | kelch-like ECH-associated protein 1 | 610 | WK~I~QQ | 430 | 23 | -3.62 |
| | FLNILKELAVNLTQD | 485 | DRB0401 | kinesin heavy chain isoform 5C | 487 | LK~L~VN | 453 | 23 | 0.54 |
| | KSLFQALKELALNPV | 508 | DRB0701 | kinesin heavy chain isoform 5C | 485 | QA~K~LA | 452 | 21 | 1.11 |
| | LKKQEPTAFQCLLII | 515 | DRB0701 | nephrocystin-4 isoform a | 38 | EP~A~QC | 463 | 21 | -3.12 |
| | RPQFFFMLAWNNRLR | 500 | DRB0701 | peroxisomal acyl-coenzyme A oxidase 1 | 119 | FF~L~WN | 438 | 23 | -3.12 |
| | ALKMMTAIIEELSPS | 488 | DRB0401 | phosphatidylinositol 3 | 12 | MT~I~EE | 457 | 23 | -3.62 |
| | FILLDKCSELRADTP | 487 | DRB0401 | symplekin | 1062 | DK~S~LR | 455 | 22 | 0.60 |
| 2 | GVYLRAQLSSAPIPA | 503 | DRB0701 | angiomotin isoform 1 | 408 | RA~L~SA | 442 | 18 | 0.99 |
| | LFHYPEEKKRKNLRK | 482 | DRB0401 | coiled-coil domain-containing protein 50 | 118 | PE~K~RK | 449 | 22 | 0.19 |
| | DSLGYRLMLYSDQGD | 468 | DRB0401 | dipeptidyl peptidase 4 | 49 | YR~M~YS | 433 | 11 | -3.62 |
| | FAFRYRLMLYSKQEF | 495 | DRB0701 | dipeptidyl peptidase 4 | 49 | YR~M~YS | 433 | 11 | -3.62 |
| | QIIYKNTYRLMLDGL | 466 | DRB0401 | dipeptidyl peptidase 4 | 46 | KN~Y~LM | 431 | 21 | -1.08 |
| | MLMWCWKQIDQNHQY | 465 | DRB0401 | kelch-like ECH-associated protein 1 | 609 | CW~Q~DQ | 429 | 23 | -1.08 |
| | HEKMLKELAVNPNFL | 509 | DRB0701 | kinesin heavy chain isoform 5C | 487 | LK~L~VN | 453 | 23 | 0.54 |
| | DFYVPTAFQCVPKTQ | 492 | DRB0401 | nephrocystin-4 isoform a | 39 | PT~F~CV | 464 | 23 | -2.04 |
| | RDIQFFMLAWNHQDL | 471 | DRB0401 | peroxisomal acyl-coenzyme A oxidase 1 | 119 | FF~L~WN | 438 | 23 | -3.12 |
| | RYLTMTAIIEEYDVL | 512 | DRB0701 | phosphatidylinositol 3 | 12 | MT~I~EE | 457 | 23 | -3.62 |
| | HELWSELREPLLLIS | 511 | DRB0701 | symplekin | 1065 | SE~R~PL | 456 | 21 | 1.16 |
| 3 | FEFLQLSSASYAHCR | 504 | DRB0701 | angiomotin isoform 1 | 410 | QL~S~SY | 443 | 16 | -0.24 |
| | PALILSSASYQNSLP | 477 | DRB0401 | angiomotin isoform 1 | 411 | LS~A~YQ | 444 | 14 | 0.13 |
| | YSMWQEKELPELSYS | 479 | DRB0401 | coiled-coil domain-containing protein 50 | 113 | QE~E~PE | 446 | 22 | 0.82 |
| | QIWSNTYRLMLTTVG | 467 | DRB0401 | dipeptidyl peptidase 4 | 47 | NT~R~ML | 432 | 23 | -2.44 |
| | HRIFKNTYRLMVLLH | 494 | DRB0701 | dipeptidyl peptidase 4 | 46 | KN~Y~LM | 431 | 21 | -1.08 |
| | RKIHMLYSLRWGLAQ | 470 | DRB0401 | dipeptidyl peptidase 4 | 52 | ML~S~RW | 435 | 24 | -1.54 |
| | SLNLEVLQALKGTGL | 483 | DRB0401 | kinesin heavy chain isoform | 482 | EV~Q~LK | 450 | 23 | 1.04 |
| | SLNVQPWKEPTLVIM | 513 | DRB0701 | nephrocystin-4 isoform a | 34 | QP~K~PT | 461 | 22 | -2.04 |

TABLE 9-continued

Recommended grouping for application of MHC II peptides or nucleotides encoding the same to Patient X

| Sub groups | Peptide | SEQ ID NO: | Allele | Protein Target | position | TCEM | SEQ ID NO: | Fc | Human Freq |
|---|---|---|---|---|---|---|---|---|---|
| | RQIRQERFFMLQRYF | 498 | DRB0701 | peroxisomal acyl-coenzyme 5CA oxidase 1 | 116 | QE~F~ML | 436 | 22 | -2.04 |
| | PDLWEEIVSRNLQLA | 491 | DRB0401 | phosphatidylinositol 3 | 17 | EE~V~RN | 460 | 20 | -0.19 |
| 4 | LPLLMPRAQLSQSQD | 474 | DRB0401 | angiomotin isoform 1 | 406 | MP~A~LS | 441 | 21 | -0.06 |
| | TLLILQEKELPALNT | 478 | DRB0401 | coiled-coil domain-containing protein 50 | 112 | LQ~K~LP | 445 | 22 | |
| | TLPHLMLYSLRSENG | 469 | DRB0401 | dipeptidyl peptidase 4 | 51 | LM~Y~LR | 434 | 19 | -2.04 |
| | PTLPEVLQALKAMLE | 506 | DRB0701 | kinesin heavy chain isoform 5C | 482 | EV~Q~LK | 450 | 23 | 1.04 |
| | ELWYKELAVNYWRLP | 510 | DRB0701 | kinesin heavy chain isoform 5C | 488 | KE~A~NY | 454 | 16 | -0.41 |
| | RMPLVLQALKEVRSI | 507 | DRB0701 | kinesin heavy chain isoform 5C | 483 | VL~A~KE | 451 | 22 | 1.11 |
| | KPLYPTAFQCVPYQM | 516 | DRB0701 | nephrocystin-4 isoform a | 39 | PT~F~CV | 464 | 23 | -2.04 |
| | SYTFMLAWNLESDTE | 472 | DRB0401 | peroxisomal acyl-coenzyme A oxidase 1 | 121 | ML~W~LE | 439 | 22 | -1.75 |
| | RRWLLAWNLEICDLD | 502 | DRB0701 | peroxisomal acyl-coenzyme A oxidase 1 | 122 | LA~N~EI | 440 | 22 | -0.02 |
| | SYMRLAWNLEISSEI | 473 | DRB0401 | peroxisomal acyl-coenzyme A oxidase 1 | 122 | LA~N~EI | 440 | 22 | -0.02 |
| | MWLRIEEIVSRNSDL | 490 | DRB0401 | phosphatidylinositol 3 | 16 | IE~I~SR | 459 | 22 | -0.02 |
| 5 | DQMWQLSSASYLDTT | 476 | DRB0401 | angiomotin isoform 1 | 410 | QL~S~SY | 443 | 16 | -0.24 |
| | KFLHLSSASYQWRIM | 505 | DRB0701 | angiomotin isoform 1 | 411 | LS~A~YQ | 444 | 14 | 0.13 |
| | PKLFLPEEKKRPQLP | 481 | DRB0401 | coiled-coil domain-containing protein 50 | 117 | LP~E~KR | 448 | 21 | 1.05 |
| | MQPQLMLYSLRIDKV | 496 | DRB0701 | dipeptidyl peptidase 4 | 51 | LM~Y~LR | 434 | 19 | -2.04 |
| | SIQWKELAVNYYKKE | 486 | DRB0401 | kinesin heavy chain isoform 5C | 488 | KE~A~NY | 454 | 16 | -0.41 |
| | FSRWQALKELALARP | 484 | DRB0401 | kinesin heavy chain isoform 5C | 485 | QA~K~LA | 452 | 21 | 1.11 |
| | DKFRWKEPTAFFKVC | 514 | DRB0701 | nephrocystin-4 isoform a | 36 | WK~P~AF | 462 | 19 | -1.75 |
| | QVSHMLAWNLEFIQE | 501 | DRB0701 | peroxisomal acyl-coenzyme A oxidase 1 | 121 | ML~W~LE | 439 | 22 | -1.75 |
| | KMLEERFFMLAKLYP | 499 | DRB0701 | peroxisomal acyl-coenzyme A oxidase 1 | 117 | ER~F~LA | 437 | 16 | 0.39 |
| | ARFFAIIEEIVQEAE | 489 | DRB0401 | phosphatidylinositol 3 | 14 | AI~E~IV | 458 | 18 | -0.24 |

TABLE 10

Patient X Advisory list for potential MHC II off target effects; no immediate cautions were flagged

| TCEM II A Motif | SEQ ID NO: | Protein Annotation | UniProt Identifier |
|---|---|---|---|
| RD~K~AL | 517 | 5-hydroxytryptamine receptor 6 | 5HT6R_HUMAN |
| SE~R~PL | 456 | Actin-binding protein anillin | ANLN_HUMAN |
| LQ~K~LP | 445 | AF4 FMR2 family member 2 | AFF2_HUMAN |
| ER~F~LA | 437 | Alanine aminotransferase 1 | ALAT1_HUMAN |
| EV~Q~LK | 450 | Aldehyde oxidase | ADO_HUMAN |
| QL~S~SY | 443 | CDK5 regulatory subunit-associated protein 3 | J3KS63_HUMAN |
| LK~L~VN | 453 | Cellular retinoic acid-binding protein 1 | RABP1_HUMAN |
| LK~L~VN | 453 | Cellular retinoic acid-binding protein 2 | RABP2_HUMAN |
| VL~A~KE | 451 | Centrosomal protein of 152 kDa | CE152_HUMAN |
| RA~L~SA | 442 | Coiled-coil domain-containing protein 9 | CCDC9_HUMAN |
| EV~Q~LK | 450 | Copine-3 | CPNE3_HUMAN |
| QE~E~PE | 446 | Cullin-4A | CUL4A_HUMAN |

TABLE 10 -continued

Patient X Advisory list for potential MHC II off target effects;
no immediate cautions were flagged

| TCEM II A Motif | SEQ ID NO: | Protein Annotation | UniProt Identifier |
|---|---|---|---|
| AI~E~IV | 458 | DNA polymerase theta | DPOLQ_HUMAN |
| KE~L~QF | 518 | E3 ubiquitin-protein ligase UBR4 | UBR4_HUMAN |
| MP~A~LS | 441 | Endoplasmic reticulum-Golgi intermediate compartment protein 3 | ERGI3_HUMAN |
| LQ~K~LP | 445 | ERC protein 2 | ERC2_HUMAN |
| KE~P~EK | 447 | Ermin | ERMIN_HUMAN |
| MP~A~LS | 441 | Gamma-glutamyltranspeptidase 1 | GGT1_HUMAN |
| MP~A~LS | 441 | Gamma-glutamyltranspeptidase 2 | GGT2_HUMAN |
| QE~E~PE | 446 | General transcription factor IIF subunit 1 | T2FA_HUMAN |
| LK~L~VN | 453 | Glycerophosphocholine phosphodiesterase GPCPD1 | GPCP1_HUMAN |
| MP~A~LS | 441 | GPI mannosyltransferase 4 | PIGZ_HUMAN |
| AI~E~IV | 458 | HCF N-terminal chain 5 | A6NEM2_HUMAN |
| AI~E~IV | 458 | Host cell factor 1 | HCFC1_HUMAN |
| KE~L~QF | 518 | Inositol hexakisphosphate kinase 2 | IP6K2_HUMAN |
| RA~L~SA | 442 | Inverted formin-2 | INF2_HUMAN |
| ML~W~LE | 439 | Laminin subunit alpha-3 | LAMA3_HUMAN |
| RA~L~SA | 442 | MAP kinase-interacting serine_threonine-protein kinase 2 | MKNK2_HUMAN |
| LK~L~VN | 453 | Midasin | MDN1_HUMAN |
| CS~L~EP | 519 | N-acetyltransferase ESCO1 | ESCO1_HUMAN |
| LQ~K~LP | 445 | Oxysterols receptor LXR-beta | NR1H2_HUMAN |
| LP~E~KR | 448 | Probable G-protein coupled receptor 111 | GP111_HUMAN |
| MP~A~LS | 441 | Probable G-protein coupled receptor 61 | GPR61_HUMAN |
| LS~A~YQ | 444 | Prolyl 4-hydroxylase subunit alpha-1 | P4HA1_HUMAN |
| RS~R~RK | 520 | Protamine-2 | PRM2_HUMAN |
| AV~D~CS | 521 | Protein NOV homolog | NOV_HUMAN |
| QE~E~PE | 446 | Protein phosphatase 1 regulatory subunit 14B | F5H2U0_HUMAN |
| RS~R~RK | 520 | Receptor-binding cancer antigen expressed on SiSo cells | RCAS1_HUMAN |
| VL~A~KE | 451 | SH3 domain-binding protein 5 | 3BP5_HUMAN |
| LK~L~VN | 453 | Small nuclear ribonucleoprotein polypeptide A' | H0YKK0_HUMAN |
| ML~W~LE | 439 | Spectrin beta chain | SPTN5_HUMAN |
| QA~K~LA | 452 | Talin-1 | TLN1_HUMAN |
| QL~S~SY | 443 | Taste receptor type 2 member 5 | TA2R5_HUMAN |
| LK~L~VN | 453 | Transcription factor BTF3 | BTF3_HUMAN |
| RD~K~AL | 517 | Transducin beta-like protein 3 | TBL3_HUMAN |
| RA~L~SA | 442 | Translation initiation factor eIF-2B subunit alpha | EI2BA_HUMAN |
| LK~L~VN | 453 | Tubulin-specific chaperone E | TBCE_HUMAN |
| LK~L~VN | 453 | U2 small nuclear ribonucleoprotein A' | RU2A_HUMAN |

TABLE 10 -continued

|  | Patient X Advisory list for potential MHC II off target effects; no immediate cautions were flagged | | |
|---|---|---|---|
| TCEM II A Motif | SEQ ID NO: | Protein Annotation | UniProt Identifier |
| VL~A~KE | 451 | Ubiquitin carboxyl-terminal hydrolase 19 | UBP19_HUMAN |
| DK~S~LR | 455 | Ubiquitin thioesterase ZRANB1 | ZRAN1_HUMAN |
| ML~W~LE | 439 | Zinc finger BED domain-containing protein 6 | ZBED6_HUMAN |
| QL~S~SY | 443 | Zinc finger protein PLAGL2 | PLAL2_HUMAN |

Example 5: Increasing Personalized T Cell Targeting Options for Melanoma Patients A recent report documented a group of patients with metastatic melanoma, whose biopsies were sequenced and mutations identified in several proteins [29]. Peptides encompassing the mutations were produced and used to identify T cells reactive to MHC tetramers carrying the peptides of interest, demonstrating that T cell populations reactive to epitopes in the cancer expressed proteins were generated at detectable levels. Tetramers were only available for a limited number of HLA. Peptides were selected based on the predicted MHC binding using publicly available algorithms. A limited number of peptides comprising the mutated amino acids were identified which bound to the A0201, A0101 and A1101 alleles carried by these patients. However, very few of the peptides had the mutated amino acid located in a position which would expose that amino acid to the TCR. Hence the T cell responses would not have differentiated tumor-mutated from normal protein. Using this patient data, we addressed the question of whether peptides could be generated which would potentially stimulate cytotoxic T cells targeting tumor cells, within the limited allele and mutation information available. The natural binding affinity for the mutant protein did not permit selection of peptides that would bind MHC and achieve this differential targeting by exposing T cell exposed motifs containing the mutant amino acids. We therefore sought to design peptides which could bind the available MHC with sufficient affinity and expose the mutated amino acids. Affinity predictions were generated for all sequential peptides in each protein. This allowed identification of which T cell exposed motifs comprising the mutated amino acid had any likelihood of being transiently bound in an MHC. For these TCEM we then generated 10,000 simulated peptides for each allele TCEM combination, by changing the four flanking amino acids which determine binding, and identified peptides with sufficient binding affinity which could be used as vaccine components to stimulate T cells cognate for the presented TCEM. We document below for each patient how the limited information does permit potential tumor targeting neoantigens to be created which would stimulate CTLs targeting the tumor, and enabling the preparation of a multi-peptide vaccine targeting the melanoma of these patients.

Patient A: Patient A is A0201; other alleles are unknown. This patient has mutations in SPRX (sushi repeat-containing protein SRPX isoform 1 precursor) and WDR46 (WD repeat-containing protein 46 isoform 1). The mutation in SPRX is a P to L at position 1275 in SPRX; T cells reactive to a peptide TLWCSPIKV were identified. The mutation in WDR46 is a T to I at position 300 and T cells reactive to peptide FLIYLDVSV were identified. In both cases the mutant amino acid is in a binding position not exposed to the TCR. We identified the TCEM comprising the mutant peptides and generated simulated peptides for A0201 designed to stimulate cytotoxic T cells to each of the 5 TCEM which have the mutant amino acid and are exposed to the TCR. Simulation of 10,000 peptides, after elimination of duplicates and non-binders, generated 2,417 unique peptides which correspond to TCEM that would be presented by A0201 naturally, and which are soluble. Of these, 88 are predicted to bind better than 1.5 SD below the mean for the protein and collectively these peptides encode the 6 different TCEM which would be naturally presented from these two proteins and which contain the mutated amino acids differentiating the tumor from the normal protein. One exemplar peptide simulated and its predicted binding for A0201 is shown below for each TCEM core. A vaccine comprising these 6 peptides would elicit CTL targeting Patient A's melanoma.

TABLE 11

| | | | | | Patient A peptides. | | | |
|---|---|---|---|---|---|---|---|
| ID | Posi-tion | Protein curation | Proposed peptide | SEQ ID NO: | Affinity for A0201# | TCEM Core pentamer | SEQ ID NO: |
| 256773176-63-mut | 294 | WDR46-WD repeat- | KDKGFLIYV | 522 | -1.53 | GFLIY | 528 |
| | 296 | containing protein | KMKLIYLDA | 523 | -2.27 | LIYLD | 529 |
| | 297 | 46 isoform 1 | KLKIYLDVG | 524 | -1.51 | IYLDV | 530 |
| 5454086-292- mut | 48 | SRPX-sushi repeat- | KLLYKDTLV | 525 | -2.35 | YKDTL | 531 |
| | 51 | containing protein | KMSTLWCSG | 526 | -2.01 | TLWCS | 532 |
| | 52 | SRPX isoform 1 precursor | KLRLWCSPA | 527 | -1.53 | LWCSP | 533 |

Affinity predicted in standard deviation units below the mean for the respective protein Patient B: Patient B carries alleles A0201 and A1101; other alleles are unknown. This patient has mutations in NSDHL (sterol-4-alpha-carboxylate 3-dehydrogenase). The mutation in NSDHL is a A to V at position 290 and T cells were identified that are cognate for a peptide ILTGLNYEV. The mutant amino acid is in a binding position not exposed to the TCR. We identified the TCEM comprising the mutant peptides and generated simulated peptides for A0201 and A1101 designed to stimulate cytotoxic T cells to each of the 5 TCEM which have the mutant amino acid and are exposed to the TCR. Simulation of 10,000 peptides for each allele, after elimination of duplicates and non-binders, generated 3,046 peptides which correspond to the only TCEM (~~~YEVPK~) (SEQ ID NO: 534) that would be presented by A0201 naturally, and which are soluble. Of these, 445 bind better than −1.5 SD below the mean. One peptide was selected as shown in Table 12 below. The same process generated 13,306 peptides which bind A1101 across 4 TCEM (~~~LNYEV~(SEQ ID NO: 535), ~~~NYEVP~ (SEQ ID NO: 536), ~~~YEVPK~(SEQ ID NO: 534), ~~~EVPKY~ (SEQ ID NO: 537)) which would be naturally presented. Of these, 3,514 bind better than −1.5 SD below the mean. A vaccine comprising these 5 peptides would elicit CTL targeting Patient B's melanoma.

TABLE 12

Patient B peptides.

| ID | Position | Protein curation | Allele | Proposed peptide | SEQ ID NO: | Affinity for allele# | TCEM Core pentamer | SEQ ID NO: |
|---|---|---|---|---|---|---|---|---|
| 8393516- | 283 | NSDHL-sterol-4- | A1101 | LELLNYEVK | 538 | −2.00 | LNYEV | 535 |
| 151-mut | 284 | alpha-carboxylate | A1101 | KATNYEVPR | 539 | −2.05 | NYEVP | 536 |
| | 285 | 3-dehydrogenase | A1101 | SIVYEVPKP | 540 | −2.02 | YEVPK | 534 |
| | 285 | | A0201 | DMLYEVPKI | 541 | −2.10 | YEVPK | 534 |
| | 286 | | A1101 | TIAEVPKYR | 542 | −2.14 | EVPKY | 537 |

Affinity predicted in standard deviation units below the mean for the respective protein Patient C: Patient C is A0201; other alleles are unknown. This patient has mutations in ERBB2 (receptor tyrosine-protein kinase erbB-2 isoform a precursor), COL181A (collagen alpha-1(XVIII) chain isoform 1 preproprotein), and TEAD1(transcriptional enhancer factor TEF-). The mutation in ERBB2 is a H to Y at position 473 and T cells were identified with a peptide ALIHHNTYL (SEQ ID NO: 543). The mutation in TEAD1 is a L to F at position 388 and T cells were identified with peptides VLENFTIFLV (SEQ ID NO: 544) and SVLENFTIFL (SEQ ID NO: 545). COL181A is mutated S to F at position 306 and T cells were identified with VLLGVKLFGV (SEQ ID NO: 546). The mutant amino acid is only not exposed to the TCR in VLENFTIFLV (SEQ ID NO: 544) and VLLGVKLFGV (SEQ ID NO: 546), utilizing in each case only one of 5 potential peptides due to the limitations of natural binding. We identified the TCEM comprising the mutant peptides and generated simulated peptides for A0201 designed to stimulate cytotoxic T cells to each of the 5 TCEM in each protein which have the mutant amino acid and are exposed to the TCR. Simulation of 10,000 peptides for each protein, after elimination of duplicates and non-binders, generated 13,425 peptides which correspond to TCEM that would be presented by A0201 naturally, and which are soluble. Of these 1200 bind better than −1.5SD below the mean and represent 14 different TCEM. Table 13 below shows 14 peptides simulated to bind at approximately 2 SD below the mean where possible. For two TCEM positions where there were no peptides generated that bind at this affinity; the two highest affinity peptides are shown. A vaccine comprising these 14 peptides would elicit CTL targeting Patient C's melanoma.

TABLE 13

Patient C peptides.

| ID | Position | Protein curation | Proposed peptide | SEQ ID NO: | Affinity for A0201 | TCEM Core pentamer | SEQ ID NO: |
|---|---|---|---|---|---|---|---|
| 110611235- | 299 | COL18A1-collagen | QMRGVKLFG | 547 | −2.03 | GVKLF | 561 |
| 186-mut | 300 | alpha-1(XVIII) chain | GMDVKLFGG | 548 | −1.96 | VKLFG | 562 |
| | 302 | isoform 1 | RMRLFGVQA | 549 | −1.97 | LFGVQ | 563 |
| | 303 | preproprotein | KLVFGVQDA | 550 | −2.01 | FGVQD | 564 |

TABLE 13-continued

| | | | | | | |
|---|---|---|---|---|---|---|
| | | | | Patient C peptides. | | |
| ID | Position | Protein curation | Proposed peptide | SEQ ID NO: | Affinity for A0201 | TCEM Core pentamer | SEQ ID NO: |
| 54792096-5-mut | 466 | ERBB2-receptor | GMIHHNTYG | 551 | -2.01 | HHNTY | 565 |
| | 467 | tyrosine-protein | QTIHNTYLV | 552 | -2.00 | HNTYL | 566 |
| | 468 | kinase erbB-2 | KGVNTYLCV | 553 | -2.08 | NTYLC | 567 |
| | 469 | isoform a | KLRTYLCFS | 554 | -2.01 | TYLCF | 568 |
| | 470 | precursor | KQQYLCFVG | 555 | -1.04 | YLCFV | 569 |
| 296434319-303-mut | 378 | TEAD1-transcriptional | RLKVLENFV | 556 | -2.10 | VLENF | 570 |
| | 379 | enhancer factor TEF-1 | ALPLENFTG | 557 | -1.98 | LENFT | 571 |
| | 380 | | YSAENFTIV | 558 | -2.02 | ENFTI | 572 |
| | 381 | | KTPNFTIFA | 559 | -2.06 | NFTIF | 573 |
| | 382 | | RQKFTIFLG | 560 | -0.87 | FTIFL | 574 |

Patient D: Patient D carries A0101 and A0201; other alleles are unknown. This patient has mutations in GANAB (neutral alpha-glucosidase AB isoform 2 precursor). The mutation in a S to F at position 298 and T cells were originally identified with a peptide ALYGFVPVL (SEQ ID NO: 575). In this instance, the mutant amino acid is exposed to the TCR. We identified all the TCEM comprising the mutant peptides and generated simulated peptides for A0101 and A0201 designed to stimulate cytotoxic T cells to each of the 5 TCEM for each protein which have the mutant amino acid and are exposed to the TCR. 10,000 peptides were simulated for each TCEM/allele combination, after elimination of duplicates and non-binders, generated 2713 peptides which correspond to TCEM that would be presented by A0101 or A0201 naturally, and which are soluble. Of those binding better than −1.0 SD below the mean 5 different TCEM are represented. Notably there were no very high binders generated for A0201 among the 50,000 original peptides simulated, with only 33 of −1 SD or better; This underscores the difficulty of finding naturally binding peptides which allow targeting of mutants and the value of simulation to maximize potential binding allele TCEM combinations which can stimulate appropriate T cells. Representative simulated peptides are shown in Table 14. A vaccine comprising these 7 peptides would elicit CTL targeting Patient D's melanoma.

Patient E: Patient E is A0101; other alleles are unknown. This patient has mutations in TRIP12 (E3 ubiquitin-protein ligase TRIP12 isoform a). The mutation in a F to S at position 1592 and was originally targeted with a peptide PSDTRQMLFY (SEQ ID NO: 590). The mutant amino acid in this peptide is not exposed to the TCR. We identified the TCEM comprising the mutant peptides and generated simulated peptides for A0101 designed to stimulate cytotoxic T cells to each of the 5 TCEM in which have the mutant amino acid is exposed to the TCR. However, we found that only 1 of the TCEM would be naturally presented in the context of the mutant protein. This and the fact we have only one known allele only provides one combination which can generate relevant T cells. However, even this single peptide is an advantage over the naturally bound peptides which do not expose the mutated amino acid and which therefore would generate T cells which cannot differentiate the tumor from normal cells. Over 4000 unique peptides were simulated for this single TCEM which are soluble; 650 of these bind better than −1.5 SD below the mean for the protein. Three peptides were selected with different predicted affinities (Table 15). These have essentially the same function but illustrate that the desired binding can be selected from the bank of simulated peptides.

TABLE 14

| | | | | | | | |
|---|---|---|---|---|---|---|---|
| | | | | Patient D peptides | | | |
| ID | Position | Protein curation | Allele | Proposed peptide | SEQ ID NO: | Affinity for Allele | TCEM Core pentamer | SEQ ID NO: |
| 38202257-12-mut | 291 | GANAB- | A0201 | RTRALYGFV | 576 | -1.35 | ALYGF | 583 |
| | 292 | neutral | A0101 | SSDLYGFVR | 577 | -2.03 | LYGFV | 584 |
| | 292 | alpha- | A0201 | KDELYGFVV | 578 | -1.13 | LYGFV | 585 |
| | 293 | glucosidase | A0101 | LADYGFVPD | 579 | -2.06 | YGFVP | 586 |
| | 293 | AB isoform | A0201 | KLRYGFVPA | 580 | -1.88 | YGFVP | 587 |
| | 294 | 2 precursor | A0201 | KVDGFVPVA | 581 | -1.55 | GFVPV | 588 |
| | 295 | | A0101 | RSDFVPVLN | 582 | -2.04 | FVPVL | 589 |

TABLE 15

| | | | | | | | |
|---|---|---|---|---|---|---|---|
| | | | | Patient E peptides | | | |

| ID | Position | Protein curation | Proposed peptide | SEQ ID NO: | Affinity for A0101 | TCEM Core pentamer | SEQ ID NO: |
|---|---|---|---|---|---|---|---|
| 545746335- | 1586 | E3 ubiquitin- | EGDFFPSDP | 591 | -3.00 | FFPSD | 594 |
| 228-mut | 1586 | protein ligase | FEDFFPSDL | 592 | -2.02 | FFPSD | 594 |
| | 1586 | TRIP12 | WDDFFPSDE | 593 | -1.75 | FFPSD | 594 |

Example 6: Personalized Neoepitope Peptides for Small Cell Lung Cancer

A recent report of a small cell lung cancer case, in which the patient alleles were well documented, identified mutations in five proteins (EGFR, STK11, NAV3, EPHB1 and PTCH2) [11]. Four of these were simple amino acid substitutions; STK11 was a frameshift. Peptides had been selected for use as neoantigens, but notably several of the peptides placed the mutated amino acid in a binding pocket position. This means that the T cell exposed motif in the mutant and the wildtype protein is unchanged. We therefore elected to explore whether additional peptides could be generated which provide high binding to the patient alleles and also place the mutant amino acid in a position exposed to the T cell to allow a differential response between mutant and wildtype proteins. Small cell lung cancers are often associated with highly mutated proteins, requiring a personalized approach to neoepitope vaccination.

We elected to design an array of vaccine or T cell stimulating peptides or encoding nucleic acids for this patient (Patient Y). For the four proteins with simple SNP mutations we assembled wildtype and mutant sequences and determined the predicted binding of all sequential peptides. Based on this we determined which TCEM comprising the mutant amino acid would be presented in vivo in this patient as the result of binding of the flanking region by the patient's alleles to expose that amino acid in the T cell exposed motif. We then identified the TCEM comprising the mutant amino acid and generated an array of 1000 peptides for each TCEM with randomly replaced flanking amino acids. Peptides were selected based on predicted affinity, solubility and likelihood of stimulating T cells which target naturally presented mutant TCEM. Peptides were selected to have a predicted affinity near 2 SD below the mean of the respective proteins; however other affinities may be selected and so this example is not considered limiting. Table 15 below summarizes the findings for the four proteins and this patient's MEW I and MEW II alleles.

Simulated binding peptides were then selected for each TCEM allele combination in the desired predicted affinity range. These are shown for MHC I in Table 16 and for MEW II in Table 17.

The TCEM for both MHC I and II were mapped onto the human protein reference database to review potential off target effects. A total of 348 unique proteins comprised TCEM which would be presented as the result of binding and presentation by one or more of Patient Ys alleles. This list would be provided to a clinician as the basis for a risk assessment of that patient. We do not include the complete advisory list here in the interests of space. Two proteins potentially targeted were flagged as being of immediate concern and for which T cell stimulating peptides would not be advised. These are shown in Table 18.

TABLE 15

| Small cell lung cancer patient-summary of available TCEM targets and peptides available | | | | | | | |
|---|---|---|---|---|---|---|---|
| | Proteins with identified mutations 4 | | | | | | |
| | TCEM with mutations 20 | | | | | | |
| Patient Alleles | A1101 | A3101 | B3501 | C0303 | DRB0405 | DRB1501 | DQB0602 |
| TCEM naturally presented for allele | 7 | 9 | 10 | 8 | 12 | 11 | 11 |
| Mutated proteins in which natural presentation occurs | 3 | 4 | 3 | 3 | 3 | 4 | 4 |
| Proteins omitted as no natural presentation | 1 | 0 | 1 | 1 | 1 | 1 | 0 |
| Unique peptides simulated with any binding | 14543 | 16585 | 17952 | 17925 | 17954 | 17964 | 17816 |
| Subset for which TCEM is naturally presented | 3916 | 9872 | 11022 | 4718 | 7040 | 7175 | 7382 |
| Filtered by polarity score <1 indicating solubility | 2195 | 6320 | 7420 | 3920 | 4127 | 4252 | 6459 |
| Peptides selected in desired binding window <-1.75> -2.25 | 254 | 273 | 209 | 298 | 261 | 135 | 607 |
| Represent TCEM allele combos <-1.75> -2.25 | 7 | 9 | 9 | 7 | 12 | 11 | 11 |
| Removed due to immediate off target caution; or high frequency Fc # | 1 | 1 | 1 | 1 | 0 | 0 | 1 |

TABLE 15-continued

| Small cell lung cancer patient-summary of available TCEM targets and peptides available | | | | | | | |
|---|---|---|---|---|---|---|---|
| | Proteins with identified mutations | | | | | | |
| | 4 | | | | | | |
| | TCEM with mutations | | | | | | |
| | 20 | | | | | | |
| Patient Alleles | A1101 | A3101 | B3501 | C0303 | DRB0405 | DRB1501 | DQB0602 |
| Net TCEM allele combos available <−1.75> −2.25 | 7 | 8 | 8 | 6 | 12 | 11 | 11 |
| Potential vaccine peptides per patient for all mutated proteins | | 29 | | | | 33 | |

One removed due to TCEM I match to Complement C4; One removed for DQB0602 match to Coagulation factor VIII

TABLE 16

Peptides available to stimulate CD8 T cells specific to
Patient Y mutations and alleles.

| Protein ID | Protein | Position | Allele MHC I | Simulated binding peptide | SEQ ID NO: | Predicted Affinity | TCEM I target | SEQ ID NO: |
|---|---|---|---|---|---|---|---|---|
| m-P00533 | EGFR_HUMAN | 852 | A_1101 | AVDDFGRAR | 595 | −2.15 | ~~~DFGRA~ | 629 |
| | Epidermal growth | 852 | A_3101 | SRDDFGRAR | 596 | −2.23 | ~~~DFGRA~ | 630 |
| | factor receptor | 853 | B-3501 | LSHFGRAKF | 597 | −1.92 | ~~~FGRAK~ | 631 |
| | | 854 | B-3501 | FAEGRAKLH | 598 | −2.07 | ~~~GRAKL~ | 632 |
| | | 855 | B-3501 | YGHRAKLLL | 599 | −2.17 | ~~~RAKLL~ | 633 |
| | | 851 | C0303 | LAITDFGRA | 600 | −2.17 | ~~~TDFGR~ | 634 |
| | | 852 | C0303 | VAADFGRAY | 601 | −1.98 | ~~~DFGRA~ | 635 |
| | | 853 | C0303 | WGIFGRAKA | 602 | −1.83 | ~~~FGRAK~ | 636 |
| | | 854 | C0303 | LEVGRAKLL | 603 | −2.16 | ~~~GRAKL~ | 637 |
| m-P54762 | EPHB1_HUMAN | 458 | A_3101 | PESSGIILR | 604 | −2.25 | ~~~SGIIL~ | 638 |
| | Ephrin type-B | 454 | B-3501 | QQMPEQPSF | 605 | −2.07 | ~~~PEQPS~ | 639 |
| | receptor 1 | 455 | B-3501 | GLCEQPSGF | 606 | −1.97 | ~~~EQPSG~ | 640 |
| | | 456 | B-3501 | HAPQPSGIF | 607 | −2.16 | ~~~QPSGI~ | 641 |
| | | 454 | C0303 | PAGPEQPST | 608 | −2.14 | ~~~PEQPS~ | 642 |
| | | 455 | C0303 | ASGEQPSGF | 609 | −2.14 | ~~~EQPSG~ | 643 |
| m-Q8IVL0 | NAV3_HUMAN Neuron | 2236 | A_1101 | SGCGPRLLR | 610 | −1.95 | ~~~GPRLL~ | 644 |
| | navigator 3 | 2237 | A_1101 | YQQPRLLLR | 611 | −1.92 | ~~~PRLLL~ | 645 |
| | | 2238 | A_1101 | NTGRLLLPP | 612 | −2.13 | ~~~RLLLP~ | 646 |
| | | 2239 | A_1101 | KTQLLLPCR | 613 | −2.01 | ~~~LLLPC~ | 647 |
| | | 2236 | A_3101 | RVTGPRLLD | 614 | −2.06 | ~~~GPRLL~ | 648 |
| | | 2237 | A_3101 | QGGPRLLLK | 615 | −2.23 | ~~~PRLLL~ | 649 |
| | | 2238 | A_3101 | SDWRLLLPK | 616 | −2.15 | ~~~RLLLP~ | 650 |
| | | 2239 | A_3101 | SHELLLPCR | 617 | −2.14 | ~~~LLLPC~ | 651 |
| | | 2236 | B-3501 | KACGPRLLY | 618 | −2.08 | ~~~GPRLL~ | 652 |
| | | 2237 | B-3501 | RGPPRLLLY | 619 | −2.17 | ~~~PRLLL~ | 653 |
| | | 2238 | B-3501 | DPTRLLLPY | 620 | −2.07 | ~~~RLLLP~ | 654 |
| | | 2236 | C0303 | PGSGPRLLS | 621 | −2.02 | ~~~GPRLL~ | 655 |
| | | 2239 | B-3501 | RSGLLLPCR | 622 | −1.30 | ~~~LLLPC~ | 656 |
| | | 2237 | C0303 | SSSPRLLLP | 623 | −1.59 | ~~~PRLLL~ | 657 |
| m-Q9Y6C5 | PTC2_HUMAN | 804 | A_1101 | RSLRHSYCR | 624 | −2.10 | ~~~RHSYC~ | 658 |
| | Protein patched | 805 | A_1101 | SKLHSYCNK | 625 | −2.06 | ~~~HSYCN~ | 659 |
| | homolog 2 | 804 | A_3101 | GARRHSYCR | 626 | −1.95 | ~~~RHSYC~ | 660 |
| | | 805 | A_3101 | PLGHSYCNR | 627 | −2.21 | ~~~HSYCN~ | 661 |
| | | 807 | A_3101 | GLTYCNGSR | 628 | −1.94 | ~~~YCNGS~ | 662 |

Predicted affinity in standard deviation units below the mean

TABLE 17

Peptides available to stimulate CD8 T cells specific to
Patient Y mutations and alleles.

| Protein ID | Protein | Position | Allele MHC I | Simulated binding peptide | SEQ ID NO: | Predicted Affinity | TCEM IA target | SEQ ID NO: |
|---|---|---|---|---|---|---|---|---|
| m-P00533 | EGFR_HUMAN | 848 | DQB0602 | LCMGKITDFGRANHE | 663 | -1.75 | KI~D~GR | 697 |
|  | Epidermal | 848 | DRB0405 | RLVFKITDFGRENIM | 664 | -1.96 | KI~D~GR | 697 |
|  | growth factor | 848 | DRB1501 | KLLLKITDFGRGQYL | 665 | -1.95 | KI~D~GR | 697 |
|  | receptor | 849 | DQB0602 | LDFIITDFGRASTQT | 666 | -2.09 | IT~F~RA | 698 |
|  |  | 849 | DRB0405 | PGFWITDFGRAELMD | 667 | -2.00 | IT~F~RA | 698 |
|  |  | 849 | DRB1501 | QTLLITDFGRASMYT | 668 | -1.99 | IT~F~RA | 698 |
|  |  | 854 | DQB0602 | VMEKRAKLLGAPKYS | 669 | -2.00 | RA~L~GA | 699 |
| m-P54762 | EPHB1_HUMAN | 451 | DQB0602 | PHLLPQPEQPSLHYC | 670 | -1.94 | PQ~E~PS | 700 |
|  | Ephrin type-B | 451 | DRB0405 | LKWFPQPEQPSIMSF | 671 | -1.59 | PQ~E~PS | 700 |
|  | receptor 1 | 451 | DRB1501 | WNILPQPEQPSQILK | 672 | -1.74 | PQ~E~PS | 700 |
|  |  | 452 | DQB0602 | LGSAQPEQPSGSYAC | 673 | -1.69 | QP~Q~SG | 701 |
|  |  | 452 | DRB0405 | RLIFQPEQPSGLSIV | 674 | -1.53 | QP~Q~SG | 701 |
|  |  | 452 | DRB1501 | GSLMQPEQPSGLLFS | 675 | -1.27 | QP~Q~SG | 701 |
|  |  | 454 | DQB0602 | LSTLEQPSGIISRNS | 676 | -2.01 | EQ~S~II | 702 |
|  |  | 454 | DRB0405 | HPFWEQPSGIIQQID | 677 | -1.58 | EQ~S~II | 702 |
|  |  | 454 | DRB1501 | SYLFEQPSGIITINS | 678 | -1.75 | EQ~S~II | 702 |
|  |  | 456 | DRB0405 | FTWRPSGIILDNIRN | 679 | -2.20 | PS~I~LD | 703 |
|  |  | 457 | DQB0602 | SNPASGIILDYLKAV | 680 | -2.11 | SG~I~DY | 704 |
|  |  | 457 | DRB0405 | FSTYSGIILDYPRHM | 681 | -1.87 | SG~I~DY | 704 |
|  |  | 457 | DRB1501 | KLPISGIILDYHVDS | 682 | -1.78 | SG~I~DY | 704 |
| m-Q8IVL0 | NAV3_HUMAN | 2233 | DRB0405 | RTYMTIGPRLLIARQ | 683 | -1.97 | TI~P~LL | 705 |
|  | Neuron | 2233 | DRB1501 | RLGETIGPRLLLVRQ | 684 | -2.01 | TI~P~LL | 705 |
|  | navigator 3 | 2234 | DRB0405 | PKEYIGPRLLLTVQT | 685 | -1.99 | IG~R~LL | 706 |
|  |  | 2234 | DRB1501 | DSRFIGPRLLLPSAN | 686 | -2.04 | IG~R~LL | 706 |
|  |  | 2236 | DRB0405 | NILTPRLLLPCPECE | 687 | -2.10 | PR~L~PC | 707 |
|  |  | 2236 | DRB1501 | DEYLPRLLLPCAQYD | 688 | -2.09 | PR~L~PC | 707 |
|  |  | 2238 | DRB0405 | YEEYLLLPCPMPRTA | 689 | -2.15 | LL~P~PM | 708 |
|  |  | 2238 | DRB1501 | PRRPLLLPCPMQTAT | 690 | -2.00 | LL~P~PM | 708 |
|  |  | 2239 | DQB0602 | QQVSLLPCPMDPEFS | 691 | -2.12 | LL~C~MD | 709 |
|  |  | 2239 | DRB0405 | NGILLLPCPMDSSES | 692 | -1.98 | LL~C~MD | 709 |
|  |  | 2239 | DRB1501 | KHSLLLPCPMDKVLD | 693 | -2.01 | LL~C~MD | 709 |
| m-Q9Y6C5 | PTC2_HUMAN | 802 | DQB0602 | LCFRTRHSYCNTRTI | 694 | -1.94 | TR~S~CN | 710 |
|  | Protein patched | 804 | DQB0602 | MIAGHSYCNGSVACG | 695 | -2.00 | HS~C~GS | 711 |
|  | homolog 2 | 806 | DQB0602 | HEAMYCNGSEDAQIT | 696 | -2.04 | YC~G~ED | 712 |

TABLE 18

TCEMs identified as of immediate concern for Patient Y

| Protein ID | pos | TCEM IIA | TCEM I | | Protein annotation | UniProt ID | Immediate Caution |
|---|---|---|---|---|---|---|---|
| P0C0L5 | 18 |  | ~~~PRLLL~ (SEQ ID NO: 645) | I | Complement C4-B | CO4B_HUMAN | Caution |
| P0C0L4 | 18 |  | ~~~PRLLL~ (SEQ ID NO: 645) | I | Complement C4-A | CO4A_HUMAN | Caution |
| P00748 | 390 | HS~C~GS (SEQ ID NO: 711) |  | IIA | Coagulation factor XII | FA12_HUMAN | Caution |

After removal of peptides comprising these TCEM the peptides in Tables 16 and 17 provide an array of T cell stimulating peptides which could be used as a neoepitope vaccine or in vitro stimulant of autologous dendritic cells or T cells for Patient Y. This provides an example of how this approach could be used in a small cell lung cancer case. This provides many more options for stimulating T cells specifically targeting the unique tumor epitopes than reliance on naturally bound peptides.

Example 7: Application to Common Mutations Found in Many Cancers

This example describes the generation of "ready to go" neoantigens which are applicable to patients of known alleles who share common mutations found in many cancers. While the description is provided for five proteins which have common mutations across over 30 cancers, the approach is equally applicable to other mutations shared between different cancers and thus the example should not be considered limiting. Similarly, the set of alleles selected and shown in the Example is not considered limiting and this process can be executed for other combinations of alleles.

Figure 5:
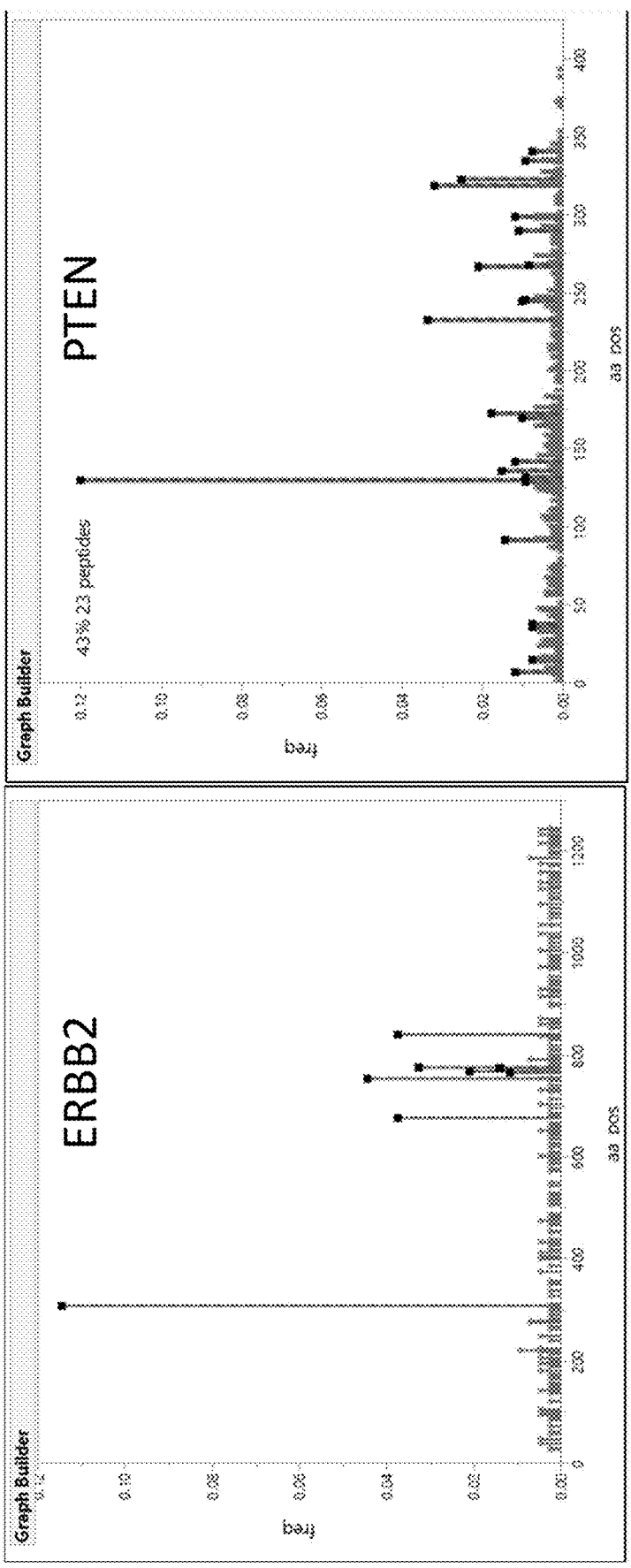
FIG. 5: The location of the dominant mutations in five proteins in which mutations are shared across multiple cancers. Although the proteins are subject to mutation at many locations there are some amino acid positions that are clearly more susceptible than others.
Figure 5:
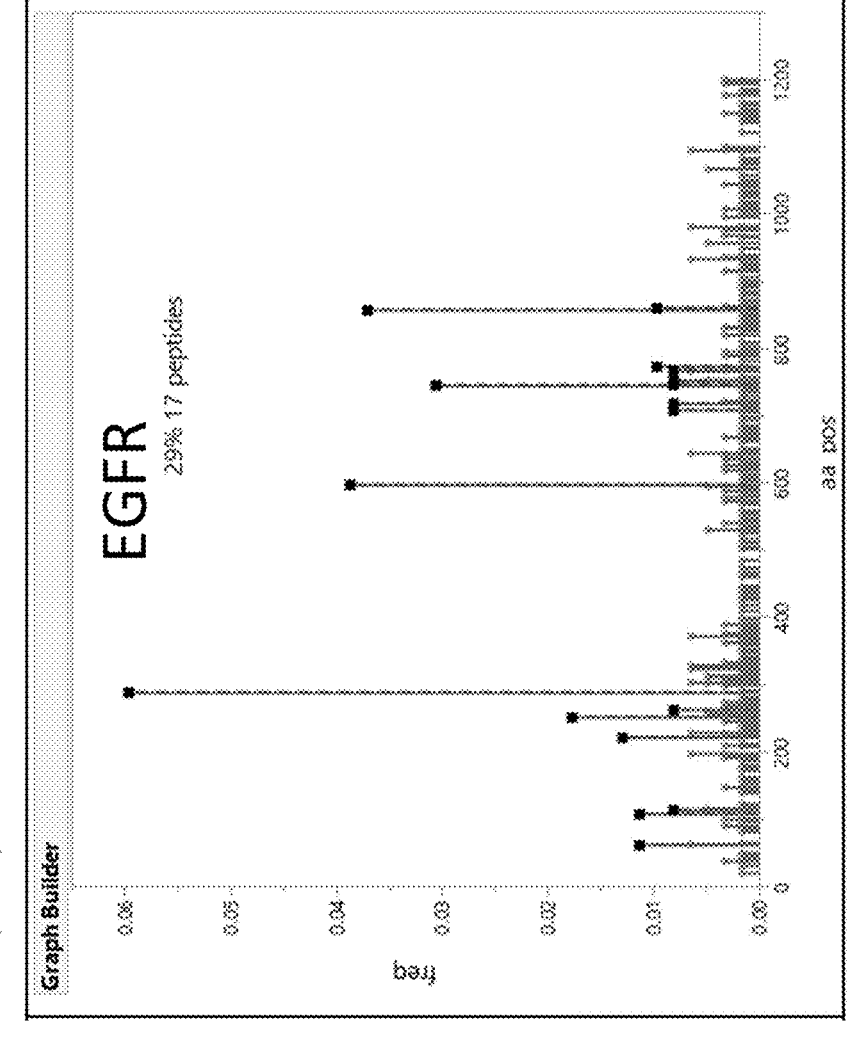
Figure 5:
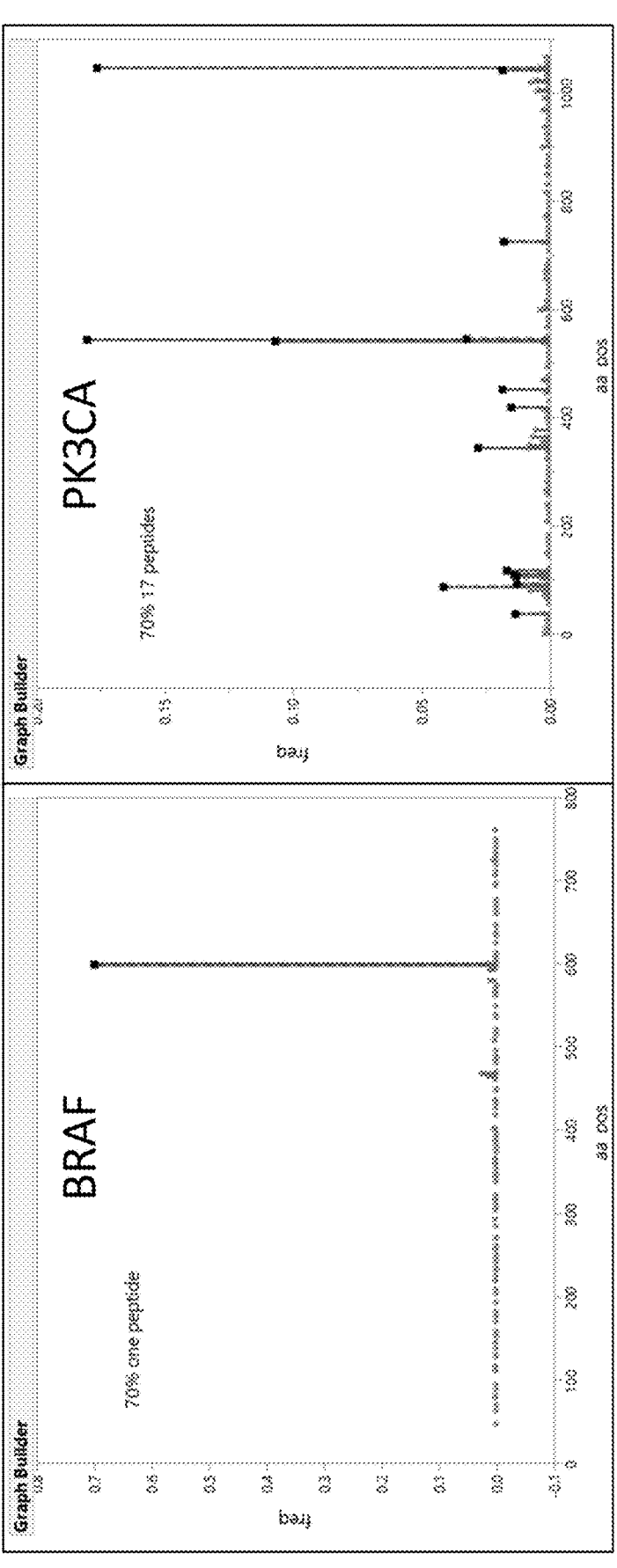

Table 19 identifies five proteins commonly mutated in many different cancers. The location of the dominant mutations is shown in FIG. 5. The preponderance of mutations at a few positions indicate it is possible to design peptides in anticipation of many different patient allele combinations, thereby providing a bank of peptides ready-to-use as soon as patient HLA typing and sequencing is available to identify mutational biomarkers.

TABLE 19

| | | | Frequency of mutations in selected proteins | | | |
| mutant type | N Rows | N, BRAF | N, EGFR | N, ERBB2 | N, PK3CA | N, PTEN |
| --- | --- | --- | --- | --- | --- | --- |
| deletion | 116 | 7 | 29 | 1 | 19 | 7 |
| duplication | 13 | 0 | 5 | 3 | 0 | 0 |
| frameshift | 856 | 8 | 4 | 7 | 3 | 294 |
| SNP | 8604 | 898 | 583 | 417 | 1764 | 883 |
| splice | 414 | 7 | 4 | 7 | 2 | 80 |

Rows: Number of records of mutations in this protein in the TCGA at present date In this Example we demonstrate the application of this approach to 10 common mutations in 5 proteins. These common mutations have been documented in the 32 common cancers shown in Table 20. The examples of mutated proteins, common mutation positions, and alleles we show below provide illustrations, but are not considered in any way limiting.

TABLE 20

| | | Cancers in which mutations in the indicated proteins are documented | | | | |
| Cancer type | CODE | BRAF | EGFR | ERBB | PK3CA | PTEN |
| --- | --- | --- | --- | --- | --- | --- |
| Adrenocortical carcinoma | ACC | 1 | 4 | | 1 | 1 |
| Bladder urothelial carcinoma | BLCA | 17 | 19 | 78 | 109 | 22 |
| Breast adenocarcinoma | BRCA | 10 | 25 | 38 | 407 | 67 |
| Cervical squamous cell carcinoma | CESC | 5 | 16 | 22 | 101 | 45 |
| Cholangiocarcinoma | CHOL | 2 | 2 | 3 | 3 | 1 |
| Colon carcinoma | COAD | 66 | 30 | 27 | 171 | 43 |
| Diffuse Large B-cell Lymphoma | DLBC | 1 | | | | 2 |
| Esophageal carcinoma | ESCA | 2 | 6 | 13 | 20 | 14 |
| Glioblastoma multiforme | GBM | 9 | 133 | 12 | 43 | 142 |
| Head and neck squamous cell carcinoma | HNSC | 13 | 27 | 18 | 108 | 14 |
| Kidney Chromophobe | KICH | | 1 | | | 6 |
| kidney renal clear cell carcinoma | KIRC | 1 | 2 | 4 | 5 | 15 |
| Kidney renal papillary cell carcinoma | KIRP | 6 | 3 | 7 | 4 | 9 |
| Acute myeloid leukaemia | LAML | | | 1 | | |
| Brain Lower Grade Glioma | LGG | 5 | 46 | 2 | 50 | 26 |
| Liver hepatocellular carcinoma | LIHC | | 9 | 3 | 13 | 10 |
| Lung adenocarcinoma | LUAD | 52 | 101 | 20 | 37 | 17 |
| Lung squamous cell carcinoma | LUSC | 18 | 24 | 15 | 73 | 63 |
| Mesothelioma | MESO | 1 | | | 2 | 2 |
| Ovarian serous carcinoma | OV | 2 | 13 | 6 | 11 | 7 |
| Pancreatic adenocarcinoma | PAAD | 2 | 2 | 6 | 5 | |
| Pheochromocytoma and Paraganglioma | PCPG | 1 | | | 1 | |
| Prostate adenocarcinoma | PRAD | 8 | 4 | 6 | 16 | 19 |
| Rectal carcinoma | READ | 7 | 8 | 8 | 26 | 13 |
| Sarcoma | SARC | 1 | 4 | 3 | 7 | 9 |

TABLE 20-continued

Cancers in which mutations in the indicated proteins are documented

| Cancer type | CODE | BRAF | EGFR | ERBB | PK3CA | PTEN |
|---|---|---|---|---|---|---|
| Skin Cutaneous Melanoma | SKCM | 314 | 111 | 57 | 31 | 49 |
| Stomach adenocarcinoma | STAD | 25 | 35 | 41 | 102 | 53 |
| Testicular Germ Cell Tumors | TGCT | | 1 | 1 | 3 | |
| Thyroid carcinoma | THCA | 314 | | | 5 | 3 |
| Thymoma | THYM | | | 2 | | |
| Uterine corpus endometrial carcinoma | UCEC | 45 | 110 | 62 | 406 | 702 |
| Uterine Carcinosarcoma | UCS | 1 | 1 | 1 | 22 | 17 |

A cancer patient with one of the common mutations and a known set of alleles could benefit from the availability of a "ready to go" set of peptides designed and selected to allow stimulation of that patient's cytotoxic T cells and cross presented helper T cells. Thus once these mutations are identified, they provide a starting point for an immunotherapy approach to these cancers. The examples include both amino acid substitutions and amino acid duplications.

Predictions of binding affinity are currently made for 31 MEW I A alleles, 31 MHC I B alleles, 8 MHC I C alleles plus for MHC II predictions are currently made for 13 DP alleles or allele combinations, 28 DQ Alleles or allele combinations and 24 DRB alleles. This allows peptides to be designed for a very wide diversity of potential patients; indeed this combination of alleles represents over 85% of the world human population. Additional alleles may be added in future and the same process applied for them.

We applied predictions of MHC binding affinity and T cell exposed motif analysis methods previous developed (See e.g., PCT Appl. US 14/41523, incorporated by reference herein its entirety). From the selected commonly mutated proteins in Table 20, we chose 2 common mutation sites in each as examples. The T cell exposed motifs which comprise the mutant amino acid were identified for both CD8 and CD4 T cells. Peptides were designed to demonstrate application for 4 MEW I alleles (A0101, A2301, A3001, A8001) and 4 MEW II alleles (B2705, B3801, B4801, B5701. These are non-limiting examples, chosen to show how this approach can be generalized to all 122 alleles for which binding affinity predictions are currently performed. While CD8 T cells are critical to generating a cytotoxic response, CD4 cells may facilitate this as helper cells.

Figure 6:
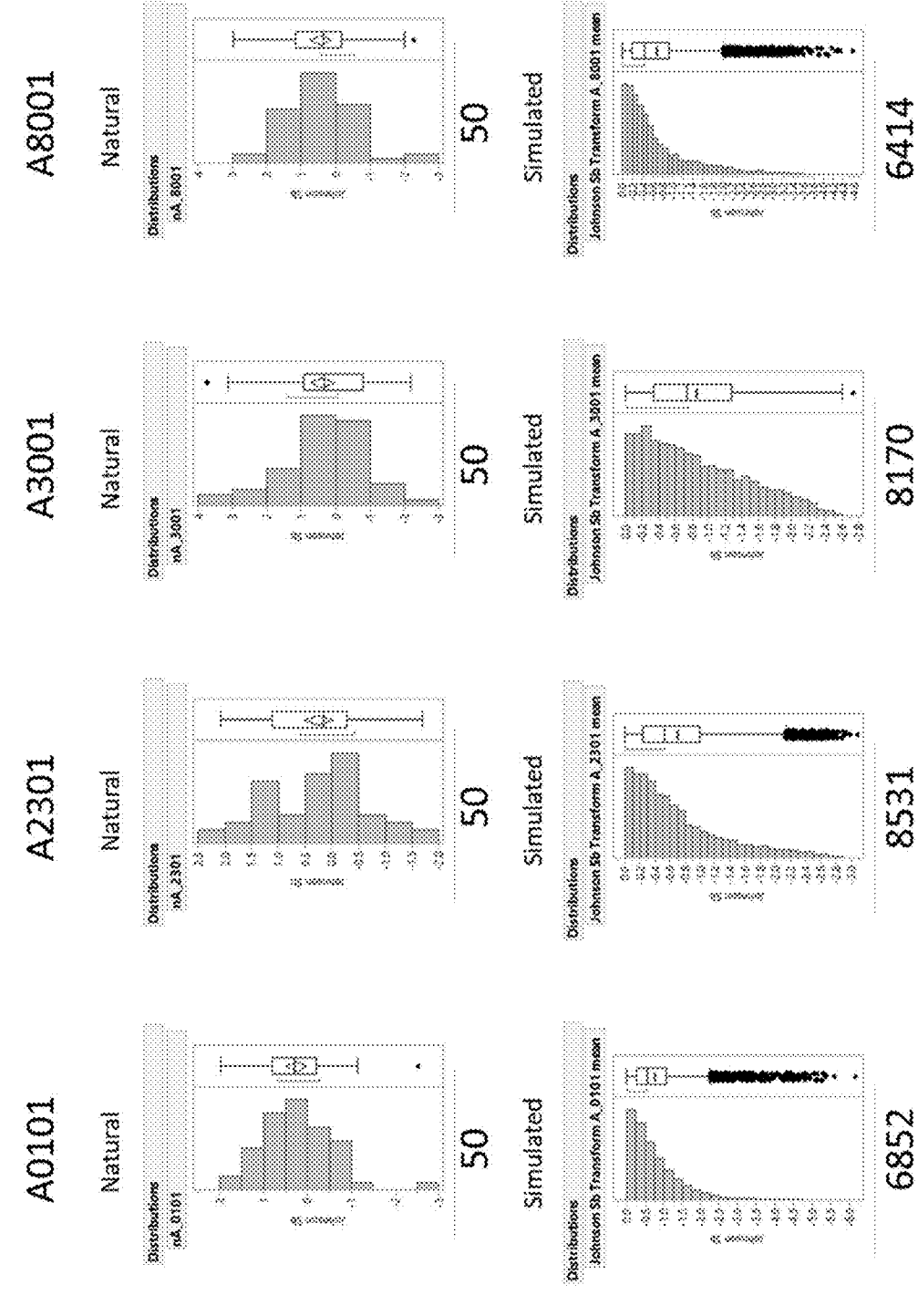
FIG. 6: Binding affinity of native peptides comprising exposed TCEM mutant compared to peptides generated by simulation. Note the Y axis is centered at zero (the mean) for the natural peptides whereas simulated peptides figures only show those below zero because peptides with binding affinities lower than the mean are deemed to be not useful and selected against in the simulation process. Numbers at bottom indicate the number of available peptides from which to select.
Figure 7:
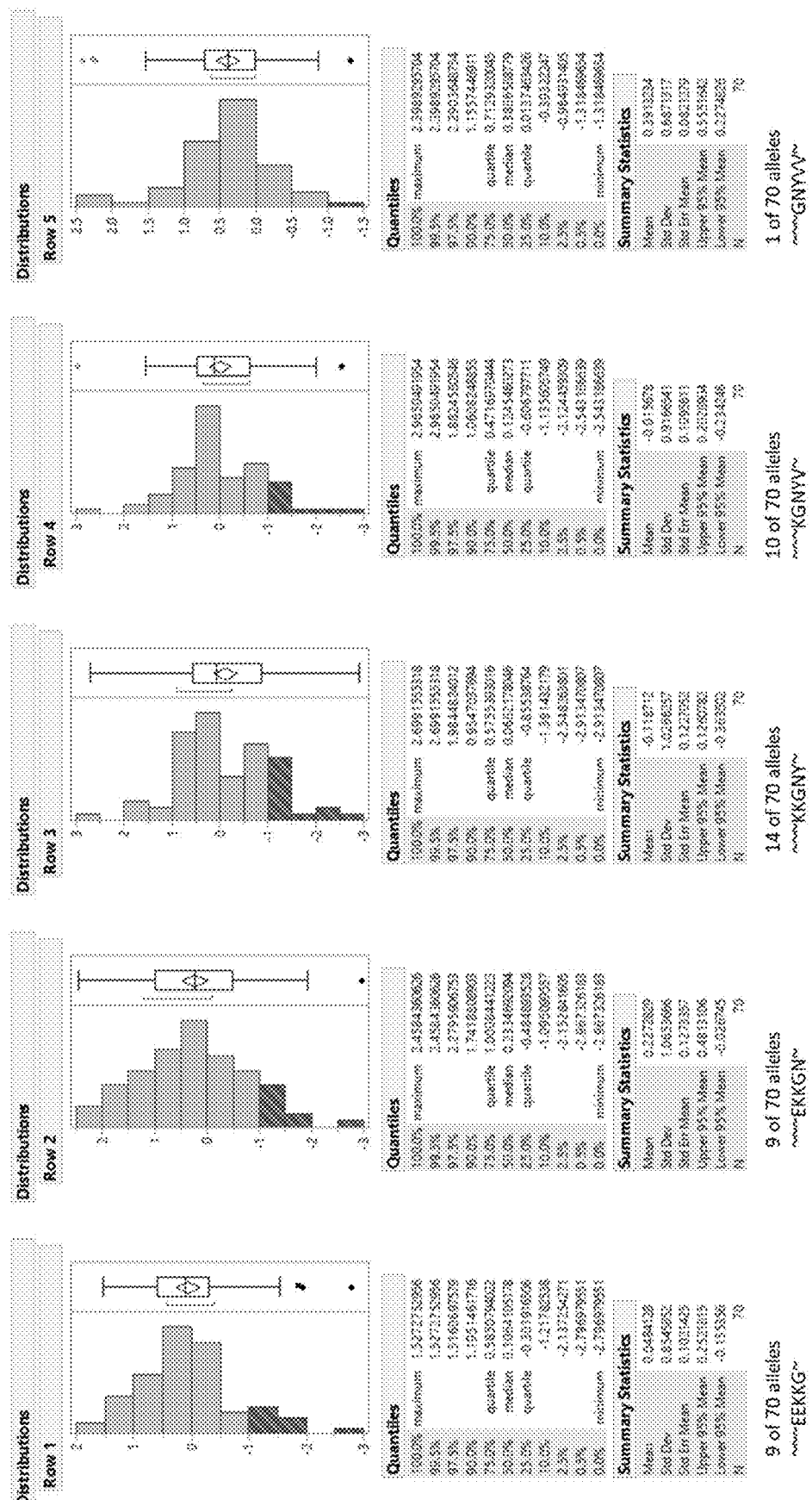
FIG. 7: Few MHC I alleles bind naturally at each of the five unique TCEM positions in the EGFRviii variant. The figure highlights those binding at better than 1 SD units below the mean for the protein (approx. 500 nm). TCEM amino acid motif is shown below each figure.

For each TCEM-selected allele combination, 1000 peptides were generated to provide a choice of high affinity peptides. Duplicates and non-binding peptides were eliminated as were potentially low solubility peptides. The choice of 1000 peptides is shown as a non-limiting example; this number could be 5000 or 10,000 or more and would result in a wider selection. Table 21 shows the number of such peptides generated for each selected allele. FIG. 6 shows (for the A alleles) how this simulation process generates peptides with a preponderance of high MEW binding relative to the native mutant peptide.

Binding affinity is measured in standard deviation units below the mean of all peptides in that protein. For example purposes, peptides with a predicted binding affinity of near 2SD below the mean for each protein and allele-TCEM combination were selected, or as near to that as feasible. This places these peptides in the top ~5% of binding peptides relative to others in the protein. These peptides are show in in Table 22 for MHC I A example alleles, Table 23 for MHC I B example alleles, and Table 24 for MHC II example alleles. We have discussed elsewhere in the Description whether MHC binding affinities higher than this are beneficial or not; the approach we show here allows selection of peptides of whatever predicted binding affinity is desired. Hence, the criteria applied in this example are not considered limiting.

Not all proteins will have TCEM that will be accessible to T cells when the mutant protein is naturally presented, depending on the MHC alleles of that patient, but as every patient has multiple loci it is anticipated that it is possible to locate suitable peptides for every patient for one or more alleles. The peptides shown in Tables 23, 24 and 25 would elicit T cells specifically targeting the TCEM unique to the proteins with these mutations regardless of the type of cancer in which they occur. These peptides thus serve as examples of multi-cancer neoepitope peptides for use in vaccines, or as in vitro T cell stimulants. These peptides may be deployed singly or in groups together selected to stimulate T cells to target a maximum number of allele-TCEM combinations, or may be applied in groups at different time points. When used as a vaccine the peptides may be delivered intradermally, by injection or microneedle array, subcutaneously, parenterally or by any other route deemed appropriate by the clinician. The peptides may be applied in conjunction with an adjuvant or local inflammatory agent. Peptide application may be followed by a checkpoint inhibitor or other immunomodulatory intervention. The peptides may also be used in vitro to prime autologous dendritic cells or T cells that are then administered to the patient.

TABLE 21

| | Group of 5 proteins; overall 10 protein mutation combinations Overall number of potential TCEM targets = 50 | | | | | | | | | | | |
|---|---|---|---|---|---|---|---|---|---|---|---|---|
| Allele | A0101 | A2301 | A3001 | A8001 | B2705 | B3801 | B4801 | B5701 | DRB1 1201 | DRB3 0101 | DQB 0302 | DQB 0602 |
| TCEM naturally presented for allele | 18 | 22 | 21 | 16 | 19 | 18 | 24 | 24 | 22 | 19 | 22 | 23 |
| # protein mutation combo with TCEM presented | 9/10 | 6/10 | 9/10 | 10/10 | 10/10 | 10/10 | 10/10 | 9/10 | 8/10 | 7/10 | 7/10 | 10/10 |
| Candidate peptides, bound, presented and soluble | 6852 | 8531 | 8170 | 6414 | 7197 | 7608 | 9014 | 10197 | 10559 | 9784 | 13752 | 11376 |

TABLE 21-continued

Group of 5 proteins; overall 10 protein mutation combinations
Overall number of potential TCEM targets = 50

| Allele | A0101 | A2301 | A3001 | A8001 | B2705 | B3801 | B4801 | B5701 | DRB1 1201 | DRB3 0101 | DQB 0302 | DQB 0602 |
|---|---|---|---|---|---|---|---|---|---|---|---|---|
| Candidate peptides binding at −1.75-2.25 SD | 407 | 463 | 846 | 406 | 466 | 470 | 512 | 383 | 554 | 581 | 708 | 662 |
| Candidate peptides binding at <−3 SD | 132 | 1 | 0 | 85 | 185 | 9 | 148 | 359 | 10 | 34 | 40 | 3 |

TABLE 22

Exemplar peptides stimulating CD8 T cell responses to multi cancer
mutated proteins for the indicated MHC I A alleles

| Protein ID | Protein Curation | Muta-tion | Allele | Binding peptide | SEQ ID NO. | Predicted binding | Position | TCEM | SEQ ID NO. |
|---|---|---|---|---|---|---|---|---|---|
| P00533_A289V | EGFR_HUMAN | A289V | A_0101 | IGEYSFGVS | 713 | −2.03 | 282 | YSFGV | 1 |
| | Epidermal growth | A289V | A_0101 | KSESFGVAR | 714 | −2.02 | 283 | SFGVA | 2 |
| | factor receptor | A289V | A_0101 | FQSGVATCP | 715 | −2.02 | 285 | GVATC | 3 |
| | OS_Homo sapiens | A289V | A_0101 | DSSVATCVL | 716 | −2.01 | 286 | VATCV | 4 |
| | OX_9606 GN_EGFR | A289V | A_2301 | DKYSFGVAF | 717 | −1.74 | 283 | SFGVA | 5 |
| | PE_1 SV_2 | A289V | A_2301 | ERYFGVATL | 718 | −1.64 | 284 | FGVAT | 6 |
| | | A289V | A_2301 | HKWGVATCW | 719 | −2.11 | 285 | GVATC | 7 |
| | | A289V | A_3001 | IGRYSFGVQ | 720 | −2.00 | 282 | YSFGV | 8 |
| | | A289V | A_3001 | EQRSFGVAG | 721 | −2.00 | 283 | SFGVA | 9 |
| | | A289V | A_3001 | KGQVATCVP | 722 | −2.02 | 286 | VATCV | 10 |
| | | A289V | A_8001 | LNGFGVATR | 723 | −1.91 | 284 | FGVAT | 11 |
| P00533_L858R | EGFR_HUMAN | L858R | A_0101 | IKDFGRLAY | 724 | −2.00 | 853 | FGRLA | 12 |
| | Epidermal growth | L858R | A_2301 | EYHTDFGRL | 725 | −2.05 | 851 | TDFGR | 13 |
| | factor receptor | L858R | A_2301 | SLKDFGRLI | 726 | −2.01 | 852 | DFGRL | 14 |
| | OS_Homo sapiens | L858R | A_2301 | DVFGRLAKF | 727 | −2.02 | 854 | GRLAK | 15 |
| | OX_9606 GN_EGFR | L858R | A_2301 | RLRRLAKLL | 728 | −2.01 | 855 | RLAKL | 16 |
| | PE_1 SV_2 | L858R | A_3001 | TARDFGRLE | 729 | −2.01 | 852 | DFGRL | 17 |
| | | L858R | A_3001 | TNKFGRLAD | 730 | −2.05 | 853 | FGRLA | 18 |
| | | L858R | A_8001 | HGNDFGRLR | 731 | −2.00 | 852 | DFGRL | 19 |
| | | L858R | A_8001 | CPRFGRLAY | 732 | −2.00 | 853 | FGRLA | 20 |
| | | L858R | A_8001 | KCIRLAKLR | 733 | −2.05 | 855 | RLAKL | 21 |
| P04626_R678Q | ERBB2_HUMAN | R678Q | A_0101 | RSELIKRQL | 734 | −2.04 | 671 | LIKRQ | 22 |
| | Receptor tyrosine- | R678Q | A_2301 | SFAIKRQRL | 735 | −2.02 | 672 | IKRQR | 23 |
| | protein kinase | R678Q | A_2301 | PRLKRQRQI | 736 | −2.03 | 673 | KRQRQ | 24 |
| | erbB-2 | R678Q | A_2301 | VINRQRQQF | 737 | −2.02 | 674 | RQRQQ | 25 |
| | OS_Homo sapiens | R678Q | A_2301 | LSYQRQQKF | 738 | −2.03 | 675 | QRQQK | 26 |
| | OX_9606 | R678Q | A_3001 | SGKIKRQRN | 739 | −2.01 | 672 | IKRQR | 27 |
| | GN_ERBB2 PE_1 | R678Q | A_3001 | TMRRQRQQS | 740 | −1.99 | 674 | RQRQQ | 28 |
| | SV_1 | R678Q | A_8001 | AVELIKRQY | 741 | −2.02 | 671 | LIKRQ | 29 |
| P04626_S310F | ERBB2_HUMAN | S310F | A_0101 | RGNTDVGFL | 742 | −2.00 | 303 | TDVGF | 30 |
| | Receptor | S310F | A_0101 | YGQDVGFSQ | 743 | −2.09 | 304 | DVGFS | 31 |
| | tyrosine- | S310F | A_0101 | YTDVGFSCA | 744 | −2.02 | 305 | VGFSC | 32 |
| | protein kinase | S310F | A_2301 | HKLTDVGFF | 745 | −2.01 | 303 | TDVGF | 33 |
| | erbB-2 | S310F | A_2301 | QRTDVGFSF | 746 | −2.06 | 304 | DVGFS | 34 |
| | OS_Homo sapiens | S310F | A_2301 | PRYGFSCTF | 747 | −2.13 | 306 | GFSCT | 35 |
| | OX_9606 | S310F | A_3001 | VVKTDVGFA | 748 | −2.00 | 303 | TDVGF | 36 |
| | GN_ERBB2 PE_1 | S310F | A_3001 | SIKVGFSCS | 749 | −2.00 | 305 | VGFSC | 37 |
| | SV_1 | S310F | A_3001 | TIRFSCTLQ | 750 | −2.00 | 307 | FSCTL | 38 |
| | | S310F | A_8001 | ISTFSCTLR | 751 | −2.06 | 307 | FSCTL | 39 |
| P15056_V600E | BRAF_HUMAN | V600E | A_0101 | LLDATEVKP | 752 | −2.09 | 595 | AIEVK | 40 |
| | Serine_threonine- | V600E | A_0101 | FKCEVKSRP | 753 | −2.02 | 597 | EVKSR | 41 |
| | protein kinase | V600E | A_2301 | YLKGLAIEW | 754 | −2.02 | 593 | GLATE | 42 |
| | B-raf | V600E | A_2301 | KPPLAIEVF | 755 | −1.83 | 594 | LATEV | 43 |
| | OS_Homo sapiens | V600E | A_2301 | LFKAIEVKL | 756 | −2.01 | 595 | AIEVK | 44 |
| | OX_9606 GN_BRAF | V600E | A_2301 | LQFEVKSRL | 757 | −2.04 | 597 | EVKSR | 45 |
| | PE_1 SV_4 | V600E | A_3001 | AVKAIEVKA | 758 | −2.01 | 595 | AIEVK | 46 |
| | | V600E | A_8001 | VGLIEVKSY | 759 | −2.04 | 596 | IEVKS | 47 |
| | | V600E | A_8001 | IEIEVKSRY | 760 | −2.03 | 597 | EVKSR | 48 |
| P15056_V600M | BRAF_HUMAN | V600M | A_0101 | ASDLATMVE | 761 | −2.01 | 594 | LATMV | 49 |
| | Serine_threonine- | V600M | A_0101 | MSNATMVKL | 762 | −2.03 | 595 | ATMVK | 50 |
| | protein kinase | V600M | A_0101 | IAEMVKSRV | 763 | −1.99 | 597 | MVKSR | 51 |
| | B-raf | V600M | A_2301 | KWDGLATML | 764 | −1.98 | 593 | GLATM | 52 |

TABLE 22-continued

Exemplar peptides stimulating CD8 T cell responses to multi cancer
mutated proteins for the indicated MHC I A alleles

| Protein ID | Protein Curation | Muta-tion | Allele | Binding peptide | SEQ ID NO. | Predicted binding | Position | TCEM | SEQ ID NO. |
|---|---|---|---|---|---|---|---|---|---|
| | OS Homo sapiens | V600M | A_2301 | RMSATMVKF | 765 | -2.00 | 595 | ATMVK | 53 |
| | OX_9606 GN_BRAF | V600M | A_2301 | IRRTMVKSI | 766 | -2.02 | 596 | TMVKS | 54 |
| | PE_1 SV_4 | V600M | A_2301 | VRTMVKSRF | 767 | -2.08 | 597 | MVKSR | 55 |
| | | V600M | A_3001 | NMKLATMVG | 768 | -2.01 | 594 | LATMV | 56 |
| | | V600M | A_3001 | YGKATMVKA | 769 | -2.09 | 595 | ATMVK | 57 |
| | | V600M | A_8001 | VELTMVKSY | 770 | -1.99 | 596 | TMVKS | 58 |
| | | V600M | A_8001 | TVIMVKSRR | 771 | -2.01 | 597 | MVKSR | 59 |
| P42336_E545K | PIK3CA_HUMAN | E545K | A_0101 | CPEITKEQY | 772 | -2.03 | 540 | ITKEQ | 60 |
| | Phos-phatidylinositol 4 | E545K | A_8001 | RGIEITKER | 773 | -2.02 | 539 | EITKE | 61 |
| P42336_H1047R | PIK3CA_HUMAN | H1047R | A_0101 | PSDMNDARL | 774 | -2.05 | 1040 | MNDAR | 62 |
| | Phos-phatidylinositol 4 | H1047R | A_0101 | YADARHHGC | 775 | -2.03 | 1043 | ARHHG | 63 |
| | | H1047R | A_3001 | APRDARHHK | 776 | -2.00 | 1042 | DARHH | 64 |
| | | H1047R | A_3001 | KARARHHGA | 777 | -2.06 | 1043 | ARHHG | 65 |
| | | H1047R | A_8001 | WKIRHHGGR | 778 | -2.04 | 1044 | RHHGG | 66 |
| P60484_R130G | PTEN_HUMAN | R130G | A_0101 | FGDKGGRTG | 779 | -2.01 | 125 | KGGRT | 67 |
| | Phos-phatidylinositol 3 | R130G | A_3001 | QGKAGKGGP | 780 | -2.08 | 123 | AGKGG | 68 |
| | | R130G | A_3001 | DNRKGGRTK | 781 | -2.00 | 125 | KGGRT | 69 |
| | | R130G | A_3001 | NNRGGRTGA | 782 | -2.00 | 126 | GGRTG | 70 |
| | | R130G | A_8001 | LITAGKGGY | 783 | -1.97 | 123 | AGKGG | 71 |
| | | R130G | A_8001 | EHFKGGRTY | 784 | -2.10 | 125 | KGGRT | 72 |
| | | R130Q | A_3001 | PAKAGKGQP | 785 | -2.07 | 123 | AGKGQ | 73 |
| | | R130Q | A_3001 | PDRKGQRTG | 786 | -2.03 | 125 | KGQRT | 74 |
| | | R130Q | A_3001 | RAWGQRTGP | 787 | -2.00 | 126 | GQRTG | 75 |
| | | R130Q | A_8001 | GVLAGKGQY | 788 | -2.00 | 123 | AGKGQ | 76 |
| | | R130Q | A_8001 | QECKGQRTY | 789 | -2.05 | 125 | KGQRT | 77 |

TABLE 23

Exemplar peptides eliciting CD8 T cell responses to multi cancer mutated
proteins for the indicated MHC I B alleles

| Protein ID | Protein Curation | Mu-tation | Allele | Binding peptide | SEQ ID NO: | Posi-tion | Pre-dicted binding | TCEM | SEQ ID NO. |
|---|---|---|---|---|---|---|---|---|---|
| P00533_A289V | EGFR_HUMAN | A289V | B_2705 | PDKSFGVAY | 790 | 283 | -2.04 | SFGVA | 162 |
| | Epidermal growth | A289V | B_2705 | WKTFGVATS | 791 | 284 | -2.03 | FGVAT | 163 |
| | factor receptor | A289V | B_2705 | PEFGVATCK | 792 | 285 | -2.00 | GVATC | 164 |
| | OS Homo sapiens | A289V | B_3801 | FEHSFGVAS | 793 | 283 | -2.01 | SFGVA | 165 |
| | OX_9606 GN_EGFR | A289V | B_3801 | YRPGVATCV | 794 | 285 | -1.93 | GVATC | 166 |
| | PE_1 SV_2 | A289V | B_4801 | GKTSFGVAG | 795 | 283 | -2.00 | SFGVA | 167 |
| | | A289V | B_4801 | GKHFGVATL | 796 | 284 | -2.01 | FGVAT | 168 |
| | | A289V | B_4801 | REQGVATCL | 797 | 285 | -2.04 | GVATC | 169 |
| | | A289V | B_5701 | RGSYSFGVY | 798 | 282 | -2.08 | YSFGV | 170 |
| | | A289V | B_5701 | GGSGVATCY | 799 | 285 | -2.01 | GVATC | 171 |
| P00533_L858R | EGFR_HUMAN | L858R | B_2705 | DRLTDFGRE | 800 | 851 | -2.00 | TDFGR | 172 |
| | Epidermal growth | L858R | B_2705 | YEMDFGRLY | 801 | 852 | -2.00 | DFGRL | 173 |
| | factor receptor | L858R | B_2705 | VRGGRLAKR | 802 | 854 | -2.03 | GRLAK | 174 |
| | OS Homo sapiens | L858R | B_3801 | FRFTDFGRT | 803 | 851 | -1.83 | TDFGR | 175 |
| | OX_9606 GN_EGFR | L858R | B_3801 | QELGRLAKP | 804 | 854 | -2.00 | GRLAK | 176 |
| | PE_1 SV_2 | L858R | B_4801 | KQYTDFGRL | 805 | 851 | -1.81 | TDFGR | 177 |
| | | L858R | B_4801 | RCYDFGRLW | 806 | 852 | -2.01 | DFGRL | 178 |
| | | L858R | B_4801 | YKLGRLAKI | 807 | 854 | -1.96 | GRLAK | 179 |
| | | L858R | B_4801 | ENPRLAKLI | 808 | 855 | -2.01 | RLAKL | 180 |
| | | L858R | B_5701 | ELNTDFGRW | 809 | 851 | -2.03 | TDFGR | 181 |
| | | L858R | B_5701 | CSNGRLAKF | 810 | 854 | -2.08 | GRLAK | 182 |
| P04626_R678Q | ERBB2_HUMAN | R678Q | B_2705 | IRSLIKRQL | 811 | 671 | -2.00 | LIKRQ | 183 |
| | Receptor | R678Q | B_3801 | THWQRQQKL | 812 | 675 | -1.97 | QRQQK | 184 |
| | tyrosine- | R678Q | B_4801 | RCLKRQRQL | 813 | 673 | -1.70 | KRQRQ | 185 |
| | protein kinase | R678Q | B_4801 | RDLQRQQKV | 814 | 675 | -2.03 | QRQQK | 186 |

TABLE 23-continued

Exemplar peptides eliciting CD8 T cell responses to multi cancer mutated
proteins for the indicated MHC I B alleles

| Protein ID | Protein Curation | Mu-tation | Allele | Binding peptide | SEQ ID NO: | Posi-tion | Pre-dicted binding | TCEM | SEQ ID NO. |
|---|---|---|---|---|---|---|---|---|---|
| | erbB-2 | R678Q | B_5701 | SPWLIKRQI | 815 | 671 | -2.03 | LIKRQ | 187 |
| | OS_Homo sapiens | R678Q | B_5701 | TAAQRQQKY | 816 | 675 | -2.00 | QRQQK | 188 |
| | OX_9606 | | | | | | | | |
| | GN_ERBB2 PE_1 | | | | | | | | |
| | SV_1 | | | | | | | | |
| P04626_S310F | ERBB2_HUMAN | S310F | B_2705 | TKRGFSCTK | 817 | 306 | -2.00 | GFSCT | 189 |
| | Receptor | S310F | B_3801 | TRKDVGFSI | 818 | 304 | -2.00 | DVGFS | 190 |
| | tyrosine- | S310F | B_3801 | LRHGFSCTC | 819 | 306 | -2.01 | GFSCT | 191 |
| | protein kinase | S310F | B_4801 | QDEDVGFSM | 820 | 304 | -2.01 | DVGFS | 192 |
| | erbB-2 | S310F | B_4801 | QNEGFSCTA | 821 | 306 | -2.00 | GFSCT | 193 |
| | OS_Homo sapiens | S310F | B_4801 | PNQFSCTLS | 1093 | 307 | -2.00 | FSCTL | 194 |
| | OX_9606 | S310F | B_5701 | HSKDVGFSI | 1094 | 304 | -2.00 | DVGFS | 195 |
| | GN_ERBB2 PE_1 | S310F | B_5701 | GSKGFSCTM | 1095 | 306 | -2.00 | GFSCT | 196 |
| | SV_1 | | | | | | | | |
| P15056_V600E | BRAF_HUMAN | V600E | B_2705 | DQFGLATEK | 822 | 593 | -2.00 | GLATE | 197 |
| | Serine_threonine- | V600E | B_2705 | LRDEVKSRE | 823 | 597 | -2.03 | EVKSR | 198 |
| | protein kinase | V600E | B_3801 | IRKGLAIEY | 824 | 593 | -2.02 | GLAIE | 199 |
| | B-raf | V600E | B_4801 | PNVGLATEI | 825 | 593 | -2.02 | GLATE | 200 |
| | OS_Homo sapiens | V600E | B_4801 | AKAAIEVKL | 826 | 595 | -2.01 | AIEVK | 201 |
| | OX_9606 GN_BRAF | V600E | B_5701 | PSCGLATEM | 827 | 593 | -2.04 | GLATE | 202 |
| | PE_1 SV_4 | V600E | B_5701 | LSKATEVKL | 828 | 595 | -2.02 | AIEVK | 203 |
| | | V600E | B_5701 | SCITEVKSF | 829 | 596 | -2.00 | IEVKS | 204 |
| | | V600E | B_5701 | ESPEVKSRY | 830 | 597 | -2.01 | EVKSR | 205 |
| P15056_V600M | BRAF_HUMAN | V600M | B_2705 | DKVGLATMA | 831 | 593 | -2.03 | GLATM | 206 |
| | Serine_threonine- | V600M | B_2705 | IRGMVKSRN | 832 | 597 | -2.00 | MVKSR | 207 |
| | protein kinase | V600M | B_3801 | LRQGLATMQ | 833 | 593 | -2.01 | GLATM | 208 |
| | B-raf | V600M | B_4801 | ENPGLATMI | 834 | 593 | -2.06 | GLATM | 209 |
| | OS_Homo sapiens | V600M | B_4801 | SKGATMVKL | 835 | 595 | -1.98 | ATMVK | 210 |
| | OX_9606 GN_BRAF | V600M | B_4801 | GQVTMVKSI | 836 | 596 | -2.06 | TMVKS | 211 |
| | PE_1 SV_4 | V600M | B_5701 | KAKGLATMM | 837 | 593 | -2.04 | GLATM | 212 |
| | | V600M | B_5701 | RGDATMVKI | 838 | 595 | -2.02 | ATMVK | 213 |
| | | V600M | B_5701 | VGCTMVKSM | 839 | 596 | -2.03 | TMVKS | 214 |
| | | V600M | B_5701 | TITMVKSRW | 840 | 597 | -2.00 | MVKSR | 215 |
| P42336_E545K | PIK3CA_HUMAN | E545K | B_2705 | KKAEITKES | 841 | 539 | -2.00 | EITKE | 216 |
| | Phos- | E545K | B_2705 | MRPTKEQEQ | 842 | 541 | -2.02 | TKEQE | 217 |
| | phatidylinositol | E545K | B_4801 | ADLSEITKV | 843 | 538 | -2.07 | SEITK | 218 |
| | 4 | E545K | B_4801 | NKLITKEQL | 844 | 540 | -2.09 | ITKEQ | 219 |
| P42336_H1047R | PIK3CA_HUMAN | H1047R | B_2705 | LRVNDARHI | 845 | 1041 | -2.03 | NDARH | 220 |
| | Phos- | H1047R | B_2705 | LKPRHHGGN | 846 | 1044 | -2.03 | RHHGG | 221 |
| | phatidylinositol | H1047R | B_3801 | IRMDARHHV | 847 | 1042 | -1.60 | DARHH | 222 |
| | 4 | H1047R | B_3801 | PEWARHHGW | 848 | 1043 | -2.02 | ARHHG | 223 |
| | | H1047R | B_4801 | SQARHHGGC | 849 | 1044 | -2.02 | RHHGG | 224 |
| | | H1047R | B_5701 | IEQNDARHF | 850 | 1041 | -2.00 | NDARH | 225 |
| | | H1047R | B_5701 | FGHRHHGGR | 851 | 1044 | -2.01 | RHHGG | 226 |
| P60484_R130G | PTEN_HUMAN | R130G | B_2705 | KQLAGKGGP | 852 | 123 | -2.01 | AGKGG | 227 |
| | Phos- | R130G | B_2705 | REWGRTGVE | 853 | 127 | -2.02 | GRTGV | 228 |
| | phatidylinositol | R130G | B_3801 | VHCAGKGGL | 854 | 123 | -2.03 | AGKGG | 229 |
| | 3 | R130G | B_3801 | MCWGKGGRA | 855 | 124 | -1.62 | GKGGR | 230 |
| | | R130G | B_3801 | ARQGRTGVS | 856 | 127 | -2.00 | GRTGV | 231 |
| | | R130G | B_4801 | KTWKGGRTL | 857 | 125 | -2.02 | KGGRT | 232 |
| | | R130G | B_4801 | FKCGRTGVL | 858 | 127 | -2.02 | GRTGV | 233 |
| | | R130G | B_5701 | NITAGKGGW | 859 | 123 | -2.00 | AGKGG | 234 |
| | | R130G | B_5701 | LSHKGGRTR | 860 | 125 | -2.02 | KGGRT | 235 |
| | | R130G | B_5701 | GGPGGRTGM | 861 | 126 | -2.02 | GGRTG | 236 |
| | | R130Q | B_2705 | DRTAGKGQE | 862 | 123 | -2.00 | AGKGQ | 237 |
| P60484_R130Q | PTEN_HUMAN | R130Q | B_3801 | LRKAGKGQP | 863 | 123 | -2.03 | AGKGQ | 238 |
| | Phos- | R130Q | B_3801 | LRTQRTGVP | 864 | 127 | -2.02 | QRTGV | 239 |
| | phatidylinositol | R130Q | B_4801 | GMFKGQRTL | 865 | 125 | -2.04 | KGQRT | 240 |
| | 3 | R130Q | B_4801 | PDLQRTGVL | 866 | 127 | -1.98 | QRTGV | 241 |
| | | R130Q | B_5701 | GDFAGKGQF | 867 | 123 | -2.04 | AGKGQ | 242 |
| | | R130Q | B_5701 | QANKGQRTL | 868 | 125 | -2.00 | KGQRT | 243 |
| | | R130Q | B_5701 | EGMGQRTGL | 869 | 126 | -2.00 | GQRTG | 244 |

TABLE 24

Exemplar peptides elicting CD4 T cell responses to
multi cancer mutated proteins for the indicated MHC II alleles

| Protein ID | Protein Curation | Mu-tation | Allele | Binding peptide | SEQ ID NO: | Pre-dicted binding | Posi-tion | TCEM | SEQ ID NO. |
|---|---|---|---|---|---|---|---|---|---|
| P00533_A289V | EGFR_HUMAN | A289V | DQB0302 | SSDAGKYSFGVLRLM | 870 | -2.11 | 279 | GKySfGV | 78 |
| | Epidermal growth | A289V | DQB0302 | GEQQKYSFGVAQNWC | 871 | -2.01 | 280 | KYsFgVA | 79 |
| | factor receptor | A289V | DQB0302 | RAEPSFGVATCGHFN | 872 | -2.00 | 282 | SFgVaTC | 80 |
| | OS_Homo sapiens | A289V | DQB0302 | AISKGVATCVKGKFV | 873 | -2.00 | 284 | GVAtcVK | 81 |
| | OX_9606 GN_EGFR | A289V | DQB0302 | MNCNVATCVKKACVF | 874 | -2.00 | 285 | VAtCyKK | 82 |
| | PE_1 SV_2 | A289V | DQB0602 | LDLLGKYSFGVSAPG | 875 | -1.90 | 279 | GKySfGV | 83 |
| | | A289V | DQB0602 | VVNRGVATCVKAVNE | 876 | -2.00 | 284 | GVAtcVK | 84 |
| | | A289V | DQB0602 | LFQKVATCVKKAESS | 877 | -2.00 | 285 | VAtCyKK | 85 |
| | | A289V | DRB1201 | RCHFGVATCVKTMDF | 878 | -1.50 | 284 | GVAtcVK | 86 |
| | | A289V | DRB3_0101 | IRRHSFGVATCELVC | 879 | -1.88 | 282 | SFgVaTC | 87 |
| | | A289V | DRB3_0101 | HSDHGVATCVKPMYT | 880 | -1.92 | 284 | GVAtcVK | 88 |
| P00533_L858R | EGFR_HUMAN | L858R | DQB0602 | LSTPITDFGRLAGHA | 881 | -2.04 | 849 | ITdFgRL | 89 |
| | Epidermal growth | L858R | DQB0602 | FDQKGRLAKLLTWIC | 882 | -1.52 | 853 | GR1AkLL | 90 |
| | factor receptor | L858R | DRB1201 | FVIWKITDFGRVKYN | 883 | -2.00 | 848 | KItDfGR | 91 |
| | OS_Homo sapiens | L858R | DRB1201 | IVSWITDFGRLWKRN | 884 | -2.02 | 849 | ITdFgRL | 92 |
| | OX_9606 GN_EGFR | L858R | DRB1201 | TLLMDFGRLAKRTMK | 885 | -2.02 | 851 | DFgRlAK | 93 |
| | PE_1 SV_2 | L858R | DRB1201 | SEMFGRLAKLLEYAI | 886 | -2.00 | 853 | GR1AkLL | 94 |
| | | L858R | DRB1201 | SQEIRLAKLLGYRSR | 887 | -2.01 | 854 | RLaKlLG | 95 |
| | | L858R | DRB3_0101 | SAYEKITDFGRKIVI | 888 | -2.00 | 848 | KItDfGR | 96 |
| | | L858R | DRB3_0101 | LGYEITDFGRLRVGY | 889 | -2.07 | 849 | ITdFgRL | 97 |
| | | L858R | DRB3_0101 | NKIFDFGRLAKRLII | 890 | -2.00 | 851 | DFgRlAK | 98 |
| P04626_R678Q | ERBB2_HUMAN | R678Q | DQB0602 | LNLLIKRQRQQPPNC | 891 | -1.55 | 671 | IKrQrQQ | 99 |
| | Receptor | R678Q | DRB1201 | LGVHGILIKRQACHC | 892 | -2.00 | 668 | GIlIkRQ | 100 |
| | tyrosine-protein | R678Q | DRB1201 | YMCLILIKRQRLTNR | 893 | -2.01 | 669 | ILiKrQR | 101 |
| | kinase erbB-2 | R678Q | DRB1201 | FALFIKRQRQQSQCW | 894 | -1.83 | 671 | IKrQrQQ | 102 |
| | OS_Homo sapiens | R678Q | DRB1201 | LIVWQRQQKIRALTE | 895 | -1.90 | 674 | QRqQkIR | 103 |
| | OX_9606 GN_ERBB2 | R678Q | DRB3_0101 | DAWYIKRQRQQRLTC | 896 | -2.02 | 671 | IKrQrQQ | 104 |
| | PE_1 SV_1 | R678Q | DRB3_0101 | PGLDRQRQQKIIVQD | 897 | -2.01 | 673 | RQrQqKI | 105 |
| | | R678Q | DRB3_0101 | GFKTQRQQKIRVFLE | 898 | -2.00 | 674 | QRqQkIR | 106 |
| P04626_S310F | ERBB2_HUMAN | S310F | DQB0302 | GVDVLSTDVGFQDIC | 899 | -2.02 | 300 | LStDvGF | 107 |
| | Receptor | S310F | DQB0302 | PGTSSTDVGFSGEFH | 900 | -2.00 | 301 | STdVgFS | 108 |
| | tyrosine-protein | S310F | DQB0302 | SENYDVGFSCTYDLV | 901 | -2.00 | 303 | DVgFsCT | 109 |
| | kinase erbB-2 | S310F | DQB0302 | GFGNGFSCTLVQHDT | 902 | -2.01 | 305 | GFsCtLV | 110 |
| | OS_Homo sapiens | S310F | DQB0602 | LALQLSTDVGFSAPS | 903 | -2.05 | 300 | LStDvGF | 111 |
| | OX_9606 GN_ERBB2 | S310F | DQB0602 | SNISSTDVGFSPLAV | 904 | -2.02 | 301 | STdVgFS | 112 |
| | PE_1 SV_1 | S310F | DQB0602 | SATVDVGFSCTDHLT | 905 | -2.00 | 303 | DVgFsCT | 113 |
| | | S310F | DQB0602 | AEILGFSCTLVATRS | 906 | -1.95 | 305 | GFsCtLV | 114 |
| | | S310F | DRB1201 | DHFFLSTDVGFRIER | 907 | -2.05 | 300 | LStDvGF | 115 |
| | | S310F | DRB1201 | LMRISTDVGFSVKVC | 908 | -2.09 | 301 | STdVgFS | 116 |
| | | S310F | DRB1201 | LSRMFSCTLVCQSGH | 909 | -2.02 | 306 | FSctlVC | 117 |
| | | S310F | DRB3_0101 | SSWELSTDVGFYSEI | 910 | -2.03 | 300 | LStDvGF | 118 |
| | | S310F | DRB3_0101 | STLYSTDVGFSYITG | 911 | -1.96 | 301 | STdVgFS | 119 |
| | | S310F | DRB3_0101 | IERKGFSCTLVTMIQ | 912 | -2.00 | 305 | GFsCtLV | 120 |
| P15056_V600E | BRAF_HUMAN | V600E | DQB0302 | ANKKEVKSRWSAQLC | 913 | -2.00 | 596 | EVkSrWS | 121 |
| | Serine_threonine- | V600E | DQB0602 | LCKSLATEVKSPFKQ | 914 | -2.01 | 593 | LAtEvKS | 122 |
| | protein kinase | V600E | DQB0602 | FNLLTEVKSRWPYCD | 915 | -1.60 | 595 | TEvKsRW | 123 |
| | B-raf OS_Homo | V600E | DQB0602 | AQLPEVKSRWSTDWE | 916 | -1.99 | 596 | EVkSrWS | 124 |
| | sapiens OX_9606 | V600E | DRB1201 | SVLRDFGLAIELYKI | 917 | -2.04 | 590 | DFgLaTE | 125 |
| | GN_BRAF PE_1 | V600E | DRB1201 | GMRYFGLAIEVPASM | 918 | -2.08 | 591 | FGlAtEV | 126 |
| | SV_4 | V600E | DRB1201 | CPFCIEVKSRWFLLK | 919 | -2.02 | 595 | TEvKsRW | 127 |
| P15056_V600M | BRAF_HUMAN | V600M | DQB0302 | PRHRFGLATMVCCTG | 920 | -2.05 | 591 | FGlAtMV | 128 |
| | Serine_threonine- | V600M | DQB0302 | DCQDLATMVKSVCSS | 921 | -2.03 | 593 | LAtMvKS | 129 |
| | protein kinase | | | | | | | | |
| | B-raf OS_Homo | V600M | DQB0302 | FRKTMVKSRWSRCLC | 922 | -2.05 | 596 | MVkSrWS | 130 |
| | sapiens OX_9606 | V600M | DQB0602 | LNPTLATMVKSLEES | 923 | -2.01 | 593 | LAtMvKS | 131 |
| | GN_BRAF PE_1 SV_4 | V600M | DQB0602 | LALLMVKSRWSTGEV | 924 | -1.91 | 596 | MVkSrWS | 132 |
| | | V600M | DRB1201 | NYGVDFGLATMLTHH | 925 | -2.02 | 590 | DFgLaTM | 133 |
| | | V600M | DRB1201 | KYISFGLATMVKNVD | 926 | -2.01 | 591 | FGlAtMV | 134 |
| | | V600M | DRB1201 | VCEILATMVKSYRLD | 927 | -2.03 | 593 | LAtMvKS | 135 |
| | | V600M | DRB1201 | LNELTMVKSRWLPLK | 928 | -2.02 | 595 | TMvKsRW | 136 |
| P42336_E545K | PIK3CA_HUMAN | E545K | DQB0302 | DGENEITKEQEQCLE | 929 | -1.80 | 538 | EItKeQE | 137 |
| | Phos- | E545K | DQB0602 | LYFSLSEITKELGQC | 930 | -1.93 | 536 | LSeItKE | 138 |
| | phatidylinositol | E545K | DQB0602 | LCLGKEQEKDFVARA | 931 | -2.01 | 541 | KEqEkDF | 139 |
| | 4 | E545K | DRB3_0101 | FILLEITKEQERVYC | 932 | -2.01 | 538 | EItKeQE | 140 |
| | | E545K | DRB3_0101 | SYWQTKEQEKDRLVT | 933 | -2.02 | 540 | TKeQeKD | 141 |
| | | E545K | DRB3_0101 | KNLDKEQEKDFIIII | 934 | -2.00 | 541 | KEqEkDF | 142 |

TABLE 24-continued

Exemplar peptides elicting CD4 T cell responses to
multi cancer mutated proteins for the indicated MHC II alleles

| Protein ID | Protein Curation | Mu-tation | Allele | Binding peptide | SEQ ID NO: | Pre-dicted binding | Posi-tion | TCEM | SEQ ID NO. |
|---|---|---|---|---|---|---|---|---|---|
| P42336_H1047R | PIK3CA_HUMAN | H1047R | DQB0602 | LDLTRHHGGWTASID | 935 | -1.98 | 1043 | RHhGgWT | 143 |
| | Phos- | H1047R | DRB3_0101 | DFNEKQMNDARYIIE | 936 | -2.00 | 1037 | KQmNdAR | 144 |
| | phatidylinositol | H1047R | DRB3_0101 | CPVVQMNDARHQLIV | 937 | -2.00 | 1038 | QMnDaRH | 145 |
| | 4 | H1047R | DRB3_0101 | KKYLNDARHHGIILV | 938 | -2.02 | 1040 | NDaRhHG | 146 |
| | | | | | | | | | |
| P60484_R130G | PTEN_HUMAN | R130G | DQB0302 | GQLRCKAGKGGYRPN | 939 | -2.00 | 120 | CKaGkGG | 147 |
| | Phos- | R130G | DQB0302 | LEENGKGGRTGPINC | 940 | -2.00 | 123 | GKgGrTG | 148 |
| | phatidylinositol | R130G | DQB0302 | NKEFGGRTGVMWCII | 941 | -2.04 | 125 | GGrTgVM | 149 |
| | 3 | R130G | DQB0302 | SNQDGRTGVMIMEID | 942 | -2.04 | 126 | GRtGyMI | 150 |
| | | R130G | DQB0602 | ICLLCKAGKGGSSES | 943 | -2.03 | 120 | CKaGkGG | 151 |
| | | R130G | DQB0602 | LVAQGKGGRTGLPIG | 944 | -2.06 | 123 | GKgGrTG | 152 |
| | | R130G | DQB0602 | LPAYGGRTGVMSYEG | 945 | -2.03 | 125 | GGrTgVM | 153 |
| | | R130Q | DQB0302 | TNNPCKAGKGQFEVW | 946 | -2.00 | 120 | CKaGkGQ | 154 |
| | | R130Q | DQB0302 | QFEKGKGQRTGGHVM | 947 | -2.01 | 123 | GKgQrTG | 155 |
| | | R130Q | DQB0302 | AELAGQRTGVMACYD | 948 | -1.76 | 125 | GQrTgVM | 156 |
| | | R130Q | DQB0302 | SQRLQRTGVMIPCFI | 949 | -2.00 | 126 | QRtGyMI | 157 |
| | | R130Q | DQB0602 | LVPTGKGQRTGAYYS | 950 | -1.97 | 123 | GKgQrTG | 158 |
| | | R130Q | DRB_1201 | SCIFKAGKGQRPHIT | 951 | -1.42 | 121 | KAgKgQR | 159 |
| | | R130Q | DRB3_0101 | FQRPGQRTGVMCMGM | 952 | -1.91 | 125 | GQrTgVM | 160 |
| | | R130Q | DRB3_0101 | LTQDQRTGVMIYDFC | 953 | -2.02 | 126 | QRtGyMI | 161 |

TCEM IIA motifs are shown with exposed amino acids in capital letters and hidden bound amino acids in lower case letters.

Example 8: Bespoke Peptides Spanning the Oncogenic Deletion in Epidermal Growth Factor Receptor viii (EGFRviii)

EGFR is upregulated in 54% pf glioblastomas [34]. Various deletion mutants are recognized with EGFRviii being the most common, and like EGFRvii being oncogenic. In EGFRviii exons 2 and 7 are deleted leading to removal of amino acids 6-273 of the mature protein; a glycine is inserted in the bridge and the downstream sequence remains in frame. The adverse effects of EGFRviii are well documented [34] An effort was made to use a peptide spanning the deletion junction as a vaccine. This peptide, comprising 14 amino acids comprises a B cell epitope and was viewed as a way of inducing antibody dependent cytotoxicity. Despite initially promising results, a large phase III trial of the vaccine used in combination with temozolomide failed to show any benefit. Patients were HLA typed but no significant associations in benefit were reported [28].

Upon closer examination of the unique T cell exposed motifs spanning the deletion junction in EGFRviii we noted that relatively few MEW I alleles bound at least one of the five possible unique T cell exposed motifs. Overall 31 of 70 MHC I alleles bound at less than ~500 nM (1 SD), comprising 17 binding sites among the 31 B alleles, 9 of 31 A allele and 5 of 8 C alleles evaluated had binding less than 500 nM at any of the possible T cell exposed motifs. In particular, no binding of A0201 was predicted. In addition, A0101, B4001 and B 1542 had predicted binding in excess of 2.75 SD below the mean equivalent of approximately 20 nM which may be an affinity so high it could induce suppression or exhaustion.

Therefore, EGFRviii is a candidate for a personalized peptide vaccine approach in which peptides are selected specifically for to optimize binding to a patient's alleles. Among the 70 alleles for which predicted binding was evaluated in the natural mutated EGFRviii, 65 alleles have some probability of presentation of the native epitope based on at least a low level of binding of the natural peptide. These are candidates for using a synthetic bespoke peptide to stimulate T cells which are cognate for and can therefore target these T cell exposed motifs. Following the process laid out in the prior examples we generated a set of 10,000 peptides for each of the possible T cell exposed positions ~~~EEKKG~(SEQ ID NO: 252), ~~~EKKGN~(SEQ ID NO: 246), ~~~KKGNY~(SEQ ID NO: 245), ~~~KGNYV~ (SEQ ID NO: 250), ~~~GNYVV~ (SEQ ID NO: 247).

Soluble peptides were selected, and those with binding affinity in two ranges of approximately -2.25 to -1.75 SD below the mean and -2.75 to -2.5 SD below the mean for all peptides in the protein, equivalent to approximately 25 nM and 50 nM selected. This binding affinity was selected from a range of affinities, other affinities could have been chosen for this example and thus this example is considered non limiting.

Table 25 shows the process of down selection of candidate peptides from the total simulated. Examples of peptides with selected predicted binding affinity are shown in Table 26 for a set of example alleles. These are assigned SEQ ID NOs.: 245-284.

TABLE 25

| Allele | Simulated peptides with above median binding of protein | TCEM presented | Available presented peptides | Soluble | Predicted binding −2.5 to −2.75 ~25 nM | Predicted binding −1.75-−2.25 ~50 nM |
|---|---|---|---|---|---|---|
| B0702 | 21507 | 2 | 12229 | 11685 | 112 | 793 |
| B3501 | 23863 | 2 | 9892 | 9892 | 69 | 524 |
| B4402 | 21851 | 2 | 8466 | 7930 | 273 | 397 |
| B5701 | 23521 | 2 | 7255 | 7255 | 65 | 165 |
| A0101 | 22473 | 3 | 15202 | 12359 | 125 | 636 |
| A0201 | 20727 | 1 | 3420 | 3420 | 37 | 153 |
| A2402 | 22574 | 2 | 11461 | 10828 | 58 | 850 |
| A6901 | 20524 | 1 | 4953 | 4410 | 91 | 324 |
| C0401 | 23755 | 2 | 10004 | 9683 | 47 | 488 |
| C0602 | 24416 | 3 | 16119 | 14895 | 164 | 969 |

TABLE 26

| Binding group | Allele | Peptide | SEQ ID NO: | Predicted binding in SD units | Polarity/ solubility | TCEM core amino acids | SEQ ID NO. |
|---|---|---|---|---|---|---|---|
| High | A0101 | LADKKGNYV | 954 | −2.59 | −1.09 | KKGNY | 245 |
| | A0101 | KASEKKGNY | 955 | −2.57 | −3.36 | EKKGN | 246 |
| | A0101 | DGDGNYVVS | 956 | −2.55 | −0.94 | GNYVV | 247 |
| | A0201 | KLAEKKGNV | 957 | −2.67 | −2.08 | EKKGN | 248 |
| | A2402 | QYTKKGNYF | 958 | −2.72 | −1.28 | KKGNY | 249 |
| | A2402 | KYTKGNYVW | 959 | −2.67 | −0.47 | KGNYV | 250 |
| | A6901 | ESDKGNYVC | 960 | −2.54 | −1.86 | KGNYV | 251 |
| | B0702 | APGEEKKGG | 961 | −2.66 | −2.93 | EEKKG | 252 |
| | B0702 | PPDKGNYVA | 962 | −2.64 | −1.09 | KGNYV | 253 |
| | B3501 | LLREEKKGF | 963 | −2.62 | −1.27 | EEKKG | 254 |
| | B3501 | FAMEKKGNY | 964 | −2.57 | −1.06 | EKKGN | 255 |
| | B4402 | ECRKGNYVE | 965 | −2.72 | −2.22 | KGNYV | 256 |
| | B4402 | PCQKKGNYV | 966 | −2.72 | −1.44 | KKGNY | 257 |
| | B5701 | LGDEKKGNF | 967 | −2.66 | −1.91 | EKKGN | 258 |
| | B5701 | PASEEKKGF | 968 | −2.65 | −2.25 | EEKKG | 259 |
| | C0401 | IRQKGNYVS | 969 | −2.65 | −1.19 | KGNYV | 260 |
| | C0401 | LWSEKKGNG | 970 | −2.64 | −1.70 | EKKGN | 261 |
| | C0602 | TKSKKGNYR | 971 | −2.74 | −3.66 | KKGNY | 262 |
| | C0602 | IRRGNYVVS | 972 | −2.66 | −0.17 | GNYVV | 263 |
| | C0602 | LKEEEKKGD | 973 | −2.23 | −4.15 | EEKKG | 264 |
| Medium | A0101 | RAEGNYVVR | 974 | −2.01 | −1.17 | GNYVV | 265 |
| | A0101 | MGEKKGNYD | 975 | −2.01 | −2.69 | KKGNY | 266 |
| | A0101 | TADEKKGNF | 976 | −2.01 | −2.64 | EKKGN | 267 |
| | A0201 | RLKEKKGNV | 977 | −1.99 | −2.86 | EKKGN | 268 |
| | A2402 | QLPKKGNYI | 978 | −2.00 | −0.74 | KKGNY | 269 |
| | A2402 | TKGKGNYVI | 979 | −2.00 | −0.74 | KGNYV | 270 |
| | A6901 | EVSKGNYVA | 980 | −2.00 | −0.81 | KGNYV | 271 |
| | B0702 | NVRKGNYVA | 981 | −1.99 | −1.06 | KGNYV | 272 |
| | B0702 | RTQEEKKGI | 982 | −1.99 | −3.40 | EEKKG | 273 |
| | B3501 | QSCEKKGNW | 983 | −2.00 | −2.55 | EKKGN | 274 |
| | B3501 | FPMEEKKGR | 984 | −1.99 | −2.28 | EEKKG | 275 |
| | B4402 | SEEKKGNYQ | 985 | −2.00 | −3.77 | KKGNY | 276 |
| | B4402 | LELKGNYVP | 986 | −2.00 | 0.34 | KGNYV | 277 |
| | B5701 | EGPEEKKGY | 987 | −2.00 | −3.27 | EEKKG | 278 |
| | B5701 | ISKEKKGNF | 988 | −1.99 | −2.18 | EKKGN | 279 |
| | C0401 | EHMKGNYVG | 989 | −2.01 | −1.03 | KGNYV | 280 |
| | C0401 | RELEKKGNA | 990 | −2.00 | −3.21 | EKKGN | 281 |
| | C0602 | AEHGNYVVT | 991 | −2.01 | −0.21 | GNYVV | 282 |
| | C0602 | TRVKKGNYS | 992 | −2.01 | −2.39 | KKGNY | 283 |
| | C0602 | WKEEEKKGR | 993 | −2.01 | −4.28 | EEKKG | 284 |

Example 9: Determination of HLA Haplotypes Determined from Whole Exome Sequences A 'BAM slice' of the exome file containing the HLA locus (GRch38=chr6:29722700-33143300) was used. The principles outlined for the Optitype [35] which focuses on the read matches to exons 2 and 3 of the MEW molecules was used in conjunction with the magicBLAST [36] aligner. magicBLAST has features that are particularly suited for this type of application. Optitype has been shown to be one of the most accurate methods [37] but only has prediction capabilities for MHC I and thus teaches away from MEW II typing. This general approach was modified as follows to provide MHC II typing also.

Figure 8:
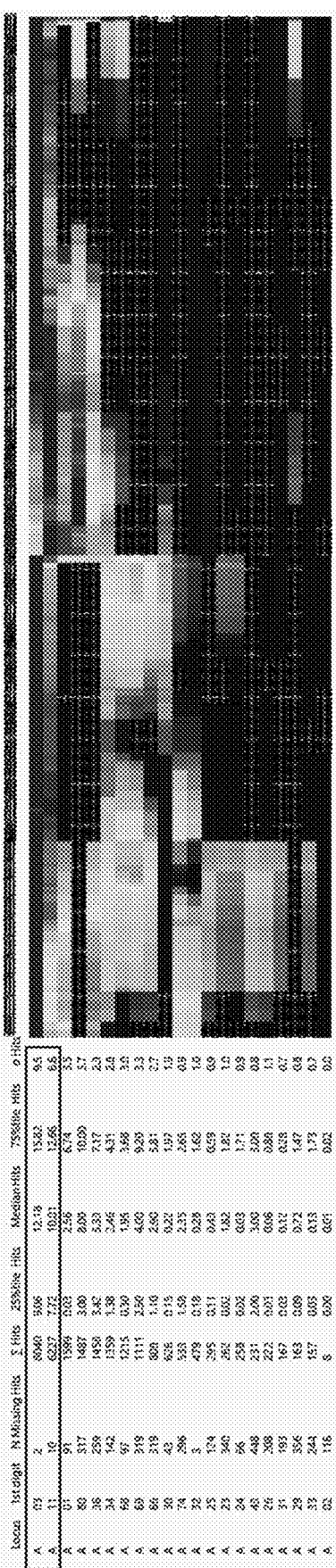
FIG. 8: Shows an example of determination of a subject's HLA alleles from a chromosome 6 BAM slice. MHC I ABC alleles and DRB1 showing sequential hits matching the IMGT database. Alleles shown in boxes are the clear highest matches for this individual. Figure shows 2 digits of HLA for space; four digit resolution was determined.
Figure 8:
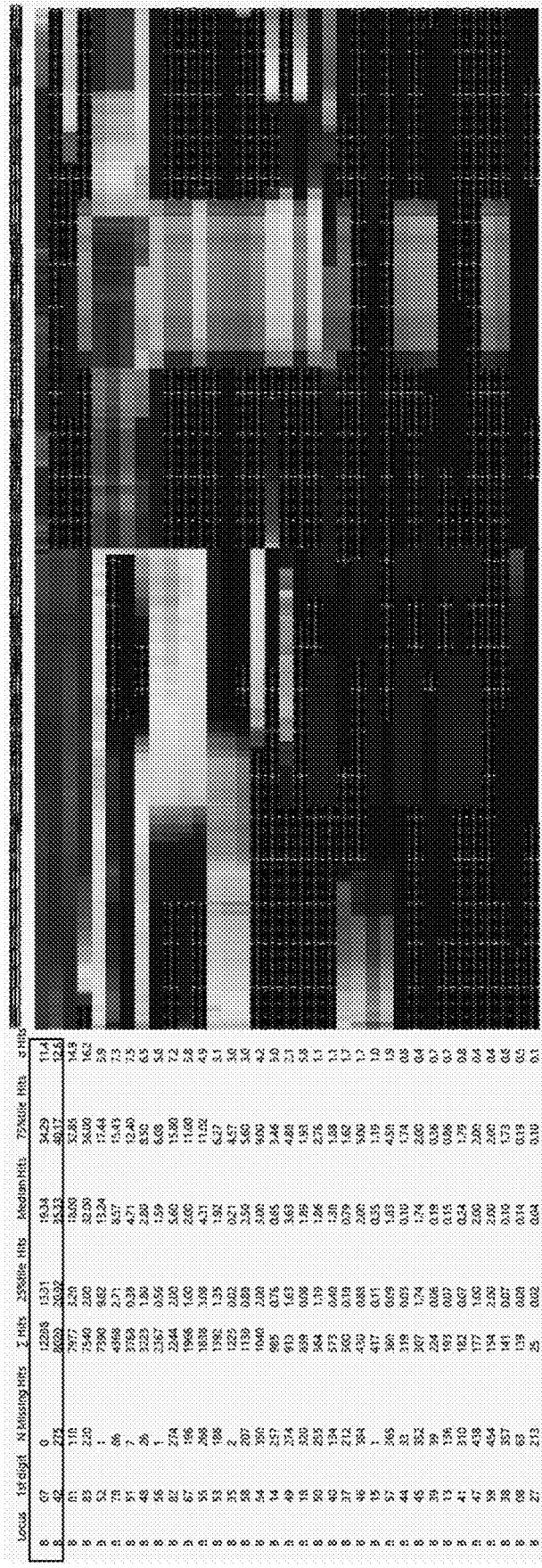

The BAM formatted 'slice' was converted to a fastq split read format required by magicBLAST using tools from GATK (Broad Institute). A special magicBLAST database for both MHC I and MEW II needed for the alignment process was created from the IMGT HLA sequence database (imgt.org). Exons 2 and 3 are each 270 nucleotides and code for the amino acid variations that form the basis of the different HLA haplotypes. A matrix 540×N (N=number of reads) was created and was used to tally the 100% read match at each nucleotide position produced by magicBLAST. The magicBLAST 100% alignment statistics in the matrix were then tallied across all reads and matched to the different MEW genotypes. Whereas Optitype uses a special integer linear programming approach with the hit matrix to assign the best fit HLA, we demonstrated that a simple tally of the hits in the matrix are adequate to clearly identify the haplotype of the exome data. FIG. 8 shows an example of the output.

Example 10: Fusion Peptide Constructs

Peptides when delivered alone are usually poor immunogens. This can be overcome by delivery with an adjuvant, as described above. An alternative approach is to deliver selected peptides linked to a fusion partner which tends to facilitate nanoparticle formation, enhancing uptake by macrophages and dendritic cells. The design of such a peptide-linker-fusion partner combination must ensure that the selected peptide is excised precisely within the macrophage, dendritic cell or other antigen presenting cell to ensure that the intended binding register that exposes the desired T cell exposed motif. Several different linkers may be used, including but not limited to single amino acids, amino acid multimers, elastin, and cathepsin cleavable linkers. In one embodiment lysine and arginine residues are used which are readily cleaved by trypsin. An alternative, but more complex, approach is to design the selected peptide to terminate at a cathepsin cleavage site. Typically, an octomer must be considered that places the cathepsin scissile bond between amino acids 4 and 5 of that octomer. The fusion partner may be a polyhydrophobic amino acid peptide. In some embodiments a polyleucine may be used. Other hydrophobic amino acids maybe used in place of leucine, including but not limited to phenylalanine, isoleucine or tryptophan. Alternatively, various hydrophobic unnatural amino acids may be linked to as the fusion partner. In some embodiments a lipid core peptide system comprising a lipoamino acid (LAA) moiety may be used to favor nanoparticle formation, facilitating uptake by antigen presenting cells. Other approaches to nanoparticle delivery may also be used in which the selected peptides are incorporated in liposomes or virosomes [38-41].

In another approach to enhancing uptake of neoepitope peptides of interest by antigen presenting cells the peptides, including the bespoke peptide antigens, may be linked to an immunoglobulin or to an immunoglobulin Fc region.

In preferred embodiments the selected peptide fusion constructs comprise one T cell stimulating peptide of interest. In yet other embodiments several T cell epitope peptides may be linked by linkers and attached to one fusion partner. In yet other embodiments one or more T cell stimulating peptides of interest may be linked to a B cell epitope peptide as a fusion partner.

Example 11: Analysis of Glioblastoma and Lung Cancer Cases

Two sets of cancer cases were analyzed comprising 30 glioblastoma (GBM) and 30 squamous cell lung cancer cases (LUSC), for which all mutated protein sequences were downloaded from the Genome Data Commons which records the mutations in TCGA. As the mutations recorded in TCGA reflect the mutations detected in clinically presenting patients, they can be considered the "surviving mutations" which have not been previously eliminated by immune surveillance or by having rendered the cell apoptotic. Mutated proteins were designated as oncogenes, tumor suppressors, or passengers based on the application of that designation by Vogelstein et al [42] and each was aligned to its normal counterpart sequences. Pairs of mutated and unmutated protein sequences were created and analyzed to determine predicted MHC binding, location of B cell linear epitopes, topology and predicted cathepsin cleavage sites as previously described [43-47]. Binding affinities were predicted for all peptide registers for each of 70 MHC class I alleles in loci A, B, and C and 70 class II alleles in loci DR, DQ and DP. Frequency of T cell exposed motifs was determined relative to both the human immunoglobulinome and the complete human proteome [44, 45]. This was done for both MHC I TCEM and MHC II TCEM. There was no significant difference observed in the patterns of TCEM frequency or topology between GBM and LUSC; tumor proteins of both sets of cases behaved similarly. Several salient observations were made upon further analysis.

Figure 9A:
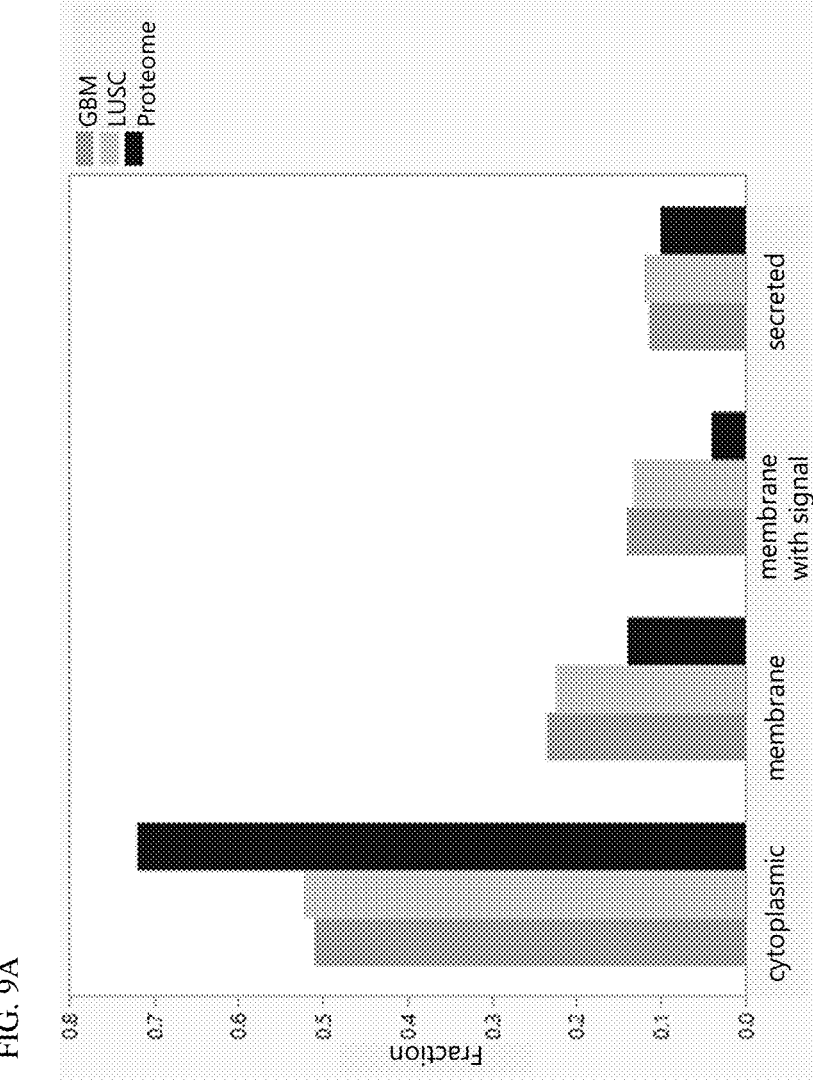
FIG. 9A-B: Distribution of tumor mutations in protein topological domains. A: Relative fraction of proteins of four different topological types in two different cancers. Compared to the distribution in the human proteome (red, hg19 including all isoforms). The data is combined from 30 cases each of GBM (blue) and LUSC (yellow). B: Distribution of mutations in protein domains for a) all mutated proteins b) oncogenes and c) tumor suppressors in the intracellular (i), membrane (m) extracellular (o) and secreted (sp) domains relative to the length of each domain. The Y axis indicates the domain length as C—N (C-terminal minus N-terminal) positions of the amino acid within the protein molecules.
Figure 9B:
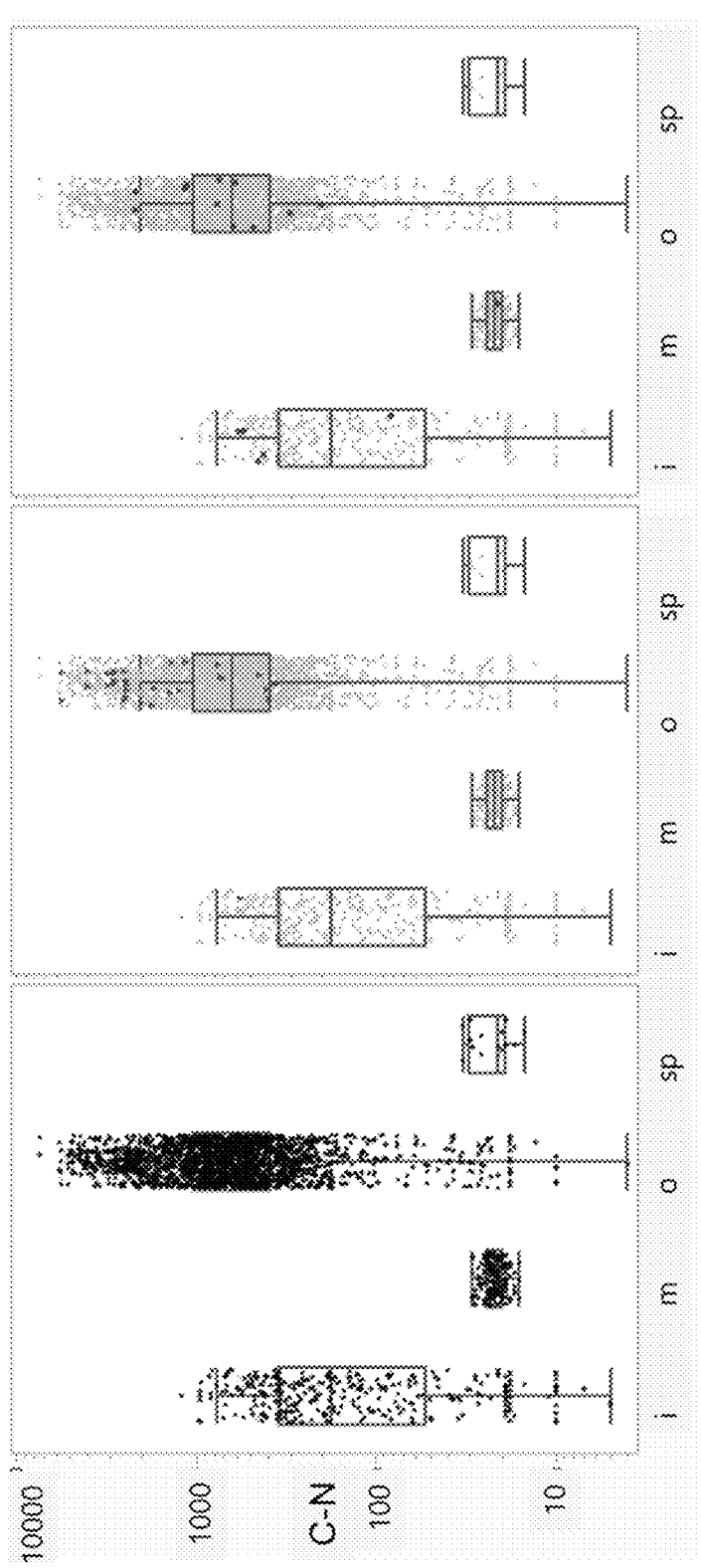
Figure 10:
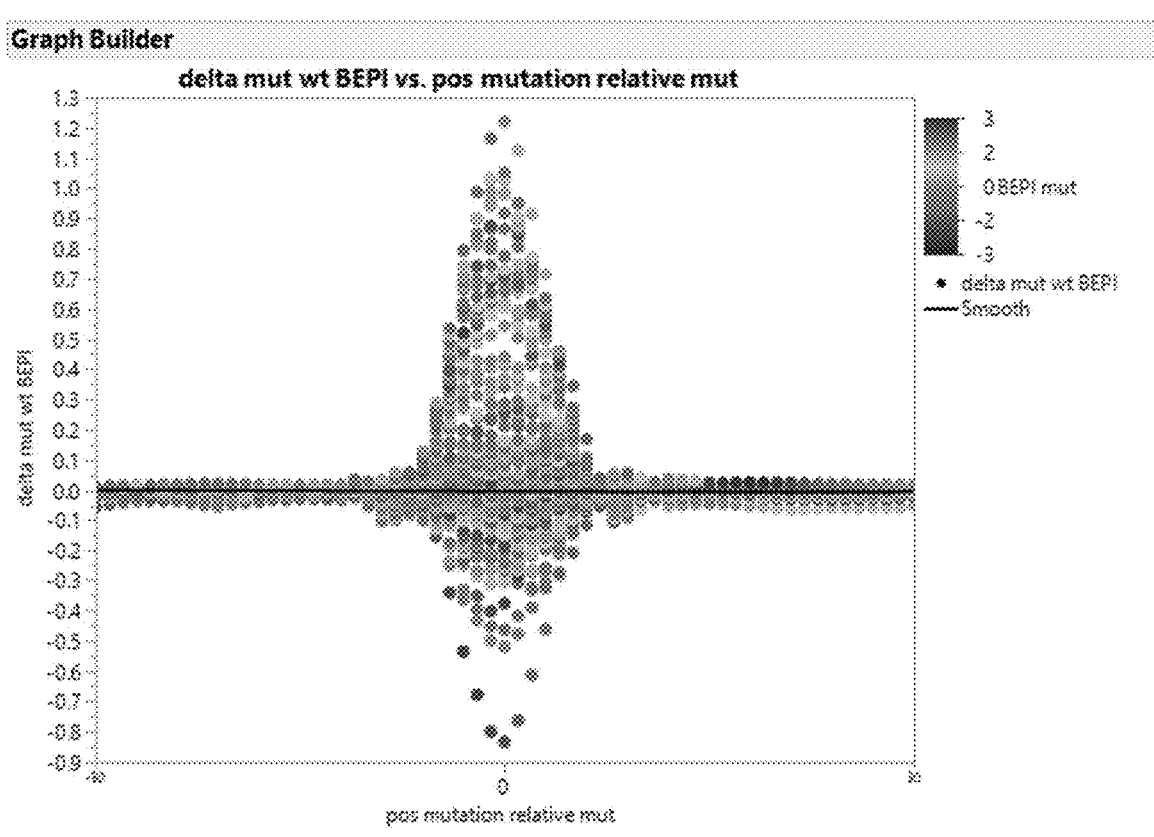
FIG. 10: Shows the creation of new higher probability B cell epitopes in one LUSC case example. Mutation positions in the 104 mutated proteins in this case were centered at zero. The Y axis shows the difference in the probability that a mutant vs a wildtype peptide 9mer centered at each position comprises part of a B cell epitope (in standard deviation units). The highest probability B cell epitopes are colored blue. Hence the graphic shows that for some proteins the mutation created new prominent B cell epitopes, whereas in other proteins there is a reduction in B cell epitope probability.

In the proteins with transmembrane domains, the mutations were more likely to be present in extracellular domains than in the portions of those proteins located in the cytoplasm. This is shown in FIG. 9, where it is seen that, among the mutated tumor proteins, the ratio of cytoplasmic to membrane or extracellular domain proteins is reversed as compared to the distribution in the proteome as a whole. As also shown in FIG. 1 in those proteins with extracellular domains and transmembrane domains, the mutations are more likely to be in the extracellular domain. This is the case for oncogenes, tumor suppressor proteins and proteins with passenger mutations alike of both GBM and LUSC cases. In addition, many of the mutated proteins have very extensive extracellular domain segments. As a result tumor proteins are more likely than the proteome as a whole to have exposed B cell epitopes, which in some cases comprised the mutated amino acid and in other instances were in close proximity to T cell epitopes with mutated amino acids, providing a unique immunologic signal. In some proteins the mutations generate de novo high probability B cell epitopes as shown in FIG. 10.

In 60% of cases, peptides which comprised mutant amino acids were not predicted to be in the top 15% of highest MHC binding affinity for either MHC I or MHC II alleles. Mutated amino acids only affected binding when they occurred in pocket position. In the case of MHC I this was particularly marked when the mutant amino acid was in pocket position 2 or 9, as shown in FIG. 11.

Mutations consistently generated motifs which were absent or less frequent in the total human proteome database than in their non mutated normal counterparts. This is shown in FIG. 12 where the residuals are all outside the 95% boundary of the regression.

These findings confirmed the observations in individual cancer patients cited in prior examples by demonstrating that mutations present in tumor proteins by the time of clinical diagnosis have developed several means of camouflage from immune surveillance and elimination and that strategies to overcome such camouflage must be employed to achieve effective immunotherapy. The present invention provides such strategies by devising means to expose and present the tumor specific peptides to T cell recognition on as many MEW alleles as possible, and by utilizing the B cell epitopes also exposed.

Example 12: Immunopathologies

The ability to generate bespoke peptides to "tune" the T cell response of an individual subject of known HLA has applications outside the field of cancer immunology. Immunomodulation of excessive T cell responses can assist in the management of allergy and autoimmune diseases and other immunopathologies. To investigate this, we generated bespoke peptides for a commonly recognized peanut allergen Ara h6 and for two proteins recognized as drivers of rheumatoid arthritis. In both cases the goal was to design peptides which could down regulate CD4+T helper cells.

Based on Genome Wide association studies there is evidence that peanut allergies may be linked to both DRB1 and DQB alleles [48, 49]. We modelled the design of novel peptides around the dominant T helper motif in ara6 h to create peptides with very high binding to DRB_1_0101 and DQA1_0101 DQB1_0501. The choice of these alleles is not considered limiting as a similar approach could be used to generate peptides if a desired binding affinity for any of the DQA DQB combinations or any DRB allele.

Peanut Ara h6

The ara h6 protein contains a number of T cell exposed motifs which are very rare in the human proteome and in the gastrointestinal microbiome. This is not unusual in proteins of allergens and it appears that the exposure of an individual to a sudden large pulse of such rare antigens has the effect of triggering an allergic reaction. This is in contradistinction to the previously cited situation in cancer where a single rare motif may be present but evade immune surveillance.

Table 27 provides non limiting examples of peptides with enhanced binding to various MEW II alleles (examples shown are nonlimiting), demonstrating and increase of approximately 2 standard deviations in predicted binding affinity over the natural peptide at that position. Such very high affinity binding peptides would be expected to induce exhaustion and anergy of the cognate T cell clonal population.

Proteins Associated with Rheumatoid Arthritis

The two proteins we examined are vimentin and Alpha enolase. In both cases peptides have been identified which are drivers of the autoimmune reaction when citrullinated at specific arginine residues [50-52]. Rheumatoid arthritis is predominantly found in individuals who carry the DRB1_0401 allele [53, 54]. Our goal was therefore to design peptides which would retain a T cell exposed motif that exposes the citrullinated residue to the T cell receptor, while modifying the flanking regions to create a very high binding peptide capable to leading to exhaustion and anergy of the T cell response. While the example shows design of high biding peptides for DRB1_0401 given that RA is the example of interest, for other autoimmune conditions other alleles may be relevant and thus the example is not considered limiting.

Table 28 shows the increased binding achieved by designing peptides to expose the citrullinated residues but alter amino acids in the flanking regions. An approximately two standard deviation unit increase in binding is achieved, making the bespoke peptides "super binders" likely to induce exhaustion and anergy of the corresponding Th clones

TABLE 27

| Allele | Index amino acid | original binding SD units | original peptide | SEQ ID NO: | Enhanced binding SD units | bespoke peptide | SEQ ID NO: | TCEM IIa | SEQ ID NO: |
|---|---|---|---|---|---|---|---|---|---|
| DRB1_0101 | 117 | −1.23 | FKRELMNLPQQCNFR | 994 | −3.81 | LNRLLMNLPQQATLI | 1013 | LM~L~QQ | 1032 |
| DRB1_0101 | 116 | −0.97 | QFKRELMNLPQQCNF | 995 | −3.31 | IRQLELMNLPQIYLN | 1014 | EL~N~PQ | 1033 |
| DRB1_0101 | 115 | −0.54 | QQFKRELMNLPQQCN | 996 | −2.88 | MIRLRELMNLPVARC | 1015 | RE~M~LP | 1034 |
| DRB1_0101 | 48 | −0.51 | EQHIMQRIMGEQEQY | 997 | −2.78 | VQAMMQRIMGELLLE | 1016 | MQ~I~GE | 1035 |
| DRB1_0101 | 116 | −0.97 | QFKRELMNLPQQCNF | 998 | −2.76 | RQMQELMNLPQLILI | 1017 | EL~N~PQ | 1036 |
| DRB1_0101 | 88 | −0.34 | NTQRCMCEALQQIME | 999 | −2.73 | MQFMCMCEALQALLV | 1018 | CM~E~LQ | 1037 |
| DRB1_0401 | 115 | −0.87 | QQFKRELMNLPQQCN | 1000 | −3.66 | PMLLRELMNLPRTRR | 1019 | RE~M~LP | 1038 |
| DRB1_0401 | 117 | −0.88 | FKRELMNLPQQCNFR | 1001 | −3.46 | LILLLMNLPQQNTVN | 1020 | LM~L~QQ | 1039 |
| DRB1_0401 | 116 | −0.78 | QFKRELMNLPQQCNF | 1002 | −3.16 | FLIFELMNLPQMRNI | 1021 | EL~N~PQ | 1040 |
| DRB1_0401 | 45 | −1.10 | KPCEQHIMQRIMGEQ | 1003 | −2.81 | IMFLQHIMQRIELQY | 1022 | QH~M~RI | 1041 |
| DRB1_0401 | 48 | −1.66 | EQHIMQRIMGEQEQY | 1004 | −2.75 | LRMLMQRIMGENQRV | 1023 | MQ~I~GE | 1042 |
| DQA1_0101-DQB1_0501 | 47 | −1.14 | CEQHIMQRIMGEQEQ | 1005 | −3.46 | RELQIMQRIMGAVLC | 1024 | IM~R~MG | 1043 |
| DQA1_0101-DQB1_0501 | 46 | −2.34 | PCEQHIMQRIMGEQE | 1006 | −3.33 | LHQRHIMQRIMAQVF | 1025 | HI~Q~IM | 1044 |
| DQA1_0101-DQB1_0501 | 45 | −1.23 | KPCEQHIMQRIMGEQ | 1007 | −3.08 | LQVDQHIMQRISCLM | 1026 | QH~M~RI | 1045 |
| DQA1_0101-DQB1_0501 | 113 | −1.01 | MVQQFKRELMNLPQQ | 1008 | −2.97 | NIILFKRELMNMHQC | 1027 | FK~E~MN | 1046 |

TABLE 27-continued

| Allele | Index amino acid | original binding SD units | original peptide | SEQ ID NO: | Enhanced binding SD units | bespoke peptide | SEQ ID NO: | TCEM IIa | SEQ ID NO: |
|---|---|---|---|---|---|---|---|---|---|
| DQA1_0101-DQB1_0501 | 116 | -0.65 | QFKRELMNLPQQCNF | 1009 | -2.44 | CCVQELMNLPQRCAA | 1028 | EL~N~PQ | 1047 |
| DQA1_0102-DQB1_0602 | 47 | -0.64 | CEQHIMQRIMGEQEQ | 1010 | -2.92 | MIMMIMQRIMGSVCG | 1029 | IM~R~MG | 1048 |
| DQA1_0102-DQB1_0602 | 45 | -0.40 | KPCEQHIMQRIMGEQ | 1011 | -2.64 | GCACQHIMQRIPCAR | 1030 | QH~M~RI | 1049 |
| DQA1_0102-DQB1_0602 | 46 | -0.62 | PCEQHIMQRIMGEQE | 1012 | -2.50 | CCSIHIMQRIMALAD | 1031 | HI~Q~IM | 1050 |

TABLE 28

| Index amino acid | curation | original binding to DRB1_0401 SD units | original peptide | SEQ ID NO: | Enhanced binding to DRB1_0401 SD units | bespoke peptide | SEQ ID NO: | TCEM IIA Core | SEQ ID NO: |
|---|---|---|---|---|---|---|---|---|---|
| 5 | alpha- | -1.19 | KIHAREIFDSXGNPT | 1051 | -3.02 | PLIFREIFDSXGVQI | 1065 | RE~F~SX | 1079 |
| 8 | enolase | -1.51 | AREIFDSXGNPTVEV | 1052 | -3.79 | KLIFFDSXGNPTADM | 1066 | FD~X~NP | 1080 |
| 8 | isoform 1 | -1.51 | AREIFDSXGNPTVEV | 1053 | -2.99 | DFNFFDSXGNPSASL | 1067 | FD~X~NP | 1081 |
| 25 | | -0.33 | FTSKGLFXAAVPSGA | 1054 | -3.05 | QLLFGLFXAAVLTKH | 1068 | GL~X~AV | 1082 |
| 27 | | -1.90 | SKGLFXAAVPSGAST | 1055 | -3.62 | ALQYFXAAVPSSGLM | 1069 | FX~A~PS | 1083 |
| 28 | | -1.98 | KGLFXAAVPSGASTG | 1056 | -2.67 | VIIFXAAVPSGGGLI | 1070 | XA~V~SG | 1084 |
| 57 | Vimentin | -0.96 | PGGVYATXSSAVXLX | 1057 | -3.09 | KQQYYATXSSAGSLF | 1071 | YA~X~SA | 1085 |
| 60 | | -0.10 | VYATXSSAVXLXSSV | 1058 | -2.88 | NAFFXSSAVXLGLST | 1072 | XS~A~XL | 1086 |
| 64 | | -0.03 | XSSAVXLXSSVPGVR | 1059 | -2.84 | RAILVXLXSSVKAQI | 1073 | VX~X~SV | 1087 |
| 65 | | -0.78 | SSAVXLXSSVPGVRL | 1060 | -2.91 | EMLWXLXSSVPGTQD | 1074 | XL~S~VP | 1088 |
| 66 | | -1.41 | SAVXLXSSVPGVRLL | 1061 | -2.91 | TLEWLXSSVPGSGLP | 1075 | LX~S~PG | 1089 |
| 414 | | -2.40 | PLPNFSSLNLXETNL | 1062 | -3.70 | PFYVFSSLNLXNNVA | 1076 | FS~L~LX | 1090 |
| 417 | | -1.27 | NFSSLNLXETNLDSL | 1063 | -3.86 | QLIWLNLXETNIQTA | 1077 | LN~X~TN | 1091 |
| 419 | | -1.64 | SSLNLXETNLDSLPL | 1064 | -2.99 | YQILLXETNLDDAPM | 1078 | LX~T~LD | 1092 |

Citrullinated amino acids represented by X

1. Lefranc M P, Giudicelli V, Ginestoux C, Jabado-Michaloud J, Folch G, Bellahcene F, et al. IMGT, the international ImMunoGeneTics information system. Nucleic acids research. 2009; 37(Database issue):D1006-12. Epub 2008/11/04. doi: 10.1093/nar/gkn838. PubMed PMID: 18978023; PubMed Central PMCID: PMC2686541.

2. Hanahan D, Weinberg R A. Hallmarks of cancer: the next generation. Cell. 2011; 144(5):646-74. Epub 2011/03/08. doi: 10.1016/j.cell.2011.02.013. PubMed PMID: 21376230.

3. Chen D S, Mellman I. Elements of cancer immunity and the cancer-immune set point. Nature. 2017; 541(7637): 321-30. Epub 2017/01/20. doi: 10.1038/nature21349. PubMed PMID: 28102259.

4. Adusumilli P S, Cha E, Cornfeld M, Davis T, Diab A, Dubensky T W, Jr., et al. New Cancer Immunotherapy Agents in Development: a report from an associated program of the 31(st) Annual Meeting of the Society for Immunotherapy of Cancer, 2016. J Immunother Cancer. 2017; 5:50. Epub 2017/06/27. doi: 10.1186/s40425-017-0253-2. PubMed PMID: 28649381; PubMed Central PMCID: PMCPMC5477277.

5. Ilyas S, Yang J C. Landscape of Tumor Antigens in T Cell Immunotherapy. J Immunol. 2015; 195(11):5117-22. Epub 2015/11/22. doi: 10.4049/jimmunol.1501657. PubMed PMID: 26589749; PubMed Central PMCID: PMCPMC4656134.

6. Aldous A R, Dong J Z. Personalized neoantigen vaccines: A new approach to cancer immunotherapy. Bioorg Med Chem. 2018; 26(10):2842-9. Epub 2017/11/08. doi: 10.1016/j.bmc.2017.10.021. PubMed PMID: 29111369.

7. Ophir E, Bobisse S, Coukos G, Harari A, Kandalaft L E. Personalized approaches to active immunotherapy in cancer. Biochim Biophys Acta. 2016; 1865(1):72-82. Epub 2015/08/05. doi: 10.1016/j.bbcan.2015.07.004. PubMed PMID: 26241169.

8. Fennemann F L, de Vries I J M, Figdor C G, Verdoes M. Attacking Tumors From All Sides: Personalized Multiplex Vaccines to Tackle Intratumor Heterogeneity. Frontiers in immunology. 2019; 10:824. Epub 2019/05/02. doi: 10.3389/fimmu.2019.00824. PubMed PMID: 31040852; PubMed Central PMCID: PMCPMC6476980.

9. Ott P A, Hu Z, Keskin D B, Shukla S A, Sun J, Bozym D J, et al. An immunogenic personal neoantigen vaccine for patients with melanoma. Nature. 2017; 547(7662): 217-21. Epub 2017/07/06. doi: 10.1038/nature22991. PubMed PMID: 28678778; PubMed Central PMCID: PMCPMC5577644.

10. Sahin U, Derhovanessian E, Miller M, Kloke B P, Simon P, Lower M, et al. Personalized RNA mutanome vaccines mobilize poly-specific therapeutic immunity against cancer. Nature. 2017; 547(7662):222-6. Epub 2017/07/06. doi: 10.1038/nature23003. PubMed PMID: 28678784.

11. Li F, Chen C, Ju T, Gao J, Yan J, Wang P, et al. Rapid tumor regression in an Asian lung cancer patient following personalized neo-epitope peptide vaccination. Onco-immunology. 2016; 5(12):e1238539. Epub 2017/01/27. doi: 10.1080/2162402X.2016.1238539. PubMed PMID: 28123873; PubMed Central PMCID: PMCPMC5214696.

12. Hilf N, Kuttruff-Coqui S, Frenzel K, Bukur V, Stevanovic S, Gouttefangeas C, et al. Actively personalized vaccination trial for newly diagnosed glioblastoma. Nature. 2019; 565(7738):240-5. Epub 2018/12/21. doi: 10.1038/s41586-018-0810-y. PubMed PMID: 30568303.

13. Keskin D B, Anandappa A J, Sun J, Tirosh I, Mathewson N D, Li S, et al. Neoantigen vaccine generates intratumoral T cell responses in phase Ib glioblastoma trial. Nature. 2019; 565(7738):234-9. Epub 2018/12/21. doi: 10.1038/s41586-018-0792-9. PubMed PMID: 30568305.

14. Rabizadeh S, Garner C, Sanborn J Z, Benz S C, Reddy S, Soon-Shiong P. Comprehensive genomic transcriptomic tumor-normal gene panel analysis for enhanced precision in patients with lung cancer. Oncotarget. 2018; 9(27):19223-32. Epub 2018/05/04. doi: 10.18632/oncotarget.24973. PubMed PMID: 29721196; PubMed Central PMCID: PMCPMC5922390.

15. Yadav M, Jhunjhunwala S, Phung Q T, Lupardus P, Tanguay J, Bumbaca S, et al. Predicting immunogenic tumour mutations by combining mass spectrometry and exome sequencing. Nature. 2014; 515(7528):572-6. Epub 2014/11/28. doi: 10.1038/nature14001. PubMed PMID: 25428506.

16. Abelin J G, Keskin D B, Sarkizova S, Hartigan C R, Zhang W, Sidney J, et al. Mass Spectrometry Profiling of HLA-Associated Peptidomes in Mono-allelic Cells Enables More Accurate Epitope Prediction. Immunity. 2017; 46(2):315-26. Epub 2017/02/24. doi: 10.1016/j.immuni.2017.02.007. PubMed PMID: 28228285; PubMed Central PMCID: PMCPMC5405381.

17. Hoof I, Peters B, Sidney J, Pedersen L E, Sette A, Lund 0, et al. NetMHCpan, a method for MHC class I binding prediction beyond humans. Immunogenetics. 2009; 61(1): 1-13. doi: 10.1007/s00251-008-0341-z [doi].

18. Havel J J, Chowell D, Chan T A. The evolving landscape of biomarkers for checkpoint inhibitor immunotherapy. Nature reviews Cancer. 2019; 19(3):133-50. Epub 2019/ 02/14. doi: 10.1038/s41568-019-0116-x. PubMed PMID: 30755690.

19. Mandal R, Samstein R M, Lee K W, Havel J J, Wang H, Krishna C, et al. Genetic diversity of tumors with mismatch repair deficiency influences anti-PD-1 immunotherapy response. Science. 2019; 364(6439):485-91. Epub 2019/05/03. doi: 10.1126/science.aau0447. PubMed PMID: 31048490.

20. Gibney G T, Weiner L M, Atkins M B. Predictive biomarkers for checkpoint inhibitor-based immunotherapy. The lancet oncology. 2016; 17(12):e542-e51. Epub 2016/12/08. doi: 10.1016/S1470-2045(16)30406-5. PubMed PMID: 27924752; PubMed Central PMCID: PMCPMC5702534.

21. Bajwa R, Cheema A, Khan T, Amirpour A, Paul A, Chaughtai S, et al. Adverse Effects of Immune Checkpoint Inhibitors (Programmed Death-1 Inhibitors and Cytotoxic T-Lymphocyte-Associated Protein-4 Inhibitors): Results of a Retrospective Study. J Clin Med Res. 2019; 11(4):225-36. Epub 2019/04/03. doi: 10.14740/jocmr3750. PubMed PMID: 30937112; PubMed Central PMCID: PMCPMC6436564.

22. Gubin M M, Zhang X, Schuster H, Caron E, Ward J P, Noguchi T, et al. Checkpoint blockade cancer immunotherapy targets tumour-specific mutant antigens. Nature. 2014; 515(7528):577-81. Epub 2014/11/28. doi: 10.1038/ nature13988. PubMed PMID: 25428507; PubMed Central PMCID: PMCPMC4279952.

23. Bailey M H, Tokheim C, Porta-Pardo E, Sengupta S, Bertrand D, Weerasinghe A, et al. Comprehensive Characterization of Cancer Driver Genes and Mutations. Cell. 2018; 173(2):371-85 e18. Epub 2018/04/07. doi: 10.1016/ j.cell.2018.02.060. PubMed PMID: 29625053; PubMed Central PMCID: PMCPMC6029450.

24. Chang M T, Asthana S, Gao S P, Lee B H, Chapman J S, Kandoth C, et al. Identifying recurrent mutations in cancer reveals widespread lineage diversity and mutational specificity. Nat Biotechnol. 2016; 34(2):155-63. Epub 2015/12/01. doi: 10.1038/nbt.3391. PubMed PMID: 26619011; PubMed Central PMCID: PMCPMC4744099.

25. Kandoth C, McLellan M D, Vandin F, Ye K, Niu B, Lu C, et al. Mutational landscape and significance across 12 major cancer types. Nature. 2013; 502(7471):333-9. Epub 2013/10/18. doi: 10.1038/nature12634. PubMed PMID: 24132290; PubMed Central PMCID: PMCPMC3927368.

26. Tamborero D, Gonzalez-Perez A, Perez-Llamas C, Deu-Pons J, Kandoth C, Reimand J, et al. Comprehensive identification of mutational cancer driver genes across 12 tumor types. Scientific reports. 2013; 3:2650. Epub 2013/ 10/03. doi: 10.1038/srep02650. PubMed PMID: 24084849; PubMed Central PMCID: PMCPMC3788361.

27. Kim H, Kim Y M. Pan-cancer analysis of somatic mutations and transcriptomes reveals common functional gene clusters shared by multiple cancer types. Scientific reports. 2018; 8(1):6041. Epub 2018/04/18. doi: 10.1038/ s41598-018-24379-y. PubMed PMID: 29662161; PubMed Central PMCID: PMCPMC5902616.

28. Weller M, Butowski N, Tran D D, Recht L D, Lim M, Hirte H, et al. Rindopepimut with temozolomide for patients with newly diagnosed, EGFRvIII-expressing glioblastoma (ACT IV): a randomised, double-blind, international phase 3 trial. The lancet oncology. 2017; 18(10):1373-85. Epub 2017/08/29. doi: 10.1016/51470-2045(17)30517-X. PubMed PMID: 28844499.

29. Cohen C J, Gartner J J, Horovitz-Fried M, Shamalov K, Trebska-McGowan K, Bliskovsky V V, et al. Isolation of neoantigen-specific T cells from tumor and peripheral lymphocytes. J Clin Invest. 2015; 125(10):3981-91. Epub 2015/09/22. doi: 10.1172/JCI82416. PubMed PMID: 26389673; PubMed Central PMCID: PMCPMC4607110.

30. Lauvau G, Soudja S M. Mechanisms of Memory T Cell Activation and Effective Immunity. Adv Exp Med Biol. 2015; 850:73-80. Epub 2015/09/02. doi: 10.1007/978-3-319-15774-0_6. PubMed PMID: 26324347; PubMed Central PMCID: PMCPMC4836952.

31. Zehn D, Lee S Y, Bevan M J. Complete but curtailed T-cell response to very low-affinity antigen. Nature. 2009; 458(7235):211-4. Epub 2009/02/03. doi: 10.1038/nature07657. PubMed PMID: 19182777; PubMed Central PMCID: PMCPMC2735344.

32. Soudja S M, Chandrabos C, Yakob E, Veenstra M, Palliser D, Lauvau G. Memory-T-cell-derived interferon-gamma instructs potent innate cell activation for protective immunity. Immunity. 2014; 40(6):974-88. Epub 2014/06/17. doi: 10.1016/j.immuni.2014.05.005. PubMed PMID: 24931122; PubMed Central PMCID: PMCPMC4105986.

33. Wucherpfennig K W, Allen P M, Celada F, Cohen I R, De Boer R, Garcia K C, et al. Polyspecificity of T cell and B cell receptor recognition. Seminars in immunology. 2007; 19(4):216-24. Epub 2007/04/03. doi: 10.1016/ j.smim.2007.02.012. PubMed PMID: 17398114; PubMed Central PMCID: PMC2034306.

34. An Z, Aksoy O, Zheng T, Fan Q W, Weiss W A. Epidermal growth factor receptor and EGFRvIII in glioblastoma: signaling pathways and targeted therapies. Oncogene. 2018; 37(12):1561-75. Epub 2018/01/13. doi: 10.1038/s41388-017-0045-7. PubMed PMID: 29321659; PubMed Central PMCID: PMCPMC5860944.

35. Szolek A, Schubert B, Mohr C, Sturm M, Feldhahn M, Kohlbacher O. OptiType: precision HLA typing from next-generation sequencing data. Bioinformatics. 2014; 30(23):3310-6. Epub 2014/08/22. doi: 10.1093/bioinformatics/btu548. PubMed PMID: 25143287; PubMed Central PMCID: PMCPMC4441069.

36. Boratyn G M, Thierry-Mieg J, Thierry-Mieg D, Busby B, Madden T L. Magic-BLAST, an accurate RNA-seq aligner for long and short reads. BMC Bioinformatics. 2019; 20(1):405. Epub 2019/07/28. doi: 10.1186/s12859-019-2996-x. PubMed PMID: 31345161; PubMed Central PMCID: PMCPMC6659269.

37. Larjo A, Eveleigh R, Kilpelainen E, Kwan T, Pastinen T, Koskela S, et al. Accuracy of Programs for the Determination of Human Leukocyte Antigen Alleles from Next-Generation Sequencing Data. Frontiers in immunology. 2017; 8:1815. Epub 2018/01/13. doi: 10.3389/fimmu.2017.01815. PubMed PMID: 29326702; PubMed Central PMCID: PMCPMC5733459.

38. Skwarczynski M, Dougall A M, Khoshnejad M, Chandrudu S, Pearson M S, Loukas A, et al. Peptide-based subunit vaccine against hookworm infection. PloS one. 2012; 7(10):e46870. Epub 2012/10/12. doi: 10.1371/journal.pone.0046870. PubMed PMID: 23056500; PubMed Central PMCID: PMCPMC3463534.

39. Skwarczynski M, Toth I. Non-invasive mucosal vaccine delivery: advantages, challenges and the future. Expert Opin Drug Deliv. 2020:1-3. Epub 2020/02/16. doi: 10.1080/17425247.2020.1731468. PubMed PMID: 32059625.

40. Nandedkar T D. Nanovaccines: recent developments in vaccination. Journal of biosciences. 2009; 34(6):995-1003. Epub 2010/01/23. doi: 10.1007/s12038-009-0114-3. PubMed PMID: 20093753.

41. Bartlett S, Eichenberger R M, Nevagi R J, Ghaffar K A, Marasini N, Dai Y, et al. Lipopeptide-based oral vaccine against hookworm infection. J Infect Dis. 2019. Epub 2019/10/18. doi: 10.1093/infdis/jiz528. PubMed PMID: 31621864.

42. Vogelstein B, Papadopoulos N, Velculescu V E, Zhou S, Diaz L A, Jr., Kinzler K W. Cancer genome landscapes. Science. 2013; 339(6127):1546-58. Epub 2013/03/30. doi: 10.1126/science.1235122. PubMed PMID: 23539594; PubMed Central PMCID: PMCPMC3749880.

43. Bremel R D, Homan E J. An integrated approach to epitope analysis II: A system for proteomic-scale prediction of immunological characteristics. ImmunomeRes. 2010; 6(1):8. doi: 1745-7580-6-8 [pii]; 10.1186/1745-7580-6-8 [doi].

44. Bremel R D, Homan E J. Frequency Patterns of T-Cell Exposed Amino Acid Motifs in Immunoglobulin Heavy Chain Peptides Presented by MHCs. Frontiers in immunology. 2014; 5:541. doi: 10.3389/fimmu.2014.00541. PubMed PMID: 25389426; PubMed Central PMCID: PMC4211557.

45. Bremel R D, Homan J. Extensive T-cell epitope repertoire sharing among human proteome, gastrointestinal microbiome, and pathogenic bacteria: Implications for the definition of self. Frontiers in immunology. 2015; 6. doi: 10.3389/fimmu.2015.00538.

46. Homan E J, Bremel R D. Patterns of Predicted T-Cell Epitopes Associated with Antigenic Drift in Influenza H3N2 Hemagglutinin. PLoSOne. 2011; 6(10):e26711. doi: 10.1371/journal.pone.0026711 [doi]; PONE-D-11-07616 [pii].

47. Hoglund R A, Torsetnes S B, Lossius A, Bogen B, Homan E J, Bremel R, et al. Human Cysteine Cathepsins Degrade Immunoglobulin G In Vitro in a Predictable Manner. Int J Mol Sci. 2019; 20(19). Epub 2019/10/02. doi: 10.3390/ijms20194843. PubMed PMID: 31569504; PubMed Central PMCID: PMCPMC6801702.

48. Asai Y, Eslami A, van Ginkel C D, Akhabir L, Wan M, Ellis G, et al. Genome-wide association study and meta-analysis in multiple populations identifies new loci for peanut allergy and establishes C1 1orf30/EMSY as a genetic risk factor for food allergy. J Allergy Clin Immunol. 2018; 141(3):991-1001. Epub 2017/10/17. doi: 10.1016/j.jaci.2017.09.015. PubMed PMID: 29030101.

49. Asai Y, Eslami A, van Ginkel C D, Akhabir L, Wan M, Yin D, et al. A Canadian genome-wide association study and meta-analysis confirm HLA as a risk factor for peanut allergy independent of asthma. J Allergy Clin Immunol. 2018; 141(4):1513-6. Epub 2018/01/13. doi: 10.1016/j.jaci.2017.10.047. PubMed PMID: 29325868.

50. Gerstner C, Dubnovitsky A, Sandin C, Kozhukh G, Uchtenhagen H, James E A, et al. Functional and Structural Characterization of a Novel HLA-DRB1*04:01-Restricted alpha-Enolase T Cell Epitope in Rheumatoid Arthritis. Frontiers in immunology. 2016; 7:494. Epub 2016/11/30. doi: 10.3389/fimmu.2016.00494. PubMed PMID: 27895642; PubMed Central PMCID: PMCPMC5108039.

51. Gerstner C, Turcinov S, Hensvold A H, Chemin K, Uchtenhagen H, Ramwadhdoebe T H, et al. Multi-HLA class II tetramer analyses of citrulline-reactive T cells and early treatment response in rheumatoid arthritis. BMC Immunol. 2020; 21(1):27. Epub 2020/05/20. doi: 10.1186/s12865-020-00357-w. PubMed PMID: 32423478; PubMed Central PMCID: PMCPMC7236297.

52. James E A, Rieck M, Pieper J, Gebe J A, Yue B B, Tatum M, et al. Citrulline-specific Th1 cells are increased in rheumatoid arthritis and their frequency is influenced by disease duration and therapy. Arthritis Rheumatol. 2014; 66(7):1712-22. Epub 2014/03/26. doi: 10.1002/art.38637. PubMed PMID: 24665079; PubMed Central PMCID: PMCPMC4248674.

53. Klareskog L, Padyukov L, Ronnelid J, Alfredsson L. Genes, environment and immunity in the development of rheumatoid arthritis. Curr Opin Immunol. 2006; 18(6): 650-5. Epub 2006/10/03. doi: 10.1016/j.coi.2006.06.004. PubMed PMID: 17010589.

54. Klareskog L, Stolt P, Lundberg K, Kallberg H, Bengtsson C, Grunewald J, et al. A new model for an etiology of rheumatoid arthritis: smoking may trigger HLA-DR (shared epitope)-restricted immune reactions to autoantigens modified by citrullination. Arthritis Rheum. 2006; 54(1):38-46. Epub 2005/12/31. doi: 10.1002/art.21575. PubMed PMID: 16385494.

All publications and patents mentioned in the above specification are herein incorporated by reference as if expressly set forth herein. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in relevant fields are intended to be within the scope of the following claims.

What is claimed is:

1. A method for treating cancer in a subject comprising designing a group of ten or more tumor-specific T-cell stimulating peptides, or nucleic acids encoding T cell stimulating peptides, which have a desired predicted binding affinity for the MHC alleles of the subject, comprising the following steps:

obtaining a biopsy of the subject's tumor;

obtaining sequences for proteins in said biopsy;

identifying proteins from the biopsy containing mutated amino acids and the peptide comprising each of said mutated amino acids;

determining T cell exposed motifs which comprise mutated amino acids in each of the proteins;

determining the predicted binding affinity to the subject's MHC alleles of peptides which comprises each of said T cell exposed motifs which comprise mutated amino acids and identifying MHC allele-T cell exposed motif combinations which bind with an affinity greater than the mean for the protein from which the peptide is derived;

generating an array of alternative peptides not present in the tumor from the identified MHC allele-T cell exposed motif combinations which bind with an affinity greater than the mean for the protein from which the peptide is derived, wherein each peptide in the array comprises the amino acids of one of said T cell exposed motifs which comprise mutated amino acids, and in which one or more of the amino acids not within the T cell exposed motif are substituted to change the predicted MHC binding affinity;

selecting a group of ten or more selected peptides from said array of alternative peptides, wherein the group of selected peptides comprises peptides collectively pre-dicted to bind to at least 4 different MHC alleles carried by the subject and further wherein the desired predicted binding affinity of each of the ten selected peptides is from 100 to 500 nM;

synthesizing said group of ten or more selected peptides, or nucleic acids encoding the selected peptides; and treating cancer in the subject by a process selected from the group consisting of 1) administering the peptides or nucleic acids to the patient to stimulate a tumor specific T cell response, 2) contacting an antigen presenting cell in vitro with said group of one or more selected peptides, or the nucleic acids that encode them and administering said antigen presenting cells to a subject, and 3) stimulating T cells in vitro with said group of one or more selected peptides, or the nucleic acids that encode them, to provide stimulated T cells and administering said stimulated T cells to a subject.

2. The method of claim 1 wherein said MHC alleles are MHC type I and said T cell response is a CD8+ response.

3. The method of claim 1 wherein said MHC alleles are MHC type II and said T cell response is a CD4+ response.

4. The method of claim 1 wherein said selected peptides are less than 20 amino acids long.

5. The method of claim 1, wherein the proteins in the subject's biopsy comprise mutations that are found in a multiplicity of cancers affecting a multiplicity of subjects.

6. The method of claim 1, wherein said group of ten or more selected peptides, or nucleic acids encoding the peptides, are prescribed for the subject of claim 1.

7. The method of claim 1, wherein said group of ten or more selected peptides, or the nucleic acids encoding them, is administered to a subject as a vaccine.

* * * * *